(12) United States Patent
Gaul et al.

(10) Patent No.: US 9,012,412 B2
(45) Date of Patent: Apr. 21, 2015

(54) DUAL SGLT1/SGLT2 INHIBITORS

(71) Applicant: Janssen Pharmaceutica NV, Beerse (BE)

(72) Inventors: Micheal Gaul, Yardley, PA (US); Gee-Hong Kuo, Scotch Plains, NJ (US); Guozhang Xu, Bensalem, PA (US); Bao-Ping Zhao, West Windsor, NJ (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 14/200,051

(22) Filed: Mar. 7, 2014

(65) Prior Publication Data
US 2014/0256657 A1 Sep. 11, 2014

Related U.S. Application Data

(60) Provisional application No. 61/775,774, filed on Mar. 11, 2013.

(51) Int. Cl.
| | | |
|---|---|---|
| *C07H 7/04* | (2006.01) | |
| *C07D 417/10* | (2006.01) | |
| *C07D 407/10* | (2006.01) | |
| *C07D 409/10* | (2006.01) | |
| *C07D 409/14* | (2006.01) | |

(52) U.S. Cl.
CPC ............ *C07D 417/10* (2013.01); *C07D 407/10* (2013.01); *C07D 409/10* (2013.01); *C07D 409/14* (2013.01)

(58) Field of Classification Search
None
See application file for complete search history.

(56) References Cited

U.S. PATENT DOCUMENTS

| | | | |
|---|---|---|---|
| 7,202,350 B2 * | 4/2007 | Imamura et al. ............. 536/1.11 | |
| 2006/0074031 A1 | 4/2006 | Eckhardt et al. | |
| 2012/0258913 A1 | 10/2012 | Nomura et al. | |

FOREIGN PATENT DOCUMENTS

| | | |
|---|---|---|
| EP | 1609785 A1 | 12/2005 |
| EP | 2530079 A1 | 12/2012 |
| WO | WO 2005/012326 A1 | 2/2005 |

OTHER PUBLICATIONS

Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, p. 596.*
International Search Report relating to corresponding International Patent Application No. PCTUS2014/021724. Date of Mailing of International Search Report: May 22, 2014.
Written Opinion of the International Searching Authority relating to corresponding International Patent Application No. PCTUS2014/021724. Date of Mailing of Written Opinion: May 22, 2014.
Berge et al., "Pharmaceutical Salts.", *J. Pharm. Sci.*, 1977, pp. 1-19, vol. 66(1).
Deetjen et al., "Renal Handling of D-Glucose and Other Sugars", *Textbook of Nephrology*, 3rd Edition, 1995, pp. 90-94. vol. 1.
Gould P.L., "Salt Selection for Basic Drugs.", *Ref. International J. Pharm.*, 1986, pp. 201-217, vol. 33.
Lee et al., "The High Affinity Na+/Glucose Cotransporter. Re-Evaluation of Function and Distribution of Expression.", *J. Biol. Chem.*, Apr. 1994, pp. 12032-12039, vol. 269(16), The American Society for Biochemistry and Molecular Biology, Inc. U.S.A.
Mackenzie et al., "Nephron Supply Is a Major Determinant of Long-Term Renal Allograft Outcome in Rats.", *J. Clin. Invest.*, Nov. 1994, pp. 2148-2152, vol. 94, The American Society for Clinical Investigation, Inc.
Silverman, R. B., "The Organic Chemistry of Drug Design and Drug Action," Academic Press, 1992, pp. 19-23.
You et al., "Molecular Characteristics of Na+-coupled Glucose Transporters in Adult and Embryonic Rat Kidney.", *J. Biol. Chem.*, Dec. 1995, pp. 29365-29371, vol. 270(49), The American Society for Biochemistry and Molecular Biology, Inc., U.S.A.

* cited by examiner

*Primary Examiner* — Traviss C McIntosh, III
(74) *Attorney, Agent, or Firm* — Jeremy K. McKown

(57) ABSTRACT

The present invention relates to compounds of Formula (I),

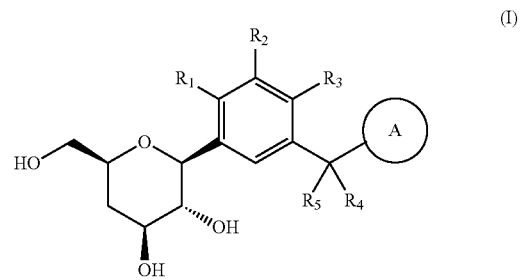

or a form thereof, wherein A, $R_1$, $R_2$, $R_3$, $R_4$, and $R_5$ are as defined herein, useful as dual SGLT1/SGLT2 inhibitors.

20 Claims, No Drawings

DUAL SGLT1/SGLT2 INHIBITORS

CROSS REFERENCE TO RELATED APPLICATIONS

This application claims the benefit of U.S. Provisional Application No. 61/775,774, filed on Mar. 11, 2013, which is incorporated by reference herein in it's entirety.

FIELD OF THE INVENTION

The present invention relates to substituted compounds useful as sodium-dependent glucose cotransporters (SGLT) inhibitors. More particularly, the present invention relates to substituted compounds useful as SGLT inhibitors and methods of preparation and use thereof.

BACKGROUND OF THE INVENTION

Diabetes is a chronic disorder affecting carbohydrate, fat and protein metabolism in animals.

Type I diabetes mellitus, which comprises approximately 10% of all diabetes cases, was previously referred to as insulin-dependent diabetes mellitus (IDDM) or juvenile onset diabetes. This disease is characterized by a progressive loss of insulin secretory function by beta cells of the pancreas. This characteristic is also shared by non-idiopathic, or "secondary", diabetes having its origins in pancreatic disease. Type I diabetes mellitus is associated with the following clinical signs or symptoms: persistently elevated plasma glucose concentration or hyperglycemia; polyuria; polydipsia and/or hyperphagia; chronic microvascular complications such as retinopathy, nephropathy and neuropathy; and macrovascular complications such as hyperlipidemia and hypertension which can lead to blindness, end-stage renal disease, limb amputation and myocardial infarction. Therapy for IDDM patients has consistently focused on administration of exogenous insulin, which may be derived from various sources (e.g., human, bovine, porcine insulin). The use of heterologous species material gives rise to formation of anti-insulin antibodies which have activity limiting effects and result in progressive requirements for larger doses in order to achieve desired hypoglycemic effects.

Type II diabetes mellitus (non-insulin-dependent diabetes mellitus or NIDDM) is a metabolic disorder involving the dysregulation of glucose metabolism and impaired insulin sensitivity. Type II diabetes mellitus usually develops in adulthood and is associated with the body's inability to utilize or make sufficient insulin. In addition to the insulin resistance observed in the target tissues, patients suffering from type II diabetes mellitus have a relative insulin deficiency—that is, patients have lower than predicted insulin levels for a given plasma glucose concentration. Type II diabetes mellitus is characterized by the following clinical signs or symptoms: persistently elevated plasma glucose concentration or hyperglycemia; polyuria; polydipsia and/or hyperphagia; chronic microvascular complications such as retinopathy, nephropathy and neuropathy; and macrovascular complications such as hyperlipidemia and hypertension which can lead to blindness, end-stage renal disease, limb amputation and myocardial infarction. Typical treatment of Type II diabetes mellitus focuses on maintaining the blood glucose level as near to normal as possible with lifestyle modification relating to diet and exercise, and when necessary, the treatment with antidiabetic agents, insulin or a combination thereof. NIDDM that cannot be controlled by dietary management is treated with oral antidiabetic agents.

Syndrome X, also termed Insulin Resistance Syndrome (IRS), Metabolic Syndrome, or Metabolic Syndrome X, is recognized in some 2% of diagnostic coronary catheterizations. Often disabling, it presents symptoms or risk factors for the development of Type II diabetes mellitus and cardiovascular disease, including impaired glucose tolerance (IGT), impaired fasting glucose (IFG), hyperinsulinemia, insulin resistance, dyslipidemia (e.g., high triglycerides, low HDL), hypertension and obesity. Although insulin resistance is not always treated in all Syndrome X patients, those who exhibit a prediabetic state (e.g., IGT, IFG), where fasting glucose levels may be higher than normal but not at the diabetes diagnostic criterion, is treated in some countries (e.g., Germany) with metformin to prevent diabetes. The anti-diabetic agents may be combined with pharmacological agents for the treatment of the concomitant co-morbidities (e.g., antihypertensives for hypertension, hypolipidemic agents for lipidemia).

Hyperglycemia is one common characteristic of these diabetic disorders. Treatments of hyperglycemia are focused on excretion of excessive glucose directly into urine, which involves sodium-glucose cotransporters (SGLTs), primarily found in the chorionic membrane of the intestine and kidney. In particular, renal reabsorption of glucose is mediated by SGLT1 and SGLT2 (Silverman et al., 1992; Deetjen et al., 1995). SGLT1, a high-affinity low-capacity transporter with a $Na^+$:glucose transport ratio of 2:1, is present in intestinal and renal epithelial cells (Lee et al., 1994). On the other hand, SGLT2, also known as SAAT1, a low-affinity high-capacity transporter with a $Na^+$:glucose transport ratio of 1:1, is found in the epithelium of the kidney (You et al., 1995, MacKenzie et al., 1994). In addition, glucose absorption in the intestine is primarily mediated by SGLT1 and SGLT2. Thus, inhibition of SGLT1 and SGLT2 reduces plasma glucose through suppression of glucose reabsorption in the kidney, which was demonstrated in rodent models of IDDM and NIDDM by increasing the excretion of glucose in urine and lowering blood glucose levels.

However, there still remains a need for SGLT inhibitor compounds that have pharmacokinetic and pharmacodynamic properties suitable for use as human pharmaceuticals.

SUMMARY OF THE INVENTION

In its many embodiments, the present invention provides novel compounds useful as, for example, SGLT inhibitors, methods of preparing such compounds, pharmaceutical compositions comprising one or more such compounds, methods of preparing pharmaceutical compositions comprising one or more such compounds, and methods of treatment, inhibition or amelioration of one or more diseases associated with SGLT using such compounds or pharmaceutical compositions.

One aspect of the present invention is directed to compounds, methods, and compositions for the treatment or prophylaxis of diabetes, Syndrome X, or associated symptoms or complications. More specifically, this invention is directed to a method of treating diabetes or Syndrome X, or associated symptoms or complications thereof, in a subject afflicted with such a condition, wherein the method comprises administering a SGLT inhibitor.

Another aspect of the present invention features a compound of Formula (I)

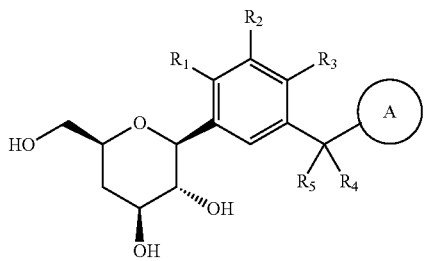

wherein
  $R_1$ is hydroxyl, $C_{1-4}$alkoxy, heteroaryl, or halogen;
  $R_2$ is H, $C_{1-2}$alkyl, or halogen;
  $R_3$ is $C_{1-4}$alkyl, halogen, $C_{1-4}$alkoxy, hydroxyl, $C_{3-5}$cycloalkyl, cyano, or $C_{1-2}$ alkenyl; wherein said $C_{1-4}$alkyl may be substituted with halogen;
  $R_4$ is H or $C_{1-4}$alkyl;
  $R_5$ is H or $C_{1-4}$alkyl; or alternatively $R_4$ is linked together to $R_5$ to form a cycloalkyl, alkenyl, or oxo;
  A is selected from the group consisting of:

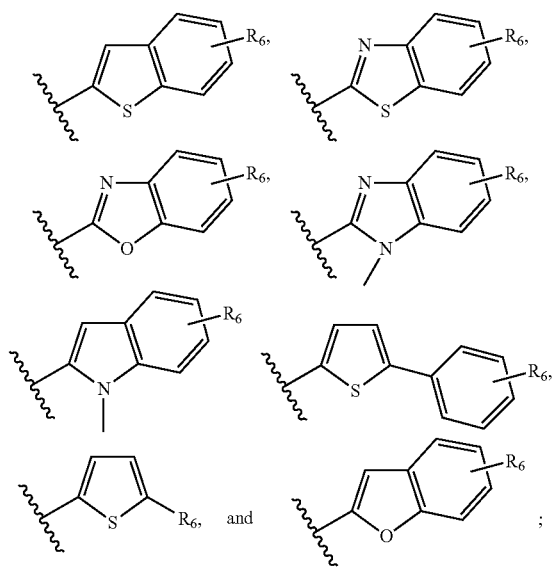

and
  $R_6$ is H, halogen, or $C_{1-4}$alkyl;
or an optical isomer, enantiomer, diastereomer, cis-trans isomer, racemate, prodrug or pharmaceutically acceptable salt thereof.

Another aspect of the present invention features a pharmaceutical composition comprising at least one compound of Formula (I) and at least one pharmaceutically acceptable carrier. The invention is also directed towards providing a process for formulating a pharmaceutical composition, comprising formulating a pharmaceutical composition of at least one compound of Formula (I) and at least one pharmaceutically acceptable carrier. The present invention further relates to a process for making a pharmaceutical composition comprising mixing any of the compounds according to Formula (I) and a pharmaceutically acceptable carrier.

The present invention also features a method of treating a subject suffering from or diagnosed with a disease, disorder, or condition mediated by SGLT activity, comprising administering to the subject a therapeutically effective amount of at least one compound of Formula (I). Such disease, disorder, or condition can include, but is not limited to diabetes, Syndrome X, or associated symptoms or complications. More specifically, diabetes, Syndrome X, and their associated symptoms or complications include, but are not limited to, IDDM, NIDDM, IGT, IFG, obesity, nephropathy, neuropathy, retinopathy, atherosclerosis, polycystic ovarian syndrome, hypertension, ischemia, stroke, heart disease, irritable bowel disorder, inflammation, and cataracts.

The invention further provides methods for using a compound or composition of the invention. For example, one embodiment of the invention is a method for treating a condition associated with SGLT activity in a subject in need thereof comprising administering to the subject an effective amount of any of the disclosed compounds or the disclosed pharmaceutical compositions.

Additional embodiments and advantages of the invention will become apparent from the detailed discussion, schemes, examples, and claims below.

DETAILED DESCRIPTION OF THE INVENTION

This invention relates to novel SGLT inhibitors and compositions thereof for the treatment, amelioration or inhibition of numerous conditions, including but not limited to diabetes and Syndrome X, and associated symptoms or complications thereof.

One aspect of the present invention features a compound of Formula (I)

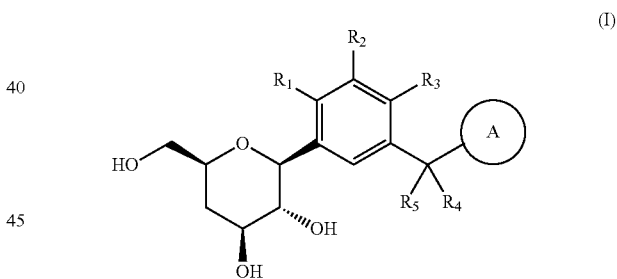

wherein
  $R_1$ is hydroxyl, $C_{1-4}$alkoxy, heteroaryl, or halogen;
  $R_2$ is H, $C_{1-2}$alkyl, or halogen;
  $R_3$ is $C_{1-4}$alkyl, halogen, $C_{1-4}$alkoxy, hydroxyl, $C_{3-5}$cycloalkyl, cyano, or $C_{1-2}$alkenyl; wherein said $C_{1-4}$alkyl may be substituted with halogen;
  $R_4$ is H or $C_{1-4}$alkyl;
  $R_5$ is H or $C_{1-4}$alkyl; or alternatively $R_4$ is linked together to $R_5$ to form a cycloalkyl, alkenyl, or oxo;
  A is selected from the group consisting of:

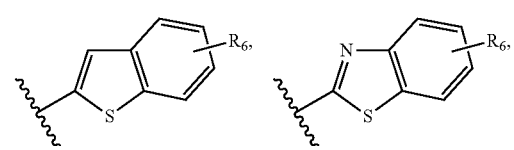

-continued

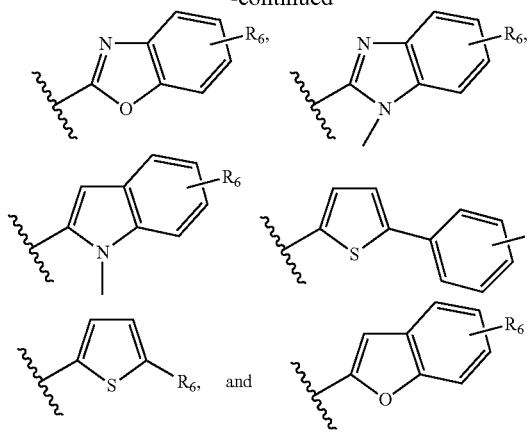

and
R$_6$ is H, halogen, or C$_{1-4}$alkyl;
or an optical isomer, enantiomer, diastereomer, cis-trans isomer, racemate, prodrug or pharmaceutically acceptable salt thereof.

In another embodiment, the present invention includes a compound of Formula (I) wherein:
R$_1$ is —OH, —OCH$_3$, —OCH$_2$—CH=CH$_2$,

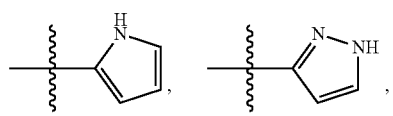

or —Br;
R$_2$ is H, —CH$_3$, or —F;
R$_3$ is —CH$_3$, —CF$_3$, —CH$_2$CH$_3$, —Cl, —OCH$_3$, —CH=CH$_2$, —CN, or

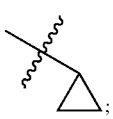

R$_4$ is H or —CH$_3$;
R$_5$ is H or —CH$_3$; or alternatively R$_4$ is linked together to R$_5$ to form

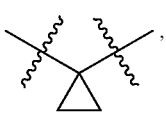 [SMILES: *C1(*)CC1]

=CH$_2$, or =O;
A is selected from the group consisting of:

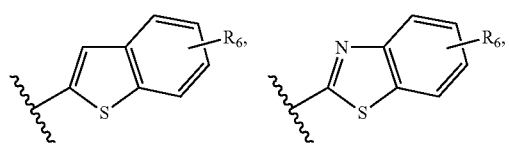

-continued

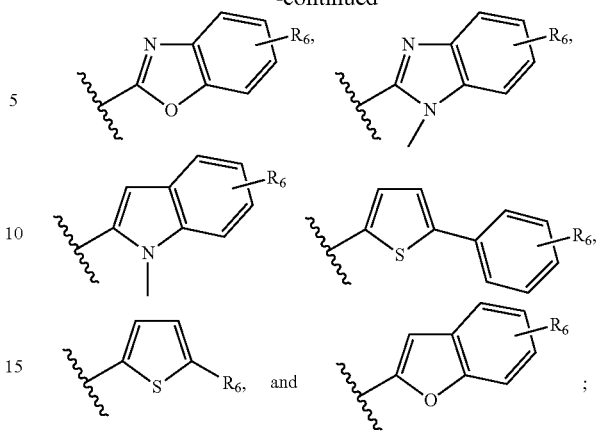

and
R$_6$ is H, —F, —Cl or —CH$_2$CH$_3$;
or an optical isomer, enantiomer, diastereomer, cis-trans isomer, racemate, prodrug or pharmaceutically acceptable salt thereof.

In another embodiment, the present invention includes a compound of Formula (I) wherein:
R$_1$ is —OH, —OCH$_3$, —OCH$_2$—CH=CH$_2$,

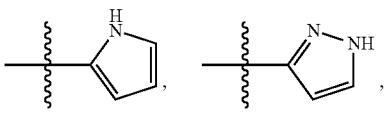 [SMILES: *c1ccc[nH]1 ; *c1cc[nH]n1]

or —Br;
R$_2$ is H, —CH$_3$, or —F;
R$_3$ is —CH$_3$, —CF$_3$, —CH$_2$CH$_3$, —Cl, —OCH$_3$, —CH=CH$_2$, —CN, or

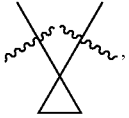

R$_4$ is H or —CH$_3$;
R$_5$ is H or —CH$_3$; or alternatively R$_4$ is linked together to R$_5$ to form =CH$_2$, or =O;
A is selected from the group consisting of:

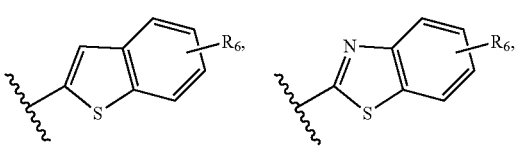

-continued

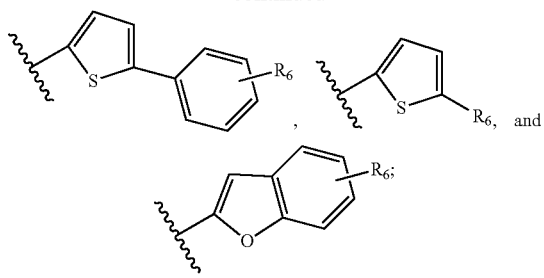

and

R$_6$ is H, —F, —Cl, or —CH$_2$CH$_3$;

or an optical isomer, enantiomer, diastereomer, cis-trans isomer, racemate, prodrug or pharmaceutically acceptable salt thereof.

In yet another embodiment, the present invention includes a compound of Formula (I) wherein:

R$_1$ is —OH;
R$_2$ is H, —CH$_3$, or —F;
R$_3$ is —CH$_3$, —CF$_3$, —CH$_2$CH$_3$, —F, —Cl, —OCH$_3$, —CH═CH2, or

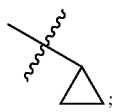 [SMILES: *C1CC1]

R$_4$ is H;
R$_5$ is H;
A is selected from the group consisting of:

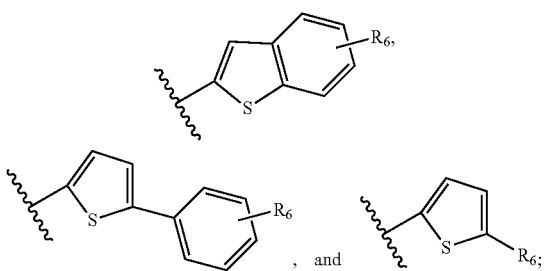

and

R$_6$ is H, —F, —Cl, or —CH$_2$CH$_3$;

or an optical isomer, enantiomer, diastereomer, cis-trans isomer, racemate, prodrug or pharmaceutically acceptable salt thereof.

In even yet another embodiment, the present invention includes a compound of Formula (I) wherein:

R$_1$ is —OH;
R$_2$ is H or —F;
R$_3$ is —CH$_3$, —CH$_2$CH$_3$, —Cl, or —OCH$_3$;
R$_4$ is H;
R$_5$ is H;
A is selected from the group consisting of:

and

R$_6$ is H, —F, or —CH$_2$CH$_3$;

or an optical isomer, enantiomer, diastereomer, cis-trans isomer, racemate, prodrug or pharmaceutically acceptable salt thereof.

In another embodiment, the present invention includes a compound of Formula (I) wherein:

R$_1$ is —OH;
R$_2$ is H or —F;
R$_3$ is —CH$_3$, —CH$_2$CH$_3$, —Cl, or —OCH$_3$;
R$_4$ is H;
R$_5$ is H;
A is

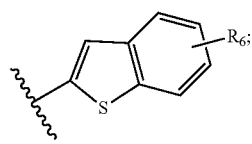

and

R$_6$ is H, —F, or —CH$_2$CH$_3$;

or an optical isomer, enantiomer, diastereomer, cis-trans isomer, racemate, prodrug or pharmaceutically acceptable salt thereof.

In even yet another embodiment, the present invention includes a compound of Formula (I) wherein:

R$_1$ is —OH;
R$_2$ is H;
R$_3$ is —CH$_3$;
R$_4$ is H;
R$_5$ is H;
A is

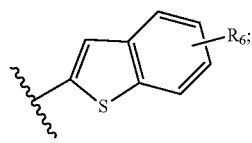

and

R$_6$ is H;

or an optical isomer, enantiomer, diastereomer, cis-trans isomer, racemate, prodrug or pharmaceutically acceptable salt thereof.

In another embodiment, the present invention includes a compound of Formula (I) wherein:

R$_1$ is —OH or —Br;
R$_2$ is H;
R$_3$ is —CH$_3$;
R$_4$ is H;
R$_5$ is H;

A is selected from the group consisting of:

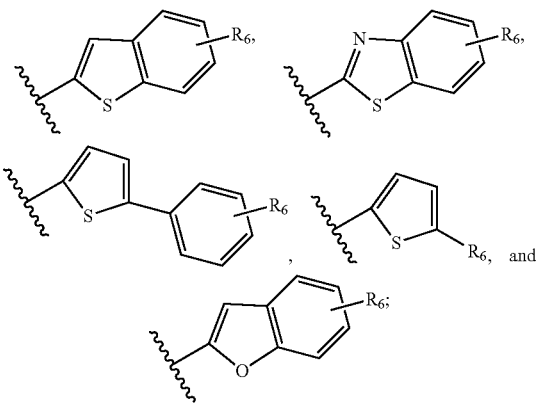

and

R$_6$ is H, CH$_2$CH$_3$, or —F
or an optical isomer, enantiomer, diastereomer, cis-trans isomer, racemate, prodrug or pharmaceutically acceptable salt thereof.

In one embodiment, A is

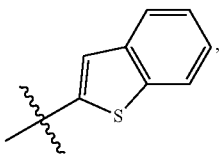 [SMILES: *c1cc2ccccc2s1]

R$_1$ is hydroxyl, R$_2$ is H, C$_{1-4}$alkyl, or fluoro, R$_3$ is C$_{1-4}$alkyl, trifluoro-C$_{1-4}$alkyl, C$_{1-4}$alkoxy, chloro, fluoro, C$_{3-5}$cycloalkyl or C$_{1-2}$alkenyl, and R$_6$ is chloro or fluoro.

In another embodiment, A is

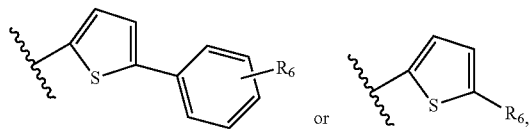

R$_1$ is hydroxyl, R$_2$ is H, R$_3$ is C$_{1-4}$alkyl, R$_4$ and R$_5$ are H.

In yet another embodiment, A is

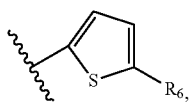

It is an embodiment of the present invention to provide a compound selected from:
(2S,3R,4S,6S)-2-(5-(benzo[b]thiophen-2-ylmethyl)-2-hydroxy-4-methylphenyl)-6-(hydroxymethyl)tetrahydro-2H-pyran-3,4-diol,
(2S,3R,4S,6S)-2-(5-(benzo[b]thiophen-2-ylmethyl)-2-hydroxy-4-methoxyphenyl)-6-(hydroxymethyl)tetrahydro-2H-pyran-3,4-diol,
(2S,3R,4S,6S)-2-(5-(benzo[b]thiophen-2-ylmethyl)-4-chloro-2-hydroxyphenyl)-6-(hydroxymethyl)tetrahydro-2H-pyran-3,4-diol,
(2S,3R,4S,6S)-2-(5-(benzo[b]thiophen-2-ylmethyl)-4-fluoro-2-hydroxyphenyl)-6-(hydroxymethyl)tetrahydro-2H-pyran-3,4-diol,
benzo[b]thiophen-2-yl(5-((2S,3R,4S,6S)-3,4-dihydroxy-6-(hydroxymethyl)tetrahydro-2H-pyran-2-yl)-4-hydroxy-2-methoxyphenyl)methanone,
benzo[b]thiophen-2-yl(5-((2S,3R,4S,6S)-3,4-dihydroxy-6-(hydroxymethyl)tetrahydro-2H-pyran-2-yl)-4-hydroxy-2-methylphenyl)methanone,
(2S,3R,4S,6S)-2-(5-(1-(benzo[b]thiophen-2-yl)vinyl)-2-hydroxy-4-methoxyphenyl)-6-(hydroxymethyl)tetrahydro-2H-pyran-3,4-diol,
(2S,3R,4S,6S)-2-(5-(1-(benzo[b]thiophen-2-yl)vinyl)-2-hydroxy-4-methylphenyl)-6-(hydroxymethyl)tetrahydro-2H-pyran-3,4-diol,
(2S,3R,4S,6S)-2-(5-(1-(benzo[b]thiophen-2-yl)cyclopropyl)-2-hydroxy-4-methoxyphenyl)-6-(hydroxymethyl)tetrahydro-2H-pyran-3,4-diol,
(2S,3R,4S,6S)-2-(5-(1-(benzo[b]thiophen-2-yl)cyclopropyl)-2-hydroxy-4-methylphenyl)-6-(hydroxymethyl)tetrahydro-2H-pyran-3,4-diol,
(2S,3R,4S,6S)-2-(5-(benzo[b]thiophen-2-ylmethyl)-4-ethyl-2-hydroxyphenyl)-6-(hydroxymethyl)tetrahydro-2H-pyran-3,4-diol,
(2S,3R,4S,6S)-2-(5-(benzo[b]thiophen-2-ylmethyl)-4-cyclopropyl-2-hydroxyphenyl)-6-(hydroxymethyl)tetrahydro-2H-pyran-3,4-diol,
2-(benzo[b]thiophen-2-ylmethyl)-4-((2S,3R,4S,6S)-3,4-dihydroxy-6-(hydroxymethyl)tetrahydro-2H-pyran-2-yl)-5-hydroxybenzonitrile,
(2S,3R,4S,6S)-2-(5-(2-(benzo[b]thiophen-2-yl)propan-2-yl)-2-hydroxy-4-methoxyphenyl)-6-(hydroxymethyl)tetrahydro-2H-pyran-3,4-diol,
(2S,3R,4S,6S)-2-(5-(2-(benzo[b]thiophen-2-yl)propan-2-yl)-2-hydroxy-4-methyl phenyl)-6-(hydroxymethyl)tetrahydro-2H-pyran-3,4-diol,
(2S,3R,4S,6S)-2-(5-(benzo[b]thiophen-2-ylmethyl)-2-hydroxy-4-(trifluoromethyl)phenyl)-6-(hydroxymethyl)tetrahydro-2H-pyran-3,4-diol,
(2S,3R,4S,6S)-2-(5-(benzo[b]thiophen-2-ylmethyl)-2-hydroxy-4-vinylphenyl)-6-(hydroxymethyl)tetrahydro-2H-pyran-3,4-diol,
benzo[b]thiophen-2-yl(5-((2S,3R,4S,6S)-3,4-dihydroxy-6-(hydroxymethyl)tetrahydro-2H-pyran-2-yl)-2,4-dihydroxyphenyl)methanone,
(2S,3R,4S,6S)-2-(5-((5-fluorobenzo[b]thiophen-2-yl)methyl)-2-hydroxy-4-methyl phenyl)-6-(hydroxymethyl)tetrahydro-2H-pyran-3,4-diol,
(2S,3R,4S,6S)-2-(5-((5-chlorobenzo[b]thiophen-2-yl)methyl)-2-hydroxy-4-methylphenyl)-6-(hydroxymethyl)tetrahydro-2H-pyran-3,4-diol,
(2S,3R,4S,6S)-2-(5-(benzo[b]thiophen-2-ylmethyl)-3-fluoro-2-hydroxy-4-methoxyphenyl)-6-(hydroxymethyl)tetrahydro-2H-pyran-3,4-diol,
(2S,3R,4S,6S)-2-(5-(benzo[b]thiophen-2-ylmethyl)-2-hydroxy-3,4-dimethylphenyl)-6-(hydroxymethyl)tetrahydro-2H-pyran-3,4-diol,
(2S,3R,4S,6S)-2-(5-(benzo[b]thiophen-2-ylmethyl)-2-methoxy-3,4-dimethylphenyl)-6-(hydroxymethyl)tetrahydro-2H-pyran-3,4-diol,
(2S,3R,4S,6S)-2-(2-(allyloxy)-5-benzo[b]thiophen-2-ylmethyl)-3,4-dimethylphenyl)-6-(hydroxymethyl)tetrahydro-2H-pyran-3,4-diol,
(2S,3R,4S,6S)-2-(5-(benzo[b]thiophen-2-ylmethyl)-2-bromo-4-methyl phenyl)-6-(hydroxymethyl)tetrahydro-2H-pyran-3,4-diol, (2S,3R,4S,6S)-2-(5-(benzo[b]thiophen-2-ylmethyl)-4-methyl-2-(1H-pyrrol-2-yl)phenyl)-6-(hydroxymethyl)tetrahydro-2H-pyran-3,4-diol, (2S,3R,4S,6S)-2-(5-(benzo[b]thiophen-2-ylmethyl)-4-methyl-2-(1H-pyrazol-3-yl)phenyl)-6-(hydroxymethyl)tetrahydro-2H-pyran-3,4-diol, (2S,3R,4S,6S)-2-(5-(benzofuran-2-ylmethyl)-2-hydroxy-4-methylphenyl)-6-(hydroxymethyl)tetrahydro-2H-pyran-3,4-diol, (2S,3R,4S,6S)-2-(5-(benzo[d]thiazol-2-ylmethyl)-2-hydroxy-4-methyl phenyl)-6-(hydroxymethyl)tetrahydro-2H-pyran-3,4-diol, (2S,3R,4S,6S)-2-(2-bromo-5-((5-(4-fluorophenyl)thiophen-2-yl)methyl)-4-methyl phenyl)-6-(hydroxymethyl)tetrahydro-2H-pyran-3,4-diol, (2S,3R,4S,6S)-2-(5-((5-(4-fluorophenyl)thiophen-2-yl)methyl)-2-hydroxy-4-methylphenyl)-6-(hydroxymethyl)tetrahydro-2H-pyran-3,4-diol, and (2S,3R,4S,6S)-2-(5-((5-ethylthiophen-2-yl)methyl)-2-hydroxy-4-methyl phenyl)-6-(hydroxymethyl)tetrahydro-2H-pyran-3,4-diol.

Particularly, an embodiment of the present invention comprises a compound selected from:

(2S,3R,4S,6S)-2-(5-(benzo[b]thiophen-2-ylmethyl)-2-hydroxy-4-methylphenyl)-6-(hydroxymethyl)tetrahydro-2H-pyran-3,4-diol, (2S,3R,4S,6S)-2-(5-(benzo[b]thiophen-2-ylmethyl)-2-hydroxy-4-methoxyphenyl)-6-(hydroxymethyl)tetrahydro-2H-pyran-3,4-diol, (2S,3R,4S,6S)-2-(5-(benzo[b]thiophen-2-ylmethyl)-4-chloro-2-hydroxyphenyl)-6-(hydroxymethyl)tetrahydro-2H-pyran-3,4-diol, (2S,3R,4S,6S)-2-(5-(benzo[b]thiophen-2-ylmethyl)-4-fluoro-2-hydroxyphenyl)-6-(hydroxymethyl)tetrahydro-2H-pyran-3,4-diol, (2S,3R,4S,6S)-2-(5-(benzo[b]thiophen-2-ylmethyl)-4-ethyl-2-hydroxyphenyl)-6-(hydroxymethyl)tetrahydro-2H-pyran-3,4-diol, (2S,3R,4S,6S)-2-(5-(benzo[b]thiophen-2-ylmethyl)-4-cyclopropyl-2-hydroxyphenyl)-6-(hydroxymethyl)tetrahydro-2H-pyran-3,4-diol, (2S,3R,4S,6S)-2-(5-(benzo[b]thiophen-2-ylmethyl)-2-hydroxy-4-(trifluoromethyl)phenyl)-6-(hydroxymethyl)tetrahydro-2H-pyran-3,4-diol, (2S,3R,4S,6S)-2-(5-(benzo[b]thiophen-2-ylmethyl)-2-hydroxy-4-vinylphenyl)-6-(hydroxymethyl)tetrahydro-2H-pyran-3,4-diol, (2S,3R,4S,6S)-2-(5-((5-fluorobenzo[b]thiophen-2-yl)methyl)-2-hydroxy-4-methylphenyl)-6-(hydroxymethyl)tetrahydro-2H-pyran-3,4-diol, (2S,3R,4S,6S)-2-(5-((5-chlorobenzo[b]thiophen-2-yl)methyl)-2-hydroxy-4-methylphenyl)-6-(hydroxymethyl)tetrahydro-2H-pyran-3,4-diol, (2S,3R,4S,6S)-2-(5-(benzo[b]thiophen-2-ylmethyl)-3-fluoro-2-hydroxy-4-methoxyphenyl)-6-(hydroxymethyl)tetrahydro-2H-pyran-3,4-diol, (2S,3R,4S,6S)-2-(5-(benzo[b]thiophen-2-ylmethyl)-2-hydroxy-3,4-dimethylphenyl)-6-(hydroxymethyl)tetrahydro-2H-pyran-3,4-diol, (2S,3R,4S,6S)-2-(5-((5-(4-fluorophenyl)thiophen-2-yl)methyl)-2-hydroxy-4-methylphenyl)-6-(hydroxymethyl)tetrahydro-2H-pyran-3,4-diol, and (2S,3R,4S,6S)-2-(5-((5-ethylthiophen-2-yl)methyl)-2-hydroxy-4-methylphenyl)-6-(hydroxymethyl)tetrahydro-2H-pyran-3,4-diol.

More particularly, an embodiment of the present invention comprises a compound selected from:

(2S,3R,4S,6S)-2-(5-(benzo[b]thiophen-2-ylmethyl)-2-hydroxy-4-methylphenyl)-6-(hydroxymethyl)tetrahydro-2H-pyran-3,4-diol, (2S,3R,4S,6S)-2-(5-(benzo[b]thiophen-2-ylmethyl)-4-chloro-2-hydroxyphenyl)-6-(hydroxymethyl)tetrahydro-2H-pyran-3,4-diol, (2S,3R,4S,6S)-2-(5-(benzo[b]thiophen-2-ylmethyl)-3-fluoro-2-hydroxy-4-methoxyphenyl)-6-(hydroxymethyl)tetrahydro-2H-pyran-3,4-diol, (2S,3R,4S,6S)-2-(5-(benzo[b]thiophen-2-ylmethyl)-4-ethyl-2-hydroxyphenyl)-6-(hydroxymethyl)tetrahydro-2H-pyran-3,4-diol, (2S,3R,4S,6S)-2-(5-((5-fluorobenzo[b]thiophen-2-yl)methyl)-2-hydroxy-4-methylphenyl)-6-(hydroxymethyl)tetrahydro-2H-pyran-3,4-diol, and (2S,3R,4S,6S)-2-(5-((5-ethylthiophen-2-yl)methyl)-2-hydroxy-4-methylphenyl)-6-(hydroxymethyl)tetrahydro-2H-pyran-3,4-diol.

The invention is also directed to a pharmaceutical composition which include, without limitation, one or more of the disclosed compounds, and pharmaceutically acceptable carriers or excipients.

Another embodiment of the present invention is a pharmaceutical composition of the present invention that comprises at least a compound selected from:

(2S,3R,4S,6S)-2-(5-(benzo[b]thiophen-2-ylmethyl)-2-hydroxy-4-methylphenyl)-6-(hydroxymethyl)tetrahydro-2H-pyran-3,4-diol, (2S,3R,4S,6S)-2-(5-(benzo[b]thiophen-2-ylmethyl)-2-hydroxy-4-methoxyphenyl)-6-(hydroxymethyl)tetrahydro-2H-pyran-3,4-diol, (2S,3R,4S,6S)-2-(5-(benzo[b]thiophen-2-ylmethyl)-4-chloro-2-hydroxyphenyl)-6-(hydroxymethyl)tetrahydro-2H-pyran-3,4-diol, (2S,3R,4S,6S)-2-(5-(benzo[b]thiophen-2-ylmethyl)-4-fluoro-2-hydroxyphenyl)-6-(hydroxymethyl)tetrahydro-2H-pyran-3,4-diol, benzo[b]thiophen-2-yl(5-((2S,3R,4S,6S)-3,4-dihydroxy-6-(hydroxymethyl)tetrahydro-2H-pyran-2-yl)-4-hydroxy-2-methoxyphenyl)methanone, benzo[b]thiophen-2-yl(5-((2S,3R,4S,6S)-3,4-dihydroxy-6-(hydroxymethyl)tetrahydro-2H-pyran-2-yl)-4-hydroxy-2-methylphenyl)methanone, (2S,3R,4S,6S)-2-(5-(1-(benzo[b]thiophen-2-yl)vinyl)-2-hydroxy-4-methoxyphenyl)-6-(hydroxymethyl)tetrahydro-2H-pyran-3,4-diol, (2S,3R,4S,6S)-2-(5-(1-(benzo[b]thiophen-2-yl)vinyl)-2-hydroxy-4-methylphenyl)-6-(hydroxymethyl)tetrahydro-2H-pyran-3,4-diol, (2S,3R,4S,6S)-2-(5-(1-(benzo[b]thiophen-2-yl)cyclopropyl)-2-hydroxy-4-methoxyphenyl)-6-(hydroxymethyl)tetrahydro-2H-pyran-3,4-diol, (2S,3R,4S,6S)-2-(5-(1-(benzo[b]thiophen-2-yl)cyclopropyl)-2-hydroxy-4-methylphenyl)-6-(hydroxymethyl)tetrahydro-2H-pyran-3,4-diol, (2S,3R,4S,6S)-2-(5-(benzo[b]thiophen-2-ylmethyl)-4-ethyl-2-hydroxyphenyl)-6-(hydroxymethyl)tetrahydro-2H-pyran-3,4-diol, (2S,3R,4S,6S)-2-(5-(benzo[b]thiophen-2-ylmethyl)-4-cyclopropyl-2-hydroxyphenyl)-6-(hydroxymethyl)tetrahydro-2H-pyran-3,4-diol, 2-(benzo[b]thiophen-2-ylmethyl)-4-((2S,3R,4S,6S)-3,4-dihydroxy-6-(hydroxymethyl)tetrahydro-2H-pyran-2-yl)-5-hydroxybenzonitrile, (2S,3R,4S,6S)-2-(5-(2-(benzo[b]thiophen-2-yl)propan-2-yl)-2-hydroxy-4-methoxyphenyl)-6-(hydroxymethyl)tetrahydro-2H-pyran-3,4-diol, (2S,3R,4S,6S)-2-(5-(2-(benzo[b]thiophen-2-yl)propan-2-yl)-2-hydroxy-4-methylphenyl)-6-(hydroxymethyl)tetrahydro-2H-pyran-3,4-diol, (2S,3R,4S,6S)-2-(5-(benzo[b]thiophen-2-ylmethyl)-2-hydroxy-4-(trifluoromethyl)phenyl)-6-(hydroxymethyl)tetrahydro-2H-pyran-3,4-diol, (2S,3R,4S,6S)-2-(5-(benzo[b]thiophen-2-ylmethyl)-2-hydroxy-4-vinylphenyl)-6-(hydroxymethyl)tetrahydro-2H-pyran-3,4-diol, benzo[b]thiophen-2-yl(5-((2S,3R,4S,6S)-3,4-dihydroxy-6-(hydroxymethyl)tetrahydro-2H-pyran-2-yl)-2,4-dihydroxyphenyl)methanone, (2S,3R,4S,6S)-2-(5-((5-fluorobenzo[b]thiophen-2-yl)methyl)-2-hydroxy-4-methyl phenyl)-6-(hydroxymethyl)tetrahydro-2H-pyran-3,4-diol, (2S,3R,4S,6S)-2-(5-((5-chlorobenzo[b]thiophen-2-yl)methyl)-2-hydroxy-4-methylphenyl)-6-(hydroxymethyl)tetrahydro-2H-pyran-3,4-diol, (2S,3R,4S,6S)-2-(5-(benzo[b]thiophen-2-ylmethyl)-3-fluoro-2-hydroxy-4-methoxyphenyl)-6-(hydroxymethyl)tetrahydro-2H-pyran-3,4-diol, (2S,3R,4S,6S)-2-(5-(benzo[b]thiophen-2-ylmethyl)-2-hydroxy-3,4-dimethylphenyl)-6-(hydroxymethyl)tetrahydro-2H-pyran-3,4-diol, (2S,3R,4S,6S)-2-(5-(benzo[b]thiophen-2-ylmethyl)-2-methoxy-3,4-dimethylphenyl)-6-(hydroxymethyl)tetrahydro-2H-pyran-3,4-diol, (2S,3R,4S,6S)-2-(2-(allyloxy)-5-(benzo[b]thiophen-2-ylmethyl)-3,4-dimethylphenyl)-6-(hydroxymethyl)tetrahydro-2H-pyran-3,4-diol, (2S,3R,4S,6S)-2-(5-(benzo[b]thiophen-2-ylmethyl)-2-bromo-4-methyl phenyl)-6-(hydroxymethyl)tetrahydro-2H-pyran-3,4-diol, (2S,3R,4S,6S)-2-(5-(benzo[b]thiophen-2-ylmethyl)-4-methyl-2-(1H-pyrrol-2-yl)phenyl)-6-(hydroxymethyl)tetrahydro-2H-pyran-3,4-diol, (2S,3R,4S,6S)-2-(5-(benzo[b]thiophen-2-ylmethyl)-4-methyl-2-(1H-pyrazol-3-yl)phenyl)-6-(hydroxymethyl)tetrahydro-2H-pyran-3,4-diol, (2S,3R,4S,6S)-2-(5-(benzofuran-2-ylmethyl)-2-hydroxy-4-methylphenyl)-6-(hydroxymethyl)tetrahydro-2H-pyran-3,4-diol, (2S,3R,4S,6S)-2-(5-(benzo[d]thiazol-2-ylmethyl)-2-hydroxy-4-methyl phenyl)-6-(hydroxymethyl)tetrahydro-2H-pyran-3,4-diol, (2S,3R,4S,6S)-2-(2-bromo-5-((5-(4-fluorophenyl)thiophen-2-yl)methyl)-4-methyl phenyl)-6-(hydroxymethyl)tetrahydro-2H-pyran-3,4-diol, (2S,3R,4S,6S)-2-(5-((5-(4-fluorophenyl)thiophen-2-yl)methyl)-2-hydroxy-4-methylphenyl)-6-(hydroxymethyl)tetrahydro-2H-pyran-3,4-diol, and (2S,3R,4S,6S)-2-(5-((5-ethylthiophen-2-yl)methyl)-2-hydroxy-4-methyl phenyl)-6-(hydroxymethyl)tetrahydro-2H-pyran-3,4-diol.

Particularly, an embodiment of the present invention is a pharmaceutical composition of the present invention that comprises at least a compound selected from:

(2S,3R,4S,6S)-2-(5-(benzo[b]thiophen-2-ylmethyl)-2-hydroxy-4-methylphenyl)-6-(hydroxymethyl)tetrahydro-2H-pyran-3,4-diol, (2S,3R,4S,6S)-2-(5-(benzo[b]thiophen-2-ylmethyl)-2-hydroxy-4-methoxyphenyl)-6-(hydroxymethyl)tetrahydro-2H-pyran-3,4-diol, (2S,3R,4S,6S)-2-(5-(benzo[b]thiophen-2-ylmethyl)-4-chloro-2-hydroxyphenyl)-6-(hydroxymethyl)tetrahydro-2H-pyran-3,4-diol, (2S,3R,4S,6S)-2-(5-(benzo[b]thiophen-2-ylmethyl)-4-fluoro-2-hydroxyphenyl)-6-(hydroxymethyl)tetrahydro-2H-pyran-3,4-diol, (2S,3R,4S,6S)-2-(5-(benzo[b]thiophen-2-ylmethyl)-4-ethyl-2-hydroxyphenyl)-6-(hydroxymethyl)tetrahydro-2H-pyran-3,4-diol, (2S,3R,4S,6S)-2-(5-(benzo[b]thiophen-2-ylmethyl)-4-cyclopropyl-2-hydroxyphenyl)-6-(hydroxymethyl)tetrahydro-2H-pyran-3,4-diol, (2S,3R,4S,6S)-2-(5-(benzo[b]thiophen-2-ylmethyl)-2-hydroxy-4-(trifluoromethyl)phenyl)-6-(hydroxymethyl)tetrahydro-2H-pyran-3,4-diol, (2S,3R,4S,6S)-2-(5-(benzo[b]thiophen-2-ylmethyl)-2-hydroxy-4-vinylphenyl)-6-(hydroxymethyl)tetrahydro-2H-pyran-3,4-diol, (2S,3R,4S,6S)-2-(5-((5-fluorobenzo[b]thiophen-2-yl)methyl)-2-hydroxy-4-methylphenyl)-6-(hydroxymethyl)tetrahydro-2H-pyran-3,4-diol, (2S,3R,4S,6S)-2-(5-((5-chlorobenzo[b]thiophen-2-yl)methyl)-2-hydroxy-4-methylphenyl)-6-(hydroxymethyl)tetrahydro-2H-pyran-3,4-diol, (2S,3R,4S,6S)-2-(5-(benzo[b]thiophen-2-ylmethyl)-3-fluoro-2-hydroxy-4-methoxyphenyl)-6-(hydroxymethyl)tetrahydro-2H-pyran-3,4-diol, (2S,3R,4S,6S)-2-(5-(benzo[b]thiophen-2-ylmethyl)-2-hydroxy-3,4-dimethylphenyl)-6-(hydroxymethyl)tetrahydro-2H-pyran-3,4-diol, (2S,3R,4S,6S)-2-(5-((5-(4-fluorophenyl)thiophen-2-yl)methyl)-2-hydroxy-4-methylphenyl)-6-(hydroxymethyl)tetrahydro-2H-pyran-3,4-diol, and (2S,3R,4S,6S)-2-(5-((5-ethylthiophen-2-yl)methyl)-2-hydroxy-4-methylphenyl)-6-(hydroxymethyl)tetrahydro-2H-pyran-3,4-diol.

More particularly, an embodiment of the present invention is a pharmaceutical composition of the present invention that comprises at least a compound selected from:

(2S,3R,4S,6S)-2-(5-(benzo[b]thiophen-2-ylmethyl)-2-hydroxy-4-methylphenyl)-6-(hydroxymethyl)tetrahydro-2H-pyran-3,4-diol, (2S,3R,4S,6S)-2-(5-(benzo[b]thiophen-2-ylmethyl)-4-chloro-2-hydroxyphenyl)-6-(hydroxymethyl)tetrahydro-2H-pyran-3,4-diol, (2S,3R,4S,6S)-2-(5-(benzo[b]thiophen-2-ylmethyl)-3-fluoro-2-hydroxy-4-methoxyphenyl)-6-(hydroxymethyl)tetrahydro-2H-pyran-3,4-diol, (2S,3R,4S,6S)-2-(5-(benzo[b]thiophen-2-ylmethyl)-4-ethyl-2-hydroxyphenyl)-6-(hydroxymethyl)tetrahydro-2H-pyran-3,4-diol, (2S,3R,4S,6S)-2-(5-((5-fluorobenzo[b]thiophen-2-yl)methyl)-2-hydroxy-4-methylphenyl)-6-(hydroxymethyl)tetrahydro-2H-pyran-3,4-diol, and (2S,3R,4S,6S)-2-(5-((5-ethylthiophen-2-yl)methyl)-2-hydroxy-4-methylphenyl)-6-(hydroxymethyl)tetrahydro-2H-pyran-3,4-diol.

The present invention also features a method of treating a subject suffering from or diagnosed with a disease, disorder, or condition mediated by SGLT activity, comprising administering to the subject a therapeutically effective amount of at least one compound of Formula (I).

The present invention also features a method for preventing or inhibiting the progression of an SGLT-mediated condition in a subject in need thereof, comprising administering to said subject a therapeutically effective amount of at least one compound of Formula (I). Such disease, disorder, or condition can include, but is not limited to diabetes, Syndrome X, and associated symptoms or complications thereof. More specifically, diabetes, Syndrome X, and their associated symptoms or complications include, but are not limited to, IDDM, NIDDM, IGT, IFG, obesity, nephropathy, neuropathy, retinopathy, atherosclerosis, polycystic ovarian syndrome, hypertension, ischemia, stroke, heart disease, irritable bowel disorder, inflammation, and cataracts.

In another embodiment, the compounds of the present invention are useful for the amelioration of symptoms associated with and/or the treatment of the following conditions and diseases: IDDM, NIDDM, IGT, IFG, obesity, nephropathy, neuropathy, retinopathy, atherosclerosis, hypertension, ischemia, stroke, and heart disease.

In another embodiment, the compounds of the present invention are useful for the amelioration of symptoms associated with and/or the treatment of diabetes.

In another embodiment, the compounds of the present invention are useful for the amelioration of symptoms associated with and/or the treatment of diabetes. wherein said diabetes is type H diabetes. In a further embodiment, the compounds of the present invention are useful for the amelioration of symptoms associated with and/or the treatment of diabetes. wherein said diabetes is type diabetes.

In another embodiment, the compounds of the present invention are useful for the amelioration of symptoms associated with and/or the treatment of impaired glucose tolerance.

In another embodiment, the compounds of the present invention are useful for the amelioration of symptoms associated with and/or the treatment of IDDM, NIDDM, and obesity.

In another embodiment, the compounds of the present invention are useful for the amelioration of symptoms associated with and/or the treatment of Type II diabetes mellitus and cardiovascular disease, including impaired glucose tolerance (IGT), impaired fasting glucose (IFG), hyperinsulinemia, insulin resistance, dyslipidemia (e.g., high triglycerides, low HDL), hypertension and obesity.

In another embodiment, the compounds of the present invention are useful for the amelioration of symptoms associated with and/or the treatment of the following conditions and diseases: polycystic ovarian syndrome, irritable bowel disorder, inflammation, and cataracts.

It is a further embodiment of the invention to provide a process for making a pharmaceutical composition comprising admixing any of the compounds according to Formula (I) and a pharmaceutically acceptable carrier.

In a further embodiment of the invention, a method for treating or ameliorating an SGLT-mediated condition in a subject in need thereof comprises administering to the subject a therapeutically effective amount of at least one compound of Formula (I), wherein the therapeutically effective amount of the compound of Formula (I) is from about 0.1 mg/dose to about 5 g/dose. In particular, the therapeutically effective amount of the compound of Formula (I) is from about 0.5 mg/dose to about 1000 mg/dose. More particularly, the therapeutically effective amount of the compound of Formula (I) is from about 1 mg/dose to about 100 mg/dose. In a further embodiment of the invention, the number of doses per day of a compound of Formula (I) is from 1 to 3 doses. In a further embodiment of the invention, the therapeutically effective amount of the compound of Formula (I) is from about 0.001 mg/kg/day to about 30 mg/kg/day. More particularly, the therapeutically effective amount of the compound of Formula (I) is from about 0.01 mg/kg/day to about 2 mg/kg/day.

The invention is further described below.

A) Terms

Some terms are defined below and by their usage throughout this disclosure.

It should also be noted that any atom with unsatisfied valences in the text, schemes, examples, structural formulae and any tables herein is assumed to have the hydrogen atom or atoms to satisfy the valences.

As used herein, the following terms are intended to have the following definitions. The definitions herein may specify that a chemical term has an indicated formula. The particular formula provided is not intended to limit the scope of the invention, but is provided as an illustration of the term. The scope of the per se definition of the term is intended to include the plurality of variations expected to be included by one of ordinary skill in the art.

The term "$C_{1-4}$alkyl" means a saturated branched or straight-chain hydrocarbon radical having from 1 up to 4 carbon atoms in a linear or branched arrangement. The term includes atom groups such as methyl, ethyl, 1-propyl, 2-propyl, 1-butyl, 2-butyl, tert-butyl and the like. An alkyl radical may be attached to a core molecule by any atom where allowed by available valences.

The term "$C_{1-4}$alkoxy" means an alkyl radical having from 1 up to 4 carbon atoms in a linear or branched arrangement, as in the formula: —O—$C_{1-4}$alkyl. The term includes atom groups such as methoxy, ethoxy, propoxy, butoxy and the like. An alkoxy radical may be attached to a core molecule by any atom where allowed by available valences.

The term "$C_{3-5}$cycloalkyl" means a saturated or partially unsaturated, monocyclic, polycyclic or benzofused hydrocarbon ring system radical. Examples include cyclopropyl, cyclobutyl, cyclopentyl, and the like. A $C_{3-5}$cycloalkyl radical may be attached to a core molecule by any ring atom where allowed by available valences.

The term "aryl" means an unsaturated, aromatic monocyclic or polycyclic hydrocarbon ring system radical. Examples of aryl ring systems include phenyl, naphthalenyl, azulenyl, anthracenyl and the like. An aryl radical may be attached to a core molecule by any ring atom where allowed by available valences.

The term "alkenyl" means an unsaturated branched or straight-chain hydrocarbon radical having from 1 up to 4 carbon atoms in a linear or branched arrangement.

The term "hetero", when used as a prefix for a ring system, refers to the replacement of at least one carbon atom member in the ring system with a heteroatom selected from N, O, S, S(O), or $SO_2$. A hetero ring may have 1, 2, 3 or 4 carbon atom members replaced by a nitrogen atom. Alternatively, a ring may have 1, 2 or 3 nitrogen atom members and 1 oxygen or sulfur atom member. Alternatively, a ring may have 1 oxygen or sulfur atom member. Alternatively, up to two adjacent ring members may be heteroatoms, wherein one heteroatom is nitrogen and the other heteroatom is selected from N, S or O.

The term "heteroaryl" means an unsaturated monocyclic, polycyclic aromatic "hetero" ring system radical. Heteroaryl ring systems include furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl and the like. A heteroaryl radical may be attached to a core molecule by any ring atom where allowed by available valences.

The term "carboxy" means a radical of the formula: —C(O)OH.

The term "halogen" or "halo" means a radical selected from the group consisting of chloro, bromo, fluoro or iodo.

The term "oxo" means a radical of the formula: =O.

The term "substituted" refers to a radical in which one or more hydrogen atoms are each independently replaced with the same or different substituent(s).

With reference to substituents, the term "independently" means that when more than one of such substituent is possible, such substituents may be the same or different from each other.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

In general, IUPAC nomenclature rules are used herein.

The term "about," whether used explicitly or not in reference to a quantitative expression given herein, means that every quantity given herein qualified with the term or otherwise is meant to refer both to the actual given value and the approximation to such given value that would reasonably be inferred based on the ordinary skill in the art, including approximations due to experimental and/or measurement conditions for such given value.

The term "form" means, in reference to compounds of the present invention, such may exist as, without limitation, a salt, stereoisomer, tautomer, crystalline, polymorph, amorphous, solvate, hydrate, ester, prodrug or metabolite form. The present invention encompasses all such compound forms and mixtures thereof.

The term "isolated form" means, in reference to compounds of the present invention, such may exist in an essentially pure state such as, without limitation, an enantiomer, a racemic mixture, a geometric isomer (such as a cis or trans stereoisomer), a mixture of geometric isomers, and the like. The present invention encompasses all such compound forms and mixtures thereof.

The term "composition" is intended to encompass a product comprising the specified ingredients in the specified amounts, as well as any product which results, directly or indirectly, from combinations of the specified ingredients in the specified amounts.

The term "subject" as used herein, refers to a patient, such as an animal, a mammal or a human, who has been the object of treatment, observation or experiment and is at risk of (or susceptible to) developing an SGLT-mediated disorder.

The term "administering" further means that the individual ingredients to be combined may be administered at the same time or at different times during the treatment period, either as one preparation or as different preparations. Accordingly, the invention should be so interpreted that it encompasses any and every administration mode at the same time or at different times. The range of the combination of the compound of the invention and the other therapeutic agent useful for the above-mentioned disorders encompasses, in principle, all combinations of the compound of the invention and any and every pharmaceutical agent useful for the above-mentioned disorders.

The term "treating" refers, without limitation, to facilitating the eradication of, preventing, ameliorating or otherwise inhibiting the progression of or promoting stasis of an SGLT-mediated disorder. Treatment of diabetes mellitus refers to the administration of a compound or combination of the present invention to treat a diabetic subject. One outcome of the treatment of diabetes is to reduce an increased plasma glucose concentration. Another outcome of the treatment of diabetes is to reduce an increased insulin concentration. Another outcome of the treatment of diabetes is to reduce an increased blood triglyceride concentration and to increase insulin sensitivity. Another outcome of the treatment of diabetes may be enhancing glucose tolerance in a subject with glucose intolerance. Another outcome of the treatment of diabetes is to reduce insulin resistance. Another outcome of the treatment of diabetes is to lower plasma insulin levels, improve glycemic control, particularly in type 2 diabetes, and increase hepatic insulin sensitivity.

The term "prodrug" means a compound of Formula (I) or a form thereof that is converted in vivo into a functional derivative form that may contribute to therapeutic biological activity, wherein the converted form may be: 1) a relatively active form; 2) a relatively inactive form; 3) a relatively less active form; or, 4) any form which results, directly or indirectly, from such in vivo conversions. Prodrugs are useful when said compound may be either too toxic to administer systemically, absorbed poorly by the digestive tract or broken down by the body before it reaches its target. Conventional procedures for the selection and preparation of suitable prodrug derivatives are described in, for example, "*Design of Prodrugs*", ed. H. Bundgaard, Elsevier, 1985.

The term "metabolite" means a prodrug form of a compound of Formula (I) or a form thereof converted by in vivo metabolism or a metabolic process to a relatively less active functional derivative of said compound.

The term "medicament" or "medicine" refers to a product containing a compound of Formula (I) or a form thereof. The present invention includes use of such a medicament for treating an SGLT-mediated disorder.

The term "combination form" refers to the use of a combination product comprising a compound of Formula (I) or a form, pharmaceutical composition, medicine or medicament thereof and at least one therapeutic agent for treating an SGLT-mediated disorder.

Methods are known in the art for determining effective doses for therapeutic and prophylactic purposes for the disclosed pharmaceutical compositions or the disclosed drug combinations, whether or not formulated in the same composition.

For therapeutic purposes, the term "therapeutically effective amount" or "effective amount" as used herein, means that amount of each active compound or pharmaceutical agent, alone or in combination, that elicits the biological or medicinal response in a tissue system, animal or human that is being sought by a researcher, veterinarian, medical doctor or other clinician, which includes alleviation of the symptoms of the disease or disorder being treated. For prophylactic purposes (i.e., inhibiting the progression of a disorder), the term "therapeutically effective amount" refers to that amount of each active compound or pharmaceutical agent, alone or in combination, that treats or inhibits in a subject the progression of a disorder as being sought by a researcher, veterinarian, medical doctor or other clinician. Thus, the present invention provides combinations of two or more drugs wherein, for example, (a) each drug is administered in an independently therapeutically or prophylactically effective amount; (b) at least one drug in the combination is administered in an amount that is sub-therapeutic or sub-prophylactic if administered alone, but is therapeutic or prophylactic when administered in combination with the second or additional drugs according to the invention; or (c) both (or more) drugs are administered in an amount that is sub-therapeutic or sub-prophylactic if administered alone, but are therapeutic or prophylactic when administered together. The effective amount of said compound is from about 0.001 mg/kg/day to about 300 mg/kg/day.

Advantageously, the effective amount of a combination product for treating an SGLT-mediated disorder may be a reduced amount of either or both, the compound or therapeutic agent, compared to the effective amount of the compound or therapeutic agent otherwise recommended for treating the condition. Therefore, it is contemplated that the compound is administered to the subject before, during or after the time the agent is administered.

The term "pharmaceutically acceptable salt" refers to non-toxic pharmaceutically acceptable salts (Ref. International J. Pharm., 1986, 33, 201-217; J. Pharm. Sci., 1997 (January), 66, 1, 1). Other salts well known to those in the art may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

The compounds of the invention may be present in the form of pharmaceutically acceptable salts. For use in medicines, the "pharmaceutically acceptable salts" of the compounds of this invention refer to non-toxic acidic/anionic or basic/cationic salt forms.

Suitable salt forms include acid addition salts which may, for example, be formed by mixing a solution of the compound according to the invention with a solution of an acid such as acetic acid, adipic acid, benzoic acid, carbonic acid, citric acid, fumaric acid, glycolic acid, hydrochloric acid, maleic acid, malonic acid, phosphoric acid, saccharinic acid, succinic acid, sulphuric acid, tartaric acid, trifluoroacetic acid and the like.

Furthermore when the compounds of the present invention carry an acidic moiety, suitable salts thereof may include alkali metal salts, e.g. sodium or potassium salts; alkaline earth metal salts, e.g. calcium or magnesium salts; and salts formed with suitable organic ligands, e.g. quaternary ammonium salts.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, 3$^{rd}$ Edition, John Wiley & Sons, 1999. The protecting groups may be removed at a convenient subsequent stage using methods known in the art. The scope of the present invention encompasses all such protected compound forms and mixtures thereof.

The invention includes compounds of various isomers and mixtures thereof. The term "isomer" refers to compounds that have the same composition and molecular weight but differ in physical and/or chemical properties. Such substances have the same number and kind of atoms but differ in structure. The structural difference may be in constitution (geometric isomers) or in an ability to rotate the plane of polarized light (optical isomers).

The term "stereoisomer" refers to isomers that have the same molecular formula and the same sequence of covalently bonded atoms but a different spatial orientation.

The term "optical isomer" means isomers of identical constitution that differ only in the spatial arrangement of their groups. Optical isomers rotate the plane of polarized light in different directions. The term "optical activity" means the degree to which an optical isomer rotates the plane of polarized light.

The term "racemate" or "racemic mixture" means an equimolar mixture of two enantiomeric species, wherein each of the isolated species rotates the plane of polarized light in the opposite direction such that the mixture is devoid of optical activity.

The term "enantiomer" means an isomer having a nonsuperimposable mirror image. The term "diastereomer" means stereoisomers that are not enantiomers.

The term "chiral" means a molecule that, in a given configuration, cannot be superimposed on its mirror image. This is in contrast to achiral molecules that can be superimposed on their mirror images.

The two distinct mirror image versions of the chiral molecule are also known as levo (left-handed), abbreviated L, or dextro (right-handed), abbreviated D, depending on which way they rotate polarized light. The symbols "R" and "S" represent the configuration of groups around a stereogenic carbon atom(s).

The term "geometric isomer" means isomers that differ in the orientation of substituent atoms in relationship to a carbon-carbon double bond, to a cycloalkyl ring, or to a bridged bicyclic system. Substituent atoms (other than hydrogen) on each side of a carbon-carbon double bond may be in an E or Z configuration according to the Cahn-Ingold-Prelog priority rules. In the "E" configuration, the substituents having the highest priorities are on opposite sides in relationship to the carbon-carbon double bond. In the "Z" configuration, the substituents having the highest priorities are oriented on the same side in relationship to the carbon-carbon double bond.

Substituent atoms (other than hydrogen) attached to a ring system may be in a cis or trans configuration. In the "cis" configuration, the substituents are on the same side in relationship to the plane of the ring; in the "trans" configuration, the substituents are on opposite sides in relationship to the plane of the ring. Compounds having a mixture of "cis" and "trans" species are designated "cis/trans".

The isomeric descriptors ("R," "S," "E," and "Z") indicate atom configurations and are intended to be used as defined in the literature.

The compounds of the invention may be prepared as individual isomers by either isomer-specific synthesis or resolved from an isomeric mixture. Conventional resolution techniques include combining the free base (or free acid) of each isomer of an isomeric pair using an optically active acid (or base) to form an optically active salt (followed by fractional crystallization and regeneration of the free base), forming an ester or amide of each of the isomers of an isomeric pair by reaction with an appropriate chiral auxiliary (followed by fractional crystallization or chromatographic separation and removal of the chiral auxiliary), or separating an isomeric mixture of either an intermediate or a final product using various well known chromatographic methods.

Furthermore, compounds of the present invention may have one or more polymorph or amorphous crystalline forms and, as such, are intended to be included in the scope of the invention. In addition, some of the compounds may form solvates with water (i.e., hydrates) or common organic solvents (e.g., organic esters such as ethanolate and the like) and, as such, are also intended to be encompassed within the scope of this invention.

B) Compounds

Representative compounds of the present invention are listed in Table 1 below:

TABLE 1

| STRUCTURE | COMPOUND # | NAME |
|---|---|---|
| 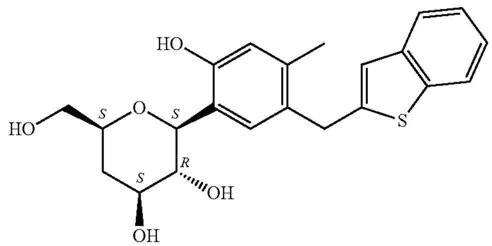 | 1 | (2S,3R,4S,6S)-2-(5-(benzo[b]thiophen-2-ylmethyl)-2-hydroxy-4-methylphenyl)-6-(hydroxymethyl)tetrahydro-2H-pyran-3,4-diol |
| 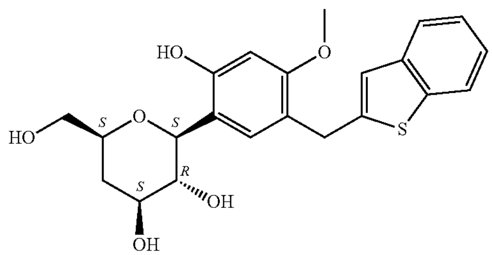 | 2 | (2S,3R,4S,6S)-2-(5-(benzo[b]thiophen-2-ylmethyl)-2-hydroxy-4-methoxyphenyl)-6-(hydroxymethyl)tetrahydro-2H-pyran-3,4-diol |
| 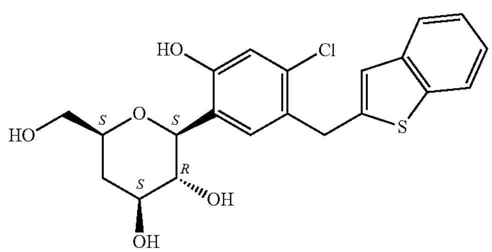 | 3 | (2S,3R,4S,6S)-2-(5-(benzo[b]thiophen-2-ylmethyl)-2-hydroxy-4-hydroxyphenyl)-6-(hydroxymethyl)tetrahydro-2H-pyran-3,4-diol |
| 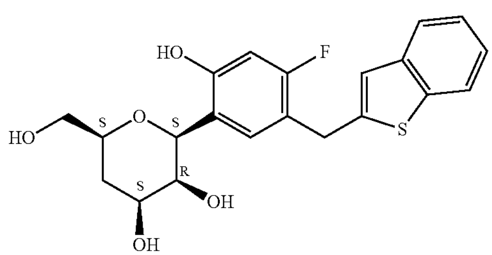 | 4 | (2S,3R,4S,6S)-2-(5-(benzo[b]thiophen-2-ylmethyl)-2-hydroxy-4-hydroxyphenyl)-6-(hydroxymethyl)tetrahydro-2H-pyran-3,4-diol |
| 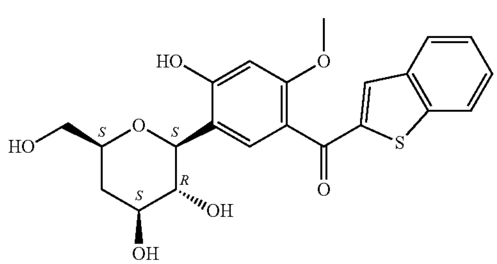 | 5 | benzo[b]thiophen-2-yl(5-((2S,3R,4S,6S)-3,4-dihydroxy-6-(hydroxymethyl)tetrahydro-2H-pyran-2-yl)-4-hydroxy-2-methoxyphenyl)methanone |

TABLE 1-continued

| STRUCTURE | COMPOUND # | NAME |
|---|---|---|
| 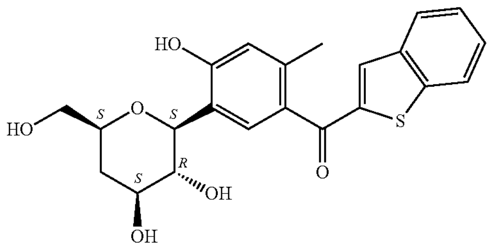 | 6 | benzo[b]thiophen-2-yl(5-((2S,3R,4S,6S)-3,4-dihydroxy-6-(hydroxymethyl)tetrahydro-2H-pyran-2-yl)-4-hydroxy-2-methoxyphenyl)methanone |
| 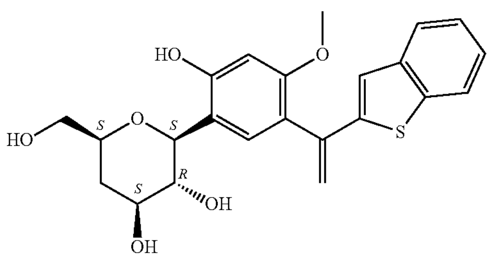 | 7 | (2S,3R,4S,6S)-2-(5-(1-(benzo[b]thiophen-2-yl)vinyl)-2-hydroxy-4-methoxyphenyl)-6-(hydroxymethyl)tetrahydro-2H-pyran-3,4-diol |
| 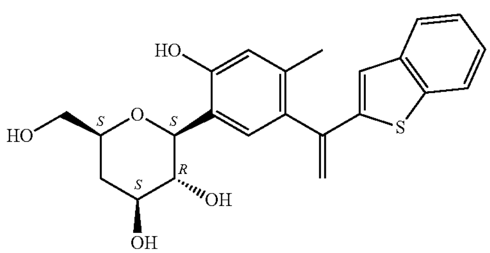 | 8 | (2S,3R,4S,6S)-2-(5-(1-(benzo[b]thiophen-2-yl)vinyl)-2-hydroxy-4-methylphenyl)-6-(hydroxymethyl)tetrahydro-2H-pyran-3,4-diol |
| 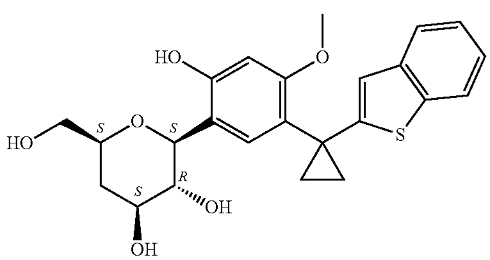 | 9 | (2S,3R,4S,6S)-2-(5-(1-(benzo[b]thiophen-2-yl)cyclopropyl)-2-hydroxy-4-methoxyphenyl)-6-(hydroxymethyl)tetrahydro-2H-pyran-3,4-diol |
| 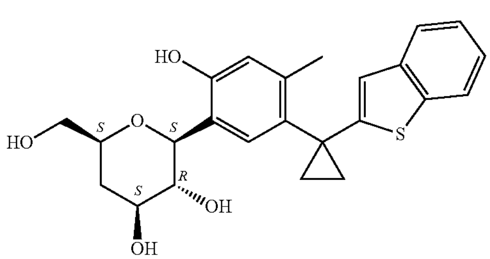 | 10 | (2S,3R,4S,6S)-2-(5-(1-(benzo[b]thiophen-2-yl)cyclopropyl)-2-hydroxy-4-methylphenyl)-6-(hydroxymethyl)tetrahydro-2H-pyran-3,4-diol |
| 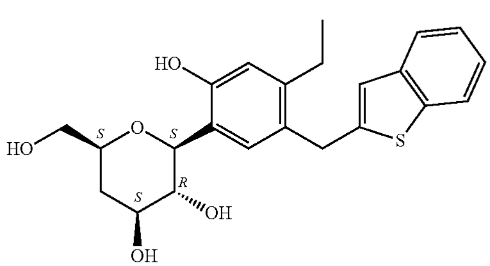 | 11 | (2S,3R,4S,6S)-2-(5-(benzo[b]thiophen-2-ylmethyl)-4-ethyl-2-hydroxyphenyl)-6-(hydroxymethyl)tetrahydro-2H-pyran-3,4-diol |

TABLE 1-continued

| STRUCTURE | COMPOUND # | NAME |
|---|---|---|
| 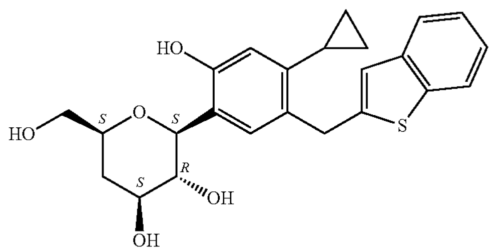 | 12 | (2S,3R,4S,6S)-2-(5-(benzo[b]thiophen-2-ylmethyl)-4-cyclopropyl-2-hydroxyphenyl)-6-(hydroxymethyl)tetrahydro-2H-pyran-3,4-diol |
| 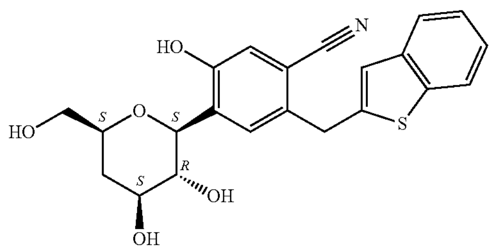 | 13 | 2-(benzo[b]thiophen-2-ylmethyl)-4-((2S,3R,4S,6S)-3,4-dihydroxy-6-(hydroxymethyl)tetrahydro-2H-pyran-2-yl)-5-hydroxybenzonitrile |
| 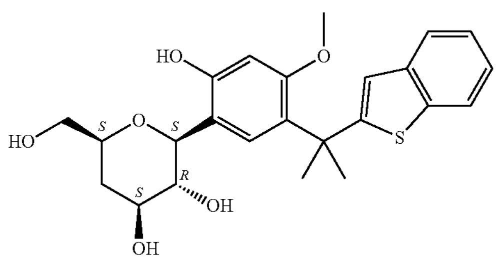 | 14 | (2S,3R,4S,6S)-2-(5-(2-(benzo[b]thiophen-2-yl)propan-2-yl)-2-hydroxy-4-methoxyphenyl)-6-(hydroxymethyl)tetrahydro-2H-pyran-3,4-diol |
| 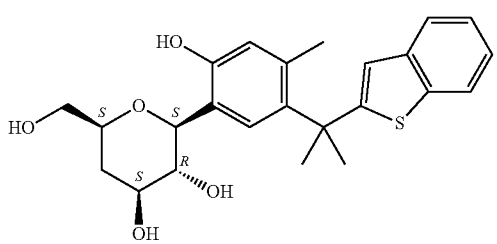 | 15 | (2S,3R,4S,6S)-2-(5-(2-(benzo[b]thiophen-2-yl)propan-2-yl)-2-hydroxy-4-methylphenyl)-6-(hydroxymethyl)tetrahydro-2H-pyran-3,4-diol |
| 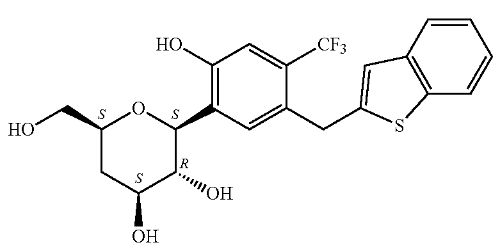 | 16 | (2S,3R,4S,6S)-2-(5-(benzo[b]thiophen-2-ylmethyl)-2-hydroxy-4-(trifluoromethyl)phenyl)-6-(hydroxymethyl)tetrahydro-2H-pyran-3,4-diol |
| 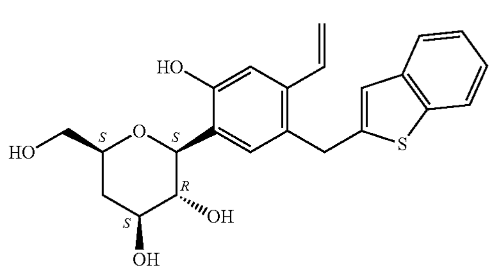 | 17 | (2S,3R,4S,6S)-2-(5-(benzo[b]thiophen-2-ylmethyl)-2-hydroxy-4-vinylphenyl)-6-(hydroxymethyl)tetrahydro-2H-pyran-3,4-diol |

TABLE 1-continued

| STRUCTURE | COMPOUND # | NAME |
|---|---|---|
| 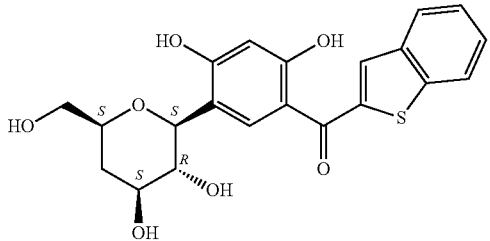 | 18 | benzo[b]thiophen-2-yl(5-((2S,3R,4S,6S)-3,4-dihydroxy-6-(hydroxymethyl)tetrahydro-2H-pyran-2-yl)-2,4-dihydroxyphenyl)methanone |
| 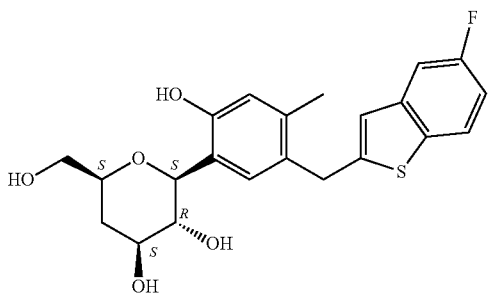 | 19 | (2S,3R,4S,6S)-2-(5-((5-fluorobenzo[b]thiophen-2-yl)methyl)-2-hydroxy-4-methylphenyl)-6-(hydroxymethyl)tetrahydro-2H-pyran-3,4-diol |
| 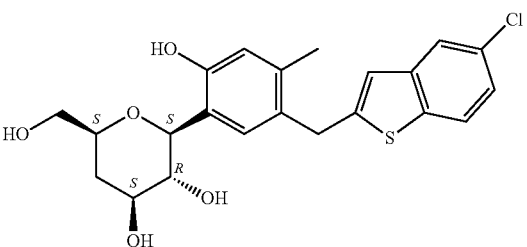 | 20 | (2S,3R,4S,6S)-2-(5-((5-chlorobenzo[b]thiophen-2-yl)methyl)-2-hydroxy-4-methylphenyl)-6-(hydroxymethyl)tetrahydro-2H-pyran-3,4-diol |
| 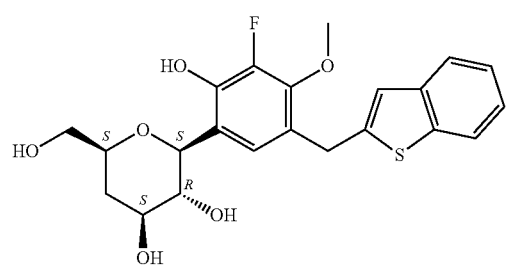 | 21 | (2S,3R,4S,6S)-2-(5-(benzo[b]thiophen-2-ylmethyl)-3-fluoro-2-hydroxy-4-methoxyphenyl)-6-(hydroxymethyl)tetrahydro-2H-pyran-3,4-diol |
| 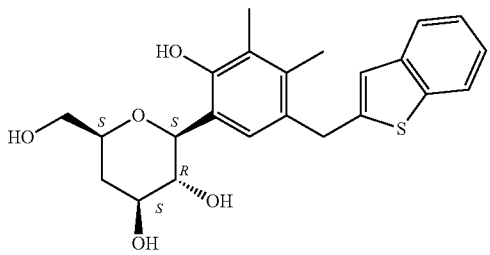 | 22 | (2S,3R,4S,6S)-2-(5-(benzo[b]thiophen-2-ylmethyl)-2-hydroxy-3,4-dimethylphenyl)-6-(hydroxymethyl)tetrahydro-2H-pyran-3,4-diol |

TABLE 1-continued

| STRUCTURE | COMPOUND # | NAME |
|---|---|---|
| 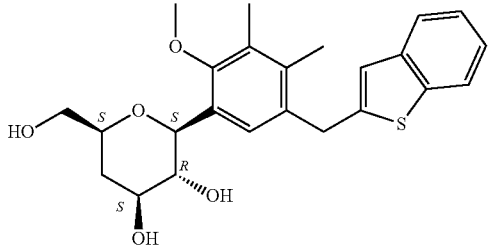 | 23 | (2S,3R,4S,6S)-2-(5-(benzo[b]thiophen-2-ylmethyl)-2-methoxy-3,4-dimethylphenyl)-6-(hydroxymethyl)tetrahydro-2H-pyran-3,4-diol |
| 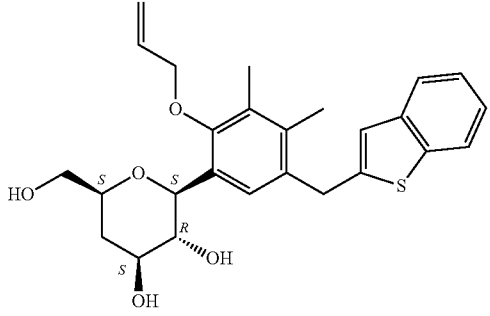 | 24 | (2S,3R,4S,6S)-2-(2-(allyloxy)-5-(benzo[b]thiophen-2-ylmethyl)-3,4-dimethylphenyl)-6-(hydroxymethyl)tetrahydro-2H-pyran-3,4-diol |
| 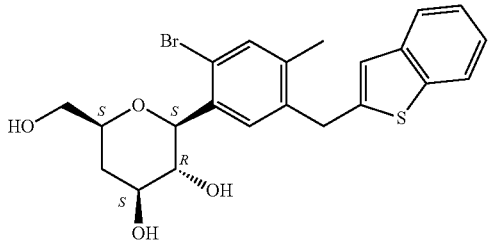 | 25 | (2S,3R,4S,6S)-2-(5-(benzo[b]thiophen-2-ylmethyl)-2-bromo-4-methylphenyl)-6-(hydroxymethyl)tetrahydro-2H-pyran-3,4-diol |
| 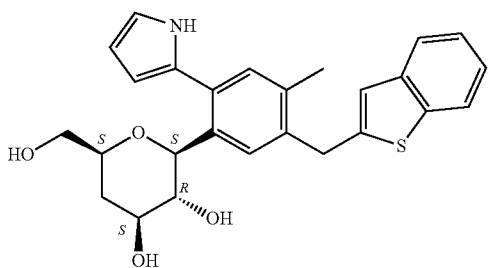 | 26 | (2S,3R,4S,6S)-2-(5-(benzo[b]thiophen-2-ylmethyl)-4-methyl-2-(1H-pyrrol-2-yl)phenyl)-6-(hydroxymethyl)tetrahydro-2H-pyran-3,4-diol |
| 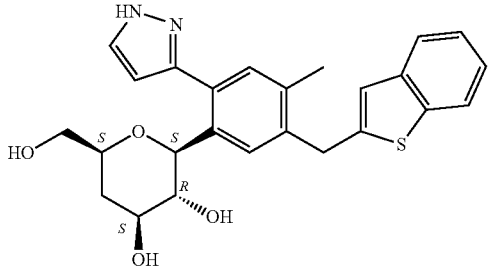 | 27 | (2S,3R,4S,6S)-2-(5-(benzo[b]thiophen-2-ylmethyl)-4-methyl-2-(1H-pyrazol-3-yl)phenyl)-6-(hydroxymethyl)tetrahydro-2H-pyran-3,4-diol |

TABLE 1-continued

| STRUCTURE | COMPOUND # | NAME |
|---|---|---|
| 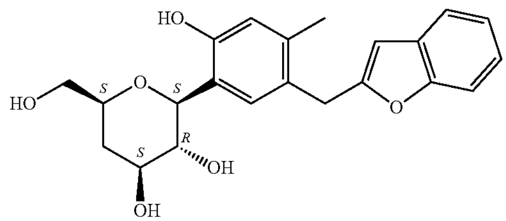 | 28 | (2S,3R,4S,6S)-2-(5-(benzofuran-2-ylmethyl)-2-hydroxy-4-methylphenyl)-6-(hydroxymethyl)tetrahydro-2H-pyran-3,4-diol |
| 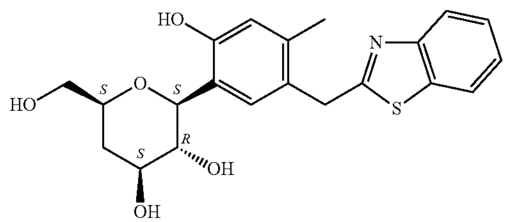 | 29 | (2S,3R,4S,6S)-2-(5-(benzo[d]thiazol-2-ylmethyl)-2-hydroxy-4-methylphenyl)-6-(hydroxymethyl)tetrahydro-2H-pyran-3,4-diol |
| 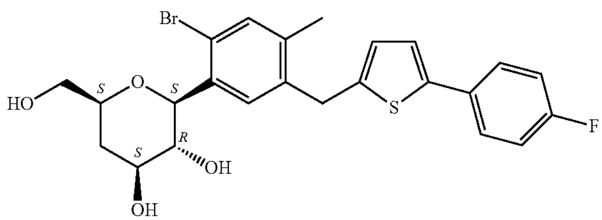 | 30 | (2S,3R,4S,6S)-2-(2-bromo-5-((5-(4-fluorophenyl)thiophen-2-yl)methyl)-4-methylphenyl)-6-(hydroxymethyl)tetrahydro-2H-pyran-3,4-diol |
| 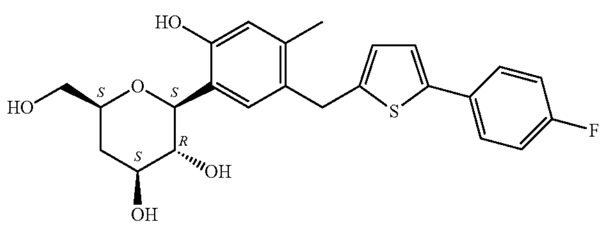 | 31 | (2S,3R,4S,6S)-2-(5-((5-(4-fluorophenyl)thiophen-2-yl)methyl)-2-hydroxy-4-methylphenyl)-6-(hydroxymethyl)tetrahydro-2H-pyran-3,4-diol |
| 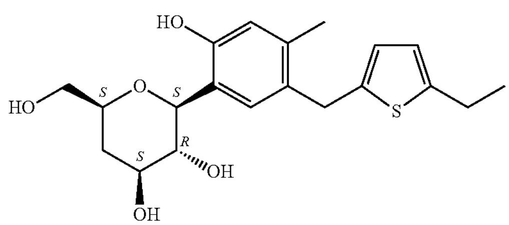 | 32 | (2S,3R,4S,6S)-2-(5-((5-ethylthiophen-2-yl)methyl)-2-hydroxy-4-methylphenyl)-6-(hydroxymethyl)tetrahydro-2H-pyran-3,4-diol |

C) Synthesis

The invention provides methods of making the disclosed compounds according to traditional organic synthetic methods as well as matrix or combinatorial synthetic methods. Schemes A-E described suggested synthetic routes. Using the schemes, the guidelines below, and the examples, a person of skill in the art may develop analogous or similar methods for a given compound that is within the invention. These methods are representative of the synthetic schemes, but are not to be construed as limiting the scope of the invention.

Where the compounds according to this invention have at least one chiral center, they may accordingly exist as enantiomers. Where the compounds possess two or more chiral centers, they may additionally exist as diastereomers. Where the processes for the preparation of the compounds according to the invention give rise to mixtures of stereoisomers, these isomers may be separated by conventional techniques such as preparative chromatography. The compounds may be prepared in racemic form or as individual enantiomers or diastereomers by either stereospecific synthesis or by resolution. The compounds may, for example, be resolved into their component enantiomers or diastereomers by standard techniques, such as the formation of stereoisomeric pairs by salt formation with an optically active base, followed by fractional crystallization and regeneration of the free acid. The compounds may also be resolved by formation of stereoisomeric esters or amides, followed by chromatographic separation and removal of the chiral auxiliary. Alternatively, the compounds may be resolved using a chiral HPLC column. It is to be understood that all stereoisomers, racemic mixtures, diastereomers, geometric isomers, and enantiomers thereof are encompassed within the scope of the present invention.

Representative compounds of the present invention can be synthesized in accordance with the general synthetic schemes described below and are illustrated more particularly in the specific synthetic examples that follow. The general schemes are offered by way of illustration; the invention should not be construed as being limited by the chemical reactions and conditions expressed. The methods for preparing the various starting materials used in the schemes and examples are well within the skill of persons versed in the art. No attempt has been made to optimize the yields obtained in any of the example reactions. One skilled in the art would know how to increase such yields through routine variations in reaction times, temperatures, solvents and/or reagents.

General: $^1$H and $^{13}$C NMR spectra were measured on a Bruker AC-300 (300 MHz) spectrometer using tetramethylsilane and the deuterated solvent respectively as internal standards. Elemental analyses were obtained by Quantitative Technologies Inc. (Whitehouse, N.J.) and the results were within 0.4% of the calculated values unless otherwise mentioned. Melting points were determined in open capillary tubes with a Mel-Temp II apparatus (Laboratory Devices Inc.) and were uncorrected. Electrospray mass spectra (MS-ESI) were recorded in the positive mode on a Hewlett Packard 59987A spectrometer. High resolution mass spectra (HRMS) were obtained on a Micromass Autospec. E spectrometer by fast atom bombardment (FAB) technique.

Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Examples of the described synthetic routes include Schemes A-E and Examples 1-33. Compounds analogous to the target compounds of these examples can be made according to similar routes. The disclosed compounds are useful as pharmaceutical agents as described herein.

Abbreviations or acronyms useful herein include:

| Abbreviation | Meaning |
|---|---|
| BOC | tert-butyloxycarbonyl |
| BOP | benzotriazol-1-yloxy-tris(dimethylamino)phosphonium hexafluorophosphate |
| Cpd | Compound |
| DCE | Dichloroethane |
| DCM | Dichloromethane |
| DMAP | Dimethylaminopyridine |
| DMF | N,N-dimethylformamide |
| DMSO | dimethyl sulfoxide |
| DPBS | Dulbecco's phosphate buffered saline |
| EDC | 1-(3-dimethylaminopropyl)-3-ethylcarbodiimide hydrochloride |
| ESI | Electrospray Ionization |
| Et$_3$N or TEA | Triethylamine |
| EtOAc | ethyl acetate |
| h/hr/hrs | hour(s) |
| HOBT | 1-hydroxybenzotriazole hydrate |
| HBTU | O-benzotriazol-1-yloxy-N,N,N',N'-tetramethyluronium hexafluorophosphate |
| LG | Leaving group |
| LiOH | lithium hydroxide |
| min | minute(s) |
| MS | mass spectroscopy |
| NMR | nuclear magnetic resonance spectroscopy |
| OTf | Triflate |
| PG | protecting group |
| RT/rt | room temperature |
| THF | Tetrahydrofuran |
| TLC | thin layer chromatography |
| Tos | p-toluenesulfonyl |

General Guidance

Representative compounds of the present invention can be synthesized in accordance with the general synthetic methods described below and are illustrated more particularly in the schemes that follow. Since the schemes are illustrations, the invention should not be construed as being limited by the chemical reactions and conditions expressed. The preparation of the various starting materials used in the schemes is well within the skill of persons versed in the art. The substituents for compounds of Formula (I) or a form thereof, represented in the schemes below, are as previously defined herein.

The compounds of Formula (I), wherein A, $R_1$, $R_2$, $R_3$, $R_4$, and $R_5$ are defined as in Formula (I), may be synthesized as outlined by the general synthetic route illustrated in Scheme A. Treatment of an aryl halide III, wherein X is Br or I, with an appropriate base such as n-butyllithium, t-butyllithium or sec-butyllithium at low temperature (−78° C.) in a solvent such as THF or Et$_2$O, followed by addition of lactone intermediate II, wherein PG is an appropriate alcohol protecting group such as benzyl, trialkylsilane or acetyl, will provide the lactol IV. The lactol intermediate IV is immediately treated with a trialkylsilane reducing agent such as triethylsilane in the presence of a Lewis acid such as BF$_3$Et$_2$O in a solvent such as dichloromethane at ambient temperature will produce the pyranoside V. Removal of the alcohol protecting group (PG) from intermediate V under standard conditions will provide the final compound I.

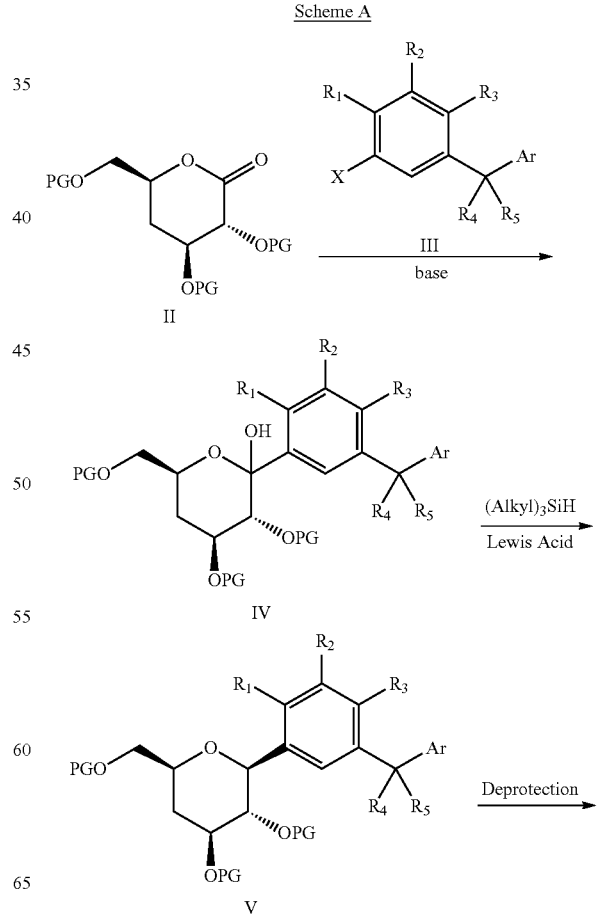

Scheme A

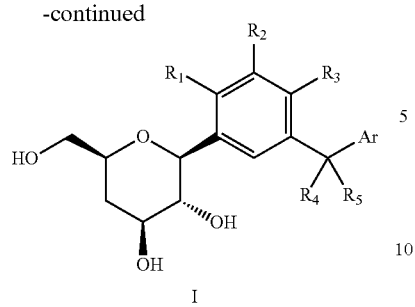

I

The preparation of lactone intermediate II may be synthesized as outlined by the general synthetic route illustrated in Scheme B. Protection of the hydroxyl groups of the benzylidene galactopyranoside VI with a suitable alcohol protecting group reagent, wherein PG is an appropriate alcohol protecting group such as benzyl will provide the intermediate VII. Treatment of intermediate VII with a reducing agent such as sodium cyanoborohydride in the presence of a solution of HCl/Et$_2$O in a solvent such as THF, Et$_2$O or dioxane will produce the pyranoside VIII. Alternatively treatment of VII with a reducing agent such as BH$_3$Et$_3$N in the presence of a Lewis acid such as TMS triflate in a solvent such as MeOH or EtOH will provide the intermediate VIII. Treatment of alcohol intermediate VIII with Tf$_2$O and an appropriate base such as pyridine or Et$_3$N in a solvent such as dichloromethane or 1,2 dichloroethane will provide the intermediate triflate IX. Treatment of triflate IX with a metal hydride such as NaBH4 in a solvent such as dichloromethane or 1,2 dichloroethane will provide the pyranoside intermediate X. Hydrolysis of intermediate X with aqueous acid such as 3N HCl in the presence of a solvent such as dioxane, THF or Et$_2$O will provide the lactol intermediate XI, which can then be oxidized under conditions such as Ac$_2$O/DMSO will provide the lactone intermediate II.

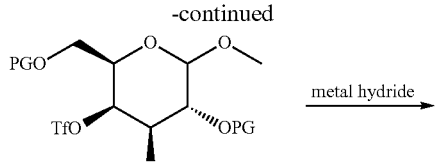

IX

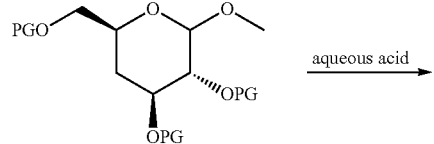

X

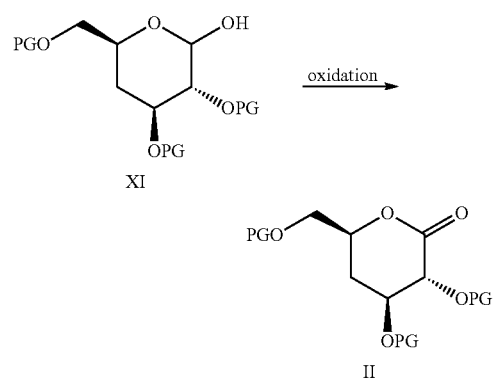

XI

II

The preparation of aryl halide III when R$_4$ and R$_5$ are H is outlined by the general synthetic route illustrated in Scheme C. Halogenation of the substituted benzaldehyde XII with a suitable halogenating reagent such as N-bromosuccinimide, Br$_2$, pyridinium hydrobromide perbromide, I$_2$, or N-iodosuccinimide will provide the intermediate aryl halide XIII. Reaction of an appropriate ArY, wherein Y is Br, I or H with a strong base such as n-butyllithium, t-butyllithium or sec-butyllithium at low temperature (−78° C.) in a solvent such as THF or Et$_2$O, followed by addition of benzaldehyde intermediate XII, will provide the alcohol intermediate XIV. Treatment of alcohol XIV with a trialkylsilane reducing agent such as triethylsilane in the presence of an acid such as TFA or HCl in a solvent such as dichloromethane at ambient temperature will produce the aryl halide III.

Scheme B

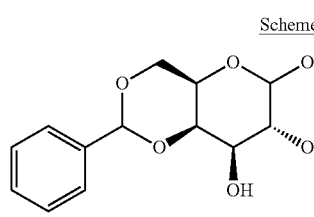

VI

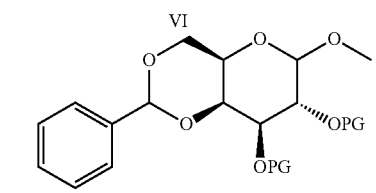

VII

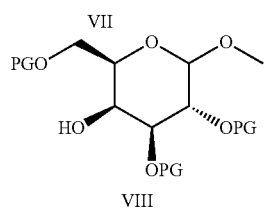

VIII

Scheme C

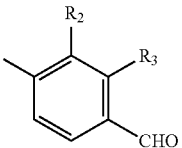

XII

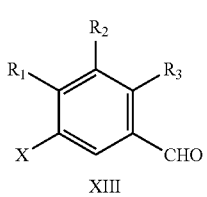

XIII

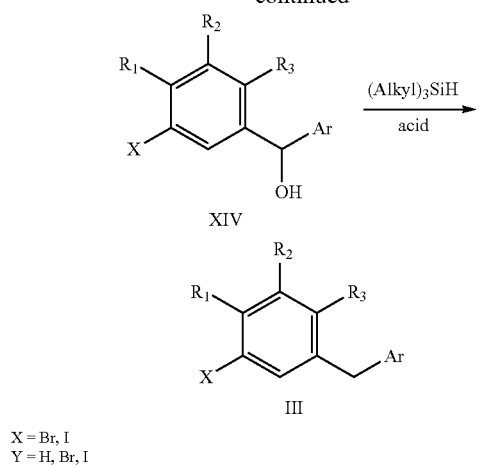

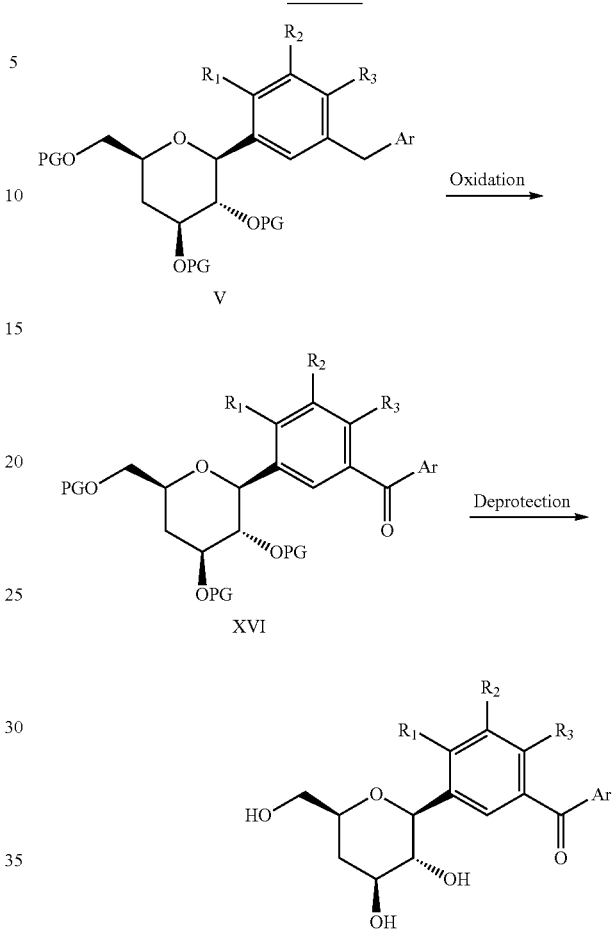

The preparation of aryl halide III when $R_4$ and $R_5$ are linked together to form an alkenyl is outlined by the general synthetic route illustrated in Scheme D. Oxidation of the substituted alcohol intermediate XIV, derived from Scheme C, with a suitable oxidation reagent such as PCC or $MnO_2$ will provide the intermediate ketone XV. Reaction of ketone XV with an appropriate methylidene ylid known in the art will produce the aryl halide III.

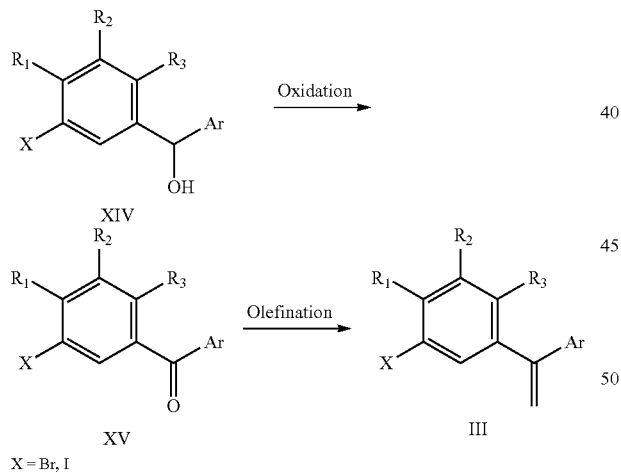

The preparation of aryl halide III when $R_4$ and $R_5$ are linked together to form an oxo is outlined by the general synthetic route illustrated in Scheme E. Oxidation of the intermediate V, derived from Scheme A, with a suitable oxidation reagent such as $SeO_2$ will provide the intermediate ketone XVI. Removal of the alcohol protecting group (PG) from intermediate XVI under standard conditions will provide the final compound I.

EXAMPLES

The following examples are offered by way of illustration; the invention should not be construed as being limited by the chemical reactions and conditions expressed.

Example 1

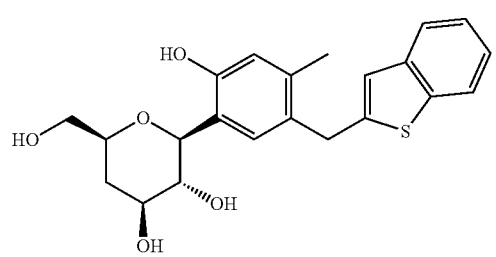 [SMILES: Cc1cc(O)c([C@@H]2O[C@H](CO)C[C@H](O)[C@H]2O)cc1Cc1cc2ccccc2s1]

39

2S,3R,4S,6S)-2-(5-(benzo[b]thiophen-2-ylmethyl)-2-hydroxy-4-methylphenyl)-6-(hydroxymethyl)tetrahydro-2H-pyran-3,4-diol (Cmp 1

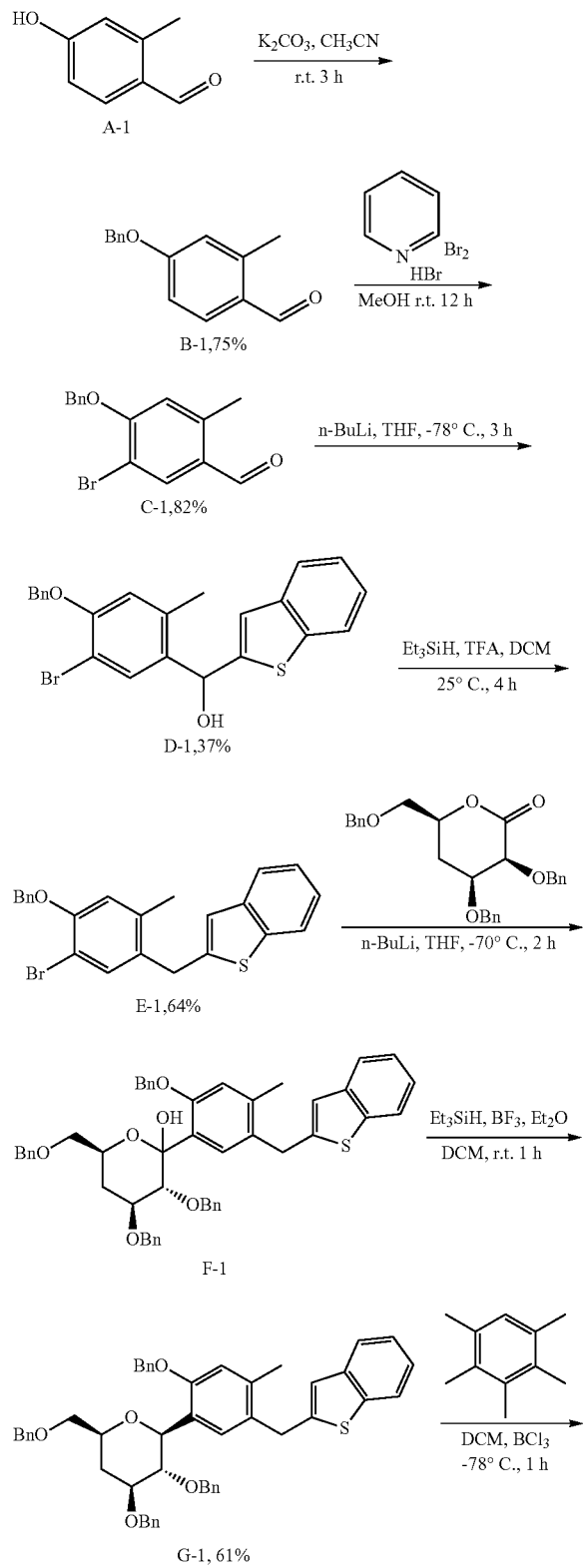

40

-continued

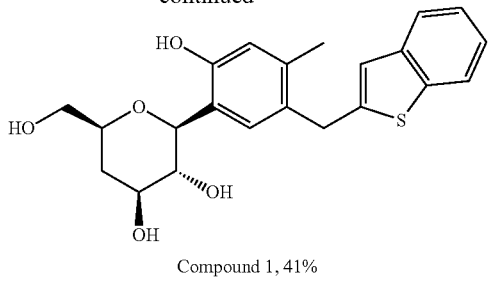

Compound 1, 41%

To a mixture of A-1 (2.72 g, 19.98 mmol, 1.00 equiv) in CH3CN (30 mL) with $K_2CO_3$ (4.14 g, 29.95 mmol, 1.50 equiv) was added BnBr (3.8 g, 22.22 mmol, 1.11 equiv). The reaction was stirred for 3 h at room temperature. Water was added and the mixture was extracted with EtOAc thrice. Concentration and chromatograph on silica gel (10:1 PE/EA) gave 3.4 g (75%) of B-1 as white solid.

To a mixture of B-1 (2.26 g, 9.99 mmol, 1.00 equiv) in methanol (50 mL) was added pyridinium hydrobromide perbromide (90% purity, 3.52 g, 10 mmol, 1.00 equiv) at 0° C. The reaction was stirred for 12 h at room temperature. Concentration and chromatograph on silica gel (10:1 PE/EA) gave 2.5 g (82%) of C-1 as white solid.

With an inert atmosphere of nitrogen, to a mixture of 1-benzothiophene (900 mg, 6.71 mmol, 1.20 equiv) in tetrahydrofuran (20 mL) was added n-BuLi (2.5M in hexane, 2.7 mL, 1.2 equiv) dropwise with stirring at −78° C., the mixture was stirred for 20 mins at −78° C. After that, C-1 (1.7 g, 5.57 mmol, 1.00 equiv) in THF (5 mL) was added to the solution. The reaction was stirred at −78° C. for 3 h. $NH_4Cl$/$H_2O$ was added and the mixture was extracted with EtOAc thrice. The combined extracts were washed with brine and dried over $Na_2SO_4$. Concentration and chromatograph on silica gel (5:1 PE/EA) gave 0.9 g (37%) of D-1 as light yellow oil.

To a mixture of D-1 (1 g, 2.28 mmol, 1.00 equiv) in dichloromethane (20 mL) with $Et_3SiH$ (530 mg, 4.56 mmol, 2.00 equiv) was added $CF_3COOH$ (520 mg, 4.56 mmol, 2.00 equiv) dropwise at 0° C. The reaction was stirred for 4 h at room temperature. sodium bicarbonate/$H_2O$ was added and the mixture was extracted with DCM thrice. The combined extracts were washed with brine and dried over $Na_2SO_4$. Concentration and chromatograph on silica gel (5:1 PE/EA) gave 0.62 g (64%) of E-1 as white solid.

With an inert atmosphere of nitrogen, to a mixture of E-1 (1.07 g, 2.53 mmol, 1.10 equiv) in THF (15 mL) was added n-BuLi (2.5M in hexane, 1.02 mL, 1.10 equiv) dropwise at −78° C., the mixture was stirred at −78° C. for 20 min. After that, (3R,4S,6S)-3,4-bis(benzyloxy)-6-[(benzyloxy)methyl]-5-methylideneoxan-2-one (1 g, 2.31 mmol, 1.00 equiv) in THF (5 mL) was added to the solution. The reaction was stirred at −78° C. for 2 h. $NH_4Cl$/$H_2O$ was added and the mixture was extracted with EtOAc thrice. The combined extracts were washed with brine and dried over $Na_2SO_4$. Concentration and This resulted in 2 g (crude) F-1 of as yellow oil. MS (ES) m/z: 799 (M+$Na^+$).

With an inert atmosphere of nitrogen, to a mixture of F-1 (2 g, 1.29 mmol, 1.00 equiv, 50%) in DCM/$CH_3CN$ (1:1 v/v, 40 mL) with $Et_3SiH$ (900 mg, 7.74 mmol, 3.00 equiv) was added $BF_3 \cdot Et_2O$ (1.1 g, 7.74 mmol, 3.00 equiv) at 0° C. The reaction was stirred at 0° C. for 1 h. Sodium bicarbonate/$H_2O$ was added and the mixture was extracted with dichloromethane thrice. The combined extracts were washed with brine and dried over $Na_2SO_4$. Concentration and chromatograph on silica gel (5:1 PE/EA) gave 0.6 g (61%) of G-1 as light yellow oil. MS (ES) m/z: 783 (M+Na⁺).

With an inert atmosphere of nitrogen, to a mixture of G-1 (600 mg, 0.79 mmol, 1.00 equiv) in dichloromethane (20 mL) with 1,2,3,4,5-pentamethylbenzene (1.2 g, 8.09 mmol, 10.27 equiv) was added BCl₃ (1M in DCM, 12 mL) dropwise at −78° C. The reaction was stirred at −78° C. for 1 h. 5 mL of methanol was added. Concentration and chromatograph on a C18 reversed phase column gave 130 mg (41%) of compound 1 as white solid. ¹H-NMR (400 MHz, CD₃OD) δ 7.73 (d, J=7.6 Hz, 1H), 7.63 (d, J=7.6 Hz, 1H), 7.29-7.20 (m, 3H), 6.92 (s, 1H), 6.70 (s, 1H), 4.50 (d, J=9.6 Hz, 1H), 4.17 (s, 2H), 3.76-3.67 (m, 2H), 3.64-3.58 (m, 2H), 3.48 (t, J=8.8 Hz, 1H), 2.24 (s, 3H), 2.03 (dd, J=12, 4.4 Hz, 1H), 1.56 (q, J=11.6 Hz, 1H); MS (ES) m/z: 423 (M+Na⁺).

Example 2

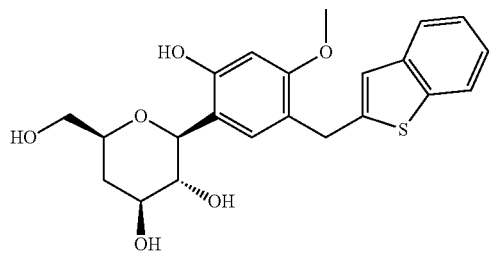 [SMILES: COc1cc(O)c([C@@H]2O[C@H](CO)C[C@H](O)[C@H]2O)cc1Cc1cc2ccccc2s1]

2S,3R,4S,6S)-2-(5-(benzo[b]thiophen-2-ylmethyl)-2-hydroxy-4-methoxyphenyl)-6-(hydroxymethyl) tetrahydro-2H-pyran-3,4-diol (Cmp. 2

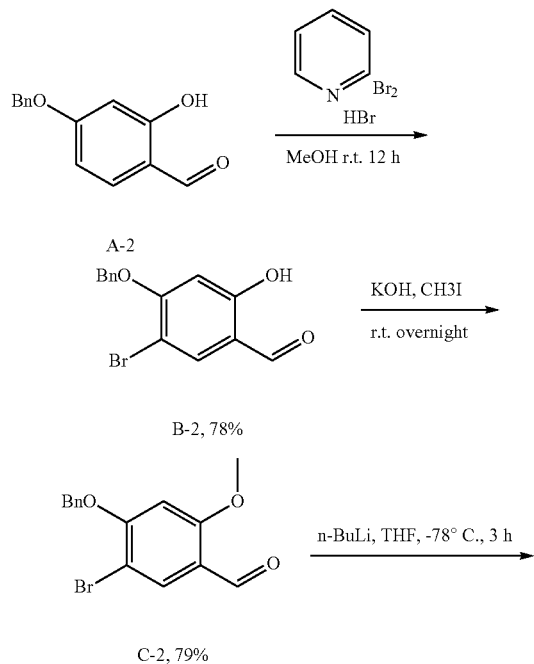

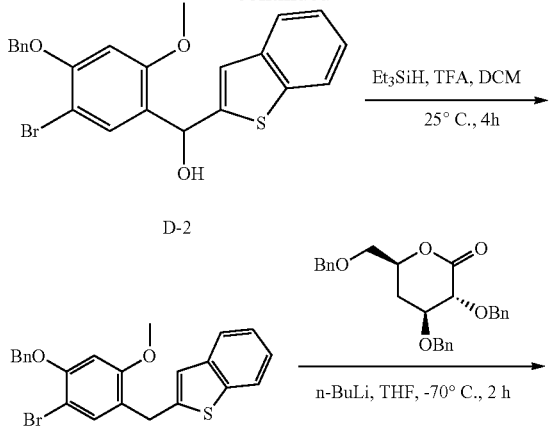

To a mixture of A-2 (228 mg, 0.98 mmol, 1.00 equiv, 98%) in methanol (20 mL) was added pyridinium hydrobromide perbromide (90% purity, 345.2 mg, 0.98 mmol, 1.00 equiv) in several batches at 0° C. The reaction was stirred for 12 h at room temperature. Concentration and chromatograph on silica gel (10:1 PE/EA) gave 240 mg (78%) of B-2 as yellow solid.

To a mixture of B-2 (1.2 g, 3.91 mmol, 1.00 equiv) in N,N-dimethylformamide (20 mL) with potassium hydroxide (263 mg, 4.69 mmol, 1.30 equiv) was added iodomethane (1.67 g, 11.77 mmol, 3.00 equiv) at room temperature. The reaction was stirred at room temperature for overnight. Water was added and the mixture was extracted with EtOAc thrice. Concentration and chromatograph on silica gel (2:1 PE/EA) gave 0.997 g (79%) of C-2 as white solid.

With an inert atmosphere of nitrogen, to a mixture of 1-benzothiophene (410 mg, 3.06 mmol, 1.00 equiv) in tetrahydrofuran (30 mL) was added n-BuLi (2.5M in hexane, 1.2 mL, 1.05 equiv) dropwise at −78° C., the mixture was stirred at −78° C. for 30 mins. After that, C-2 (973 g, 3.03 mol, 1.05 equiv) in tetrahydrofuran (5 mL) was added dropwise at −78° C. The reaction was stirred at −78° C. for 2 h. NH$_4$Cl/H$_2$O was added and the mixture was extracted with EtOAc thrice. The combined extracts were washed with brine and dried over Na$_2$SO$_4$. Concentration and chromatograph on silica gel (5:1 PE/EA) gavel 0.2 g (crude) of D-2 as yellow oil.

To a mixture of D-2 (1.2 g, 2.64 mmol, 1.00 equiv) in dichloromethane (20 mL) with Et$_3$SiH (368 mg, 3.16 mmol, 1.20 equiv) was added CF$_3$COOH (600 mg, 5.26 mmol, 2.00 equiv) at 0° C. The reaction was stirred at room temperature for 2 h. sodium bicarbonate/H$_2$O was added and the mixture was extracted with DCM thrice. Concentration and chromatograph on silica gel (2:1 PE/EA) gave 0.812 g (70%) of E-2 as a yellow solid.

With an inert atmosphere of nitrogen, to a mixture of E-2 (304 mg, 0.69 mmol, 1.10 equiv) in tetrahydrofuran (10 mL) was added n-BuLi (2.5M in hexane, 0.33 mL, 1.10 equiv) dropwise at −78° C., the mixture was stirred at −78° C. for 20 min. After that, (3R,4S,6S)-3,4-bis(benzyloxy)-6-[(benzyloxy)methyl]-5-methylideneoxan-2-one (300 mg, 0.69 mmol, 1.00 equiv) in THF (5 mL) was added dropwise at −78° C., The reaction was stirred at −78° C. for 2 h. NH$_4$Cl/H$_2$O was added and the mixture was extracted with EtOAc thrice. The combined extracts were washed with brine and dried over Na$_2$SO$_4$. Concentration and This resulted in 2 g (crude) F-2 of as yellow oil. MS (ES) m/z: 815 (M+Na$^+$).

With an inert atmosphere of nitrogen, to a mixture of F-2 (400 mg, 0.50 mmol, 1.00 equiv) in dichloromethane (12 mL) with Et$_3$SiH (160 mg, 1.38 mmol, 3.00 equiv) was added BF$_3$·Et$_2$O (600 mg, 9.00 equiv) dropwise at 0° C. The reaction was stirred at 0° C. for 1 h. Sodium bicarbonate/H$_2$O was added and the mixture was extracted with dichloromethane thrice. The combined extracts were washed with brine and dried over Na$_2$SO$_4$. Concentration and chromatograph on silica gel (5:1 PE/EA) gave 270 mg (69%) of G-2 as yellow oil. MS (ES) m/z: 799[M+Na]$^+$ With an inert atmosphere of nitrogen, to a mixture of G-2 (160 mg, 0.21 mmol, 1.00 equiv) in dichloromethane (10 mL) with 1,2,3,4,5-pentamethylbenzene (320 mg, 2.16 mmol, 10.48 equiv) was added BCl$_3$ (1M in DCM, 3.2 mL) dropwise at −78° C. The reaction was stirred at −60° C. for 1 h. 5 mL of methanol was added. Concentration and chromatograph on a C18 reversed phase column gave 9 mg (10%) of compound 2 as white solid. H-NMR (300 MHz, CD$_3$OD) δ7.59 (d, J=7.8 Hz, 1H), 7.51 (d, J=7.8 Hz, 1H), 7.17-7.06 (m, 3H), 6.87 (s, 1H), 6.38 (s, 1H), 4.35 (d, J=9.6 Hz, 1H), 4.06-3.95 (m, 2H), 3.70 (s, 3H), 3.63-3.53 (m, 2H), 3.47-3.44 (m, 2H), 3.33 (t, J=9.0 Hz, 1H), 1.93-1.84 (m, 1H), 1.44 (q, J=11.7 Hz, 1H); MS (ES) m/z: 439 [M+Na].

Example 3

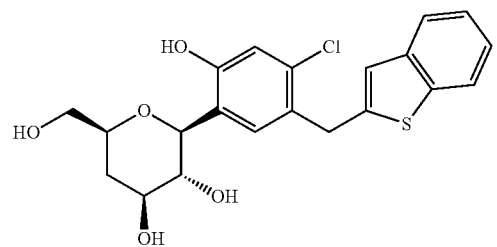 [SMILES: OC[C@@H]1C[C@H](O)[C@@H](O)[C@H](c2cc(Cc3cc4ccccc4s3)c(Cl)cc2O)O1]

2S,3R,4S,6S)-2-(5-(benzo[b]thiophen-2-ylmethyl)-4-chloro-2-hydroxyphenyl)-6-(hydroxymethyl)-tetrahydro-2H-pyran-3,4-diol (Cmp. 3

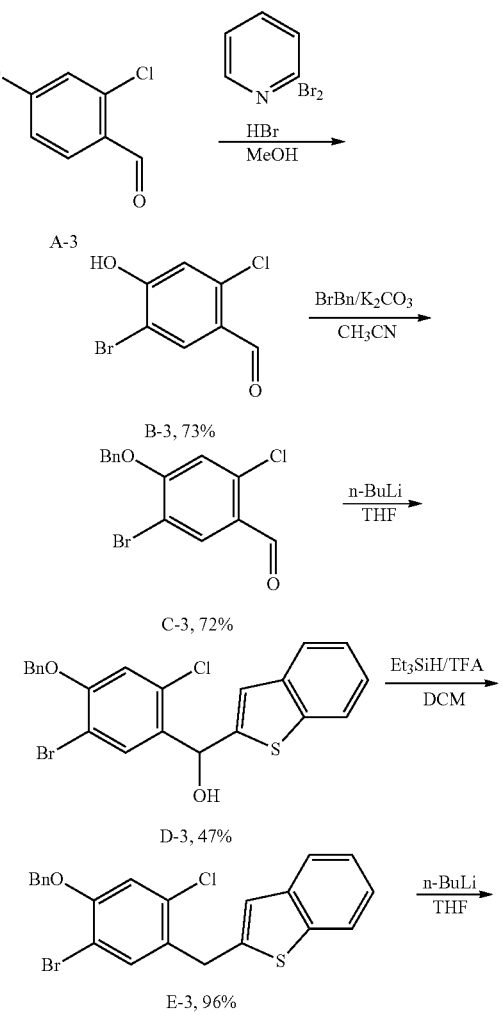

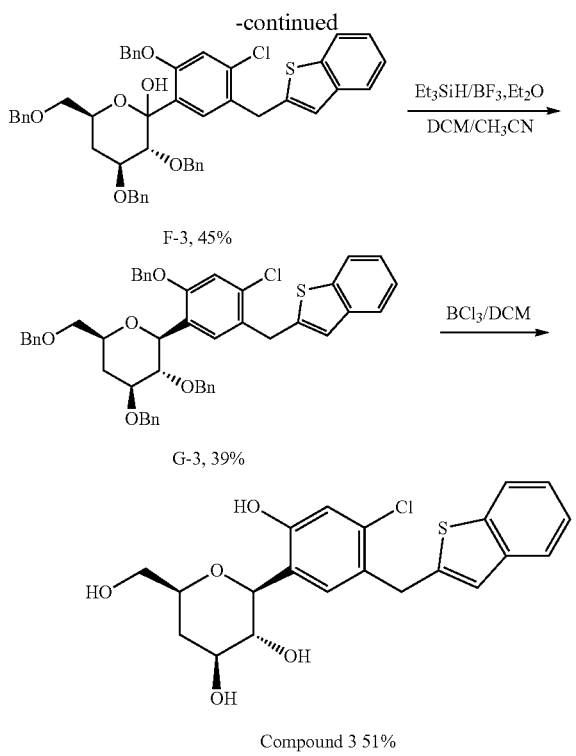

F-3, 45%

G-3, 39%

Compound 3 51%

To a mixture of A-3 (10 g, 63.87 mmol) in methanol (200 mL) was added Pyridinium Bromide Perbromide (21.4 g, 67.30 mmol) in several batches at 0° C. The reaction was stirred at 0° C. for 5 h. Water was added and the mixture was extracted with EtOAc thrice. The combined extracts were washed with 1N hydrogen chloride, H₂O, brine and dried over Na₂SO₄. Concentration and chromatograph on silica gel (5:1 PE/EA) gave 11 g (73%) of B-3 as yellow solid. GS (EI) m/z: 234 (M⁺).

To a mixture of B-3 (11 g, 46.72 mmol) in CH₃CN (100 mL) was added BnBr (8.75 g, 51.47 mmol) and potassium carbonate (8.4 g). The reaction was heated to reflux for 5 hr. The solids were filtered out. Concentration and chromatograph on silica gel (5:1 PE/EA) gave 11 g (72%) of C-3 as a yellow solid.

With an inert atmosphere of nitrogen, to a solution of 1-benzothiophene (1.36 g, 10.13 mmol) in tetrahydrofuran (20 mL) was added n-BuLi (2.5M in hexane, 4.2 mL, 1.15 equiv) dropwise at −78° C. It was reacted 20 min at −78° C. After that, C-3 (3 g, 9.21 mmol) in tetrahydrofuran (10 mL) was added dropwise at −78° C. The reaction was stirred at −78° C. for 1 h. NH₄Cl/H₂O was added and the mixture was extracted with EtOAc thrice. The combined extracts were washed with brine and dried over Na₂SO₄. Concentration and chromatograph on silica gel (5:1 PE/EA) gave 2 g (47%) of D-3 as a light yellow solid.

To a mixture of D-3 (2 g, 4.35 mmol) in dichloromethane (20 mL) with Et₃SiH (1 g, 8.62 mmol) was added trifluoroacetic acid (1 g, 8.77 mmol) dropwise at 0° C. The mixture was stirred at room temperature for 2 h. NaHCO₃/H₂O was added and the mixture was extracted with DCM thrice. The combined extracts were washed with brine and dried over Na₂SO₄. Concentration and chromatograph on silica gel (acetate/petroleum ether (0:1-1:5) gave 1.85 g (96%) of E-3 as a yellow solid. ¹H NMR (300 MHz, CDCl₃) δ 7.76-7.60 (m, 2H), 7.49-7.19 (m, 8H), 6.99-6.90 (m, 2H), 5.13 (s, 2H), 4.25 (s, 2H)

With an inert atmosphere of nitrogen, to a mixture of E-3 (100 mg, 0.23 mmol, 1.10 equiv) in tetrahydrofuran (8 mL) was added n-BuLi (2.5M in hexane, 0.1 mL, 1.15 equiv) dropwise at −78° C. it was reacted 10 min at −78° C. To this was added a solution of (3R,4S,6S)-3,4-bis(benzyloxy)-6-[(benzyloxy)methyl]oxan-2-one (88.56 mg, 0.20 mmol) in tetrahydrofuran (2 mL) dropwise at −78° C. The mixture was stirred at −78° C. for 1 h. NH₄Cl/H₂O was added and the mixture was extracted with EtOAc thrice. The combined extracts were washed with brine and dried over Na₂SO₄. Concentration and chromatograph on silica gel (acetate/petroleum ether (0:1-1:5) gave 72 mg (45%) F-3 as yellow oil. MS (ES) m/z: 819 (M+Na⁺).

With an inert atmosphere of nitrogen, to a mixture of F-3 (318 mg, 0.40 mmol) in DCM/CH₃CN (1:1 v/v, 10 mL) with Et₃SiH (93 mg, 0.80 mmol, 2.00 equiv) was added BF₃.Et₂O (114 mg, 0.80 mmol, 2.00 equiv) dropwise at 0° C. The reaction was stirred for 2 h at 0° C. NaHCO₃/H₂O was added and the mixture was extracted with DCM thrice. The combined extracts were washed with brine and dried over Na₂SO₄. Concentration and chromatograph on silica gel (5:1, PE/EA) gave 120 mg (39%) of G-3 as yellow oil. MS (ES) m/z: 803 (M+Na⁺).

To a mixture of G-3 (100 mg, 0.13 mmol) in dichloromethane (20 ml) with 1,2,3,4,5-pentamethylbenzene (200 mg) was added BCl₃ (1M in DCM, 2 mL) dropwised at −78° C. The mixture was stirred for 2 h at −78° C. The reaction was then quenched by the addition of 5 mL of methanol. The mixture was concentrated under vacuum. The crude product (300 mg) was purified by Prep-HPLC with the following conditions (1#-Waters 2767-1): Column, SunFire Prep C18, 5 um, 19*100 mm; mobile phase: water in 0.05% TFA and MeCN (15% MeCN up to 55% in 12 min, up to 100% in 1 min, down to 15% in 1 min); Detector, UV 254 nm. This resulted in 27.3 mg (51%) of compound 3 as a white solid. ¹H NMR (400 MHz, CD3OD) δ 7.74 (d, J=8.0 Hz, 1H), 7.65 (d, J=7.6 Hz, 1H), 7.46 (s, 1H), 7.30-7.22 (m, 2H), 7.11 (s, 1H), 6.91 (s, 1H), 4.52 (d, J=9.6 Hz, 1H), 4.33-4.23 (m, 2H), 3.75-3.67 (m, 2H), 3.59 (d, J=4.8 Hz, 2H), 3.41 (t, J=9.2 Hz, 1H), 2.05-2.00 (m, 1H), 1.54 (q, J=11.6 Hz, 1H); MS (ES) m/z: 443 (M+Na⁺).

Example 4

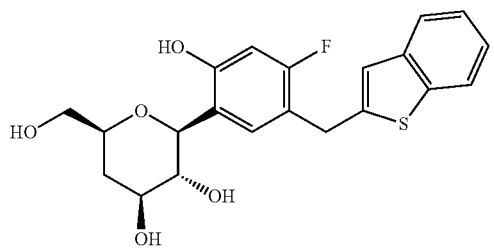 [SMILES: OC[C@@H]1C[C@H](O)[C@@H](O)[C@H](c2cc(Cc3cc4ccccc4s3)c(F)cc2O)O1]

(2S,3R,4S,6S)-2-(5-(benzo[b]thiophen-2-ylmethyl)-4-fluoro-2-hydroxyphenyl)-6-(hydroxymethyl)-tetrahydro-2H-pyran-3,4-diol (Cmp. 41

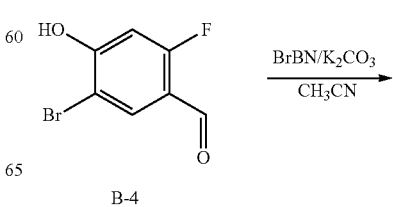

B-4

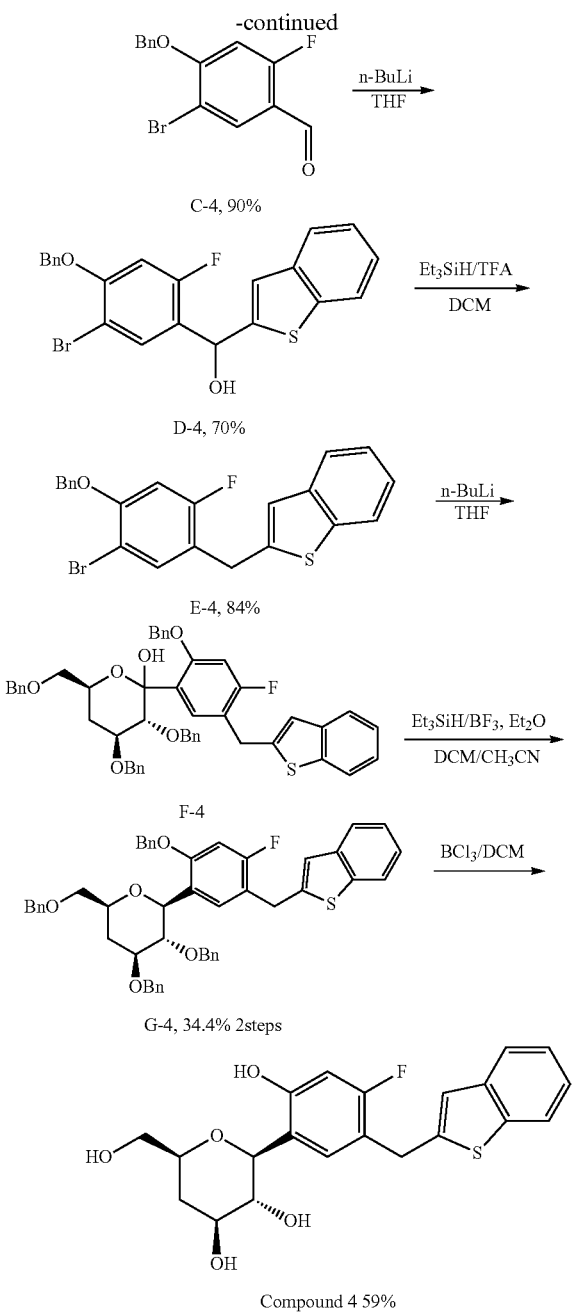

combined extracts were washed with brine and dried over $Na_2SO_4$. Concentration and chromatograph on silica gel (5:1, PE/EA) gave 0.73 g (70%) of D-4 as yellow solid.

To a mixture of D-4 (710 mg, 1.60 mmol) in dichloromethane (10 mL) with $Et_3SiH$ (373 mg, 3.22 mmol) was added trifluoroacetic acid (275 mg, 2.41 mmol) at 0° C. The reaction was stirred for 2 hours at room temperature. $NaHCO_3/H_2O$ was added and the mixture was extracted with DCM thrice. The combined extracts were washed with brine and dried over $Na_2SO_4$. Concentration and chromatograph on silica gel (5:1, PE/EA) gave 577 mg (84%) of E-4 as a white solid. $^1H$ NMR (300 MHz, $CDCl_3$) δ 7.78-7.71 (m, 2H), 7.68-7.29 (m, 7H), 7.05 (s, 1H), 6.76-6.72 (d, J=12 Hz, 1H), 4.18 (s, 2H).

With an inert atmosphere of nitrogen, to a mixture of E-4 (577 mg, 1.35 mmol) in tetrahydrofuran (8 mL) was added n-BuLi (2.5M in hexane, 0.56 mL, 1.15 equiv) dropwise at −78° C. it was reacted 25 min at −78° C. To this was added (3R,4S,6S)-3,4-bis(benzyloxy)-6-[(benzyloxy)methyl]oxan-2-one (530 mg, 1.23 mmol) in tetrahydrofuran (1 mL) dropwise at −78° C. The reaction was stirred for 1 h at −78° C. $NH_4Cl/H_2O$ was added and the mixture was extracted with EtOAc thrice. The combined extracts were washed with brine and dried over $Na_2SO_4$. Concentration and chromatograph on silica gel (5:1, PE/EA) gave 1 g (crude) of F-4 as yellow oil. MS (ES) m/z: 803 $(M+Na^+)$.

With an inert atmosphere of nitrogen, To a mixture of F-4 1 g (crude) in $DCM/CH_3CN$ (1:1, v/v, 20 mL) with $Et_3SiH$ (297 mg) was added $BF_3Et_2O$ (364 mg) at 0° C. The reaction was stirred for 1 h at 0° C. $NaHCO_3/H_2O$ was added and the mixture was extracted with DCM thrice. The combined extracts were washed with brine and dried over $Na_2SO_4$. Concentration and chromatograph on silica gel (5:1, PE/EA) gave 356 mg (34.4%) of G-4 as yellow oil. MS (ES) m/z: 787 $(M+Na^+)$.

With an inert atmosphere of nitrogen, To a mixture of G-4 (160 mg, 0.21 mmol) in dichloromethane (8 ml) with 1,2,3,4,5-pentamethylbenzene (320 mg) was added $BCl_3/DCM$ (1M in DCM, 3.2 ml) at −78° C. The reaction was stirred for 1 h at −78° C. The reaction was then quenched by the addition of 5 mL of methanol. Concentration and chromatograph on C18 (10%-50% $CH_3CN/H_2O$) gave 50 mg (59%) of compound 4 as a white solid. (300 MHz, CD3OD) δ 7.73 (d, J=7.6 Hz, 1H), 7.65 (d, J=7.6 Hz, 1H), 7.36-7.21 (m, 3H), 7.03 (s, 1H), 6.59 (d, J=11.4 Hz, 1H), 4.51 (d, J=9.3 Hz, 1H), 4.17 (s, 2H), 3.73-3.67 (m, 2H), 3.58 (d, J=5.1 Hz, 2H), 3.42 (t, J=9.3 Hz, 1H), 2.01-1.99 (m, 1H), 1.54 (q, J=12.6 Hz, 1H); MS (ES) m/z: 427 $(M+Na^+)$.

To a mixture of B-4 (1.5 g, 6.85 mmol) in $CH_3CN$ (30 mL) was added BnBr (1.3 g, 7.65 mmol), potassium carbonate (1.234 g, 8.94 mmol). The reaction was heated to reflux for 5 hr. The reaction mixture was cooled. The solids were filtered out. Water was added and the mixture was extracted with EtOAc thrice. The combined extracts were washed with brine and dried over $Na_2SO_4$. Concentration and chromatograph on silica gel (5:1, PE/EA) gave 1.92 g (90%) of C-4 as a white solid. MS (ES) m/z: 308 $(M^+)$.

With an inert atmosphere of nitrogen, To a mixture of 1-benzothiophene (350 mg, 2.61 mmol) in tetrahydrofuran (5 mL) was added n-BuLi (1.1 mL, 1.15 equiv) dropwise at −78° C. It was reacted 25 min at −78. To this was added C-4 (730 mg, 2.36 mmol) in tetrahydrofuran (1 mL) dropwise at −78° C. The reaction was stirred for 1 h at −78° C. $NH_4Cl/H_2O$ was added and the mixture was extracted with EtOAc thrice. The Example 5

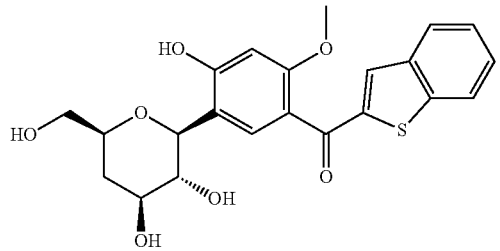 [SMILES: COc1cc(O)c([C@@H]2O[C@H](CO)C[C@H](O)[C@H]2O)cc1C(=O)c1cc2ccccc2s1]

benzo[b]thiophen-2-yl(5-((2S,3R,4S,6S)-3,4-dihydroxy-6-(hydroxymethyl)-tetrahydro-2H-pyran-2-yl)-4-hydroxy-2-methoxyphenyl)methanone (cmp. 5)

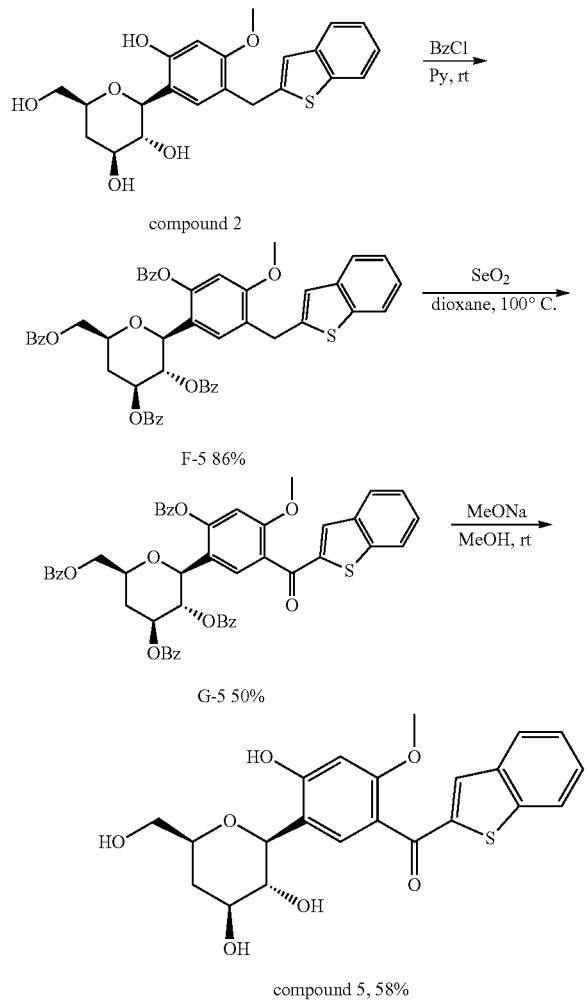

To a mixture of compound 2 (29 mg, 0.07 mmol) in pyridine (1 mL) was added BzCl (98 mg, 0.70 mmol) at 0° C., the reaction was stirred at room temperature for overnight, Water was added and the mixture was extracted with EtOAc thrice. The combined extracts were washed with 1N HCl, brine and dried over $Na_2SO_4$. Concentration and chromatograph on silica gel (5:1, PE/EA) gave 50 mg (86%) of F-5 as a white solid.

To a mixture of F-5 (50 mg, 0.06 mmol) in 1,4-dioxane (2 ml) was added $SeO_2$ (13.5 mg, 0.12 mmol), the reaction was stirred at 100° C. for 3 h, Concentration and chromatograph on silica gel (5:1, PE/EA) gave 25.4 mg (50%) of G-5 as a yellow oil.

To a mixture of G-5 (25.4 mg, 0.03 mmol) in MeOH (2 mL) was added MeONa (2.5 mg), the reaction was stirred at room temperature for 3 h. Concentration and chromatograph on C18 (10%-50% $CH_3CN/H_2O$) gave 7.5 mg (58.1%) of compound 5 as a white solid. (300 MHz, CD3OD) δ 7.89 (t, J=8.4 Hz, 2H), 7.79 (s, 1H), 7.51 (s, 1H), 7.48-7.35 (m, 2H), 6.58 (s, 1H), 4.51 (d, J=9.6 Hz, 1H), 3.74 (s, 1H) 3.71-3.63 (m, 2H), 3.54 (d, J=4.8 Hz, 2H), 3.40 (t, J=9.3 Hz, 1H), 2.01-1.91 (m, 1H), 1.48 (q, J=11.4 Hz, 1H); MS (ES) m/z: 431 (M+H$^+$).

Example 6 benzo[b]thiophen-2-yl(5-((2S,3R,4S,6S)-3,4-dihydroxy-6-(hydroxymethyl)-tetrahydro-2H-pyran-2-yl)-4-hydroxy-2-methylphenyl)methanone (cmp. 6)

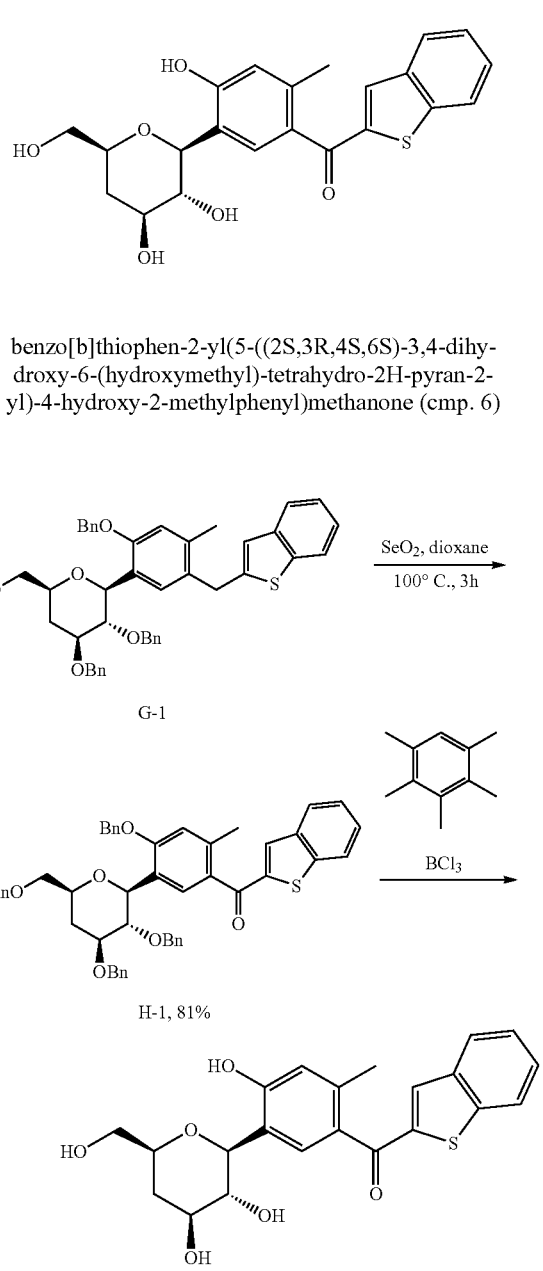

To a mixture of G-1 (600 mg, 0.79 mmol, 1.00 equiv) in dioxane (100 mL) was added $SeO_2$ (177 mg, 1.60 mmol, 2.02 equiv). The reaction was stirred for 3 h at 100° C. The solids were filtered out. Concentration and chromatograph on silica gel (5:1, PE/EA) gave 550 mg (81%) of H-1 as yellow oil. MS (ES) m/z: 793 (M+H$_2$O)$^+$.

With an inert atmosphere of nitrogen, To a mixture of H-1 (300 mg, 0.35 mmol, 1.00 equiv) in dichloromethane (10 mL) with 1,2,3,4,5-pentamethylbenzene (600 mg) was added $BCl_3$ (1M in DCM, 6 ml) at −78° C. The reaction was stirred for 1 h at −78° C. The reaction was then quenched by the addition of 5 mL of methanol. Concentration and chromatograph on C18 (10%-50% CH$_3$CN/H$_2$O) gave 50 mg (34%) of compound 6 as a white solid. $^1$H-NMR (300 MHz, CD3OD) δ 7.95 (t, J=7.8 Hz, 2H), 7.84 (s, 1H), 7.68 (s, 1H), 7.51-7.43 (m, 2H), 6.82 (s, 1H), 4.58 (d, J=9.6 Hz, 1H), 3.77-3.69 (m, 2H), 3.57 (d, J=4.8 Hz, 2H), 3.44 (t, J=9.2 Hz, 1H), 2.38 (s, 3H), 2.04-1.98 (m, 1H), 1.53 (q, J=12.6 Hz, 1H); MS (ES) m/z: 415 (M+H$^+$).

Example 7

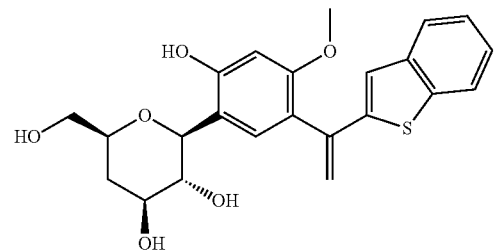 [SMILES: C=C(c1cc2ccccc2s1)c1cc([C@@H]2O[C@H](CO)C[C@H](O)[C@H]2O)c(O)cc1OC]

(2S,3R,4S,6S)-2-(5-(1-(benzo[b]thiophen-2-yl)vinyl)-2-hydroxy-4-methoxyphenyl)-6(hydroxymethyl)tetrahydro-2H-pyran-3,4-diol (cmp. 7)

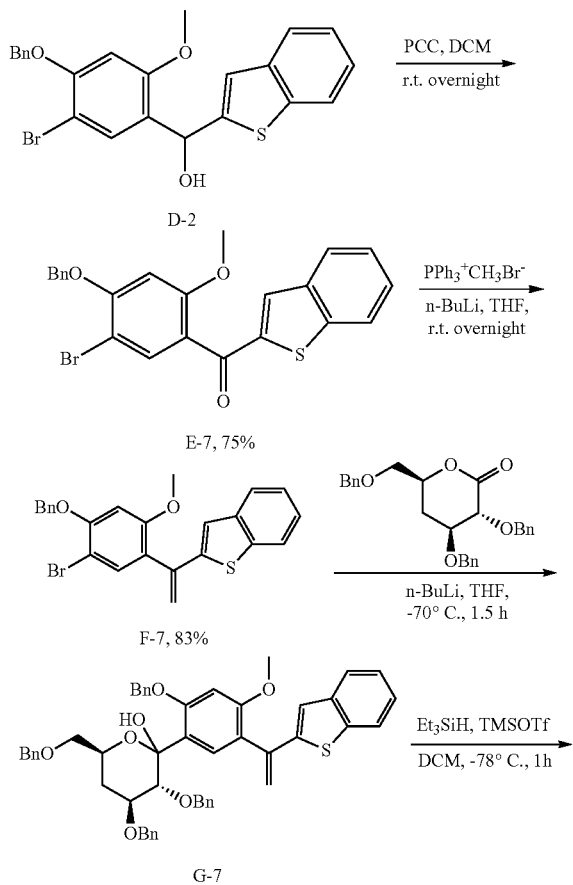

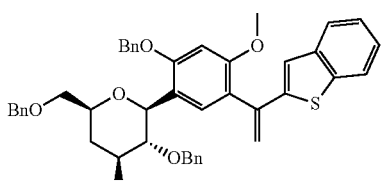

H-7, 11%

compound 7, 6%

To a mixture of D-2 (4 g, 8.78 mmol, 1.00 equiv) in dichloromethane (100 mL) was added PCC (3 g, 13.92 mmol, 1.58 equiv) in several batches at room temperature. The reaction was stirred for 12 h at room temperature. H$_2$O was added and the mixture was extracted with EtOAc thrice. The combined extracts were washed with brine and dried over Na$_2$SO$_4$. Concentration and chromatograph on silica gel (5:1 PE/EA) gave 3 g (75%) of E-7 as a light yellow solid.

With an inert atmosphere of nitrogen, to a mixture of PPh$_3$CH$_3$Br (5.36 g, 15.06 mmol, 2.00 equiv) in tetrahydrofuran (100 mL) was added n-BuLi (2.5M in hexane, 6 mL, 2.00 equiv) dropwise at −78° C., the mixture was stirred for 30 mins at 0° C. After that, E-7 (3.4 g, 7.50 mmol, 1.00 equiv) in tetrahydrofuran (20 mL) was added dropwise at −78° C. The reaction was stirred at room temperature for overnight. NH$_4$Cl/H$_2$O was added and the mixture was extracted with EtOAc thrice. The combined extracts were washed with brine and dried over Na$_2$SO$_4$. Concentration and chromatograph on silica gel (5:1, PE/EA) gave 2.8 g (83%) of F-7 as white solid.

With an inert atmosphere of nitrogen, to a mixture of F-7 (300 mg, 0.66 mmol, 1.00 equiv) in THF (5 mL) was added n-BuLi (2.5M in hexane, 0.29 mL, 1.10 equiv) dropwise at −78° C. The mixture was stirred for 20 min at −78° C. After that, to this was added (3R,4S,6S)-3,4-bis(benzyloxy)-6-[(benzyloxy)methyl]-5-methylideneoxan-2-one (287 mg, 0.66 mmol, 1.00 equiv) in THF (2 mL) dropwise at −78° C. The reaction was stirred for 1.5 h at −78° C. NH$_4$Cl/H$_2$O was added and the mixture was extracted with EtOAc thrice. The combined extracts were washed with brine and dried over Na$_2$SO$_4$. Concentration and chromatograph on silica gel (5:1, PE/EA) gave 700 mg (crude) of G-7 as yellow oil. MS (ES) m/z: 827 (M+Na$^+$).

With an inert atmosphere of nitrogen, to a mixture of G-7 (660 mg, 0.82 mmol, 1.00 equiv) in dichloromethane (10 mL) with Et$_3$SiH (104.7 mg, 0.90 mmol, 1.10 equiv) was added TMSOTf (200.5 mg, 0.90 mmol, 1.10 equiv) dropwise at −78° C. The reaction was stirred for 1 h at 78° C. NaHCO$_3$/H$_2$O was added and the mixture was extracted with dichloromethane thrice. The combined extracts were washed with brine and dried over Na$_2$SO$_4$. Concentration and chromatograph on silica gel (5:1, PE/EA) gave 70 mg (11%) of H-7 as yellow oil. MS (ES) m/z: 811 (M+Na⁺).

With an inert atmosphere of nitrogen, to a mixture of H-7 (160 mg, 0.20 mmol, 1.00 equiv) in dichloromethane (10 mL) with 1,2,3,4,5-pentamethylbenzene (320 mg, 2.16 mmol, 10.64 equiv) was added BCl₃ (1M in DCM, 3.2 mL) at −78° C. The reaction was stirred for 1 h at −78° C. 2 mL of methanol was added. Concentration and chromatograph on C18 (10%-50% CH₃CN/H₂O) gave 5.2 mg (6%) of compound 7 as white solid. ¹H-NMR (400 MHz, CD₃CN) δ 7.83 (t, J=5.2 Hz, 1H), 7.69 (t, J=5.6 Hz, 1H), 7.32-7.34 (m, 2H), 7.15 (s, 1H), 6.98 (s, 1H), 6.58 (s, 1H), 5.81 (s, 1H), 5.25 (s, 2H), 4.37 (d, J=9.6 Hz, 1H), 3.68-3.64 (m, 5H), 3.54 (d, J=5.2 Hz, 2H), 3.35 (t, J=9.2 Hz, 2H), 1.52 (q, J=12.0 Hz, 1H); MS (ES) m/z: 451 (M+Na⁺).

Example 8

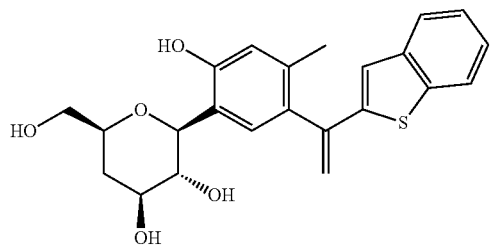 [SMILES: C=C(c1cc2ccccc2s1)c1cc([C@@H]2O[C@H](CO)C[C@H](O)[C@H]2O)c(O)cc1C]

(2S,3R,4S,6S)-2-(5-(1-(benzo[b]thiophen-2-yl)vinyl)-2-hydroxy-4-methylphenyl)-6-(hydroxymethyl)tetrahydro-2H-pyran-3,4-diol (cmp. 8)

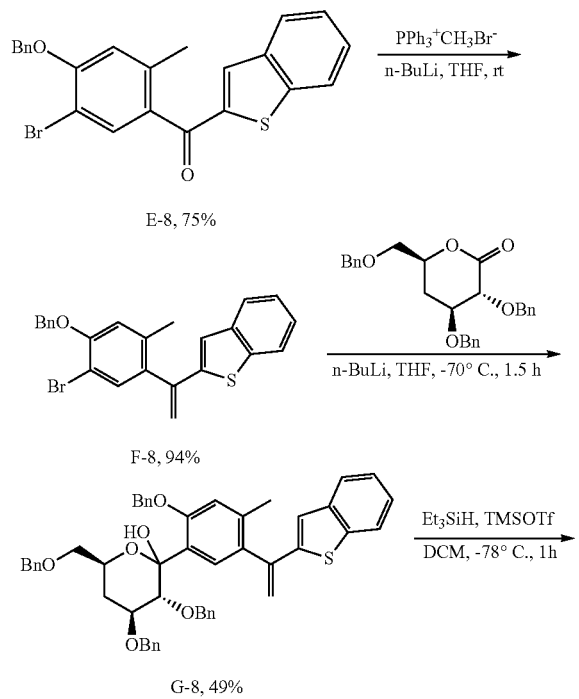

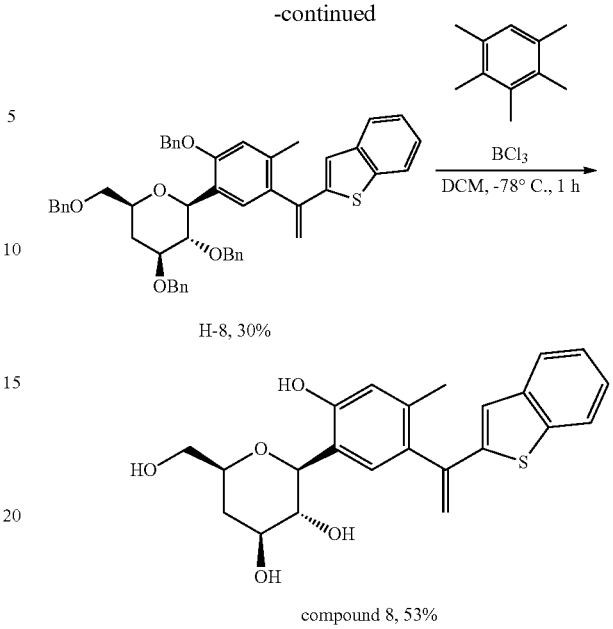

With an inert atmosphere of nitrogen, to a mixture of PPh₃CH₃Br (6 g, 16.85 mmol, 2.00 equiv) in tetrahydrofuran (100 mL) was added n-BuLi (2.5M in hexane, 6.7 mL, 2.00 equiv) dropwise at −78° C., the mixture was stirred for 30 mins at 0° C. After that, E-8 (3 g, 6.86 mmol, 1.00 equiv) in tetrahydrofuran (5 mL) was added dropwise at −78° C. The reaction was stirred at room temperature for overnight. NH₄Cl/H₂O was added and the mixture was extracted with EtOAc thrice. The combined extracts were washed with brine and dried over Na₂SO₄. Concentration and chromatograph on silica gel (5:1, PE/EA) gave 2.8 g (94%) of F-8 as white solid.

With an inert atmosphere of nitrogen, to a mixture of F-8 (300 mg, 0.69 mmol, 1.10 equiv) in THF (5 mL) was added n-BuLi (2.5M in hexane, 0.28 mL, 1.10 equiv) dropwise at −78° C. The mixture was stirred for 20 min at −78° C. After that, to this was added (3R,4S,6S)-3,4-bis(benzyloxy)-6-[(benzyloxy)methyl]-5-methylideneoxan-2-one (271 mg, 0.63 mmol, 1.00 equiv) in THF (2 mL) dropwise at −78° C. The reaction was stirred for 1.5 h at −78° C. NH₄Cl/H₂O was added and the mixture was extracted with EtOAc three times. The combined extracts were washed with brine and dried over Na₂SO₄. Concentration and chromatograph on silica gel (5:1, PE/EA) gave 240 mg (49%) of G-8 as yellow oil. MS (ES) m/z: 813 (M+Na⁺).

With an inert atmosphere of nitrogen, to a mixture of G-8 (240 mg, 0.30 mmol, 1.00 equiv) in dichloromethane (10 mL) with Et₃SiH (38.8 mg, 0.33 mmol, 1.10 equiv) was added TMSOTf (74.3 mg, 1.10 equiv) dropwise at −78° C. The reaction was stirred for 1 h at 78° C. NaHCO₃/H₂O was added and the mixture was extracted with dichloromethane. The combined extracts were washed with brine and dried over Na₂SO₄. Concentration and chromatograph on silica gel (5:1, PE/EA) gave 70 mg (30%) of H-8 as yellow oil. MS (ES) m/z: 795 (M+Na⁺).

With an inert atmosphere of nitrogen, to a mixture of H-8 (70 mg, 0.09 mmol, 1.00 equiv) in dichloromethane (5 mL) with 1,2,3,4,5-pentamethylbenzene (140 mg, 0.94 mmol, 10.43 equiv) was added BCl₃ (1M in DCM, 1.4 mL) at −78° C. The reaction was stirred for 1 h at −78° C. 2 mL of methanol was added. Concentration and chromatograph on C18 (10%-50% CH₃CN/H₂O) gave 20 mg (53%) of compound 8 as white solid. H-NMR (300 MHz, CD₃CN) δ 7.84 (t, J=5.2 Hz, 1H), 7.66 (t, J=5.6 Hz, 1H), 7.34-7.31 (m, 2H), 7.13

(s, 1H), 6.88 (s, 1H), 6.77 (s, 1H), 5.86 (s, 1H), 5.18 (s, 1H), 4.39 (d, J=9.3 Hz, 1H), 3.70-3.65 (m, 5H), 3.53 (q, J=4.0 Hz, 2H), 3.34 (t, J=9.0 Hz, 2H), 2.12 (s, 3H), 1.50 (q, J=12.6 Hz, 1H). MS (ES) m/z: 435 (M+Na$^+$)

Example 9

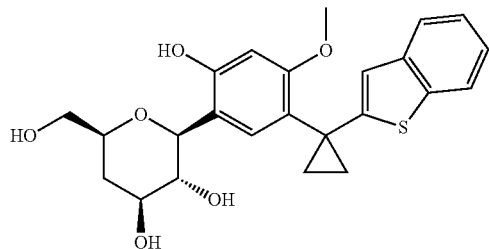 [SMILES: COc1cc(O)c([C@@H]2O[C@H](CO)C[C@H](O)[C@H]2O)cc1C1(c2cc3ccccc3s2)CC1]

(2S,3R,4S,6S)-2-(5-(1-(benzo[b]thiophen-2-yl)cyclopropyl)-2-hydroxy-4-methoxy-phenyl)-6-(hydroxymethyl)tetrahydro-2H-pyran-3,4-diol (cmp. 9)

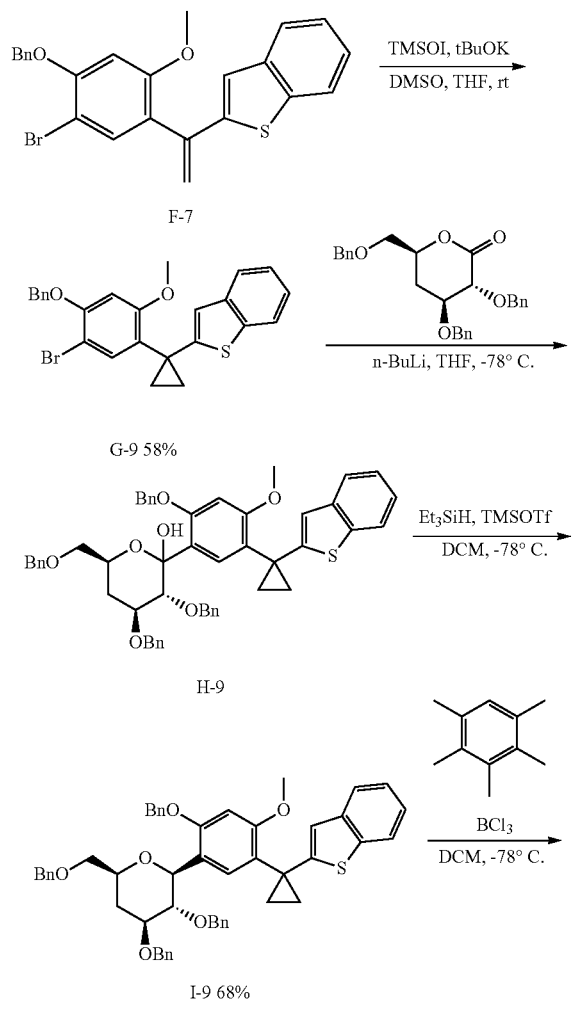

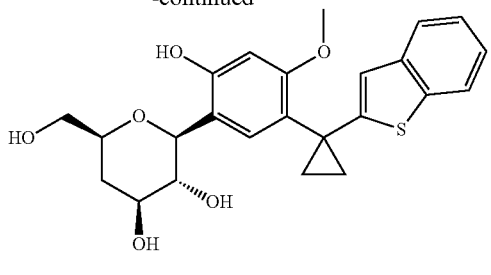

Compound 9 35%

With an inert atmosphere of nitrogen, to a mixture of Trimethyl sulfoxonium iodide (1.95 g, 8.86 mmol) in DMSO (20 mL) was added (tert-butoxy)potassium (1 M in THF, 8.9 mL). The mixture was stirred for 30 min at room temperature. After that, F-7 (800 mg, 1.77 mmol) in tetrahydrofuran (10 mL) was added at room temperature. The reaction was stirred for 48 h at room temperature. H$_2$O was added and the mixture was extracted with EtOAc thrice. The combined extracts were washed with brine and dried over Na$_2$SO$_4$. Concentration and chromatograph on silica gel (5:1, PE/EA) gave 480 mg (58%) of G-9 as a white solid.

With an inert atmosphere of nitrogen, to a mixture of G-9 (331 mg, 0.71 mmol, 1.00 equiv) in THF (5 mL) was added n-BuLi (2.5 M in hexane, 0.29 mL, 1.10 equiv) dropwise at −78° C. The mixture was stirred for 20 min at −78° C. After that, to this was added (3R,4S,6S)-3,4-bis(benzyloxy)-6-[(benzyloxy)methyl]-5-methylideneoxan-2-one (287 mg, 0.66 mmol, 1 equiv) in THF (2 mL) dropwise at −78° C. The reaction was stirred for 1.5 h at −78° C. NH$_4$Cl/H$_2$O was added and the mixture was extracted with EtOAc thrice. The combined extracts were washed with brine and dried over Na$_2$SO$_4$. Concentration and chromatograph on silica gel (5:1, PE/EA) gave 300 mg (crude) of H-9 as yellow oil. MS (ES) m/z: 841 (M+Na$^+$).

With an inert atmosphere of nitrogen, to a mixture of H-9 (300 mg, 0.37 mmol, 1 equiv) in dichloromethane (10 mL) with Et$_3$SiH (63.8 mg, 0.55 mmol, 1.50 equiv) was added TMSOTf (122 mg, 1.50 equiv) dropwise at −78° C. The reaction was stirred for 1 h at 78° C. NaHCO$_3$/H$_2$O was added and the mixture was extracted with dichloromethane thrice. The combined extracts were washed with brine and dried over Na$_2$SO$_4$. Concentration and chromatograph on silica gel (5:1, PE/EA) gave 200 mg (68%) of I-9 as yellow oil. MS (ES) m/z: 825 (M+Na$^+$).

With an inert atmosphere of nitrogen, to a mixture of I-9 (200 mg, 0.25 mmol, 1.00 equiv) in dichloromethane (10 mL) with 1,2,3,4,5-pentamethylbenzene (400 mg, 2.70 mmol, 10.83 equiv) was added BCl$_3$ (1M in DCM, 4.0 mL) at −78° C. The reaction was stirred for 1 h at −78° C. 2 mL of methanol was added. Concentration and chromatograph on C18 (10%-50% CH$_3$CN/H$_2$O) gave 39 mg (35%) of compound 9 as a pink solid. H-NMR (400 MHz, CD3OD) δ 7.66 (d, J=8.0 Hz, 1H), 7.54 (d, J=8.0 Hz, 1H), 7.37 (s, 1H), 7.25-7.15 (m, 2H), 6.81 (s, 1H), 6.48 (s, 1H), 4.50 (d, J=9.6 Hz, 1H), 3.78 (s, 3H), 3.75-3.70 (m, 2H), 3.62-3.61 (m, 2H), 3.49 (t, J=9.2 Hz, 1H), 2.04 (dd, J=11.6, 4.8 Hz, 1H), 1.57 (q, J=12.4 Hz, 1H), 1.38 (t, J=7.2 Hz, 2H), 1.32 (t, J=7.2 Hz, 2H). MS (ES) m/z: 465 (M+Na$^+$).

Example 10

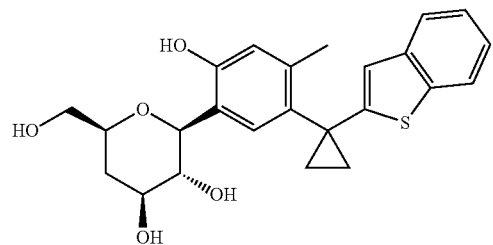 [SMILES: Cc1cc(O)c([C@@H]2O[C@H](CO)C[C@H](O)[C@H]2O)cc1C1(c2cc3ccccc3s2)CC1]

2S,3R,4S,6S)-2-(5-(1-(benzo[b]thiophen-2-yl)cyclopropyl)-2-hydroxy-4-methyl-phenyl)-6-(hydroxymethyl)tetrahydro-2H-pyran-3,4-diol (cmp. 10

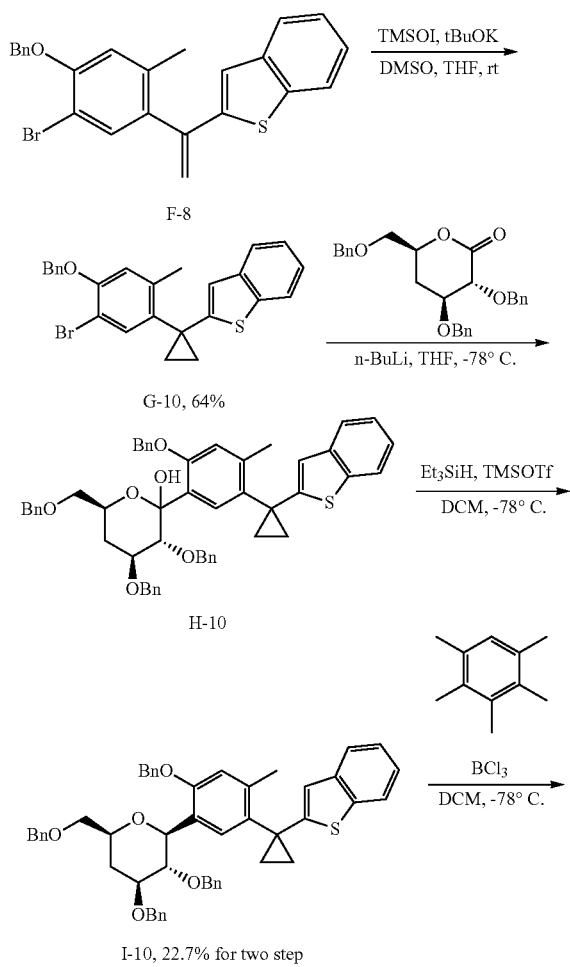

With an inert atmosphere of nitrogen, to a mixture of Trimethyl sulfoxonium iodide (2.55 g, 11.59 mmol) in DMSO (20 mL) was added (tert-butoxy)-potassium (1M in THF, 12 mL). The mixture was stirred for 30 min at room temperature. After that, F-8 (1.0 g, 2.30 mmol) in tetrahydrofuran (10 mL) was added at room temperature. The reaction was stirred for 48 h at room temperature. H₂O was added and the mixture was extracted with EtOAc thrice. The combined extracts were washed with brine and dried over $Na_2SO_4$. Concentration and chromatograph on silica gel (5:1, PE/EA) gave 660 mg (64%) of G-10 as a yellow oil.

With an inert atmosphere of nitrogen, to a mixture of G-10 (200 mg, 0.45 mmol, 1.10 equiv) in THF (5 mL) was added n-BuLi (2.5 M in hexane, 0.179 mL, 1.10 equiv) dropwise at −78° C. The mixture was stirred for 20 min at −78° C. After that, to this was added (3R,4S,6S)-3,4-bis(benzyloxy)-6-[(benzyloxy)methyl]-5-methylideneoxan-2-one (192.9 mg, 0.45 mmol, 1.00 equiv) in THF (2 mL) dropwise at −78° C. The reaction was stirred for 1.5 h at −78° C. $NH_4Cl/H_2O$ was added and the mixture was extracted with EtOAc thrice. The combined extracts were washed with brine and dried over $Na_2SO_4$. Concentration gave 360 mg (crude) of H-10 as yellow oil. MS (ES) m/z: 825 (M+Na⁺).

With an inert atmosphere of nitrogen, to a mixture of H-10 (360 mg, 0.45 mmol, 1.00 equiv) in dichloromethane (10 mL) with $Et_3SiH$ (155.4 mg, 1.34 mmol, 3.00 equiv) was added $BF_3 \cdot Et_2O$ (190.2 mg, 1.34 mmol, 3.00 equiv) dropwise at 0° C. The reaction was stirred for 1 h at 0° C. $NaHCO_3/H_2O$ was added and the mixture was extracted with dichloromethane thrice. The combined extracts were washed with brine and dried over $Na_2SO_4$. Concentration and chromatograph on silica gel (5:1, PE/EA) gave 80 mg (22.7% for two step) of I-10 as yellow oil. MS (ES) m/z: 809 (M+Na⁺).

With an inert atmosphere of nitrogen, to a mixture of I-10 (80 mg, 0.10 mmol, 1.00 equiv) in dichloromethane (5 mL) with 1,2,3,4,5-pentamethylbenzene (160 mg, 1.08 mmol, 10.83 equiv) was added $BCl_3$ (1M in DCM, 1.6 mL) at −78° C. The reaction was stirred for 1 h at −78° C. 2 mL of methanol was added. Concentration and chromatograph on C18 (10%-50% $CH_3CN/H_2O$) gave 23 mg (52%) of compound 10 as a pink solid. H-NMR (300 MHz, CD₃OD) δ 7.68 (d, J=7.5 Hz, 1H), 7.54 (d, J=8.1 Hz, 1H), 7.407 (s, 1H), 7.26-7.16 (m, 2H), 6.70 (d, J=5.1 Hz, 2H), 4.54 (d, J=9.6 Hz, 1H), 3.78-3.69 (m, 2H), 3.63 (d, J=5.1 Hz, 2H), 3.50 (t, J=9.3 Hz, 1H), 2.27 (s, 3H), 2.05 (dd, J=14.1, 6.6 Hz, 1H), 1.59 (q, J=11.4 Hz, 1H), 1.46-1.42 (m, 4H). MS (ES) m/z: 449 (M+Na⁺).

Example 11

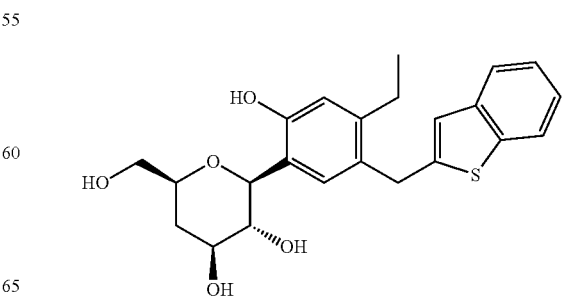

2S,3R,4S,6S)-2-(5-(benzo[b]thiophen-2-ylmethyl)-4-ethyl-2-hydroxyphenyl)-6-(hydroxymethyl)tetrahydro-2H-pyran-3,4-diol (cmp. 11

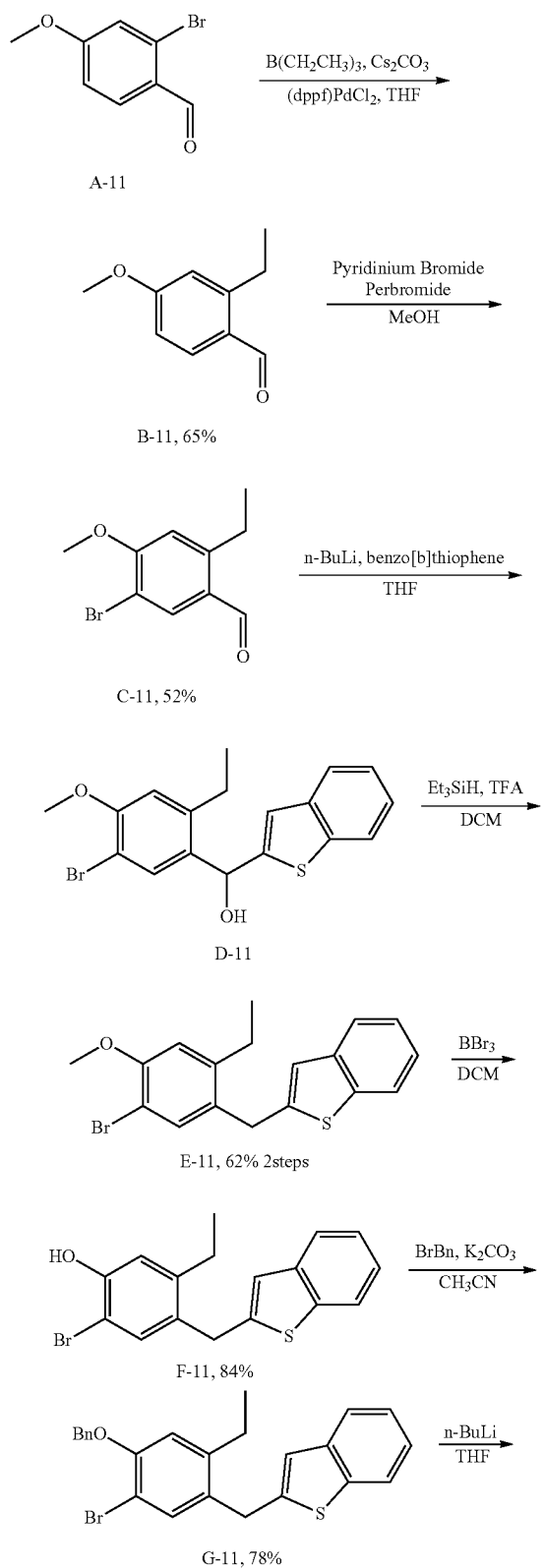

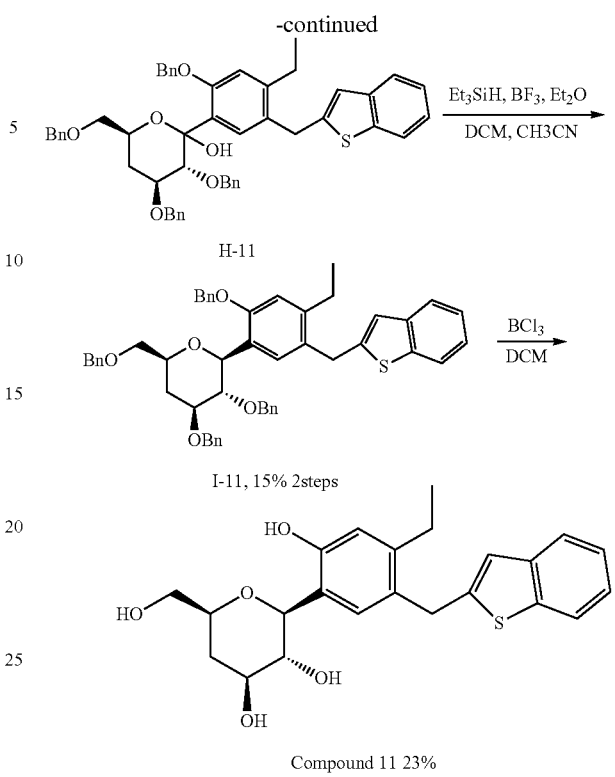

With an inert atmosphere of nitrogen, A solution of A-11 (6 g, 27.91 mmol), B(CH$_2$CH$_3$)$_3$ (4.1 g, 41.86 mmol) and Cs$_2$CO$_3$ (27.3 g, 83.72 mmol) in THF (100 ml) was treated with (dppf)PdCl$_2$ (2.3 g, 2.79 mmol). The reaction was stirred at 68° C. for 3 h. Water was added and the mixture was extracted with EtOAc thrice. The combined extracts were washed with brine and dried over Na$_2$SO$_4$. Concentration and chromatograph on silica gel (1:10 ethyl acetate/petroleum ether) gave 3.0 g (65%) of B-11 as yellow oil.

To a mixture of B-11 (3.0 g, 18.27 mmol) in MeOH (40 mL) was added pyridinium bromide perbromide (6.0 g, 18.94 mmol) at 0° C. The reaction was stirred at room temperature for 8 h. Water was added and the mixture was extracted with EtOAc thrice. The combined extracts were washed with 1N HCl, brine and dried over Na$_2$SO$_4$. Concentration and chromatograph on silica gel (1:10 ethyl acetate/petroleum ether) gave 2.3 g (52%) of C-11 as yellow oil.

With an inert atmosphere of nitrogen, To a mixture of 1-benzothiophene (1.52 g, 11.33 mmol) in THF (20 mL) was added n-BuLi (5 mL, 2.5N) dropwise at −78° C., the mixture was stirred for 30 min at −78° C. After that, C-11 (2.3 g, 9.54 mmol) in THF (3 mL) was added. The reaction was stirred for 1 h at −78° C. NH$_4$Cl/H$_2$O was added and the mixture was extracted with EtOAc thrice. The combined extracts were washed with brine and dried over Na$_2$SO$_4$. Concentration and chromatograph on silica gel gave 3.7 g (crude) of D-11 as yellow oil.

To a mixture of D-11 (3.7 g, crude) in dichloromethane (40 mL) with Et$_3$SiH (2.2 g, 19.18 mmol) was added trifluoroacetic acid (2.3 g, 19.91 mmol) at 0° C. The reaction was stirred at 0° C. for 3 h. NaHCO$_3$/H$_2$O was added and the mixture was extracted with DCM thrice. The combined extracts were washed with brine and dried over Na$_2$SO$_4$. Concentration and chromatograph on silica gel (1:20 ethyl acetate/petroleum ether) gave 2.1 g (62%) of E-11 as a white solid.

With an inert atmosphere of nitrogen, to a mixture of E-11 (1.7 g, 4.71 mmol) in dichloromethane (20 mL) was added BBr$_3$ (3.5 g, 14.13 mmol) at −78° C. The reaction was stirred at room temperature for 2 h. NaHCO$_3$/H$_2$O was added and the mixture was extracted with DCM thrice. The combined extracts were washed with brine and dried over Na$_2$SO$_4$. Concentration and chromatograph on silica gel (1:20 ethyl acetate/petroleum ether) gave 1.3 g (84%) of F-11 as yellow oil.

To a mixture of F-11 (1.3 g, 3.74 mmol) in CH3CN (20 mL) with K$_2$CO$_3$ (1.6 g, 11.21 mmol) was added BnBr (960 mg, 5.61 mmol). The reaction was stirred at room temperature for overnight. Water was added and the mixture was extracted with EtOAc thrice. The combined extracts were washed with brine and dried over Na$_2$SO$_4$. Concentration and chromatograph on silica gel (1:20 ethyl acetate/petroleum ether) gave 1.3 g (78%) of G-11 as yellow oil.

With an inert atmosphere of nitrogen, to a mixture of G-11 (300 mg, 0.69 mmol) in THF (5 mL) was added n-BuLi (0.25 mL, 2.5N) at −78° C. The mixture was stirred for 30 min at −78° C. To his was added (3R,4S,6S)-3,4-bis(benzyloxy)-6-[(benzyloxy)methyl]oxan-2-one (250 mg, 0.58 mmol) at −78° C. The reaction was stirred for 2 h at −78° C. NH$_4$Cl/H$_2$O was added and the mixture was extracted with EtOAc thrice. The combined extracts were washed with brine and dried over Na$_2$SO$_4$. Concentration gave 490 mg (crude) of H-11 as yellow solid.

To a mixture of I-11 (490 mg, crude) in DCM/CH$_3$CN (5/5 ml) with Et$_3$SiH (142 mg, 1.22 mmol) was added BF$_3$.Et$_2$O (133 mg, 0.93 mmol) dropwise at 0° C. The reaction was stirred for 2 h at 0° C. NaHCO$_3$/H$_2$O was added and the mixture was extracted with DCM thrice. The combined extracts were washed with brine and dried over Na$_2$SO$_4$. Concentration and chromatograph on silica gel (1:5 ethyl acetate/petroleum ether) gave 81 mg (15%) of J-11 as yellow oil.

With an inert atmosphere of nitrogen, To a mixture of J-11 (81 mg, 0.10 mmol) in DCM (5 ml) with 1,2,3,4,5-pentamethylbenzene (200 mg) was added BCl$_3$ (2 mL 1 M/L in DCM) dropwise at −78° C. The reaction was stirred for 1 h at −78° C. The reaction was then quenched by the addition of 3 mL of methanol. The mixture was concentrated under vacuum. The crude product was purified by Prep-HPLC with the following conditions (1#-Waters 2767-1): Column, SunFire Prep C18, 5 um, 19*100 mm; mobile phase: water in 0.05% TFA and CH3CN (30% CH3CN up to 48% in 15 min, up to 100% in 1 min, down to 30% in 1 min); Detector, UV 254 nm. This resulted in 10 mg (23%) of compound 11 as white solid. $^1$H NMR (300 MHz, CD3OD) δ 7.61 (d, J=9.6 Hz, 1H), 7.51 (d, J=9.6 Hz, 1H), 7.18-7.08 (m, 3H), 6.81 (s, 1H), 6.62 (s, 1H), 4.39 (d, J=9.9 Hz, 1H), 4.11 (s, 2H), 3.66-3.57 (m, 2H), 3.50-3.46 (m, 2H), 3.37 (t, J=9.3 Hz, 1H), 2.50 (q, J=7.2 Hz, 2H), 1.92 (dd, J=12.6, 4.2 Hz, 1H), 1.44 (q, J=11.7 Hz, 1H), 1.04 (t, J=7.2 Hz, 3H); MS (ES) m/z: 437 (M+Na$^+$).

Example 12

2S,3R,4S,6S)-2-(5-(benzo[b]thiophen-2-ylmethyl)-4-cyclopropyl-2-hydroxyphenyl)-6-(hydroxymethyl)tetrahydro-2H-pyran-3,4-diol (cmp. 12

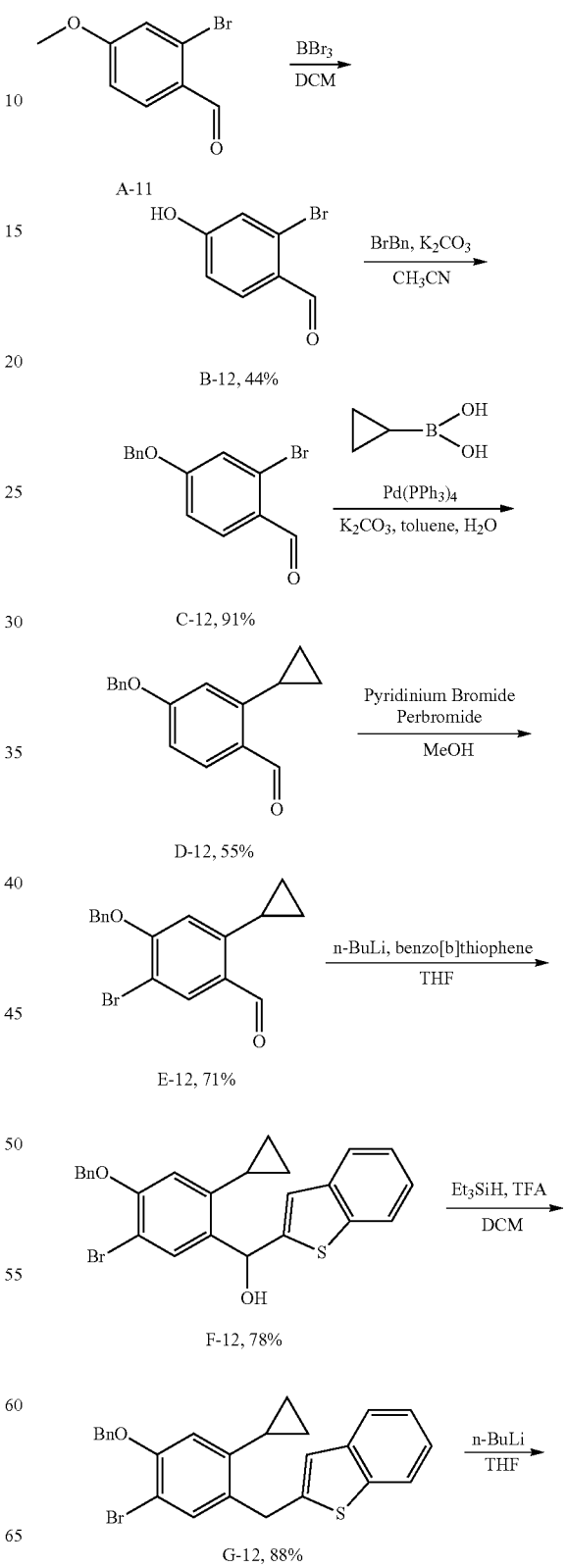

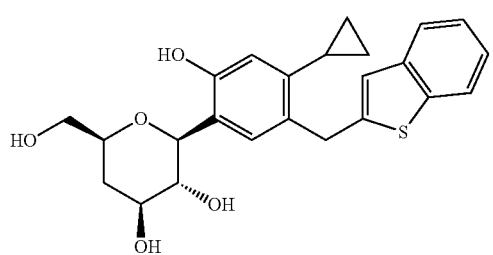 [SMILES: OC[C@@H]1C[C@H](O)[C@@H](O)[C@H](c2cc(Cc3cc4ccccc4s3)c(C3CC3)cc2O)O1]

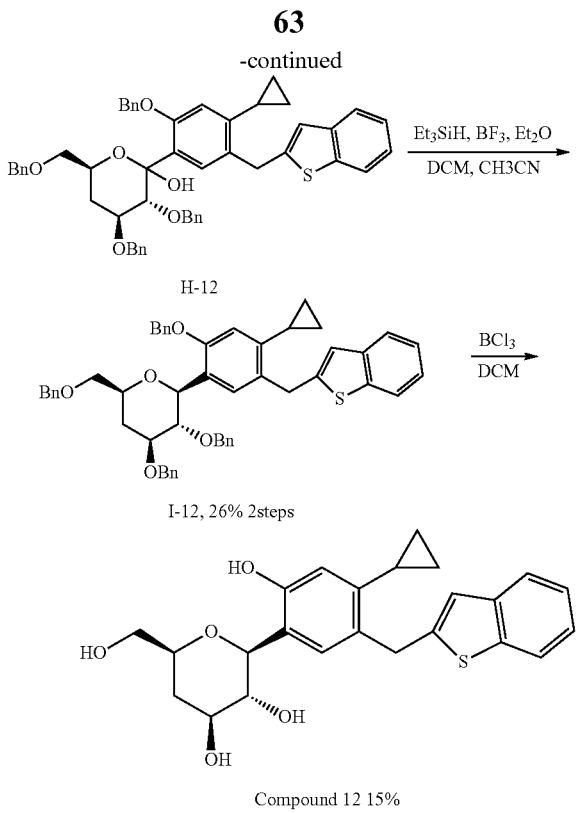

Compound 12 15%

With an inert atmosphere of nitrogen to a mixture of A-11 (16 g, 74.40 mmol) in dichloromethane (150 mL) was added BBr₃ (22 mL, 4M in DCM) at −78° C. The reaction was stirred at room temperature for overnight. NaHCO₃/H₂O was added and the mixture was extracted with DCM thrice. The combined extracts were washed with brine and dried over Na₂SO₄. Concentration and chromatograph on silica gel (1:5 acetate/petroleum ether) gave 6.6 g (44%) of B-12 as yellow oil.

To a mixture of B-12 (6.6 g, 32.83 mmol) in CH3CN (65 ml) with K₂CO₃ (13.7 g, 98.84 mmol) was added BnBr (6.8 g, 39.58 mmol). The reaction was stirred at room temperature for overnight. Water was added and the mixture was extracted with EtOAc thrice. Concentration and chromatograph on silica gel (1:10 ethyl acetate/petroleum ether) gave 8.7 g (91%) of C-12 as yellow solid.

With an inert atmosphere of nitrogen a solution of C-12 (8.4 g, 28.85 mmol), cyclopropylboronic acid (3 g, 34.93 mmol) and K₂CO₃ (12 g, 86.82 mmol) in toluene/H2O (90 mL/9 mL) was treated with Pd(PPh₃)₄ (3.4 g, 2.90 mmol). The reaction was stirred at 80° C. for 4 h. Water was added and the mixture was extracted with EtOAc thrice. Concentration and chromatograph on silica gel (1:10 ethyl acetate/petroleum ether) gave 4.0 g (55%) of D-12 as yellow oil.

To a mixture of D-12 (1.5 g, 5.95 mmol) in MeOH (15 mL) was added pyridinium bromide perbromide (2.0 g, 6.25 mmol). The reaction was stirred at room temperature for overnight. Water was added and the mixture was extracted with EtOAc thrice. The combined extracts were washed with 1N HCl, brine and dried over Na₂SO₄. Concentration and chromatograph on silica gel (1:10 acetate/petroleum ether) gave 1.4 g (71%) of E-12 as white solid.

With an inert atmosphere of nitrogen, to a mixture of 1-benzothiophene (490 mg, 3.65 mmol) in THF (10 mL) was added n-BuLi (1.5 mL, 2.5N) dropwise at −78° C., the mixture was stirred for 30 mins at −78° C. After that, E-12 (1 g, 3.02 mmol) was added to the solution. The resulting solution was stirred for 2 h at −78° C. NH₄Cl/H₂O was added and the mixture was extracted with EtOAc thrice. The combined extracts were washed with brine and dried over Na₂SO₄. Concentration and chromatograph on silica gel (1:5 ethyl acetate/petroleum ether) gave 1.1 g (78%) of F-12 as yellow oil.

To a mixture of F-12 (1.1 g, 2.36 mmol) in DCM (15 mL) was added Et₃SiH (640 mg, 5.50 mmol) and trifluoroacetic acid (650 mg, 5.70 mmol) dropwise with stirring at 0° C. The reaction was stirred at 0° C. for 2 h. NaHCO₃/H₂O was added and the mixture was extracted with DCM thrice. The combined extracts were washed with brine and dried over Na₂SO₄. Concentration and chromatograph on silica gel (1:20 ethyl acetate/petroleum ether) gave 930 mg (88%) of G-12 as yellow solid.

With an inert atmosphere of nitrogen, to a mixture of G-12 (320 mg, 0.71 mmol) in THF (5 mL) was added n-BuLi (0.26 mL, 2.5N) at −78° C. The mixture was stirred for 30 min at −78° C. Then, to this was added (3R,4S,6S)-3,4-bis(benzyloxy)-6-[(benzyloxy)methyl]oxan-2-one (260 mg, 0.60 mmol) at −78° C. The reaction was stirred for 2 h at −78° C. NH₄Cl/H₂O was added and the mixture was extracted with EtOAc thrice. The combined extracts were washed with brine and dried over Na₂SO₄. Concentration gave 520 mg (crude) of H-12 as yellow solid.

To a mixture of H-12 (520 mg, crude) in DCM/CH₃CN (5/5 mL) with Et₃SiH (150 mg, 1.29 mmol) was added BF₃.Et₂O (140 mg, 1.00 mmol) dropwise at 0° C. The reaction was stirred for 1 h at 0° C. NaHCO₃/H₂O was added and the mixture was extracted with DCM thrice. The combined extracts were washed with brine and dried over Na₂SO₄. Concentration and chromatograph on silica gel (1:5 ethyl acetate/petroleum ether) gave 120 mg (26%) of I-12 as yellow oil.

With an inert atmosphere of nitrogen to a mixture of I-12 (120 mg, 0.15 mmol) in DCM (5 mL) with 1,2,3,4,5-pentamethylbenzene (240 mg) was added BCl3 (2.5 mL) dropwise at −78° C. The reaction was stirred for 1 h at −78° C. The reaction was then quenched by the addition of 3 mL of methanol. The mixture was concentrated under vacuum. The crude product was purified by Prep-HPLC with the following conditions (1#-Waters 2767-1): Column, SunFire Prep C18, 5 um, 19*100 mm; mobile phase: water in 0.05% TFA and CH3CN (30% CH3CN up to 48% in 15 min, up to 100% in 1 min, down to 30% in 1 min); Detector, UV 254 nm. This resulted in 10 mg (15%) of compound 12 as white solid. ¹H NMR (300 MHz, CD3OD). δ 7.61 (d, J=7.5 Hz, 1H), 7.51 (d, J=6.9 Hz, 1H), 7.18-7.10 (m, 3H), 6.84 (s, 1H), 6.40 (s, 1H), 4.38 (d, J=9.3 Hz, 1H), 4.23 (d, J=3.0 Hz, 2H), 3.62-3.56 (m, 2H), 3.48 (d, J=5.4 Hz, 2H), 3.35 (t, J=9.3 Hz, 1H), 1.90-1.89 (m, 1H), 1.80-1.78 (m, 1H), 1.43 (q, J=12.6 Hz, 1H), 0.78-0.73 (m, 2H), 0.50-0.44 (m, 2H); MS (ES) m/z: 449 (M+Na⁺).

Example 13

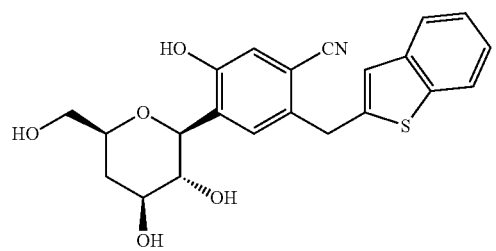 [SMILES: N#Cc1cc(O)c([C@@H]2O[C@H](CO)C[C@H](O)[C@H]2O)cc1Cc1cc2ccccc2s1]

2-(benzo[b]thiophen-2-ylmethyl)-4-((2S,3R,4S,6S)-3,4-dihydroxy-6-(hydroxymethyl)-tetrahydro-2H-pyran2-yl)-5-hydroxybenzonitrile (cmp. 13)

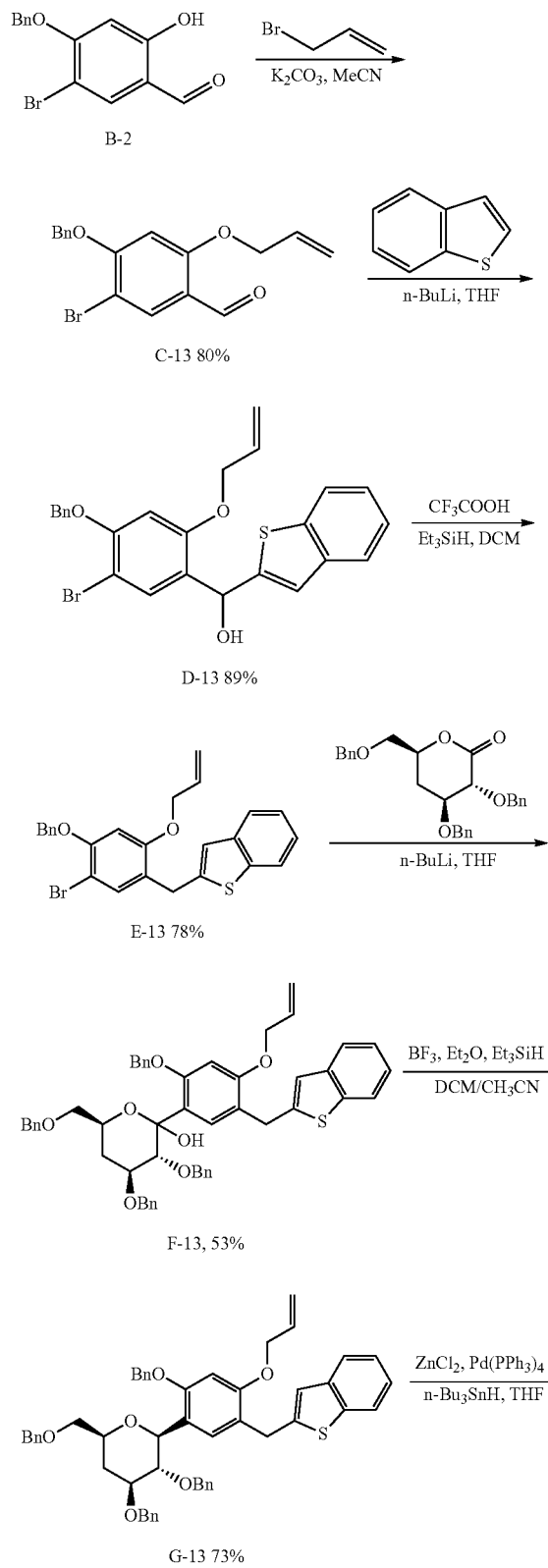

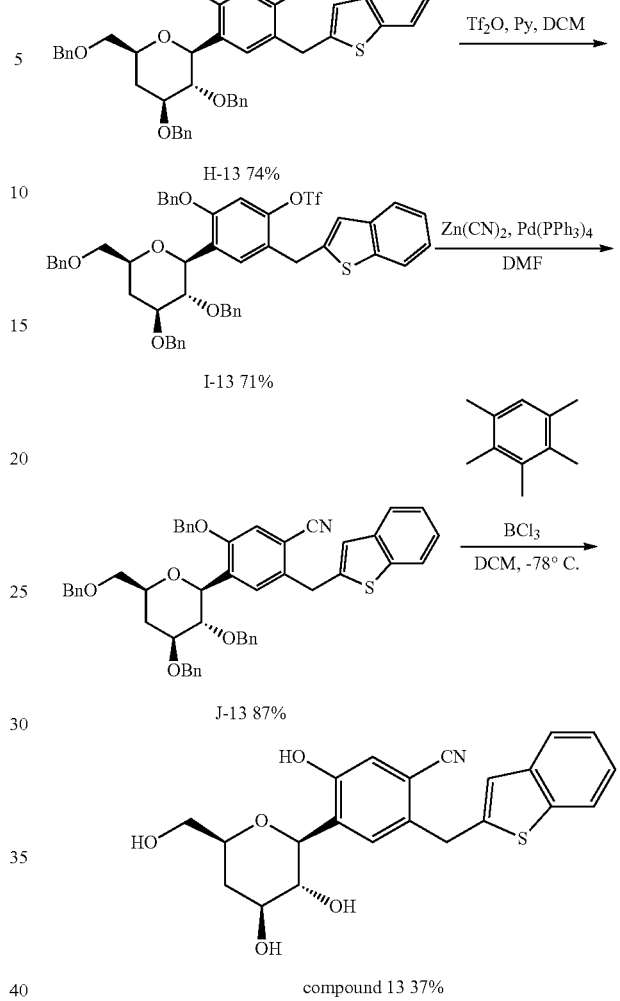

To a mixture of B-2 (4 g, 13.02 mmol) in acetonitrile (100 mL) with potassium carbonate (5.4 g, 39.07 mmol) was added 3-bromoprop-1-ene (2.4 g, 19.84 mmol). The mixture was stirred for overnight at room temperature. The solids were filtered out, concentrated and Chromatograph on silica gel (5:1 PE/EtOAc) gave 3.6 g (80%) of C-13 as a light yellow solid.

With an inert atmosphere of nitrogen to a mixture of 1-benzothiophene (600 mg, 4.47 mmol) in tetrahydrofuran (15 mL) was added n-BuLi (2.5M in hexane, 1.8 mL) dropwise at −78° C. The mixture was stirred for 30 min at −78° C. After that, C-13 (1.3 g, 3.74 mmol) in THF (3 mL) was added dropwise at −78° C. The reaction was stirred for 2 h at −78° C. Water was added, the mixture was extracted with EtOAc thrice. The combined extracts were washed with $H_2O$, brine and dried over $Na_2SO_4$. Concentration and chromatograph on silica gel (3:1 PE/EtOAc) gave 1.6 g (89%) of D-13 as yellow oil.

A solution of D-13 (1.6 g, 3.32 mmol) in dichloromethane (20 mL) with $Et_3SiH$ (1.2 g, 10.32 mmol) was treated with trifluoroacetic acid (760 mg, 6.72 mmol) at 0° C. The reaction was stirred for 2 h at room temperature. Water was added, the mixture was extracted with DCM thrice. The combined extracts were washed with $H_2O$, brine and dried over $Na_2SO_4$. Concentration and chromatograph on silica gel (5:1 PE/EtOAc) gave 1.2 g (78%) of E-13 as yellow oil.

With an inert atmosphere of nitrogen to a mixture of E-13 (829 mg, 1.78 mmol) in tetrahydrofuran (10 mL) was added n-BuLi (2.5M in hexane, 0.7 mL, 1.10 equiv) dropwise at −78° C. The mixture was stirred for 30 min at −78° C. To the mixture was added a solution of (3R,4S,6S)-3,4-bis(benzyloxy)-6-[(benzyloxy)methyl]oxan-2-one (700 mg, 1.62 mmol, 1.00 equiv) in tetrahydrofuran (5 mL) dropwise at −78° C. The reaction was stirred for 2 h at −78° C. NH$_4$Cl/H$_2$O was added, the mixture was extracted with EtOAc thrice. The combined extracts were washed with H$_2$O, brine and dried over Na$_2$SO$_4$. Concentration and chromatograph on silica gel (3:1 PE/EtOAc) gave 700 mg (53%) of F-13 as yellow oil.

A solution of F-13 (700 mg, 0.85 mmol) in dichloromethane (10 mL) with Et$_3$SiH (297 mg, 2.55 mmol) was treated with BF$_3$.Et$_2$O (242 mg, 1.70 mmol) at 0° C. The reaction was stirred for 1 h at 0° C. Water was added, the mixture was extracted with dichloromethane thrice. The combined extracts were washed with H$_2$O, brine and dried over Na$_2$SO$_4$. Concentration and chromatograph on silica gel (5:1 PE/EtOAc) gave 500 mg (73%) of G-13 as yellow oil.

With an inert atmosphere of nitrogen, to a mixture of G-13 (500 mg, 0.62 mmol) in tetrahydrofuran (15 mL) was added ZnCl$_2$ (212 mg, 1.56 mmol), the mixture was stirred for 30 min at room temperature. To this was added Pd(PPh$_3$)$_4$ (180 mg, 0.16 mmol), The mixture was stirred for 30 min at room temperature. To this was added n-Bu$_3$SnH (728 mg, 2.49 mmol). The solution was stirred for 1 h at room temperature. Water was added, the mixture was extracted with EtOAc thrice. The combined extracts were washed with 1% HCl, brine and dried over Na$_2$SO$_4$. Concentration and chromatograph on silica gel (2:1 PE/EtOAc) gave 350 mg (74%) of H-13 as yellow oil.

A solution of H-13 (300 mg, 0.39 mmol) in dichloromethane (15 mL) with pyridine (93 mg, 1.18 mmol) was treated with (trifluoromethane)sulfonyl trifluoromethanesulfonate (222 mg, 0.79 mmol). The mixture was stirred for 1 h at room temperature. Water was added, the mixture was extracted with dichloromethane thrice. The combined extracts were washed with H$_2$O, brine and dried over Na$_2$SO$_4$. Concentration and chromatograph on silica gel (5:1 PE/EtOAc) gave 250 mg (71%) of I-13 as yellow oil.

A solution of I-13 (200 mg, 0.22 mmol) in N,N-dimethylformamide (10 mL) with Zn(CN)$_2$ (260 mg, 2.24 mmol) was treated with Pd(PPh$_3$)$_4$ (516 mg, 0.45 mmol). The reaction was stirred for 2 h at 80° C. Water was added, the mixture was extracted with EtOAc thrice. The combined extracts were washed with H$_2$O, brine and dried over Na$_2$SO$_4$. Concentration and chromatograph on silica gel (2:1, PE/EtOAc) gave 150 mg (87%) of J-13 as yellow oil.

With an inert atmosphere of nitrogen, to a mixture of J-13 (150 mg, 0.19 mmol) in dichloromethane (10 mL) was added BBr$_3$ (3 mL, 20.00 equiv) at −78° C. The reaction was stirred for 1 h at −78° C. Menthol was added. Concentration and chromatograph on C18 column (1:2 MeCN/H$_2$O) gave 29.8 mg (37%) of compound 13 as a white solid. 1H NMR (300 MHz, CD$_3$OD) δ 7.75 (d, J=8.0 Hz, 1H), 7.68 (d, J=7.6 Hz, 1H), 7.57 (s, 1H), 7.24-7.32 (m, 2H), 7.13 (s, 1H), 7.08 (s, 1H), 4.60 (d, J=6.4 Hz, 1H), 4.38 (t, J=12.6 Hz, 2H), 3.77-3.68 (m, 2H), 3.60 (d, J=3.6 Hz, 2H), 3.38-3.33 (m, 1H), 2.03 (dd, J=10.2, 3.6 Hz, 1H), 1.56 (q, J=9.3 Hz, 1H). MS (ES) m/z: 434 (M+Na$^+$)

Example 14

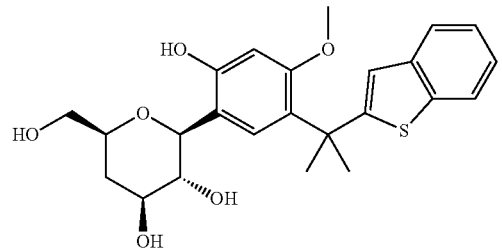 [SMILES: COc1cc(O)c([C@@H]2O[C@H](CO)C[C@H](O)[C@H]2O)cc1C(C)(C)c1cc2ccccc2s1]

(2S,3R,4S,6S)-2-(5-(2-(benzo[b]thiophen-2-yl)propan-2-yl)-2-hydroxy-4-methoxyphenyl)-6-(hydroxymethyl)-tetrahydro-2H-pyran-3,4-diol

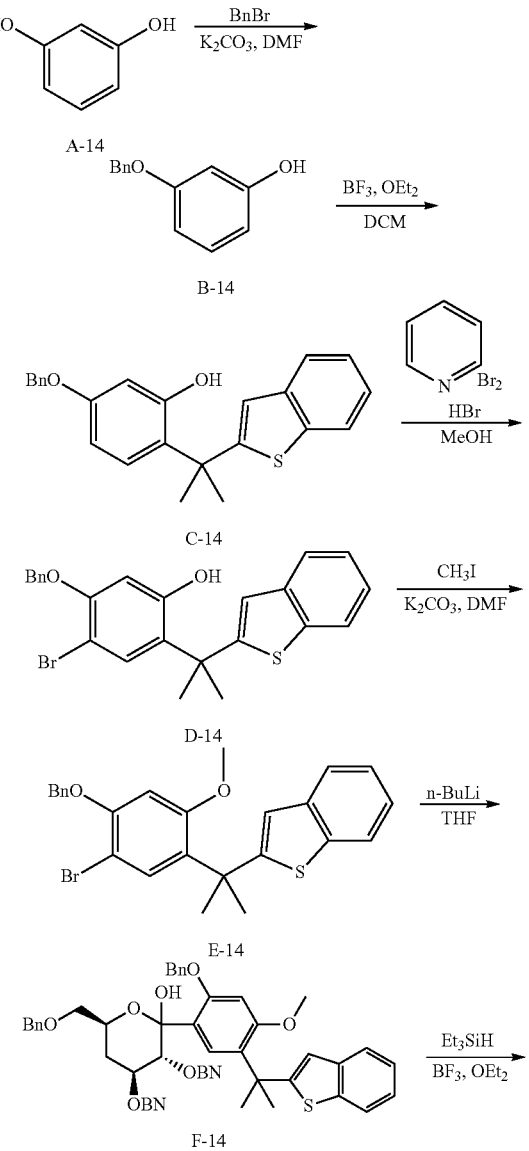

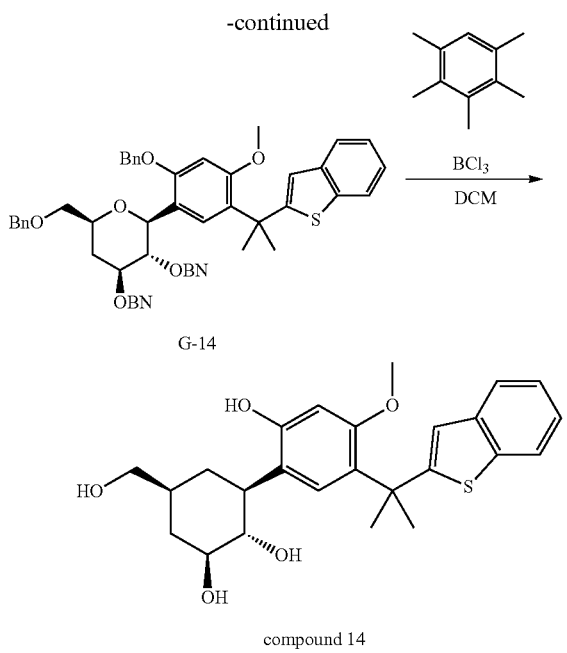

G-14 compound 14

To a mixture of A-14 (4.0 g, 36.4 mmol) in Acetone (50 mL) with K₂CO₃ (7.7 g, 56 mmol) was added BnBr (4.75 g, 28 mmol). The reaction was stirred for 2 h at 80° C. Water was added, the mixture was extracted with EtOAc thrice. The combined extracts were washed with H₂O, brine and dried over Na₂SO₄. Concentration and chromatograph on silica gel (5:1 PE/EtOAc) gave 6 g (83%) of B-14 as a white solid. ¹H NMR (400 MHz, CDCl₃) δ 7.46-7.23 (m, 5H), 7.16 (t, J=8.4 Hz, 1H), 6.60 (dd, J=8.4, 2.4 Hz, 1H), 6.51 (s, 1H), 6.47 (dd, J=8.4, 2.4 Hz, 1H), 5.04 (s, 2H).

To a mixture of B-14 (300 mg, 1.5 mmol) in DCM with 2-(benzo[b]thiophen-2-yl)propan-2-ol (288 mg. 1.5 mmol) was added BF₃.Et₂O (106 mg, 0.75 mmol) at −78° C., The reaction was stirred for 3 h at −78° C. Water was added, the mixture was extracted with EtOAc thrice. The combined extracts were washed with H₂O, brine and dried over Na₂SO₄. Concentration and chromatograph on silica gel (5:1 PE/EtOAc) gave 320 mg (59%) of C-14 as a white solid.

To a mixture of C-14 (1.9 g, 5.07 mmol) in methanol (20 mL) was added pyridinium hydrobromide perbromide (1.6 g, 5.02 mmol) at 0° C. The reaction was stirred for 3 h at 0° C. Water was added, the mixture was extracted with EtOAc thrice. The combined extracts were washed with H₂O, brine and dried over Na₂SO₄. Concentration and chromatograph on silica gel (4:1 PE/EtOAc) gave 2.0 g (87%) of D-14 as a white solid. ¹H NMR (400 MHz, CDCl₃) δ 7.75-7.21 (m, 11H), 6.46 (s, 1H), 5.07 (s, 2H), 1.80 (s, 6H).

To a mixture of D-14 (1.2 g, 2.65 mmol) in DMF (10 mL) with potassium carbonate (1.1 g, 7.96 mmol) was added iodomethane (1.13 g, 7.96 mmol). The reaction was stirred for 3 h at room temperature. Water was added, the mixture was extracted with EtOAc thrice. The combined extracts were washed with H₂O, brine and dried over Na₂SO₄. Concentration and chromatograph on silica gel (5:1 PE/EtOAc) gave 1.1 g (89%) of E-14 as a white solid. ¹H NMR (400 MHz, CDCl₃) δ 7.71-7.18 (m, 10H), 6.91 (s, 1H), 6.47 (s, 1H), 5.14 (s, 2H), 3.44 (s, 3H), 1.78 (s, 6H).

With an inert atmosphere of nitrogen, To the solution of E-14 (340 mg, 0.73 mmol) in tetrahydrofuran (5 mL) was added n-BnLi (2.5M in hexane, 0.35 mL,) at −78° C. The mixture was stirred for 30 min at −78° C. To the mixture was added a solution of (3R,4S,6S)-3,4-bis(benzyloxy)-6-[(benzyloxy)methyl]oxan-2-one (346 mg, 0.8 mmol) in tetrahydrofuran (5 mL) dropwise at −78° C. The reaction was stirred for 2 h at −78° C. NH₄Cl/H₂O was added, the mixture was extracted with EtOAc thrice. The combined extracts were washed with H₂O, brine and dried over Na₂SO₄. Concentration and chromatograph on silica gel (5:1 PE/EtOAc) gave 450 mg (75%) of F-14 as yellow oil.

To a mixture of F-14 (450 mg, 0.60 mmol) in dichloromethane (5 mL) and CH₃CN (5 mL) with Et₃SiH (124 mg, 1.07 mmol) was added BF₃.OEt₂ (152 mg, 1.07 mmol) at 0° C. The reaction was stirred for 3 h at 0° C. Water was added, the mixture was extracted with dichloromethane thrice. The combined extracts were washed with H₂O, brine and dried over Na₂SO₄. Concentration and chromatograph on silica gel (5:1 PE/EtOAc) gave 150 mg (34%) of G-14 as yellow oil.

To a mixture of G-14 (210 mg, 0.26 mmol) and 1,2,3,4,5-pentamethylbenzene (420) in dichloromethane (5 mL) was added BCl₃ (1M in DCM, 4.2 mL) at −78° C. with an inert atmosphere. The reaction was stirred for 1 h at −78° C. Methanol was added. Concentration and chromatograph on C18 column (1:2 MeCN/H₂O) gave 26.3 mg (23%) of compound 14 as a white solid. ¹H NMR (300 MHz, CD₃CN) δ 7.74 (d, J=8.1 Hz, 1H), 7.66 (d, J=7.5 Hz, 1H), 7.32-7.19 (m, 3H), 7.01 (s, 1H), 6.43 (s, 1H), 4.34 (d. J=9.9, 1 H), 3.70-3.64 (m, 2H), 3.54 (t, J=3.6 Hz, 2H), 3.47 (s, 3H), 3.36 (t, J=9.3 Hz, 1H), 2.49 (s, 1H), 1.57 (s, 6H), 1.51 (q, J=12.6 Hz, 1H). MS (ES) m/z: 467 (M+Na⁺).

Example 15

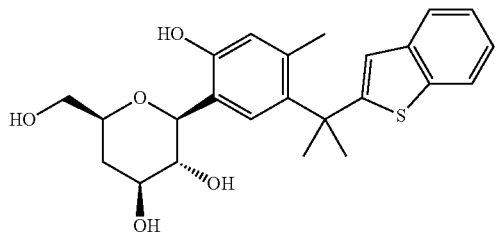 [SMILES: Cc1cc(O)c([C@@H]2O[C@H](CO)C[C@H](O)[C@H]2O)cc1C(C)(C)c1cc2ccccc2s1]

2S,3R,4S,6S)-2-(5-(2-(benzo[b]thiophen-2-yl)propan-2-yl)-2-hydroxy-4-methyl-phenyl)-6-(hydroxymethyl)tetrahydro-2H-pyran-3,4-diol (cmp. 15

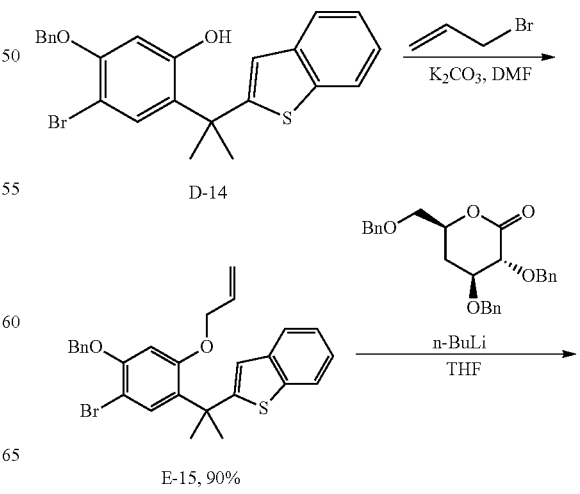

D-14

E-15, 90%

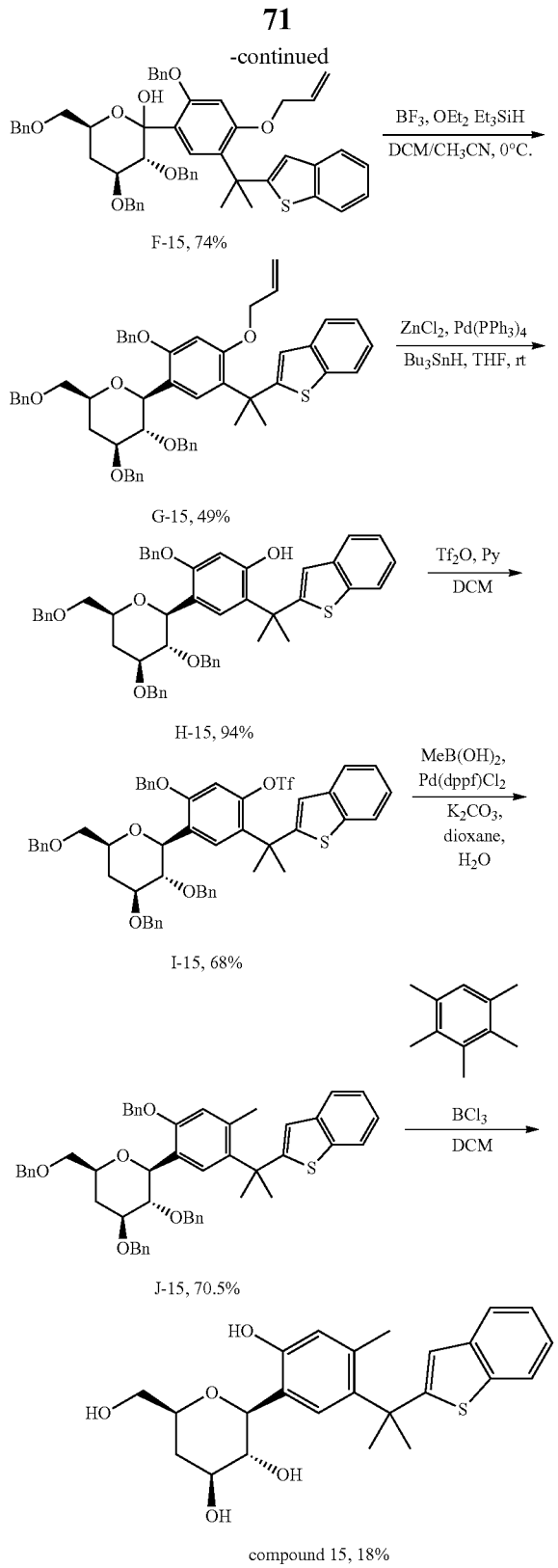

F-15, 74%

G-15, 49%

H-15, 94%

I-15, 68%

J-15, 70.5% compound 15, 18%

To a mixture of D-1 (560 mg, 1.23 mmol) and potassium carbonate (256.5 mg, 1.86 mmol) in N,N-dimethylformamide (10 mL) was added 3-bromoprop-1-ene (223 mg, 1.86 mmol) at room temperature. The reaction was stirred for 5 h at room temperature. Water was added, the mixture was extracted with EtOAc thrice. The combined extracts were washed with $H_2O$, brine and dried over $Na_2SO_4$. Concentration and chromatograph on silica gel (5:1 PE/EtOAc) gave 550 mg of E-15 as yellow oil.

With an inert atmosphere of nitrogen, To the solution of E-15 (550 mg, 1.11 mmol, 1.20 equiv) in tetrahydrofuran (10 mL) was added n-BnLi (2.5M in hexane, 0.4 mL) at −78° C. The mixture was stirred for 30 min at −78° C. To the mixture was added a solution of (3R,4S,6S)-3,4-bis(benzyloxy)-6-[(benzyloxy)methyl]oxan-2-one (412 mg, 0.95 mmol, 1.00 equiv) in tetrahydrofuran (2 mL) dropwise at −78° C. The reaction was stirred for 2 h at −78° C. $NH_4Cl/H_2O$ was added, the mixture was extracted with EtOAc thrice. The combined extracts were washed with $H_2O$, brine and dried over $Na_2SO_4$. Concentration and chromatograph on silica gel (5:1 PE/EtOAc) gave 600 mg (75%) of F-15 as yellow oil.

To a mixture of F-15 (600 mg, 0.71 mmol, 1.0 equiv) in dichloromethane (5 mL) and $CH_3CN$ (5 mL) with $Et_3SiH$ (324 mg, 2.79 mmol, 3.00 equiv) was added $BF_3\cdot OEt_2$ (216 mg, 1.52 mmol, 2.00 equiv) at 0° C. The reaction was stirred for 3 h at 0° C. Water was added, the mixture was extracted with EtOAc thrice. The combined extracts were washed with $H_2O$, brine and dried over $Na_2SO_4$. Concentration and chromatograph on silica gel (5:1 PE/EtOAc) gave 280 mg (49%) of G-15 as yellow oil.

To a mixture of G-15 (280 mg, 0.34 mmol, 1.00 equiv) in tetrahydrofuran (5 mL) was added $ZnCl_2$ (116 mg, 0.85 mmol, 2.50 equiv), the mixture was stirred at room temperature for 30 min. After that, $Pd(PPh_3)_4$ (98 mg, 0.25 equiv) was added, the mixture was stirred at room temperature for 30 min. then, $Bu_3SnH$ (393 mg, 1.36 mmol, 4.00 equiv) was added, the reaction was stirred at room temperature for 1 h. Water was added, the mixture was extracted with dichloromethane thrice. The combined extracts were washed with 1% HCl, brine and dried over $Na_2SO_4$. Concentration and chromatograph on silica gel (5:1 PE/EtOAc) gave 250 mg (94%) of H-15 as yellow oil.

To a mixture of H-15 (250 mg, 0.32 mmol, 1.00 equiv) in dichloromethane (3 mL) with pyridine (50 mg, 0.63 mmol, 2.00 equiv) was added $Tf_2O$ (134 mg, 0.47 mmol, 1.50 equiv) at 0° C., the reaction was stirred at room temperature for 3 h, Water was added, the mixture was extracted with EtOAc thrice. The combined extracts were washed with $H_2O$, brine and dried over $Na_2SO_4$. Concentration and chromatograph on silica gel (5:1 PE/EtOAc) gave 200 mg (68%) of I-16 as yellow oil.

To a mixture of I-16 (150 mg, 0.16 mmol, 1.00 equiv), $MeB(OH)_2$ (15 mg, 0.25 mmol, 1.50 equiv) and potassium carbonate (45 mg, 0.33 mmol, 2.00 equiv) in dioxane (2 mL) and water (0.5 mL) was added $Pd(dppf)Cl_2$ (12 mg, 0.02 mmol, 0.10 equiv) with an inert atmosphere of nitrogen, the reaction was stirred at 100° C. for 4 h, Water was added, the mixture was extracted with EtOAc thrice. The combined extracts were washed with $H_2O$, brine and dried over $Na_2SO_4$. Concentration and chromatograph on silica gel (5:1 PE/EtOAc) gave 120 mg (70.5%) of J-15 as yellow oil.

To a mixture of J-15 (120 mg, 0.15 mmol) and 1,2,3,4,5-pentamethylbenzene (240 mg) in dichloromethane (5 mL) was added $BCl_3$ (1M in DCM, 2.4 mL) at −78° C. with an inert atmosphere. The reaction was stirred for 1 h at −78° C. Methanol was added. Concentration and chromatograph on C18 column (1:2 $MeCN/H_2O$) gave 11.9 mg (18%) of compound 15 as a white solid. $^1H$ NMR (300 MHz, $CD_3OD$) δ 7.70 (d, J=7.8 Hz, 1H), 7.63 (d, J=7.5 Hz, 1H), 7.51 (s, 1H), 7.27-7.21 (m, 2H), 7.00 (s, 1H), 6.59 (s, 1H), 4.54 (d, J=9.6 Hz), 3.80-3.68 (m, 2H), 3.64-3.62 (m, 2H), 3.56 (t, J=9.3 Hz), 2.06 (m, 1H), 1.95 (s, 3H), 1.80 (s, 6H), 1.58 (q, J=11.0 Hz, 1H). MS (ES) m/z: 451 (M+Na+).

Example 16

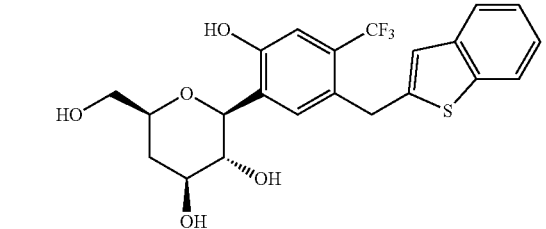 [SMILES: OC[C@@H]1C[C@H](O)[C@@H](O)[C@H](c2cc(Cc3cc4ccccc4s3)c(C(F)(F)F)cc2O)O1]

(2S,3R,4S,6S)-2-(5-(benzo[b]thiophen-2-ylmethyl)-2-hydroxy-4-(trifluoromethyl)-phenyl)-6-(hydroxymethyl)tetrahydro-2H-pyran-3,4-diol (cmp. 16)

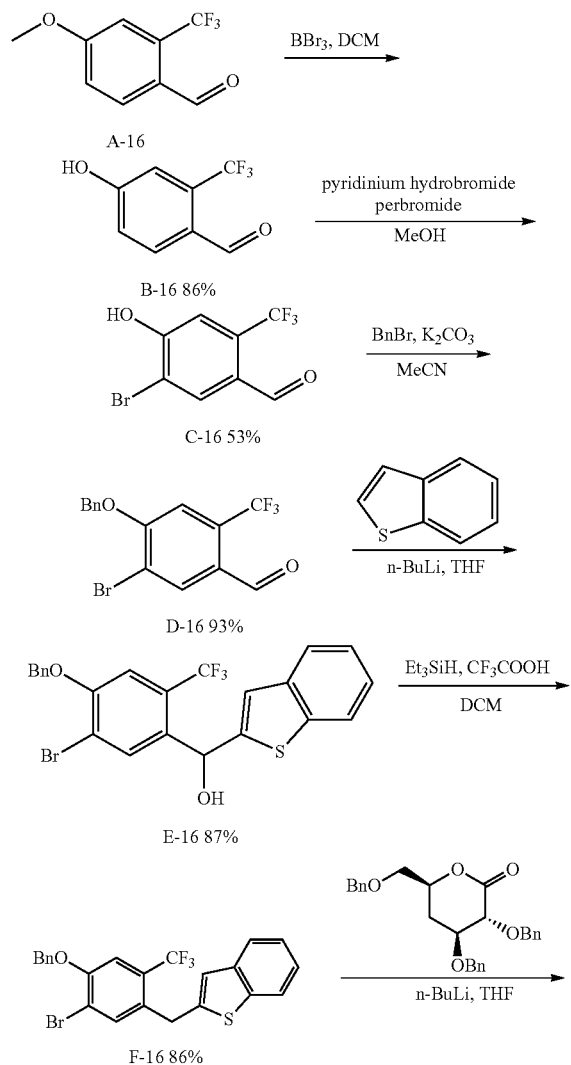

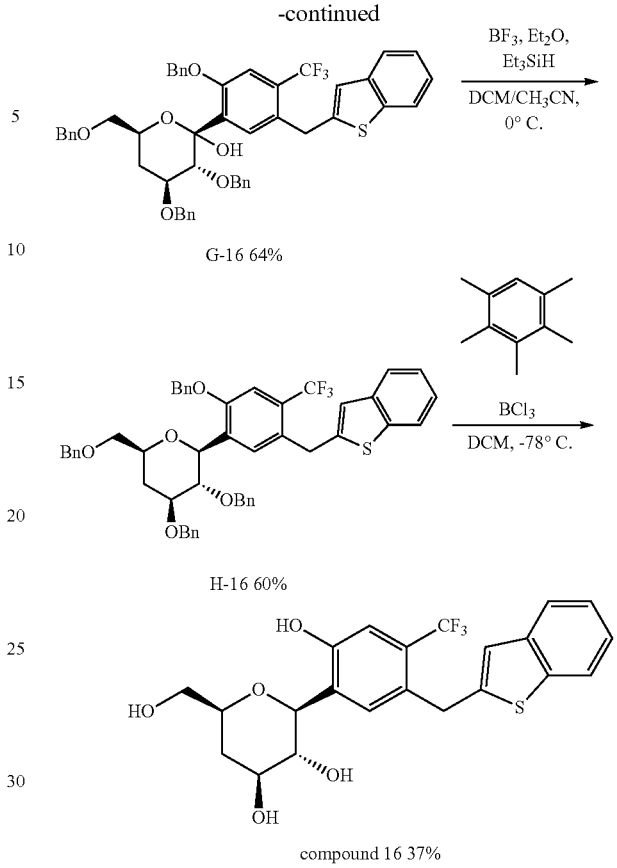

To a mixture of A-16 (2 g, 9.80 mmol) in dichloromethane (30 mL) was added BBr$_3$ (4M in DCM, 2 mL) at −78° C. The reaction was stirred for 5 h at room temperature. Water was added, the mixture was extracted with dichloromethane thrice. The combined extracts were washed with H$_2$O, brine and dried over Na$_2$SO$_4$. Concentration and chromatograph on silica gel (2:1 PE/EtOAc) gave 1.6 g (86%) of B-16 as a white solid.

To a mixture of B-16 (1.6 g, 8.42 mmol) in methanol (30 mL) was added pyridinium hydrobromide perbromide (2.7 g, 8.47 mmol). The reaction was stirred for overnight at room temperature. Water was added, the mixture was extracted with EtOAc thrice. The combined extracts were washed with H$_2$O, brine and dried over Na$_2$SO$_4$. Concentration and chromatograph on silica gel (3:1 hexane/EtOAc) gave 1.2 g (53%) of C-16 as a white solid.

To a mixture of C-16 (800 mg, 2.97 mmol) in MeCN (30 mL) with potassium carbonate (1.23 g, 8.90 mmol) was added BnBr (763 mg, 4.46 mmol). The reaction was stirred for 2 h at 85° C. The solids were filtered out. Concentration and chromatograph on silica gel (5:1 hexane/EtOAc) gave 1 g (94%) of D-16 as a white solid.

To a mixture of 1-benzothiophene (410 mg, 3.06 mmol) in tetrahydrofuran (10 mL) was added n-BuLi (2.5M in hexane, 1.23 mL) dropwise at −78° C. The mixture was stirred for 30 min at −78° C. D-16 (1 g, 2.78 mmol) in tetrahydrofuran (3 mL) was added dropwise at −78° C. The reaction was stirred for 2 h at −78° C. NH$_4$Cl/H$_2$O was added, the mixture was extracted with EtOAc thrice. The combined extracts were washed with H$_2$O, brine and dried over Na$_2$SO$_4$. Concentration and chromatograph on silica gel (3:1 PE/EtOAc) gavel 0.2 g (87%) of E-16 as yellow oil.

To a mixture of E-16 (1.2 g, 2.43 mmol) in dichloromethane (30 mL) with Et$_3$SiH (847 mg, 7.28 mmol) was added CF$_3$COOH (555 mg, 4.87 mmol). The mixture was stirred for 2 h at room temperature. Water was added, the mixture was extracted with dichloromethane thrice. The combined extracts were washed with H₂O, brine and dried over Na₂SO₄. Concentration and chromatograph on silica gel (5:1 PE/EtOAc) gave 1.0 g (86%) of F-16 as a white solid.

To a mixture of F-16 (238 mg, 0.50 mmol) in tetrahydrofuran (5 mL) was added n-BuLi (2.5M in hexane, 0.2 mL) at −78° C. The mixture was stirred for 20 min at −78° C. After that, a solution of (3R,4S,6S)-3,4-bis(benzyloxy)-6-[(benzyloxy)-methyl]-5-methylideneoxan-2-one (222 mg, 0.50 mmol) in tetrahydrofuran (1 mL) was added dropwise at −78° C. The reaction was stirred for 2 h at −78° C. NH₄Cl/H₂O was added, the mixture was extracted with EtOAc thrice. The combined extracts were washed with H₂O, brine and dried over Na₂SO₄. Concentration and chromatograph on silica gel (3:1 PE/EtOAc) gave 270 mg (64%) of G-16 as yellow oil.

A solution of G-16 (200 mg, 0.24 mmol) in dichloromethane (5 mL) with Et₃SiH (55.9 mg, 0.48 mmol) was treated with BF₃.Et₂O (68.4 mg, 0.48 mmol) at 0° C. The reaction was stirred for 1 h at 0° C. Water was added, the mixture was extracted with dichloromethane thrice. The combined extracts were washed with H₂O, brine and dried over Na₂SO₄. Concentration and chromatograph on silica gel (5:1 PE/EtOAc) gave 140 mg (71%) of H-16 as yellow oil.

To a mixture of H-16 (100 mg, 0.12 mmol) in dichloromethane (10 mL) with 1,2,3,4,5-pentamethylbenzene (100 mg, 0.67 mmol) was added BCl₃ (1M in DCM, 0.2 mL) at −78° C. The mixture was stirred for 1 h at −78° C. Methanol was added. Concentration and chromatograph on C18 column (1:1 MeCN/H₂O) gave 20 mg (35%) of compound 16 as a white solid. 1HNMR (300 MHz, CD₃OD) δ 7.74 (d, J=7.8 Hz, 1H), 7.66 (d, J=7.8 Hz, 1H), 7.51 (s, 2H), 7.32-7.21 (m, 2H), 7.15 (s, 1H), 6.98 (s, 1H), 4.57 (d, J=9.6 Hz, 1H), 4.38 (s, 2H), 3.72-3.63 (m, 2H), 3.58 (d, J=4.8 Hz, 2H), 3.38 (t, J=9.0 Hz, 1H), 2.04-2.00 (m, 1H), 1.53 (q, J=12.6 Hz, 1H). MS (ES) m/z: 477 (M+Na⁺).

Example 17

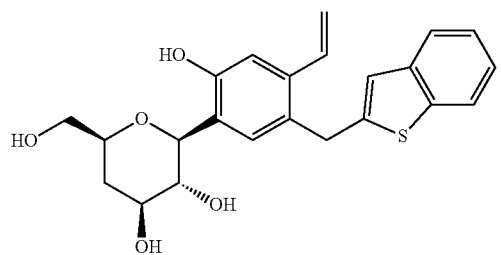 [SMILES: C=Cc1cc(O)c([C@@H]2O[C@H](CO)C[C@H](O)[C@H]2O)cc1Cc1cc2ccccc2s1]

2S,3R,4S,6S)-2-(5-(benzo[b]thiophen-2-ylmethyl)-2-hydroxy-4-vinylphenyl)-6-(hydroxyl-methyl)tetrahydro-2H-pyran-3,4-diol (cmp. 17

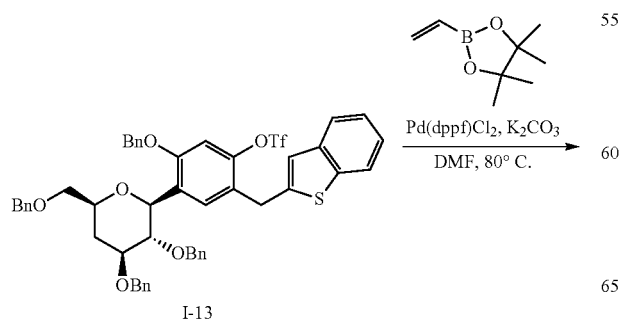

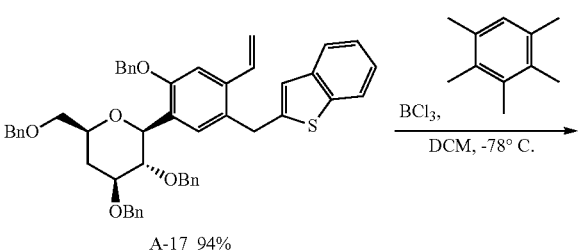

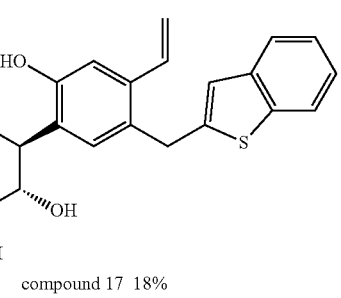

compound 17 18%

To a mixture of I-13 (270 mg, 0.30 mmol) in N,N-dimethylformamide (10 mL) was added 2-ethenyl-4,4,5,5-tetramethyl-1,3,2-dioxaborolane (93 mg, 0.60 mmol), potassium carbonate (126 mg, 0.91 mmol), Pd(dppf)Cl₂ (24 mg, 0.03 mmol). The reaction was stirred for 3 h at 80° C. Water was added, the mixture was extracted with EtOAc thrice. The combined extracts were washed with H₂O, brine and dried over Na₂SO₄. Concentration and chromatograph on silica gel (5:1 PE/EtOAc) gave 220 mg (94%) of A-17 as yellow oil.

To a mixture of A-17 (120 mg, 0.15 mmol) in dichloromethane (10 mL) with 1,2,3,4,5-pentamethylbenzene (240 mg, 1.62 mmol) was added BCl₃ (2.4 mL, 2.4 mmol) at −78° C. The reaction was stirred for 1 h at −78° C. Methanol was added. Concentration and chromatograph on C18 column (1:2 MeCN/H₂O) gave 11 mg (18%) of compound 17 as a white solid. 1H NMR (300 MHz, CD₃OD) δ 7.66 (d, J=7.2 Hz, 1H), 7.56 (d, J=7.2 Hz, 1H), 7.26-7.15 (m, 3H), 7.02 (s, 1H), 6.97-6.84 (m, 3H), 5.59 (dd, J=17.4, 1.2 Hz, 1H), 5.18 (d, J=10.8 Hz, 1H), 4.45 (d, J=9.6 Hz, 1H), 4.19 (s, 1H), 3.71-3.63 (m, 2H), 3.57-3.55 (m, 2H), 3.42 (t, J=9.3 Hz, 1H), 1.98 (dd, J=12.6, 3.6 Hz, 1H), 1.51 (q, J=12.6 Hz, 1H). MS (ES) m/z: 435 (M+Na⁺).

Example 18

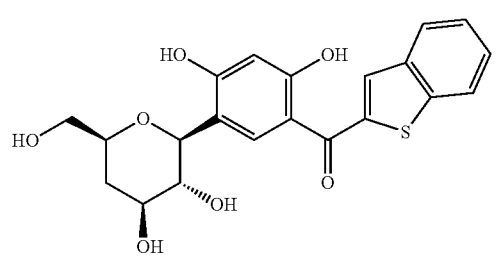 [SMILES: O=C(c1cc2ccccc2s1)c1cc([C@@H]2O[C@H](CO)C[C@H](O)[C@H]2O)c(O)cc1O]

77 benzo[b]thiophen-2-yl(5-((2S,3R,4S,6S)-3,4-dihydroxy-6-(hydroxymethyl)tetrahydro-2H-pyran-2-yl)-2,4-dihydroxyphenyl)methanone (cmp. 18)

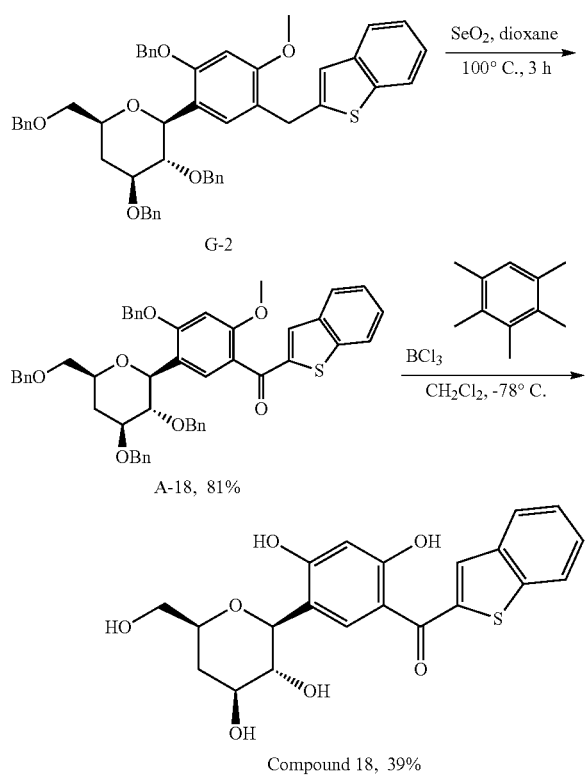

To a mixture of G-2 (613 mg, 0.79 mmol, 1.00 equiv) in dioxane (100 mL) was added SeO$_2$ (177 mg, 1.60 mmol, 2.02 equiv). The reaction was stirred for 3 h at 100° C. The solids were filtered out. Concentration and chromatograph on silica gel (5:1, PE/EA) gave 505.5 mg (81%) of A-18 as yellow oil. MS (ES) m/z: 793 (M+H$_2$O)$^+$.

With an inert atmosphere of nitrogen, To a mixture of A-18 (300 mg, 0.38 mmol) in dichloromethane (10 mL) with 1,2,3,4,5-pentamethylbenzene (600 mg) was added BCl$_3$ (1M in DCM, 6 mL) at −78° C. The reaction was stirred for 1 h at −78° C. The reaction was then quenched by the addition of 5 mL of methanol. Concentration and chromatograph on C18 (10%-50% CH$_3$CN/H$_2$O) gave 61.6 mg (39%) of compound 18 as a white solid. $^1$H NMR (300 MHz, CD$_3$OD) δ 8.11 (s, 2H), 8.01 (t, J=8.0 Hz, 2H), 7.54-7.47 (m, 2H), 6.46 (s, 1H), 4.55 (d, J=9.6 Hz, 1H), 3.78-3.70 (m, 2H), 3.59 (d, J=4.8 Hz, 2H), 3.48 (t, J=9.2 Hz, 1H), 2.06-2.01 (m, 1H), 1.51 (q, J=11.2 Hz, 1H). MS (ES) m/z: 417 (M+H$^+$).

Example 19

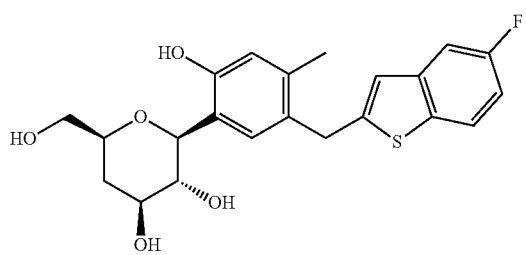 [SMILES: Cc1cc(O)c([C@@H]2O[C@H](CO)C[C@H](O)[C@H]2O)cc1Cc1cc2cc(F)ccc2s1]

78

2S,3R,4S,6S)-2-(5-((5-fluorobenzo[b]thiophen-2-yl)methyl)-2-hydroxy-4-methyl-phenyl)-6-(hydroxymethyl)tetrahydro-2H-pyran-3,4-diol (cmp. 19

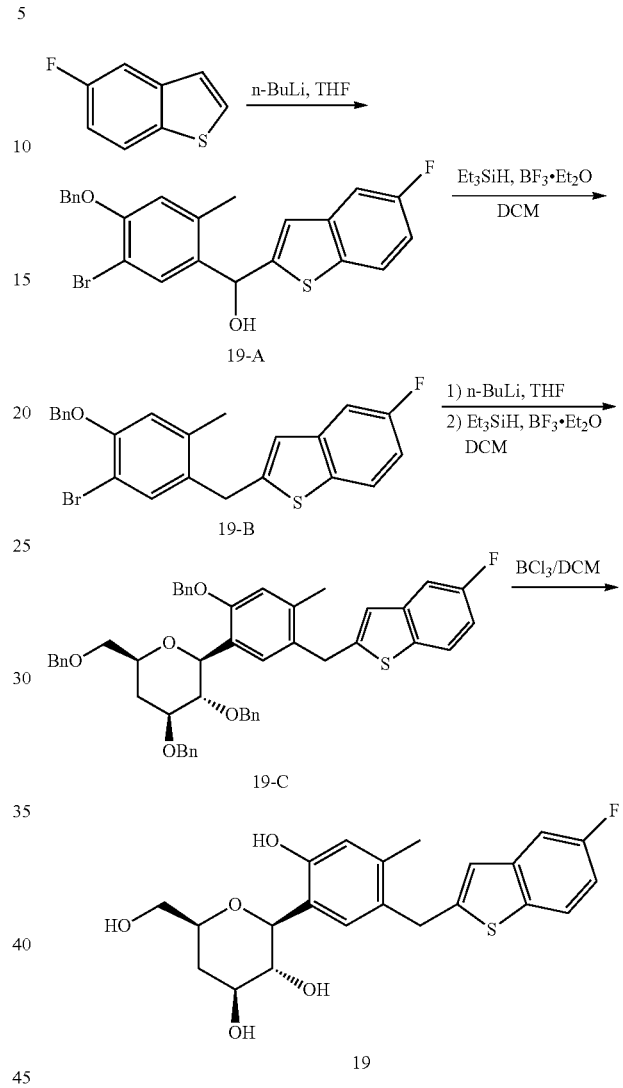

To 5-fluoro-benzo[b]thiophene (697 mg, 4.58 mmol) in 3.5 ml of anhydrous THF at −78° C. under argon was added n-BuLi (2.86 ml, 1.6 M in hexanes) and the resulting mixture was stirred at that temperature for 1 h, then 4-(benzyloxy)-5-bromo-2-methylbenzaldehyde (1.4 g, 4.58 mmol) in 2.5 ml of THF was added dropwise over 5 mins. The reaction mixture was stirred at −78° C. for 1 h, was left in −30° C. freezer overnight. It was then quenched with aq. NH$_4$Cl solution, extracted with EtOAc three times. The combined organic layer was washed with brine, dried with Na$_2$SO$_4$ and the solvent was evaporated. The residue was purified by flash column chromatography on silica gel (40 g column, EtOAc/heptane: 0>>>10%) to yield 1.99 g (95%) of 19-A as a white solid. $^1$H NMR (CDCl$_3$) δ 7.78 (s, 1H), 7.70 (dd, J=9.1, 5.1 Hz, 1H), 7.46-7.51 (2H), 7.40 (m, 2H), 7.31-7.36 (2H), 7.06 (td, J=8.6, 2.0 Hz, 1H), 7.01 (s, 1H), 6.77 (s, 1H), 6.17 (d, J=4.0 Hz, 1H), 5.16 (s, 2H), 2.40 (d, J=4.0 Hz, 1H), 2.27 (s, 3H). MS (ES) 480.0 (M+Na$^+$).

A 250 ml round bottom flask was charged with 19-A (1.99 g, 4.35 mmol) and 40 ml of DCM was added. The mixture was degassed and put under argon. To the mixture was added triethylsilane (1.74 ml, 10.90 mmol) at 0° C., followed by dropwise addition of BF$_3$.Et$_2$O (0.82 ml, 6.53 mmol). The reaction mixture was kept stirring at 0° C. for 1 h. Saturated aqueous NaHCO$_3$ was added and the mixture was extracted with DCM. The organic layer was washed with brine, dried with Na$_2$SO$_4$, and evaporated to give a colorless oil, which was purified by flash column chromatography on silica gel (80 g Combiflash column, EtOAc/heptane: 0>>>5%) to afford 1.82 g (94.7%) of 19-B as a white solid. $^1$H NMR (CDCl$_3$) δ 7.63 (dd, J=8.59, 4.55 Hz, 1H), 7.46-7.51 (2H), 7.37-7.43 (3H), 7.33 (m, 1H), 7.29 (dd, J=9.60, 2.53 Hz, 1H), 7.00 (td, J=8.59, 2.53 Hz, 1H), 6.83 (s, 1H), 6.79 (s, 1H), 5.14 (s, 2H), 4.10 (s, 2H), 2.24 (s, 3H). MS (ES) 463.1 (M+Na$^+$).

Compound 19-B (417 mg, 0.95 mmol) was dissolved in 3 ml of anhydrous THF, cooled to −78° C. in an acetone-dry ice bath. The solution was degassed and put under argon. To the above solution was added n-BuLi (0.59 ml, 1.6 M in hexanes) and the mixture was stirred at −78° C. for 1 h. Lactone (408.6 mg, 0.95 mmol) in 2 ml of anhydrous THF was added dropwise and the resulting mixture was stirred at that temperature for 4 h, quenched with aq. NH$_4$Cl, extracted with EtOAc three times. The organic extracts were dried with Na$_2$SO$_4$ and the solvent was evaporated and the residue was dried in vacuo for 2 h, then dissolved in 15 ml of anhydrous DCM, cooled to −78° C., degassed and re-filled with argon. To the solution was added 0.64 ml of triethylsilane (3.97 mmol) and the mixture was stirred for 3 min, then 0.24 ml of BF$_3$.Et$_2$O was added and the mixture was stirred at −78° C. for 5 min, warmed to 0° C. (ice-bath) and stirred at 0° C. for 2 h. It was quenched with saturated aq. NaHCO$_3$ solution, extracted with DCM three times. The extracts were dried with Na$_2$SO$_4$ and the drying agent was filtered off. The solvent was evaporated. The residue was purified by flash column chromatography on silica gel (40 g, EtOAc/heptane: 0>>>10%>>>15%) to yield 350 mg (47.6% over two steps) of 19-C as a colorless gel (white foam after dried in vacuo). $^1$H NMR (CDCl$_3$) δ 7.52 (dd, J=8.59, 4.55 Hz, 1H), 7.36-7.41 (2H), 7.23-7.35 (14H), 7.10-7.21 (4H), 6.96 (m, 2H), 6.93 (dd, J=9.09, 2.53 Hz, 1H), 6.75 (s, 2H), 5.01 (s, 2H), 4.78 (br, 1H), 4.68 (q, J=11.62 Hz, 2H), 4.58 (d, J=10.61 Hz, 1H), 4.54 (s, 2H), 4.07-4.21 (3H), 3.71-3.81 (m, 3H), 3.61 (dd, J=10.11, 5.05 Hz, 1H), 3.46 (dd, J=10.11, 5.56 Hz, 1H), 2.30 (m, 1H), 2.25 (s, 3H), 1.59 (q, J=11.62 Hz, 1H). MS (ES) 801.15 (M+Na$^+$).

To a mixture of 19-C (131 mg, 0.17 mmol) and pentamethylbenzene (249 mg, 1.7 mmol) in DCM (5 ml) was added BCl$_3$ (1 ml, 1M in DCM) at −78° C. under argon. The resulting brownish mixture was stirred at that temperature for 1.5 h, quenched with MeOH (1 ml). After stirring for 10 min, the volatiles were removed under reduced pressure and the residue was purified by flash column chromatography on silica gel (12 g column, EtOAc/heptanes: 0>>>100%, then 5% MeOH/EtOAc) to yield 58.1 mg (82%) of 19 as a white solid. $^1$H NMR (CDCl$_3$) δ 7.67 (s, 1H), 7.56 (dd, J=9.09, 5.05 Hz, 1H), 7.21 (dd, J=9.60, 2.53 Hz, 1H), 7.01 (s, 1H), 6.94 (td, J=9.60, 2.53 Hz, 1H), 6.78 (s, 1H), 6.69 (s, 1H), 4.22 (d, J=9.60 Hz, 1H), 4.04 (s, 2H), 3.43-3.71 (m, 6H), 3.33 (d, J=3.03 Hz, 1H), 2.80 (br, 1H), 2.17 (s, 3H), 1.89 (dd, J=12.13, 4.55 Hz, 1H), 1.58 (q, J=11.62 Hz, 1H). MS (ES) 441.0 (M+Na$^+$).

Example 20

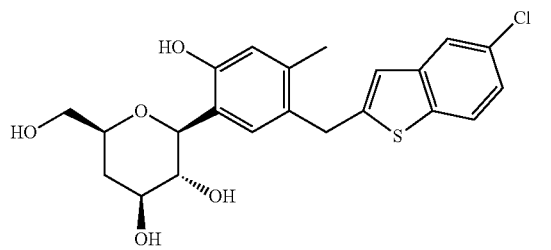 [SMILES: Cc1cc(O)c([C@@H]2O[C@H](CO)C[C@H](O)[C@H]2O)cc1Cc1cc2cc(Cl)ccc2s1]

2S,3R,4S,6S)-2-(5-((5-chlorobenzo[b]thiophen-2-yl) methyl)-2-hydroxy-4-methyl-phenyl)-6-(hydroxymethyl)tetrahydro-2H-pyran-3,4-diol (cmp. 20

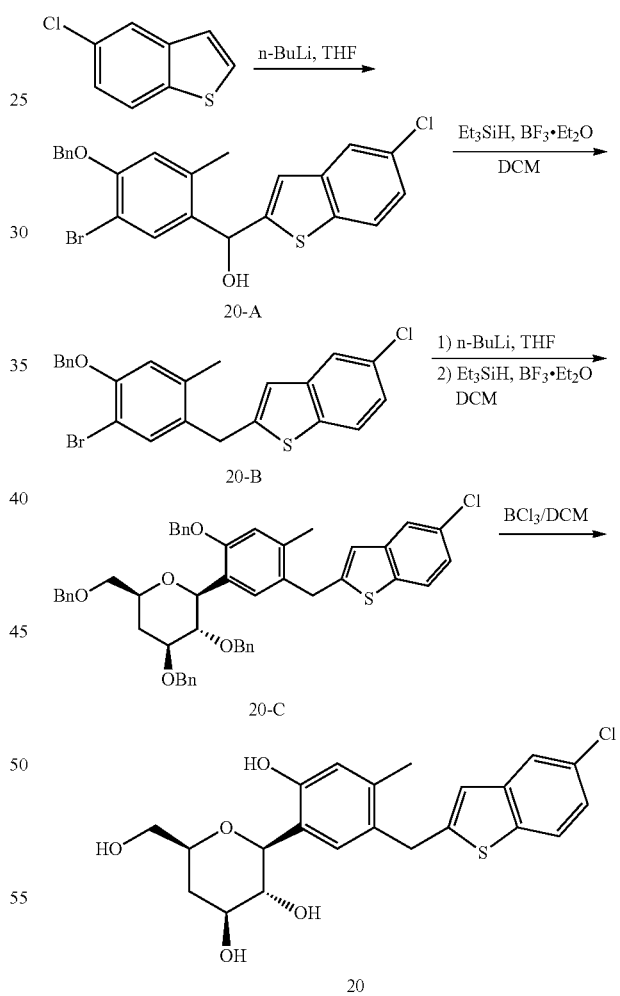

To 5-chloro-benzo[b]thiophene (702 mg, 4.16 mmol) in 3.5 ml of anhydrous THF at −78° C. under argon was added n-BuLi (2.6 ml, 1.6 M in hexanes) and the resulting mixture was stirred at that temperature for 1 h, then 4-(benzyloxy)-5-bromo-2-methylbenzaldehyde (1.27 g, 4.16 mmol) in 2.5 ml of THF was added dropwise over 5 mins. The reaction mixture was stirred at −78° C. for 1 h, then was left in −30° C.

freezer overnight. It was then quenched with aq. NH₄Cl solution, extracted with EtOAc three times. The combined organic layer was washed with brine, dried with Na₂SO₄ and the solvent was evaporated. The residue was purified by flash column chromatography on silica gel (80 g column, EtOAc/heptane: 0>>>10%) to yield 1.77 g (89.7%) of 20-A as a white solid. $^1$H NMR (CDCl₃) δ 7.75 (s, 1H), 7.65 (d, J=8.59 Hz, 1H), 7.61 (d, J=2.02 Hz, 1H), 7.45-7.51 (2H), 7.36-7.43 (2H), 7.32 (m, 1H), 7.24 (dd, J=8.08, 2.02 Hz, 1H), 6.95 (s, 1H), 6.73 (s, 1H), 6.11 (d, J=3.54 Hz, 1H), 5.13 (s, 2H), 2.60 (d, J=4.04 Hz, 1H), 2.23 (s, 3H). MS (ES) 495.0 (M+Na⁺).

A 250 ml round bottom flask was charged with 20-A (1.77 g, 3.74 mmol) and 40 ml of DCM was added. The mixture was degassed and put under argon. To the mixture was added triethylsilane (1.49 ml, 9.34 mmol) at 0° C., followed by dropwise addition of BF₃.Et₂O (0.71 ml, 5.60 mmol). The reaction mixture was kept stirring at 0° C. for 1 h. Saturated aqueous NaHCO₃ was added and the mixture was extracted with DCM. The organic layer was washed with brine, dried with Na₂SO₄, and evaporated to give a colorless oil, which was purified by flash column chromatography on silica gel (80 g Combiflash column, EtOAc/heptane: 0>>>5%) to afford 1.56 g (91.2%) of 20-B as a white solid. $^1$H NMR (CDCl₃) δ 7.63 (d, J=8.59 Hz, 1H), 7.60 (d, J=2.02 Hz, 1H), 7.46-7.52 (2H), 7.37-7.43 (3H), 7.33 (t, J=7.07 Hz, 1H), 7.21 (dd, J=8.59, 2.02 Hz, 1H), 6.82 (s, 1H), 6.79 (s, 1H), 5.14 (s, 2H), 4.10 (s, 2H), 2.24 (s, 3H). MS (ES) 480.90 (M+Na⁺).

Compound 20-B (363.5 mg, 0.79 mmol) was dissolved in 3 ml of anhydrous THF, cooled to −78° C. in an acetone-dry ice bath. The solution was degassed and put under argon. To the above solution was added n-BuLi (0.50 ml, 1.6 M in hexanes) and the mixture was stirred at −78° C. for 1 h. Lactone (343.4 mg, 0.79 mmol) in 2 ml of anhydrous THF was added dropwise and the resulting mixture was stirred at that temperature for 4 h, quenched with aq. NH₄Cl, extracted with EtOAc three times. The organic extracts were dried with Na₂SO₄ and the solvent was evaporated and the residue was dried in vacuo for 2 h, then dissolved in 8 ml of anhydrous ACN, cooled to 0° C., degassed and re-filled with argon. To the solution was added 0.38 ml of triethylsilane (2.38 mmol) and the mixture was stirred for 3 min, then 0.14 ml of BF₃.Et₂O was added and the mixture was stirred at 0° C. for 2 h. It was quenched with saturated aq. NaHCO₃ solution, extracted with DCM three times. The extracts were dried with Na₂SO₄ and the drying agent was filtered off. The solvent was evaporated. The residue was purified by flash column chromatography on silica gel (40 g, EtOAc/heptane: 0>>>10%>>>15%) to yield 361.6 mg (57.3% over two steps) of 20-C as a white foam. $^1$H NMR (CDCl₃) δ 7.51 (d, J=8.59 Hz, 1H), 7.36-7.43 (3H), 7.22-7.35 (14H), 7.11-7.20 (4H), 6.93-6.99 (2H), 6.75 (s, 1H), 6.73 (s, 1H), 5.01 (s, 2H), 4.78 (br, 1H), 4.68 (q, J=11.62 Hz, 2H), 4.58 (d, J=11.12 Hz, 1H), 4.54 (s, 2H), 4.06-4.21 (3H), 3.75 (m, 2H), 3.68 (br, 1H), 3.61 (dd, J=10.11, 5.05 Hz, 1H), 3.46 (dd, J=9.60, 5.05 Hz, 1H), 2.29 (m, 1H), 2.25 (s, 3H), 1.59 (q, J=11.62 Hz, 1H). MS (ES) 817.3 (M+Na⁺).

A 50 ml round bottom flask was charged with 20-C (362 mg, 0.46 mmol) and pentamethylbenzene (674 mg, 4.5 mmol). To which was added 5 ml of DCM and the mixture was cooled to −78° C. BCl₃ (2.7 ml, 1M in DCM) was added to the above mixture under argon and the resulting brown mixture was stirred at −78° C. for 1 h, quenched with 1 ml of MeOH. The solvents were removed under reduced pressure and the residue was purified by flash column chromatography on silica gel (12 g column, EtOAc/heptanes; 0>>>100%) to yield 168 mg (85%) of 20 as a light orange solid. $^1$H NMR (CD₃OD) δ 7.69 (d, J=8.59 Hz, 1H), 7.62 (d, J=1.52 Hz, 1H), 7.23 (s, 1H), 7.19 (dd, J=8.08, 1.52 Hz, 1H), 6.89 (s, 1H), 6.67 (s, 1H), 4.49 (d, J=9.60 Hz, 1H), 4.15 (s, 2H), 3.64-3.75 (m, 2H), 3.58 (d, J=4.04 Hz, 2H), 3.45 (t, J=9.09 Hz, 1H), 2.20 (s, 3H), 1.97-2.04 (m, 1H), 1.53 (q, J=11.62 Hz, 1H). MS (ES) 457.1 (M+Na⁺).

Example 21

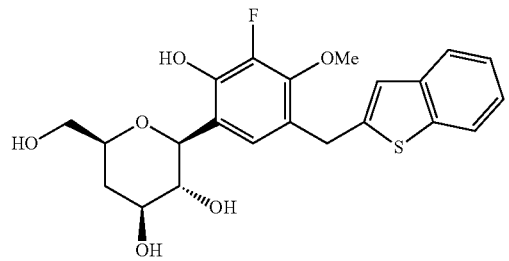 [SMILES: COc1c(Cc2cc3ccccc3s2)cc([C@@H]2O[C@H](CO)C[C@H](O)[C@H]2O)c(O)c1F]

2S,3R,4S,6S)-2-(5-(benzo[b]thiophen-2-ylmethyl)-3-fluoro-2-hydroxy-4-methoxy-phenyl)-6-(hydroxymethyl)tetrahydro-2H-pyran-3,4-diol (cmp. 21

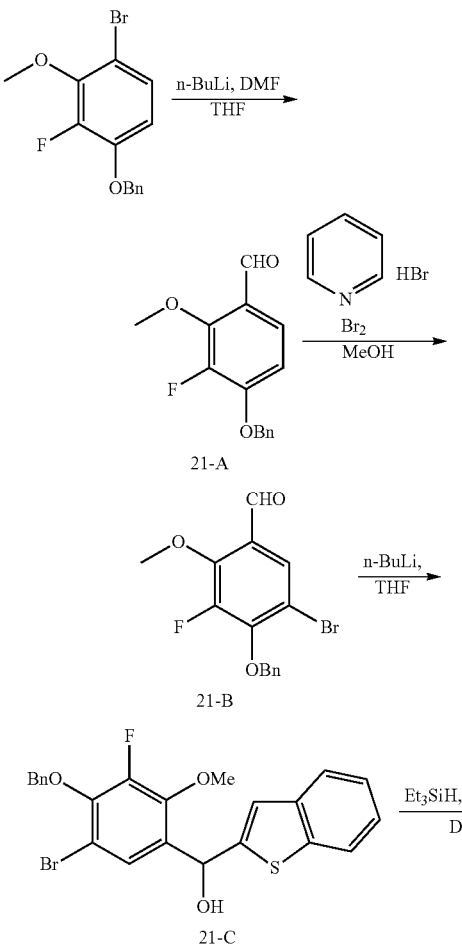

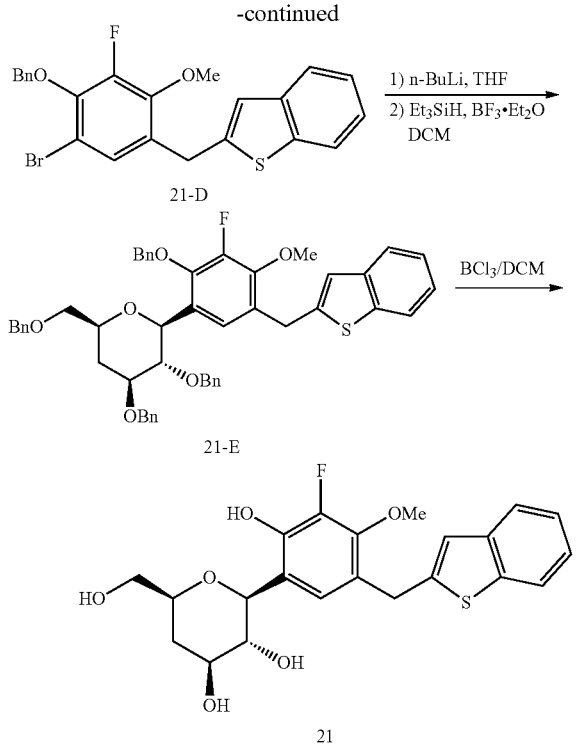

To 1-benzyloxy-4-bromo-2-fluoro-3-methoxybenzene (2 g, 6.43 mmol) in 20 ml of anhydrous THF at −78° C. was added n-BuLi (3.09 ml, 2.5 M in hexanes) under argon and the resulting mixture was stirred at −78° C. for 40 min. Thereto was added 1.5 ml of anhydrous DMF and the resulting mixture was warmed to room temperature over 30 min, stirred at room temperature for 2 h. It was quenched with 1N HCl, extracted with EtOAc three times, dried over $Na_2SO_4$, filtered and the solvent was removed under reduced pressure. The crude residue was purified by flash column chromatography on silica gel (150 g column, EtOAc/heptanes; 0>>>10%) to yield 349.3 mg (20.9%) of 21-A as a white solid. $^1$H NMR ($CDCl_3$) δ 10.23 (s, 1H), 7.56 (d, J=8.59, 2.02 Hz, 1H), 7.32-7.46 (5H), 6.79 (dd, J=8.59, 7.07 Hz, 1H), 5.19 (s, 2H), 4.10 (d, J=3.03 Hz, 3H). MS (ES) 289.2 (M+Na$^+$).

To a mixture of 21-A (352 mg, 1.35 mmol) in MeOH (10 ml) was added pyridinium bromide perbromide (721 mg, 2.03 mmol) and the resulting mixture was stirred at room temperature for 16 h. The organic solvent was removed under reduced pressure and the residue was purified by flash column chromatography on silica gel (40 g, EtOAc/heptanes; 0>>>5%) to yield 420 mg (91.6%) of 21-B as a pale white solid. $^1$H NMR ($CDCl_3$) δ 10.20 (s, 1H), 7.80 (d, J=2.53 Hz, 1H), 7.47-7.52 (2H), 7.32-7.41 (3H), 5.27 (s, 2H), 4.06 (d, J=2.53 Hz, 3H). MS (ES) 352.9 (M+2+Na$^+$).

To a solution of benzo[b]thiophene (177.1 mg, 1.32 mmol) in THF (4 mL) was added n-BuLi (0.53 mL) at −78° C. and the mixture was kept at −78° C. for 60 minutes. Compound 21-B (447.5 mg, 1.32 mmol) in THF (4 mL) was added to the above mixture and the reaction mixture was stirred at −78° C. for 1 hour and slowly warmed up to room temperature. HCl (1 N, 50 mL) was added and THF was removed under reduced pressure and the content was extracted with EtOAc three times. The organic layer was washed with brine, dried with $Na_2SO_4$ and the solution was passed into $SiO_2$ bed. EtOAc was evaporated to dryness and the residue purified by flash column chromatography on silica gel (40 g, EtOAc/heptane: 0>>>15%) to give 200 mg (32%) of 21-C as a white solid. $^1$H NMR ($CDCl_3$) δ 7.79 (dd, J=7.58, 1.01 Hz, 1H), 7.07 (dd, J=6.57, 1.52 Hz, 1H), 7.50-7.54 (2H), 7.47 (d, J=2.53 Hz, 1H), 7.34-7.42 (3H), 7.32 (dd, J=7.07, 1.52 Hz, 1H), 7.29 (dd, J=7.58, 1.52 Hz, 1H), 7.09 (s, 1H), 6.20 (d, J=6.06 Hz, 1H), 5.13 (s, 2H), 3.79 (d, J=2.02 Hz, 3H), 3.04 (d, J=6.06 Hz, 1H). MS (ES) 457 (MH$^+$-18).

$BF_3.OEt_2$ (0.35 ml, 2.8 mmol) was added to a solution of 21-C (870 mg, 1.84 mmol) and $Et_3SiH$ (0.73 ml, 4.6 mmol) in DCM (45 ml) under argon atmosphere at 0° C. and the mixture became dark and was stirred at that temperature for 30 min. TLC analysis of the reaction mixture indicated that the starting material 21-C is completely consumed. The reaction mixture was kept stirring for another 15 min (total 45 mins). Saturated aqueous $NaHCO_3$ was added and the mixture was extracted with DCM. The organic layer was washed with brine, dried with $Na_2SO_4$, and evaporated to give a brown oil, which was purified by flash column chromatography on silica gel (40 g Combiflash column, EtOAc/heptane: 0>>>5%) to afford 789.5 mg (93.9%) of 21-D as a light yellow oil. $^1$H NMR ($CDCl_3$) δ 7.74 (dd, J=7.07, 1.01 Hz, 1H), 7.67 (dd, J=7.07, 1.01 Hz, 1H), 7.50-7.54 (2H), 7.30-7.41 (3H), 7.28 (dd, J=5.56, 1.52 Hz, 1H), 7.25 (dd, J=7.07, 1.52 Hz, 1H), 7.19 (d, J=2.02 Hz, 1H), 7.00 (s, 1H), 5.11 (s, 2H), 4.15 (s, 2H), 3.88 (d, J=2.02 Hz, 3H).

Compound 21-D (315.8 mg, 0.69 mmol) was dissolved in 3 ml of anhydrous THF, cooled to −78° C. in an acetone-dry ice bath. The solution was degassed and put under argon. To the above solution was added n-BuLi (0.43 ml, 1.6 M in hexanes) dropwise and the mixture was stirred at −78° C. under argon. After 1 h, lactone (299 mg, 0.69 mmol) in 3 ml of anhydrous THF was added and the resulting mixture was stirred at that temperature for 2 h, quenched with aq. NH4Cl, extracted with EtOAc three times. The organic extracts were dried with $Na_2SO_4$ and the solvent was evaporated. The crude material was dissolved in 10 ml of DCM, cooled to −78° C., degassed and re-filled with argon. To the solution was added 0.46 ml of triethylsilane and the mixture was stirred for 3 min, then 0.17 ml of $BF_3.Et_2O$ was added and the mixture was stirred at −78° C. for 60 min, then warmed to 0° C. (ice-bath) and stirred at 0° C. for 1 h. It was quenched with saturated aq. $NaHCO_3$ solution, extracted with DCM three times. The extracts were dried with $Na_2SO_4$ and the drying agent was filtered off. The solvent was evaporated. The residue was purified by flash column chromatography on silica gel (40 g, EtOAc/heptane: 0>>>10%) to yield 92 mg (16.8%) of 21-E. MS (ES) 812.2 (M+18).

At −78° C. a 1M solution of $BCl_3$ in DCM was added dropwise to a solution of 21-E (85 mg, 0.11 mmol) and pentamethylbenzene (158.5 mg, 1.07 mmol) in DCM (5 ml). After the addition, the reaction mixture turned into brownish red and was stirred at −78° C. for 1.5 h. MeOH (1 ml) was added and the resulting solution was stirred for another 10 min, then the mixture was treated with sat. $NaHCO_3$ solution (2 ml). The mixture was concentrated and the residue was partitioned between EtOAc and water. The organic layer was separated and dried with $Na_2SO_4$, the drying agent was filtered off and the solvent was concentrated under reduced pressure. The residue was purified by preparative TLC to yield 40 mg (86.1%) of 21 as a white solid. $^1$H NMR ($CD_3OD$) δ 7.71 (d, J=8.08 Hz, 1H), 7.64 (d, J=7.58 Hz, 1H), 7.26 (td, J=7.07, 1.01 Hz, 1H), 7.21 (td, J=7.58, 1.01 Hz, 1H), 7.08 (d, J=2.02 Hz, 1H), 7.01 (s, 1H), 4.51 (d, J=9.60 Hz, 1H), 4.17 (d, J=15.66 Hz, 1H), 4.12 (d, J=15.16 Hz, 1H), 3.83 (d, J=2.02 Hz, 3H), 3.63-3.74 (m, 2H), 3.56 (dd, J=5.05, 1.01 Hz, 2H), 3.40 (t, J=9.09 Hz, 1H), 2.00 (ddd, J=12.63, 5.05, 1.52 Hz, 1H), 1.51 (q, J=11.62 Hz, 1H). MS (ES) 457.05 (M+Na+).

Example 22

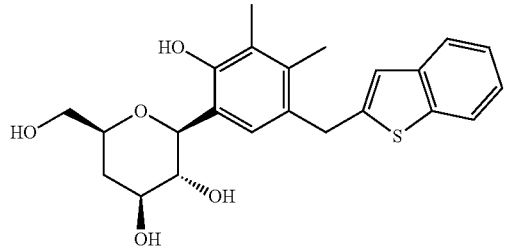 [SMILES: Cc1c(Cc2cc3ccccc3s2)cc([C@@H]2O[C@H](CO)C[C@H](O)[C@H]2O)c(O)c1C]

2S,3R,4S,6S)-2-(5-(benzo[b]thiophen-2-ylmethyl)-2-hydroxy-3,4-dimethylphenyl)-6-(hydroxymethyl)tetrahydro-2H-pyran-3,4-diol (cmp. 22

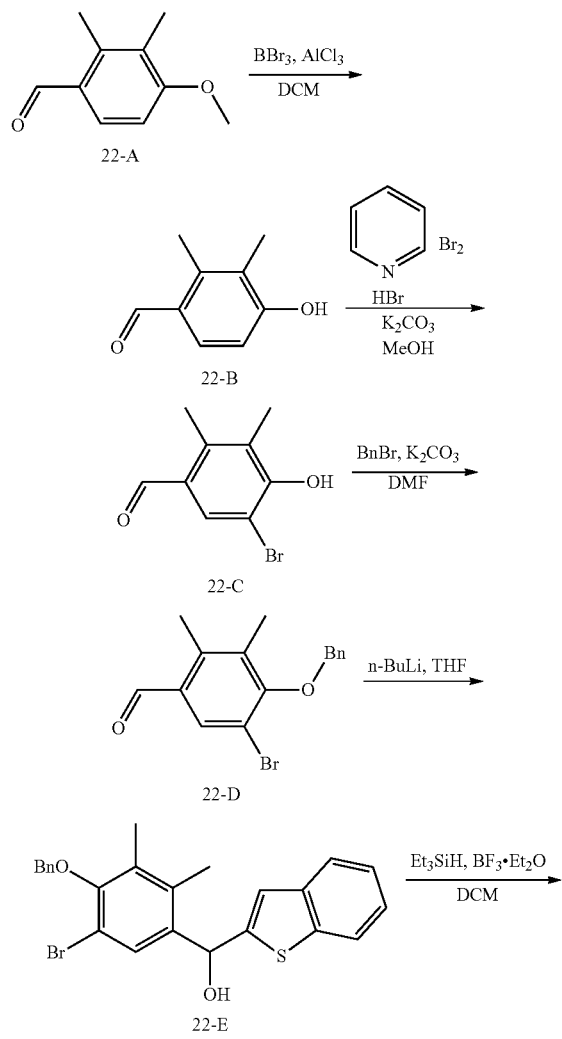

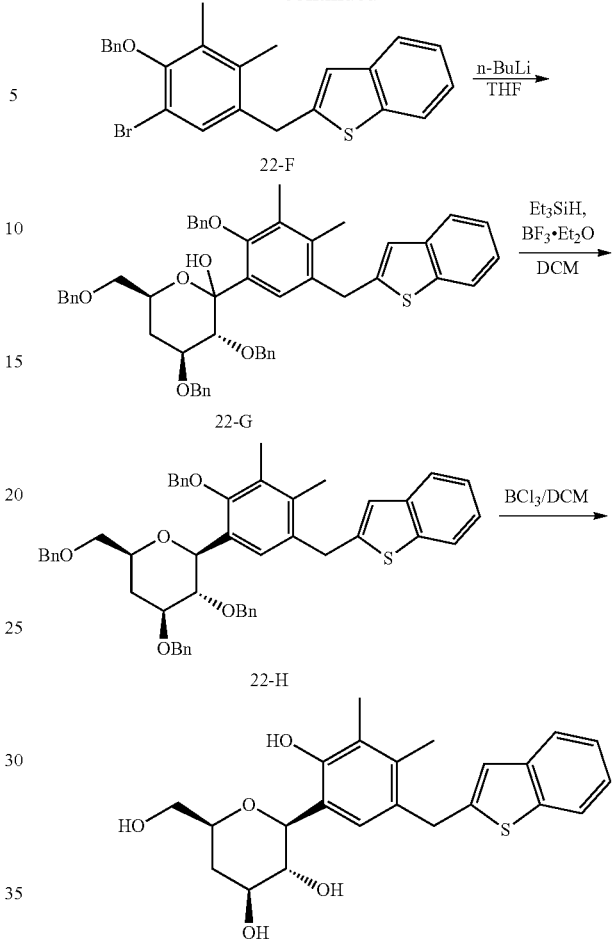

To 2,3-dimethyl-4-methoxybenzaldehyde (9.91 g, 59.7 mmol) in 100 ml of dry DCM at −78° C. under argon was added BBr$_3$ (1 M, 62.7 ml) dropwise and the mixture was stirred at that temperature for 2 h. Then one equivalent of AlCl$_3$ (7.97 g, 59.7 mmol) was added at 0° C. and the resulting mixture was stirred at room temperature for 4 h, the reaction mixture was poured into ice and the organic solvent was evaporated. It was then extracted with EtOAc three times. The combined organic layer was dried with Na$_2$SO$_4$ and the drying agent was filtered off. The solvent was evaporated and the residue was washed with DCM three times to yield 5.77 g (64.4%) of 22-B as a greenish solid. $^1$H NMR (CDCl$_3$) δ 10.14 (s, 1H), 7.60 (d, J=8.59 Hz, 1H), 6.79 (d, J=8.59 Hz, 1H), 6.19 (br, 1H), 2.61 (s, 3H), 2.23 (s, 3H).

To a mixture of 22-B (2.89 g, 19.2 mmol) in MeOH (200 ml) was added K$_2$CO$_3$ (2.66 g, 19.2 mmol) and the resulting suspension was stirred at room temperature for 5 min, then pyridinium bromide perbromide (7.52 g, 21.1 mmol) was added in several portions and the resulting mixture was stirred at room temperature for 16 h. The organic solvent was removed under reduced pressure and the residue was diluted with 1N HCl (100 ml), extracted with EtOAc three times. The combined organic layer was washed with 1N HCl (50 ml), brine, dried with Na$_2$SO$_4$. The drying agent was filtered off and the solvent was evaporated to yield 4.34 g (98.5%) of 22-C as a light orange solid. $^1$H NMR (CDCl$_3$) δ 10.13 (s, 1H), 7.83 (s, 1H), 6.07 (s, 1H), 2.57 (s, 3H), 2.28 (s, 3H).

To a solution of 22-C (4.34 g, 18.95 mmol) in DMF (20 ml) at room temperature was added solid $K_2CO_3$ (5237 mg, 37.89 mmol) then benzylbromide (2.7 ml, 22.74 mmol) dropwise. The suspension was stirred at room temperature for 2 days. Water was added and the mixture was extracted with ether three times. The organic layers were combined, washed with brine, dried with $Na_2SO_4$, and concentrated. The residue was purified by flash column chromatography on silica gel (80 g column, EtOAc/heptane: 0>>>5%) to obtain 3.84 g (63.5%) of 22-D as a white solid. $^1$H NMR ($CDCl_3$) δ 10.22 (s, 1H), 7.93 (s, 1H), 7.51-7.55 (m, 2H), 7.35-7.45 (m, 3H), 4.95 (s, 2H), 2.56 (s, 3H), 2.28 (s, 3H). MS (ES) 321.0 (M+H$^+$).

To a solution of benzo[b]thiophene (512.7 mg, 3.82 mmol) in THF (3 mL) was added n-BuLi (2.27 mL, 1.6 M in hexane) at −78° C. and the mixture was kept at −78° C. under argon for 40 minutes, 22-D (1.16 g, 3.64 mmol) in THF (5 mL) was introduced slowly by double-ended needle to the above mixture and the resulting mixture was stirred at −78° C. for 1 hr and aq. $NaHCO_3$ (10 mL) was added and THF was removed under reduced pressure and the content was extracted with EtOAc three times. The organic layer was washed with brine, dried with $Na_2SO_4$ and the solution was passed into $SiO_2$ bed. EtOAc was evaporated to dryness and the residue was triturated with DCM to yield 1.6 g (97%) of 22-E as a white solid. $^1$H NMR ($CDCl_3$) δ 7.74 (d, J=8.08 Hz, 1H), 7.69 (s, 1H), 7.64 (d, J=7.58 Hz, 1H), 7.51-7.55 (m, 2H), 7.33-7.42 (m, 3H), 7.23-7.32 (m, 2H), 6.98 (s, 1H), 6.13 (d, J=4.04 Hz, 1H), 4.88 (s, 2H), 2.82 (d, J=4.04 Hz, 1H), 2.20 (s, 3H), 2.10 (s, 3H). MS (ES) 477.0 (M+Na$^+$).

A 100 ml round bottom flask was charged with 22-E (1.60 g, 3.53 mmol) and 20 ml of DCM was added. The mixture was degassed and put under argon. To the mixture was added triethylsilane (1.41 ml, 8.82 mmol) at 0° C., followed by dropwise addition of $BF_3.Et_2O$ (0.67 ml, 5.29 mmol). The reaction mixture was kept stirring at 0° C. for 2 h. Saturated aqueous $NaHCO_3$ was added and the mixture was stirred at 0° C. for 20 min, then concentrated. The residue was extracted with EtOAc three times. The organic layer was washed with brine, dried with $Na_2SO_4$, and concentrated and the resulting residue was purified by flash column chromatography on silica gel (40 g column, EtOAc/heptane: 0>>>5%) to yield 1.48 g (96%) of 22-F as a yellow oil. $^1$H NMR ($CDCl_3$) δ 7.73 (d, J=7.58 Hz, 1H), 7.63 (d, J=7.07 Hz, 1H), 7.53-7.57 (2H), 7.33-7.43 (4H), 7.29 (td, J=7.58, 1.52 Hz, 1H), 7.24 (m, 1H), 6.86 (s, 1H), 4.90 (s, 2H), 4.15 (s, 2H), 2.26 (s, 3H), 2.16 (s, 3H). MS (ES) 460.95 (M+Na$^+$).

A solution of n-BuLi (668 μL, 1.6 M in hexanes) was added quickly to a cold (−78° C.) solution of 22-F (467.7 mg, 1.07 mmol) in THF (2 ml) and the mixture quickly turned into deep orange. The solution was stirred at that temperature for 50 min and then a solution of lactone (463 mg, 1.07 mmol) in THF (3 ml) is added to the solution. The resulting solution is stirred at −78° C. for 2 h, quenched with aqueous $NH_4Cl$ solution and the resulting mixture is extracted with ethyl acetate three times. The combined organic layer was washed with brine, dried with $Na_2SO_4$. The drying agent was filtered off and the solvent was evaporated to yield 22-G as yellow oil, which was used for the next step reaction without purification. MS (ES) 813.3 (M+Na$^+$).

Triethylsilane (0.38 ml) was added in one portion to a stirred solution of 22-G in dry DCM (5 ml) at 0° C. under argon atmosphere. After 5 min, $BF_3.Et_2O$ (148 μL) was added dropwise by syringe. The resulting mixture was stirred at 0° C. for 30 mins, then quenched with saturated $NaHCO_3$, extracted with DCM, dried with $Na_2SO_4$, and concentrated under reduced pressure to yield orange oil. This crude residue was purified by flash column chromatography on silica gel (40 g column, EtOAc/heptane: 0>>>5%>>>10%) to yield 376 mg (45.3% over two steps) of 22-H as a white foam. $^1$H NMR ($CDCl_3$) δ 7.62 (d, J=7.58 Hz, 1H), 7.45 (d, J=7.58 Hz, 1H), 7.38-7.42 (2H), 7.10-7.37 (19H), 6.94 (d, J=7.58 Hz, 2H), 6.80 (s, 1H), 4.95 (d, J=11.12 Hz, 1H), 4.60-4.73 (5H), 4.50 (s, 2H), 4.12-4.29 (3H), 3.62-3.81 (3H), 3.54 (dd, J=9.60, 5.05 Hz, 1H), 3.40 (dd, J=9.60, 5.05 Hz, 1H), 2.14-2.30 (7H), 2.25 (s, 3H), 2.21 (s, 3H), 1.58 (q, J=11.62 Hz, 1H). MS (ES) 797.4 (M+Na$^+$).

A 50 ml round bottom flask was charged with 22-H (375.9 mg, 0.49 mmol) and pentamethylbenzene (431.4 mg, 2.91 mmol). To which was added 5 ml of anhydrous DCM and the mixture was evacuated, re-filled with argon. It was cooled to −78° C. To the mixture was added $BCl_3$ (2.91 ml, 1M in DCM) dropwise and the resulting mixture turned into brown. It was stirred at that temperature for 40 mins, quenched with 2 ml of MeOH, the solvent was removed under reduced pressure and the residue was purified by flash column chromatography on silica gel (12 g column, EtOAc/heptane: 0>>>10%>>>80%>>>100%) to yield 150 mg (74.6%) of compound 22 as a white foam. $^1$H NMR ($CD_3OD$) δ 7.67 (d, J=7.58 Hz, 1H), 7.55 (d, J=7.58 Hz, 1H), 7.22 (t, J=7.07 Hz, 1H), 7.17 (t, J=7.07 Hz, 1H), 7.06 (s, 1H), 6.82 (s, 1H), 4.34 (d, J=9.09 Hz, 1H), 4.14 (m, 2H), 3.57-3.74 (4H), 3.41 (t, J=9.09 Hz, 1H), 2.16 (s, 3H), 2.13 (s, 3H), 1.96-2.04 (m, 1H), 1.59 (q, J=12.13 Hz, 1H). MS (ES) 437.2 (M+Na$^+$).

Example 23

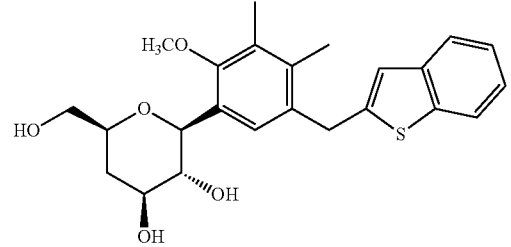 [SMILES: COc1c([C@@H]2O[C@H](CO)C[C@H](O)[C@H]2O)cc(Cc2cc3ccccc3s2)c(C)c1C]

2S,3R,4S,6S)-2-(5-(benzo[b]thiophen-2-ylmethyl)-2-methoxy-3,4-dimethylphenyl)-6-(hydroxymethyl) tetrahydro-2H-pyran-3,4-diol (cmp. 23

A 20 ml vial was charged with 22 (38.2 mg, 0.09 mmol) and $Cs_2CO_3$ (45 mg, 0.14 mmol) and to which was added 1 ml of dry acetone, followed by methyl iodide (12 μL, 0.18 mmol). The resulting mixture was stirred at room temperature for 16 h and the solid was filtered of, washed with acetone. The solvent was evaporated and the crude residue was purified by flash column chromatography on silica gel (4 g column, EtOAc/heptane: 0>>>100%) to afford 28.4 mg (71.8%) of 23 as a white solid. $^1$H NMR ($CD_3OD$) δ 7.71 (d, J=7.58 Hz, 1H), 7.60 (d, J=7.58 Hz, 1H), 7.14-7.28 (3H), 6.87 (s, 1H), 4.52 (d, J=9.60 Hz, 1H), 4.22 (s, 2H), 3.76 (s, 3H), 3.65-3.75 (2H), 3.49-3.59 (m, 3H), 2.23 (s, 3H), 2.20 (s, 3H), 2.02 (m, 1H), 1.50 (q, J=11.62 Hz, 1H). MS (ES) 451.1 (M+Na$^+$).

Example 24

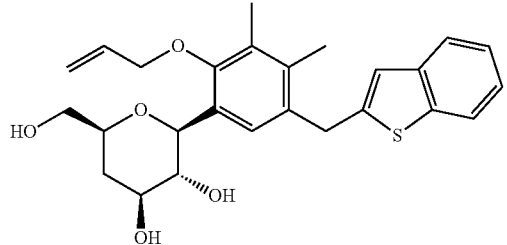 [SMILES: C=CCOc1c([C@@H]2O[C@H](CO)C[C@H](O)[C@H]2O)cc(Cc2cc3ccccc3s2)c(C)c1C]

2S,3R,4S,6S)-2-(2-(allyloxy)-5-(benzo[b]thiophen-
2-ylmethyl)-3,4-dimethylphenyl)-6-(hydroxymethyl)
tetrahydro-2H-pyran-3,4-diol (cmp 24

A 20 ml vial was charged with 22 (33.3 mg, 0.08 mmol) and Cs$_2$CO$_3$ (39.3 mg, 0.12 mmol) and to which was added 1 ml of dry acetone, followed by allyl bromide (19.4 mg, 0.16 mmol). The resulting mixture was stirred at room temperature for 16 h and the solid was filtered of, washed with acetone. The solvent was evaporated and the crude residue was purified by flash column chromatography on silica gel (4 g column, EtOAc/heptane: 0>>>100%) to afford 17.5 mg (43.1%) of 24 as a white solid. $^1$H NMR (CD$_3$OD) δ 7.71 (d, J=8.08 Hz, 1H), 7.60 (d, J=7.58 Hz, 1H), 7.13-7.28 (m, 3H), 6.87 (s, 1H), 6.14 (m, 1H), 5.47 (dd, J=17.18, 2.02 Hz, 1H), 5.24 (dd, J=10.61, 1.52 Hz, 1H), 4.51 (d, J=9.60 Hz, 1H), 4.47 (dd, J=12.63, 5.05 Hz, 1H), 4.35 (dd, J=12.63, 5.05 Hz, 1H), 4.23 (s, 2H), 3.47-3.73 (5H), 2.23 (s, 3H), 2.20 (s, 3H), 2.01 (m, 1H), 1.48 (q, J=11.12 Hz, 1H). MS (ES) 477.1 (M+Na$^+$).

Example 25

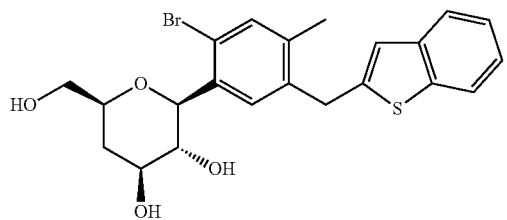 [SMILES: Cc1cc(Br)c([C@@H]2O[C@H](CO)C[C@H](O)[C@H]2O)cc1Cc1cc2ccccc2s1]

2S,3R,4S,6S)-2-(5-(benzo[b]thiophen-2-ylmethyl)-
2-bromo-4-methylphenyl)-6-(hydroxymethyl)tet-
rahydro-2H-pyran-3,4-diol (cmp. 25

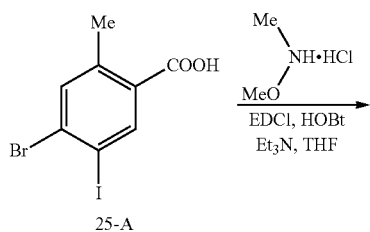

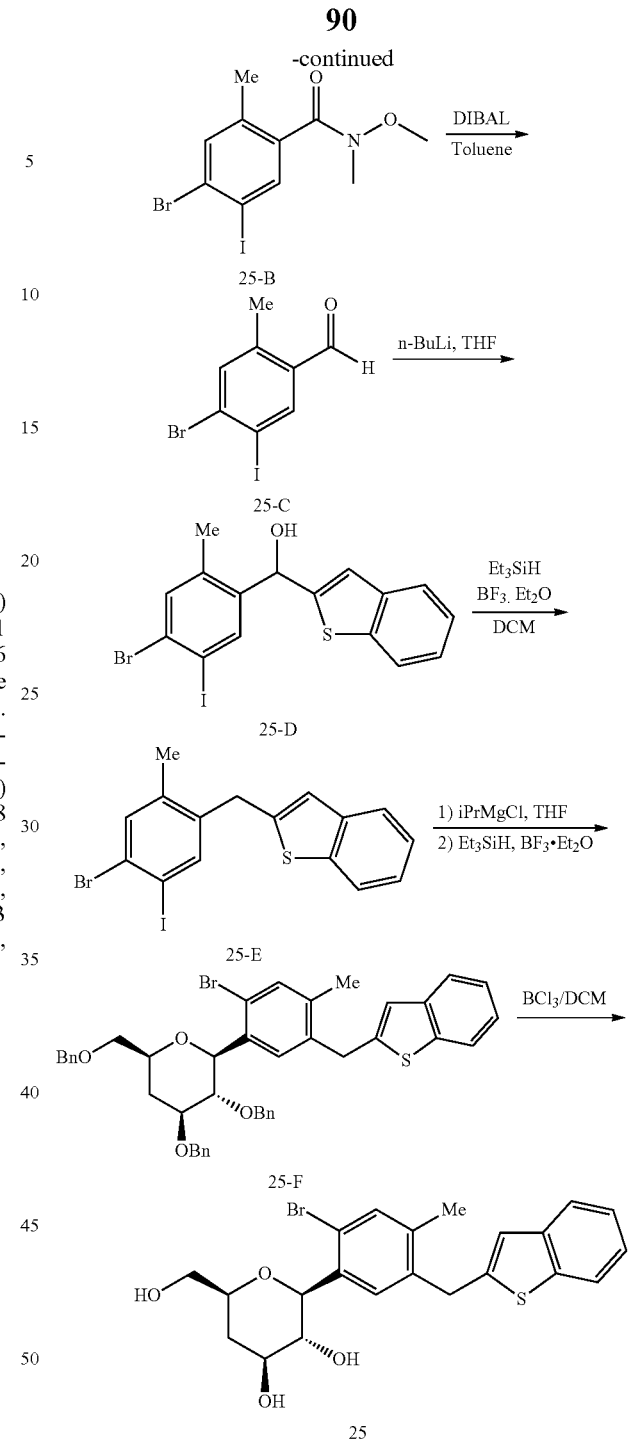

To a solution of 25-A (9.0 g, 26.4 mmol) in THF (100 ml) were added HOBt (4.08 g, 26.4 mmol), EDCl (6.13 g, 31.7 mmol), N,O-dimethylhydroxylamine hydrochloride (3.42 g, 34.3 mmol), and triethylamine (14.68 ml, 105.6 mmol) and the resulting mixture was stirred at room temperature for 20 h. It was diluted with 1N HCl (50 ml), the aqueous layer was extracted with EtOAc three times. The combined organic layer was washed with 1N NaOH, brine, dried with Na$_2$SO$_4$ and the solvent was evaporated. The residue was purified by flash column chromatography on silica gel (120 g, EtOAc/heptane: 0>>>30%). to give 8.49 g (83.8%) of 25-B as colorless syrup. $^1$H NMR (CDCl$_3$) δ 7.72 (s, 1H), 7.26 (s, 1H), 3.49 (br, 3H), 3.32 (br, 3H), 2.26 (s, 3H).

To 25-B (8.39 g, 21.85 mmol) in 100 ml of toluene at −78° C. was added 26.2 ml of DIBAL (1M in toluene) dropwise under argon. When TLC showed the starting material to be consumed (~2 h), the reaction was quenched with methanol (5 ml) and warmed to ambient temperature. Rochelle's salt solution was added and the cloudy mixture was stirred for several hours. The two layers were separated. The aqueous phase was extracted with EtOAc three times. The combined organic layers were washed with water and brine, dried over $Na_2SO_4$ and concentrated to give 6.76 g (95.2%) of 25-C as a white solid. $^1H$ NMR (CDCl$_3$) δ 10.11 (s, 1H), 8.17 (s, 1H), 7.56 (s, 1H), 2.56 (s, 3H).

To a solution of benzo[b]thiophene (876 mg, 6.53 mmol) in THF (4 mL) was added n-BuLi (3.9 mL, 1.6 M in hexanes) at −78° C. and the mixture was kept at −78° C. for 40 minutes, Compound 25-C (2.02 g, 6.22 mmol) in THF (11 mL) was introduced slowly by double-ended needle to the above mixture and the reaction mixture was stirred at −78° C. for 1 h. Aqueous. NaHCO$_3$ (10 mL) was added and THF was removed under vacuum and the content was extracted with EtOAc three times. The organic layer was washed with brine, dried with Na$_2$SO$_4$ and the drying agent was filtered off. The filtrate was concentrated under reduced pressure and the residue was purified by flash column chromatography on silica gel (40 g column, EtOAc/heptane: 0>>>10%) to yield 2.32 g (81.2%) of 25-D as a white solid. $^1H$ NMR (CDCl$_3$) δ 8.08 (s, 1H), 7.73 (dd, J=7.07 Hz, 1.52 Hz, 1H), 7.63 (dd, J=6.57, 2.02 Hz, 1H), 7.34 (s, 1H), 7.25-7.33 (m, 2H), 6.95 (s, 1H), 6.01 (d, J=4.04 Hz, 1H), 3.06 (d, J=4.04 Hz, 1H), 2.10 (s, 3H). MS (ES) 480.9 (M+Na$^+$).

A 100 ml round bottom flask was charged with 25-D (2.32 g, 5.05 mmol) and 50 ml of DCM was added. The mixture was degassed and put under argon. To the mixture was added triethylsilane (2.02 ml, 12.63 mmol) at 0° C., followed by dropwise addition of BF$_3$.Et$_2$O (0.96 ml, 7.58 mmol). The reaction mixture was kept stirring at 0° C. for 1 h. Saturated aqueous NaHCO$_3$ was added and the mixture was stirred at 0° C. for 20 min, then concentrated. The residue was extracted with EtOAc three times. The organic layer was washed with brine, dried with Na$_2$SO$_4$, and evaporated and the resulting residue was purified by flash column chromatography on silica gel (80 g column, EtOAc/heptane: 0>>>5%) to yield 1.86 g (83.1%) of 25-E as a white solid. $^1H$ NMR (CDCl$_3$) δ 7.74 (d, J=8.08 Hz, 1H), 7.70 (s, 1H), 7.64 (d, J=7.58 Hz, 1H), 7.46 (s, 1H), 7.24-7.35 (m, 2H), 6.87 (s, 1H), 4.10 (s, 2H), 2.24 (s, 3H).

A solution of iPrMgCl*LiCl in THF (1.91 ml, 1.3 M in THF) was added dropwise to a cold (−78° C.) solution of 25-E (1.10 g, 2.49 mmol) in THF (5 ml) and the mixture turned into red orange. The solution was stirred at that temperature for 40 mins and then was transferred into a solution of lactone (1.08 g, 2.49 mmol) in THF (3 ml) via cannula. The resulting solution is stirred at −78° C. for 1 h, warmed to room temperature and stirred at that temperature for 16 h, quenched with aqueous NH$_4$Cl solution and the resulting mixture is extracted with ethyl acetate three times. The combined organic layer was washed with brine, dried with Na$_2$SO$_4$. The drying agent was filtered off and the solvent was evaporated and the crude material was dissolved in 15 ml of acetonitrile, cooled to 0° C. with an ice-water bath. It was evacuated and refilled with argon. To which was added triethylsilane (1.31 ml, 8.2 mmol), followed by BF$_3$.Et$_2$O (0.63 ml, 4.97 mmol) and the resulting mixture was stirred at 0° C. for 30 min, then quenched with NaHCO$_3$ solution. The aqueous layer was extracted with EtOAc three times (20 ml each time) and the combined organic layers were dried with Na$_2$SO$_4$. The inorganic solid was filtered off and the filtrate was concentrated under reduced pressure. The crude material was purified by flash column chromatography on silica gel (120 g, EtOAc/heptane: 0>>>5%>>>10%>>>30%) to yield 724.4 mg (39.7%) of 25-F as a white solid. $^1H$ NMR (CDCl$_3$) 7.64 (d, J=7.58 Hz, 1H), 7.50 (d, J=7.58 Hz, 1H), 7.41 (s, 1H), 7.37 (s, 1H), 7.14-7.34 (15H), 7.01-7.05 (m, 2H), 6.79 (s, 1H), 4.75 (d, J=9.60 Hz, 1H), 4.67 (AB q, J=4.68 Hz, 2H), 4.55 (s, 2H), 4.51 (d, J=10.61 Hz, 1H), 4.13 (s, 2H), 4.09 (d, J=11.12 Hz, 1H), 3.75-3.85 (m, 2H), 3.60 (dd, J=10.61, 5.56 Hz, 1H), 3.54 (m, 1H), 3.48 (dd, J=10.11, 5.05 Hz, 1H), 2.29 (m, 1H), 2.26 (s, 3H), 1.61 (q, J=11.62 Hz, 1H). MS (ES) 757.05 (M+Na$^+$).

A 50 ml round bottom flask was charged with 25-F (724.4 mg, 0.99 mmol) and pentamethylbenzene (585.4 mg, 3.94 mmol). To which was added 5 ml of anhydrous DCM and the mixture was evacuated, re-filled with argon. It was cooled to −78° C. To the mixture was added BCl$_3$ (4.44 ml, 1M in DCM) dropwise and the resulting mixture turned into brown. It was stirred at that temperature for 40 mins, quenched with 2 ml of MeOH, the solvent was removed under reduced pressure and the residue was purified by flash column chromatography on silica gel (40 g column, EtOAc/heptane: 0>>>10%>>>50%>>>100%) to yield 320 mg (69.9%) of 25 as a white foam. $^1H$ NMR (CD$_3$OD) δ 7.72 (d, J=7.58 Hz, 1H), 7.62 (d, J=7.58 Hz, 1H), 7.45 (s, 1H), 7.42 (s, 1H), 7.27 (td, J=7.58 Hz, 1.01 Hz, 1H), 7.22 (td, J=7.58, 1.52 Hz, 1H), 6.92 (s, 1H), 4.61 (d, J=9.60 Hz, 1H), 4.22 (s, 2H), 3.74 (m, 1H), 3.68 (m, 1H), 3.56 (d, J=5.05 Hz, 1H), 3.55 (d, J=3.54 Hz, 1H), 3.47 (t, J=9.09 Hz, 1H), 2.27 (s, 3H), 2.03 (ddd, J=13.14, 5.05, 2.02 Hz, 1H), 1.51 (q, J=11.62 Hz, 1H). MS (ES) 487.05 (M+Na$^+$).

Example 26

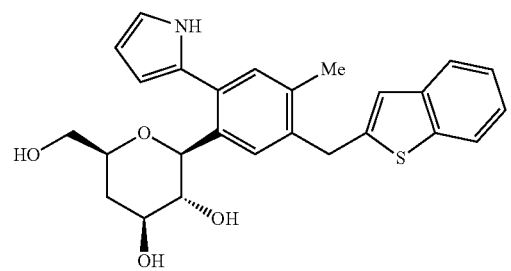 [SMILES: Cc1cc(-c2ccc[nH]2)c([C@@H]2O[C@H](CO)C[C@H](O)[C@H]2O)cc1Cc1cc2ccccc2s1]

2S,3R,4S,6S)-2-(5-(benzo[b]thiophen-2-ylmethyl)-4-methyl-2-(1H-pyrrol-2-yl)-phenyl)-6-(hydroxymethyl)tetrahydro-2H-pyran-3,4-diol (cmp. 26

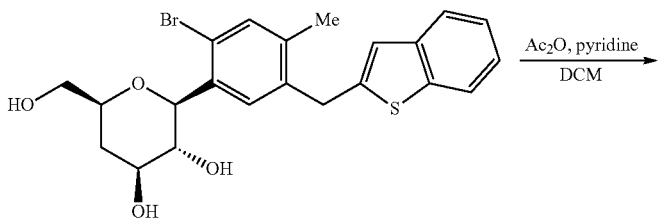

25

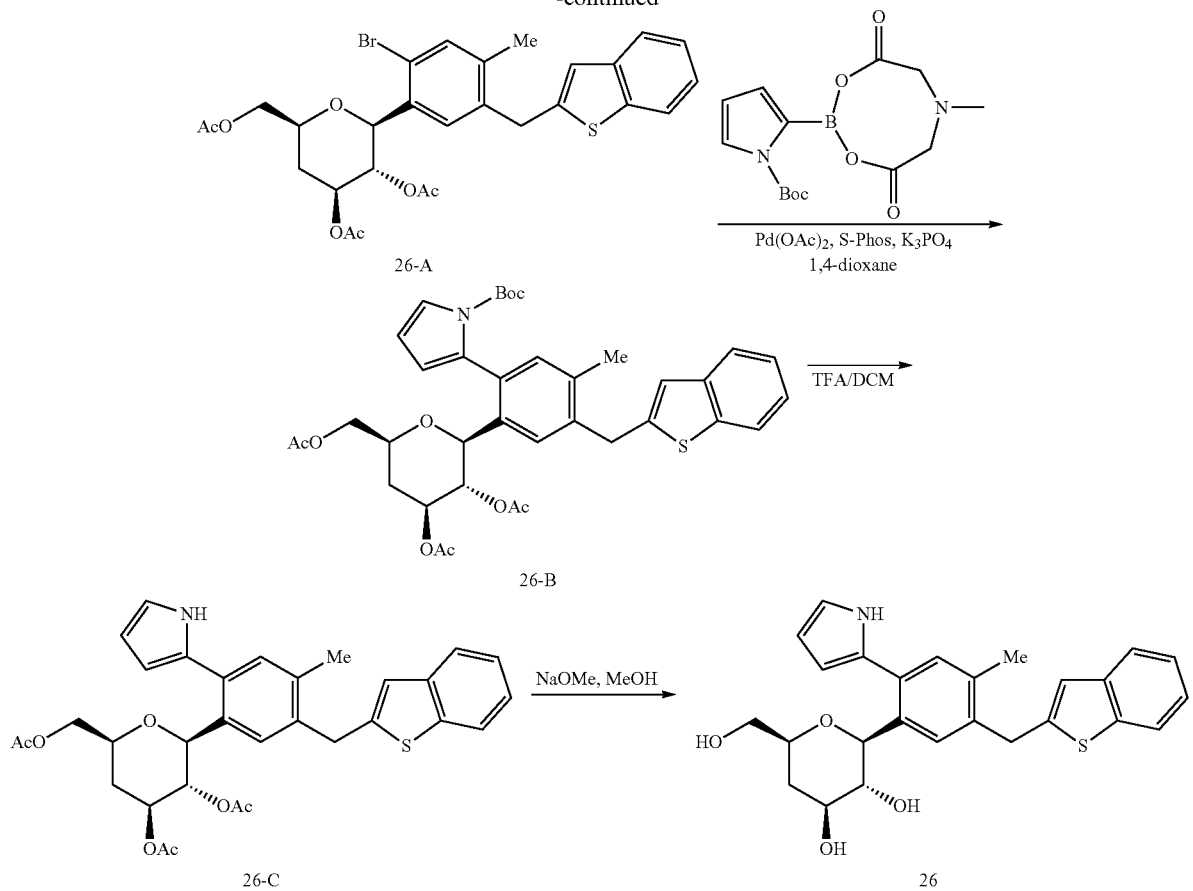

To a solution of 25 (320 mg, 0.69 mmol) in 20 ml of DCM was added pyridine (0.50 ml, 6.2 mmol) and DMAP (4.2 mg, 0.03 mmol). Then acetic anhydride (0.59 ml, 6.2 mmol) was added, and the mixture was stirred for 48 h at room temperature. The reaction was quenched by addition of aq. NaHCO$_3$ solution (20 mL). The mixture was extracted with dichloromethane (2×25 mL). The combined organic layers were washed with hydrochloric acid (1N, 30 mL), then with brine (20 mL), and then dried over sodium sulfate. After removal of volatiles, the residue was a white solid (26-A, 371.5 mg, 91.3%). MS (ES) 611.0 (M+Na$^+$).

Under ambient atmosphere, to a 20 mL vial equipped with a stir bar was added 26-A (70.4 mg, 0.12 mmol), the N-tert-butylpyrrole-derived MIDA boronate (58 mg, 0.18 mmol), 2-dicyclohexylphosphino-2',6'-dimethoxybiphenyl (SPhos) (4.9 mg, 0.012 mmol) and Pd(OAc)$_2$ (1.3 mg, 0.006 mmol). The vial was sealed with a PTFE-lined septum screw-cap and was placed under argon atmosphere. To the vial was added 1,4-dioxane (3 mL) and the resulting mixture was stirred at 23° C. for 2 min. To the vial was then added aq K$_3$PO$_4$ (3.0 M, 0.3 mL, degassed by sparging with Ar for 1 min). The vial was placed in a 80° C. with stirring for 16 h. After cooling to room temperature. The solvent was evaporated and the residue was purified by flash column chromatography (12 g column, EtOAc/heptane: 0>>>10%>>>20%) to yield 56 mg (69.4%) of 26-B as a light yellow solid. MS (ES) 698.3 (M+Na$^+$).

The compound 26-B was treated with TFA (0.5 ml) in DCM (2 ml) and the solvent was removed under reduced pressure. The crude material was purified by flash column chromatography on silica gel (40 g column, EtOAc/heptane: 0>>>20%>>>50%) to yield 25 mg (52.4%) of 26-C as a white solid.

Compound 26-C (25 mg, 0.043 mmol) was dissolved in 4 ml of MeOH and it was treated with 3 drops of NaOMe solution in MeOH (25%) and the resulting mixture was stirred at room temperature for 16 h. The solvent was removed under reduced pressure and the residue was purified by flash column chromatography on silica gel (12 g column, EtOAc/heptane: 0>>>20%>>>90%) to yield 10.1 mg (51.7%) of 26 as a slightly pink foam. $^1$H NMR (CD$_3$OD) δ 7.72 (d, J=7.58 Hz, 1H), 7.62 (d, J=7.07 Hz, 1H), 7.49 (s, 1H), 7.19-7.29 (m, 3H), 6.95 (s, 1H), 6.83 (m, 1H), 6.26 (m, 1H), 6.17 (m, 1H), 4.36 (d, J=9.60 Hz, 1H), 4.27 (s, 2H), 3.52-3.71 (5H), 2.31 (s, 3H), 1.97 (ddd, J=12.63, 5.05, 1.52 Hz, 1H), 1.53 (q, J=11.62 Hz, 1H). MS (ES) 450.15 (M+H$^+$).

Example 27

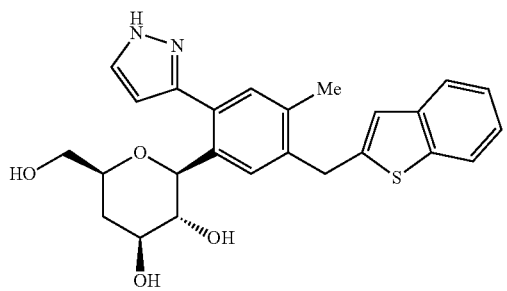 [SMILES: Cc1cc(-c2cc[nH]n2)c([C@@H]2O[C@H](CO)C[C@H](O)[C@H]2O)cc1Cc1cc2ccccc2s1]

(2S,3R,4S,6S)-2-(5-(benzo[b]thiophen-2-ylmethyl)-4-methyl-2-(1H-pyrazol-3-yl)-phenyl)-6-(hydroxymethyl)tetrahydro-2H-pyran-3,4-diol (cmp. 27)

Example 28

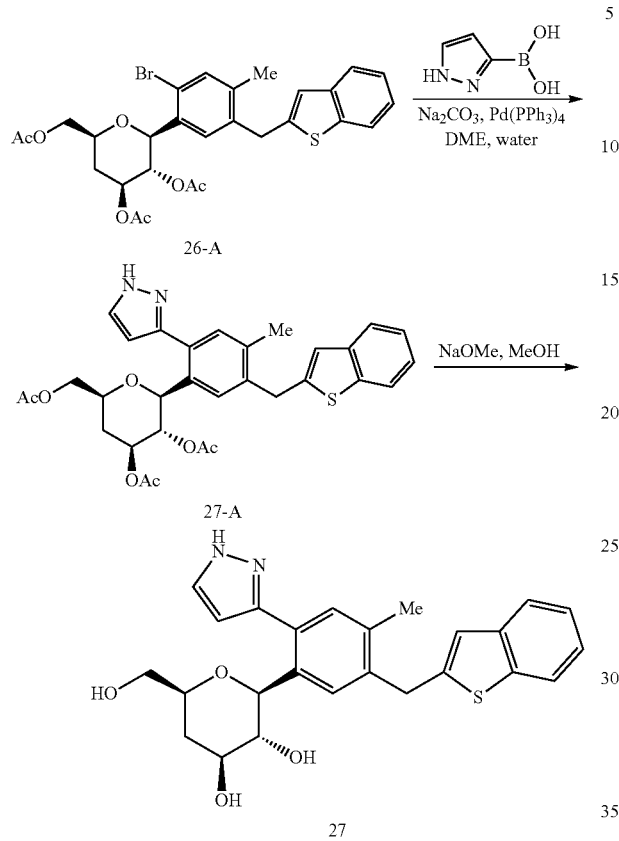

2S,3R,4S,6S)-2-(5-(benzofuran-2-ylmethyl)-2-hydroxy-4-methylphenyl)-6-(hydroxymethyl)tetrahydro-2H-pyran-3,4-diol (cmp. 28

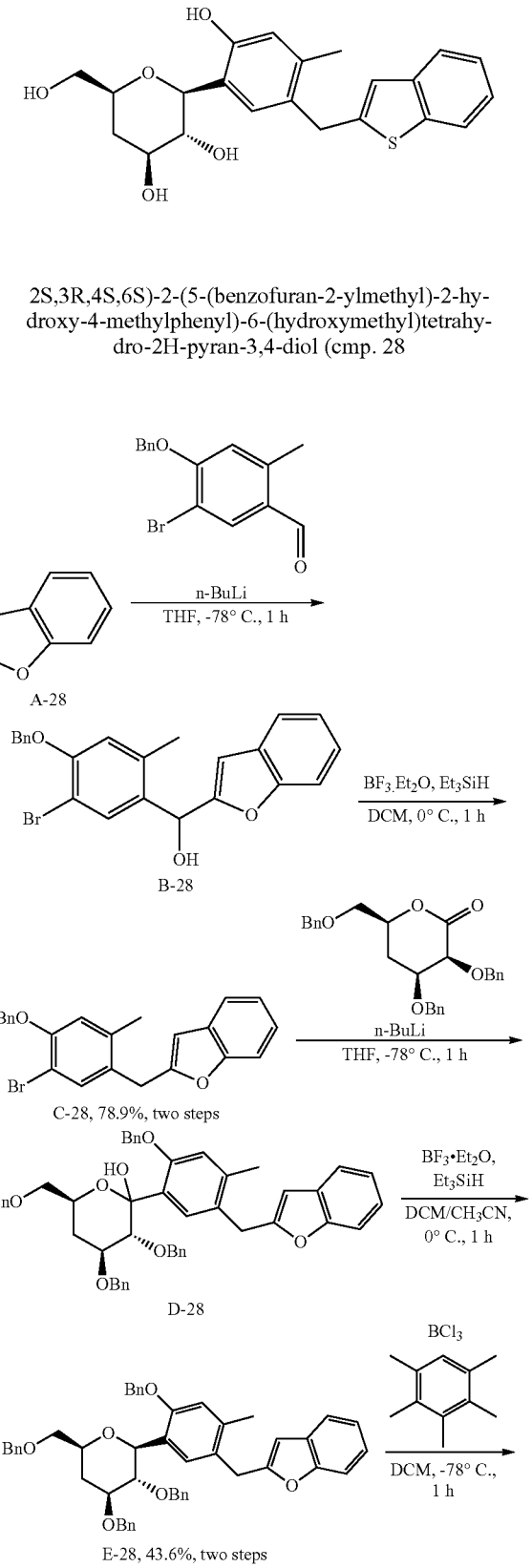

A 20 ml vial was charged with 26-A (59.4 mg, 0.101 mmol), (1H-pyrazol-3-yl)-boronic acid (22.6 mg, 0.2 mmol), $Na_2CO_3$ (25.4 mg, 0.3 mmol), $Pd(PPh_3)_4$ (5.8 mg, 0.005 mmol). The vial was sealed with a PTFE-lined septum screwcap, evacuated, refilled with argon and this process was repeated three times. To which was added DME (3 ml), followed by 0.3 ml of water and the resulting mixture was stirred at 100° C. for 3 h. The mixture was diluted with water and extracted with EtOAc three times and the combined organic extracts were concentrated under reduced pressure and the residue was purified by flash column chromatography on silica gel (12 g column, EtOAc/heptane: 0>>>50%) to yield 30 mg (51.6%) of 27-A. MS (ES) 577.20 (M+H$^+$).

Compound 27-A (30 mg, 0.052 mmol) was dissolved in 4 ml of MeOH and it was treated with three drops of NaOMe solution in MeOH (25%) and the resulting mixture was stirred at room temperature for 16 h. The solvent was removed and the residue was partitioned between EtOAc and water. The aqueous layer was extracted with EtOAc three times and the combined organic extracts were washed with brine, dried with $Na_2SO_4$ and the inorganic salt was filtered off and the filtrate was concentrated. The residue was purified by flash column chromatography on silica gel (4 g column, EtOAc/heptane: 0>>>100%) to yield 10.2 mg (43.5%) of 27 as a white foam. $^1$H NMR (CD$_3$OD) δ 7.73 (d, J=7.58 Hz, 1H), 7.62-7.68 (2H), 7.61 (s, 1H), 7.31 (s, 1H), 7.27 (td, J=7.07, 1.01 Hz, 1H), 7.22 (td, J=8.08, 2.02 Hz, 1H), 6.95 (s, 1H), 6.56 (br, 1H), 4.50 (br, 1H), 4.30 (s, 2H), 3.67 (m, 1H), 3.50-3.60 (3H), 3.46 (m, 1H), 2.34 (s, 3H), 1.98 (dd, J=12.63, 5.05 Hz, 1H), 1.52 (q, J=11.62 Hz, 1H). MS (ES) 451.10 (M+H$^+$).

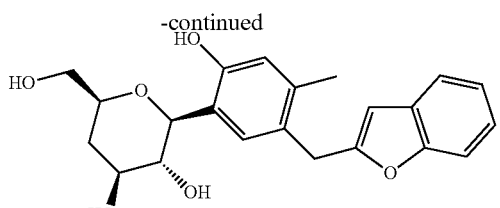

Compound 28, 20%

With an inert atmosphere of nitrogen, to a mixture of A-28 (500 mg, 4.23 mmol, 1.10 equiv) in tetrahydrofuran (5 mL). This was followed by the addition of n-BuLi (2.5M in hexane, 4.42 mmol, 1.77 mL, 1.15 equiv) dropwise with stirring at −78° C.

It was reacted 20 min at −78° C. To this was added a solution of 4-(benzyloxy)-5-bromo-2-methylbenzaldehyde (1.17 g, 3.85 mmol, 1.00 equiv) in tetrahydrofuran (10 mL) dropwise with stirring at −78° C. The resulting solution was stirred for 1 h at −78° C. NH$_4$Cl/H$_2$O was added and the mixture was extracted with EtOAc thrice. The combined extracts were washed with brine and dried over Na$_2$SO$_4$. Concentration and this resulted in 1.6 g (crude) of B-28 as light yellow oil.

With an inert atmosphere of nitrogen, to a mixture of B-28 (1.6 g, crude) in dichloromethane (20 mL), Et$_3$SiH (0.88 g, 7.58 mmol, 2.00 equiv). This was followed by the addition of BF3Et2O (1.08 g, 7.58 mmol, 2.00 equiv) dropwise with stirring at 0° C. The resulting solution was stirred for 1 h at 0° C. in a water/ice bath. Sodium bicarbonate/H$_2$O was added and the mixture was extracted with dichloromethane thrice. The combined extracts were washed with brine and dried over Na$_2$SO$_4$. Concentration and chromatograph on silica gel (5:1 PE/EA) gave 1.23 g (78.9%, two steps) of C-28 as a light yellow solid. $^1$H-NMR (300 MHz, CDCl$_3$) δ 7.35-7.52 (m, 8H), 7.14-7.32 (m, 2H), 6.81 (s, 1H), 6.28 (s, 1H), 5.16 (s, 2H), 4.01 (s, 2H), 2.30 (s, 3H).

With an inert atmosphere of nitrogen, to a mixture of C-28 (451 mg, 1.11 mmol, 1.20 equiv) in tetrahydrofuran (5 mL), n-BuLi (2.5M in hexane, 0.46 mL, 1.16 mmol, 1.25 equiv), the resulting solution was stirred for 10 min at −78° C. in a dry ice bath. (3R,4S,6S)-3,4-bis(benzyloxy)-6-[(benzyloxy)methyl]oxan-2-one (400 mg, 0.926 mmol, 1.00 equiv). The resulting solution was allowed to react, with stirring, for an additional 1 h while the temperature was maintained at −78° C. in a dry ice bath. NH$_4$Cl/H$_2$O was added and the mixture was extracted with EtOAc thrice. The combined extracts were washed with brine and dried over Na$_2$SO$_4$. Concentration and this resulted in 0.8 g (crude) of D-28 as yellow oil. MS (ES) m/z: 783 [M+Na]$^+$.

With an inert atmosphere of nitrogen, to a mixture of D-28 (800 mg, crude) in CH$_3$CN/DCM (10/10 mL). This was followed by the addition of Et$_3$SiH (244 mg, 2.10 mmol, 2.00 equiv) dropwise with stirring. To this was added BF$_3$.Et$_2$O (299 mg, 2.10 mmol, 2.00 equiv) dropwise with stirring at 0° C. The resulting solution was stirred for 1 h at 0° C. in a water/ice bath. Sodium bicarbonate/H$_2$O was added and the mixture was extracted with dichloromethane thrice. The combined extracts were washed with brine and dried over Na$_2$SO$_4$. Concentration and chromatograph on silica gel (5:1 PE/EA) gave 0.3 g (43.6%, two steps) of E-28 as colorless oil. MS (ES) m/z: 767 [M+Na]$^+$ With an inert atmosphere of nitrogen, to a mixture of E-28 (270 mg, 0.36 mmol, 1.00 equiv) in dichloromethane (30 mL), Petamethy/bezene (537 mg, 3.6 mmol, 10.00 equiv). This was followed by the addition of BCl$_3$/DCM (1M in DCM, 5.4 mL, 5.4 mmol, 15.00 equiv) at −78° C. The resulting solution was stirred for 1 h at −78° C. in a dry ice bath. 10 mL of methanol was added. Concentration and chromatograph on a C18 reversed phase column gave 28 mg (20%) of Compound 28 as a white solid. $^1$H-NMR (300 MHz, CD$_3$OD) δ 7.31-7.41 (m, 2H), 7.20 (s, 1H), 7.09-7.17 (m, 2H), 6.65 (s, 1H), 6.23 (s, 1H), 4.43-4.46 (d, J=9 Hz, 1H), 4.00 (s, 2H), 3.61-3.71 (m, 2H), 3.54-3.55 (m, 2H), 3.39-3.45 (m, 1H), 2.22 (s, 3H), 1.95-2.01 (m, 1H), 1.44-1.56 (m, 1H); MS (ES) m/z: 407 [M+Na]$^+$.

Example 29

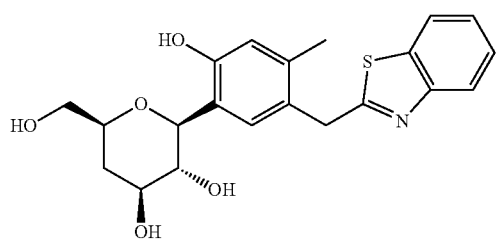 [SMILES: Cc1cc(O)c([C@@H]2O[C@H](CO)C[C@H](O)[C@H]2O)cc1Cc1nc2ccccc2s1]

2S,3R,4S,6S)-2-(5-(benzo[d]thiazol-2-ylmethyl)-2-hydroxy-4-methylphenyl)-6-(hydroxymethyl)tetrahydro-2H-pyran-3,4-diol (cmp. 29

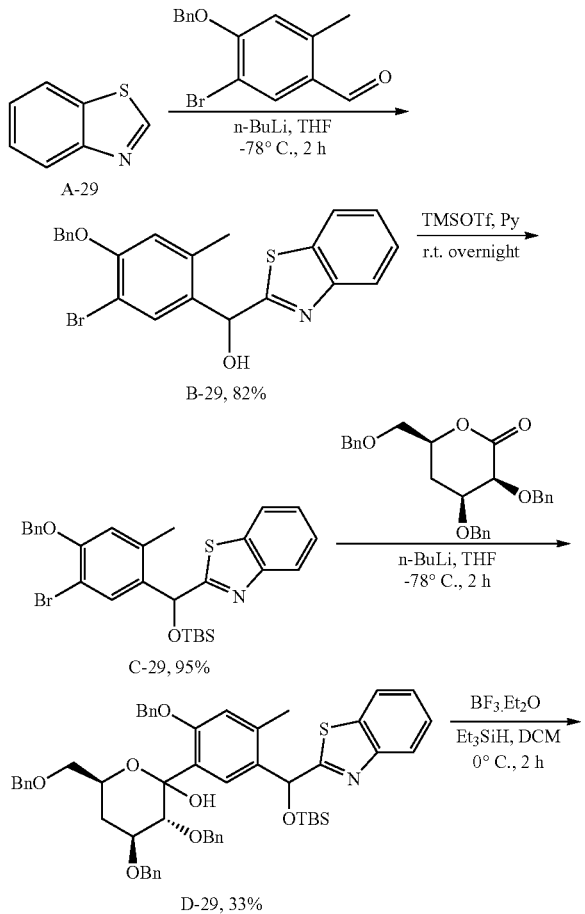

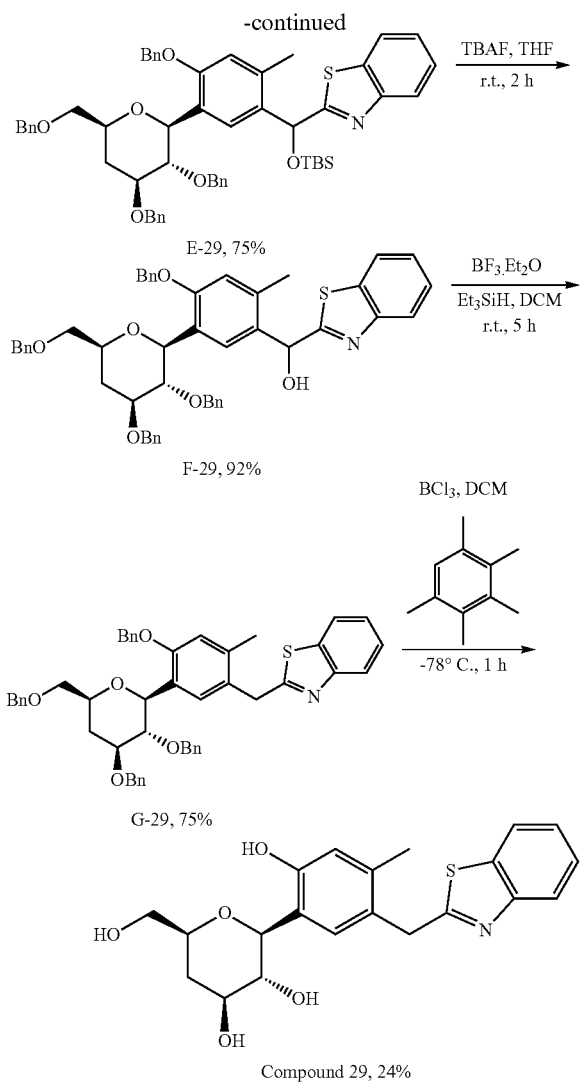

E-29, 75%

F-29, 92%

G-29, 75%

Compound 29, 24%

With an inert atmosphere of nitrogen, to a mixture of A-29 (450 mg, 3.33 mmol, 1.00 equiv) in tetrahydrofuran (15 mL) was added n-BuLi (2.5M in hexane, 1.3 mL, 1.00 equiv) at −78° C. The mixture was stirred for 1 h at −78° C. After that 4-(benzyloxy)-5-bromo-2-methylbenzaldehyde (1 g, 3.28 mmol, 1.00 equiv) in THF (5 mL) was added to the solution. The reaction was stirred for 2 h at −78° C. $NH_4Cl/H_2O$ was added and the mixture was extracted with EtOAc thrice. The combined extracts were washed with brine and dried over $Na_2SO_4$. Concentration and chromatograph on silica gel (2:1 PE/EA) gave 1.2 g (82%) of B-29 as yellow oil. $^1$H-NMR (400 MHz, DMSO) δ 8.07 (d, J=8.0 Hz, 1H), 7.89 (d, J=7.6 Hz, 1H), 7.59 (s, 1H), 7.32-7.49 (m, 8H), 7.08 (s, 1H), 6.97 (s, 1H), 6.16 (s, 1H), 5.20 (s, 2H), 2.38 (s, 3H).

To a mixture of B-29 (1 g, 2.27 mmol, 1.00 equiv) in pyridine (20 mL) was added tert-butyldimethylsilyl trifluoromethanesulfonate (3 g, 11.35 mmol, 5.00 equiv). The reaction was stirred overnight at room temperature. Water was added and the mixture was extracted with EtOAc thrice. The combined extracts were washed with brine. Concentration and chromatograph on silica gel (5:1 PE/EA) gave 1.2 g (95%) of C-29 as yellow oil. $^1$H-NMR (300 MHz, $CDCl_3$) δ 7.87-7.96 (m, 3H), 7.79 (s, 1H), 7.33-7.50 (m, 8H), 6.76 (s, 1H), 6.20 (s, 1 H), 5.14 (s, 2H), 2.46 (s, 2H), 0.94-0.99 (m, 15H).

With an inert atmosphere of nitrogen, to a mixture of C-29 (555 mg, 1.00 mmol, 1.00 equiv) in tetrahydrofuran (10 mL) was added n-BuLi (2.5M in hexane, 0.4 mL, 1.00 equiv,) at −78° C. The mixture was stirred for 5 min at −78° C. After that (3R,4S,6S)-3,4-bis(benzyloxy)-6-[(benzyloxy)methyl]oxan-2-one (432 mg, 1.00 mmol, 1.00 equiv) in tetrahydrofuran (5 mL) was added to the solution. The reaction was stirred for 2 h at −78° C. $NH_4Cl/H_2O$ was added and the mixture was extracted with EtOAc thrice. The combined extracts were washed with brine and dried over $Na_2SO_4$. Concentration and chromatograph on silica gel (2:1 PE/EA) gave 300 mg (33%) of D-29 as yellow oil. MS (ES) m/z: 908 $[M+H]^+$.

With an inert atmosphere of nitrogen, to a mixture of D-29 (300 mg, 0.33 mmol, 1.00 equiv) in dichloromethane (10 mL) with $Et_3SiH$ (120 mg, 1.03 mmol, 3.00 equiv) was added $BF_3Et_2O$ (100 mg, 0.70 mmol, 2.00 equiv) at 0° C. The reaction was stirred for 2 h at 0° C. Sodium bicarbonate/$H_2O$ was added and the mixture was extracted with dichloromethane thrice. The combined extracts were washed with brine and dried over $Na_2SO_4$. Concentration and chromatograph on silica gel (5:1 PE/EA) gave 220 mg (75%) of E-29 as yellow oil. MS (ES) m/z: 892 $[M+H]^+$.

To a mixture of E-29 (200 mg, 0.22 mmol, 1.00 equiv) in tetrahydrofuran (10 mL) was added TBAF (300 mg, 1.15 mmol, 5.00 equiv). The reaction was stirred for 2 h at room temperature. $NH_4Cl/H_2O$ was added and the mixture was extracted with EtOAc thrice. The combined extracts were washed with brine and dried over $Na_2SO_4$. Concentration and chromatograph on silica gel (2:1 PE/EA) gave 160 mg (92%) of G-29 as yellow oil. MS (ES) m/z: 778 $[M+H]^+$.

With an inert atmosphere of nitrogen, to a mixture of G-29 (150 mg, 0.19 mmol, 1.00 equiv) in dichloromethane (10 mL) with $Et_3SiH$ (67 mg, 0.58 mmol, 3.00 equiv) was added $BF_3Et_2O$ (55 mg, 0.39 mmol, 2.00 equiv). The reaction was stirred for 5 h at room temperature. Sodium bicarbonate/$H_2O$ was added and the mixture was extracted with dichloromethane thrice. The combined extracts were washed with brine and dried over $Na_2SO_4$. Concentration and chromatograph on silica gel (5:1 PE/EA) gave 110 mg (75%) of G-29 as yellow oil. MS (ES) m/z: 762 $[M+H]^+$.

With an inert atmosphere of nitrogen, to a mixture of G-29 (100 mg, 0.13 mmol, 1.00 equiv) in dichloromethane (10 mL) with 1,2,3,4,5-pentamethylbenzene (100 mg, 0.67 mmol, 5.10 equiv) was added $BCl_3$ (1 M in DCM, 2 mL, 16.00 equiv) at −78° C. The reaction was stirred for 1 h at −78° C. 5 mL of methanol was added. Concentration and chromatograph on a C18 reversed phase column gave 12.8 mg (24%) of Compound 29 as a white solid. $^1$H-NMR (300 MHz, $CD_3OD$) δ 7.88-7.93 (m, 2H), 7.34-7.57 (m, 2H), 7.33 (s, 2H), 6.75 (s, 1H), 4.51-4.54 (d, J=9.6 Hz, 1H), 4.46 (s, 1H), 3.52-3.81 (m, 5H), 1.97-2.08 (m, 1H), 1.50-1.59 (m, 1H); MS (ES) m/z); 424 $[M+Na]^+$.

Example 30

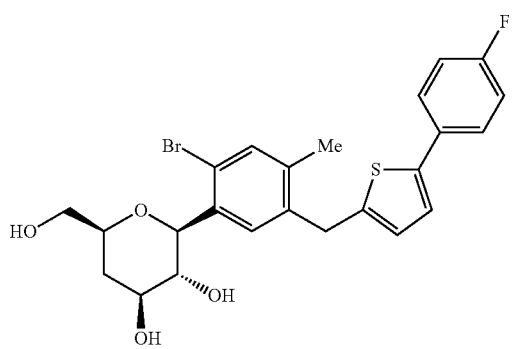 [SMILES: Cc1cc(Br)c([C@@H]2O[C@H](CO)C[C@H](O)[C@H]2O)cc1Cc1ccc(-c2ccc(F)cc2)s1]

2S,3R,4S,6S)-2-(2-bromo-5-((5-(4-fluorophenyl)thiophen-2-yl)methyl)-4-methylphenyl)-6-(hydroxymethyl)tetrahydro-2H-pyran-3,4-diol (cmp. 30

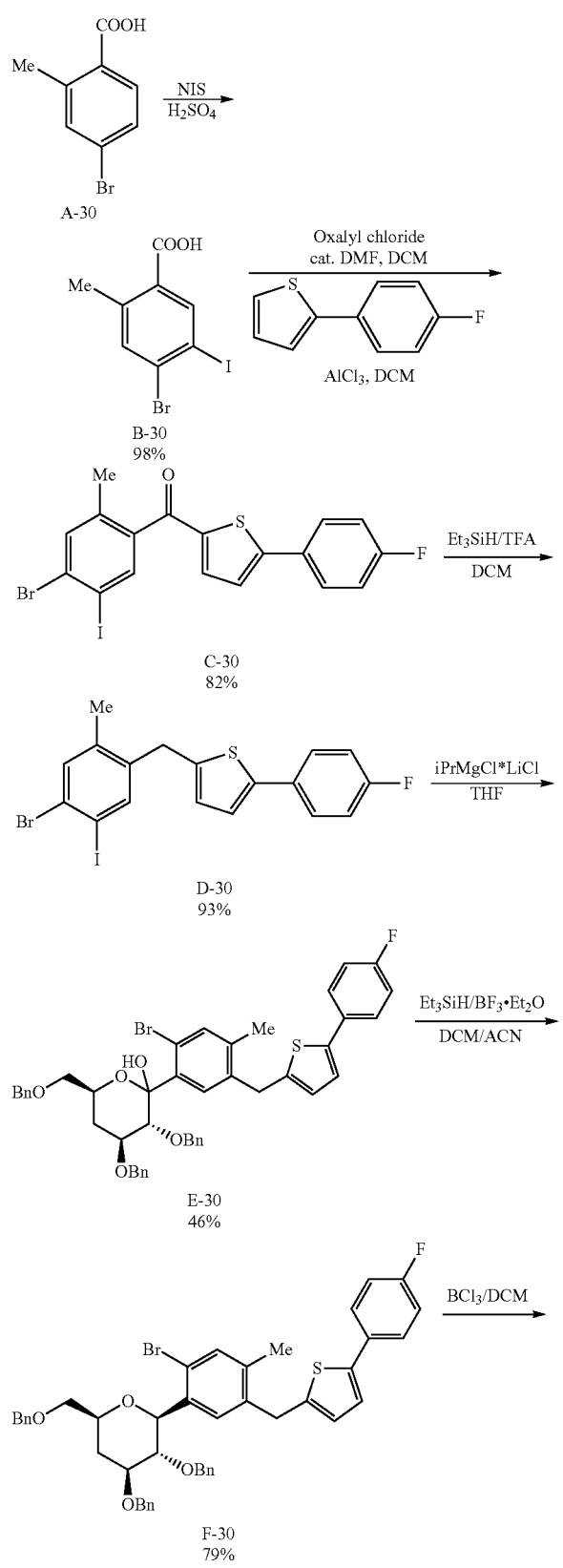

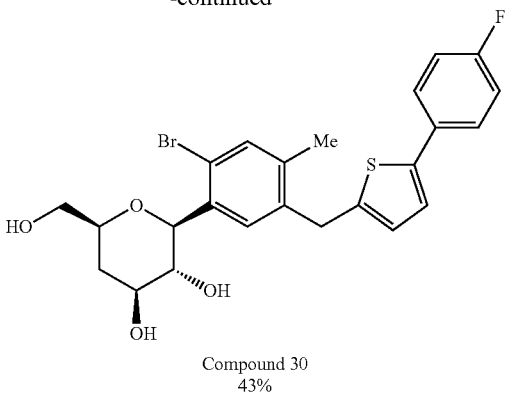

Compound 30
43%

N-Iodosuccinimide (4.26 g) is added in portions to an ice-cold solution of sulphuric acid (30 ml). The resulting mixture is stirred at that temperature for 40 min, then 4-bromo-2-methyl-benzoic acid (A-30) dissolved in 30 ml of sulphuric acid is added while the temperature maintains at 0-5° C. The mixture is stirred for 1 h, then the mixture is poured on crushed ice and the resulting precipitate was washed with water ten times, heptane three times, methanol twice, dried in vacuo to give 5.68 g (98%) of B-30 as a white solid. $^1$H NMR (CD$_3$OD) δ 8.34 (s, 1H), 7.61 (s, 1H), 2.50 (s, 3H).

The acid B-30 (1.81 g, 5.31 mmol) was suspended in DCM (35 ml) and to the mixture were added oxalyl chloride (0.59 ml, 6.75 mmol) and DMF (18 uL). The mixture was stirred at room temperature for 3 days. The solvent was evaporated under reduced pressure to give the benzoyl chloride as a white solid. This compound and 2-(4-fluorophenyl)-thiophene were dissolved in DCM (40 ml), and to the mixture was added AlCl$_3$ (939 mg, 6.37 mmol)) at 0° C. After stirring at that temperature for 30 min, the mixture was allowed to warm to room temperature and stirred for 1 h. The reaction mixture was poured into ice-water and the organic layer was separated, and the aqueous layer was extracted with DCM three times. The combined organic layers were washed with brine, dried with Na$_2$SO$_4$ and the drying agent was filtered off. The light yellow solid was washed with heptane three times to give 2.16 g (82%) C-30 as a yellow solid. $^1$H NMR (CDCl$_3$) δ 7.90 (s, 1H), 7.63-7.68 (m, 2H), 7.59 (s, 1H), 7.38 (d, J=4.04 Hz, 1H), 7.27 (d, J=4.0 Hz, 1H), 7.10-7.17 (m, 2H), 2.32 (s, 3H). MS (ES) 524.8 (M+Na$^+$).

The aryl ketone C-30 (2.16 g, 4.31 mmol) was dissolved in DCM (50 ml) and ACN (25 ml). To this solution was added triethylsilane (2.07 ml, 12.9 mmol)) and Boron trifluoride-etheral (1.36 ml, 10.8 mol) dropwise under argon at room temperature. The resulting mixture was stirred at 42° C. for 16 h. It was quenched with saturated aqueous NaHCO$_3$ and stirred at room temperature for 30 min, then the organic layer was separated and the aqueous layer was extracted with DCM three times. The combined organic layers were washed with brine, dried with Na$_2$SO$_4$. The drying agent was filtered off and the solvent was evaporated to give a light orange oil, which was purified by flash column chromatography on silica gel (40 g column, EtOAc/heptane: 0>>>5%>>>10%) to yield 1.95 g (93%) of D-30 as a white solid. $^1$H NMR (CDCl$_3$) δ

7.67 (s, 1H), 7.46-7.50 (m, 2H), 7.44 (s, 1H), 7.01-7.07 (m, 3H), 6.66 (d, J=3.5 Hz, 1H), 4.02 (s, 2H), 2.25 (s, 3H).

A solution of iPrMgCl*LiCl in THF (789 μL, 1.3 M in THF) was added dropwise to a cold (−78° C.) solution of D-30 (500 mg, 1.03 mmol) in THF (2 ml) and the mixture turned into purple, then light orange (after 10 mins). The solution was stirred at that temperature for 1 h and then a solution of lactone (426 mg, 0.99 mmol) in THF (4 ml) is added to the solution. The resulting solution is stirred at −78° C. for 30 min, then 0° C. for 2 h, quenched with aqueous NH$_4$Cl solution and the resulting mixture is extracted with ethyl acetate three times. The combined organic layer was washed with brine, dried with Na$_2$SO$_4$. The drying agent was filtered off and the solvent was evaporated. The residue was purified by flash column chromatography on silica gel (40 g column, EtOAc/heptane: 0>>>15%>>>25%) to yield 375 mg (46%) of E-30 as a colorless gel. MS (ES) 815.3 (M+Na$^+$).

E-30 was dissolved in anhydrous acetonitrile (5 ml) and the solution was degassed, filled with argon and cooled to 0° C. To which was added triethylsilane (0.23 ml), followed by BF$_3$.Et$_2$O dropwise. The resulting mixture was stirred at 0° C. for 1 h. It was quenched with saturated aqueous NaHCO$_3$, extracted with EtOAc three times. The combined organic extracts were washed with brine, dried with Na$_2$SO$_4$. The drying agent was filtered off and the solvent was evaporated under reduced pressure. The residue was purified by flash column chromatography on silica gel (12 g column, EtOAc/heptane: 0>>10%) to yield 289 mg (79%) of F-30 as a white foam. MS (ES) 799.2 (M+Na$^+$).

A 30 ml vial was charged with F-30 (87.9 mg, 0.11 mmol) and pentamethyl benzene (167.5 mg, 1.13 mmol). To which was added 5 ml of anhydrous DCM and the mixture was degassed, re-filled with argon. It was cooled to −78° C. To the mixture was added BCl$_3$ (0.68 ml, 1M in DCM) dropwise and the resulting mixture turned into brown. It was stirred at that temperature for 1 h, quenched with 1 ml of MeOH, the solvent was removed under reduced pressure and the residue was purified by flash column chromatography on silica gel (12 column, EtOAc/heptanes: 0>>>100%) to yield 24.9 mg (43%) of compound 30 as a white foam. $^1$H NMR (CD$_2$Cl$_2$) δ 7.51-7.57 (m, 2H), 7.47 (s, 1H), 7.40 (s, 1H), 7.06-7.13 (3H), 6.72 (d, J=3.5 Hz, 1H), 4.64 (d, J=9.6 Hz, 1H), 4.15 (s, 2H), 3.85 (m, 1H), 3.77 (m, 1H), 3.64 (dd, J=12.1, 3.5 Hz, 1H), 3.57 (dd, J=11.6, 6.6 Hz, 1H), 3.53 (d, J=9.1 Hz, 1H), 2.67 (br, 1H), 2.32 (s, 3H), 2.23 (br, 1H), 2.00 (m, 1H), 1.59 (q, J=11.6 Hz, 1H). MS (ES) 529.0 (M+Na$^+$).

Example 31

2S,3R,4S,6S)-2-(5-((5-(4-fluorophenyl)thiophen-2-yl)methyl)-2-hydroxy-4-methylphenyl)-6-(hydroxymethyl)tetrahydro-2H-pyran-3,4-diol (cmp. 31

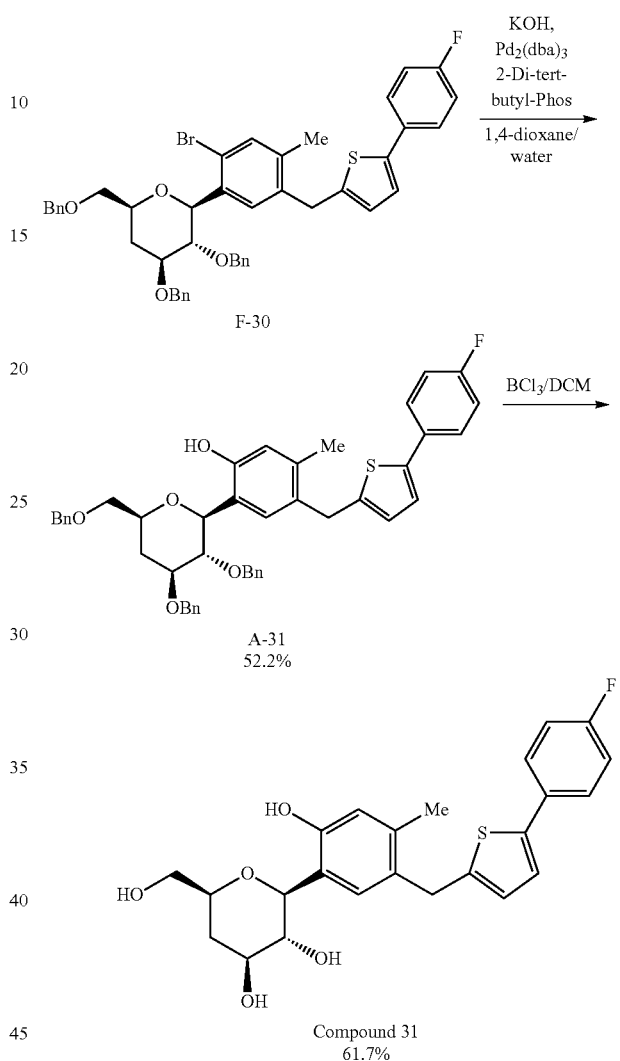

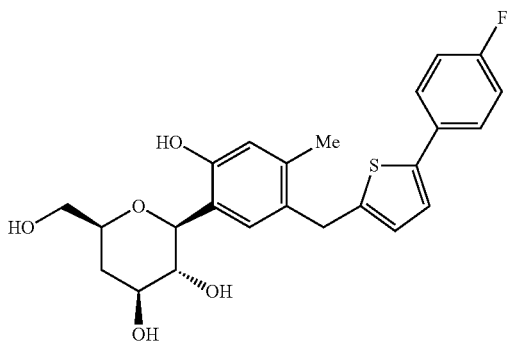 [SMILES: Cc1cc(O)c([C@@H]2O[C@H](CO)C[C@H](O)[C@H]2O)cc1Cc1ccc(-c2ccc(F)cc2)s1]

A disposable vial (30 ml) with a plastic screw cap top and Teflon septa was charged with F-30 (80.5 mg, 0.10 mmol), Pd$_2$(dba)$_3$ (1.9 mg, 0.002 mmol), 2-di-tert-butylphosphino-2',4',6'-tri-isopropyl-1,1'-biphenyl (3.6 mg, 0.008 mmol), and KOH (17.4 mg, 0.31 mmol). The vial was evacuated and backfilled with argon and this sequence was repeated three times. To the vial was added 0.5 ml of water, followed by 2 ml of 1,4-dioxane. The mixture was stirred at 95° C. for 16 h and the solvent was evaporated and the residue was purified by flash column chromatography on silica gel (40 g column, EtOAc/heptane: 0>>>10%>>>20%) to yield 38.6 mg (52.2%) of A-31 as a colorless gel. MS (ES) 732.2 (M+Na$^+$).

A 50 ml round-bottom flask was charged with A-31 (38.6 mg, 0.054 mmol) and pentamethyl benzene (80 mg, 0.54 mmol). To which was added 5 ml of anhydrous DCM and the mixture was degassed, re-filled with argon. It was cooled to −78° C. To the mixture was added BCl$_3$ dropwise and the resulting mixture turned into brown. It was stirred at that temperature for 1 h, quenched with 1 ml of MeOH, the solvent was removed under reduced pressure and the residue was purified by flash column chromatography on silica gel (12 g column, EtOAc/heptane: 0>>>10%>>>100%) to yield 14.8 mg (61.7%) of compound 31 as a white foam. $^1$H NMR (CD$_3$OD) δ 7.50-7.55 (m, 2H), 7.21 (s, 1H), 7.02-7.10 (m, 3H), 6.67 (d, J=3.5 Hz, 1H), 6.66 (s, 1H), 4.47 (d, J=9.6 Hz, 1H), 4.05 (s, 2H), 3.72 (m, 1H), 3.67 (m, 1H), 3.58 (dd, J=5.1, 1.5 Hz, 2H), 3.46 (t, J=9.60 Hz, 1H), 2.21 (s, 3H), 2.01 (ddd, J=12.6, 5.1, 1.5 Hz, 1H), 1.54 (q, J=11.6 Hz, 1H). MS (ES) 467.1 (M+Na$^+$).

Example 32

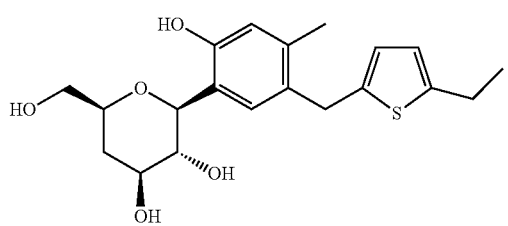 [SMILES: CCc1ccc(Cc2cc([C@@H]3O[C@H](CO)C[C@H](O)[C@H]3O)c(O)cc2C)s1]

2S,3R,4S,6S)-2-(5-((5-ethylthiophen-2-yl)methyl)-2-hydroxy-4-methylphenyl)-6-(hydroxymethyl)tetrahydro-2H-pyran-3,4-diol (cmp. 32

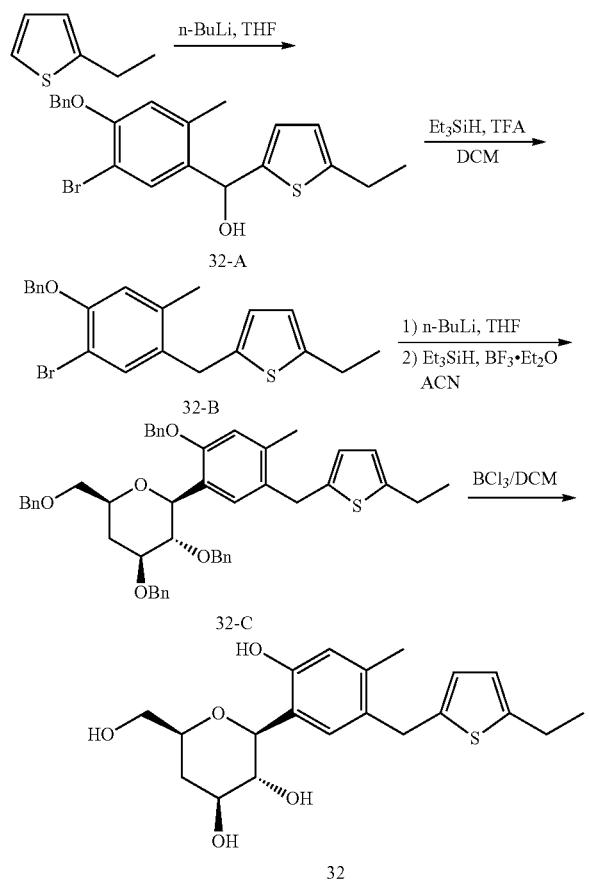

To 5-ethyl]thiophene (662 mg, 5.9 mmol) in 4 ml of anhydrous THF at −78° C. under argon was added n-BuLi (2.34 ml, 2.5 M in hexanes) and the resulting mixture was stirred at that temperature for 1 h, and then warmed up to 0° C. and stirred at the temperature for 10 minutes, then 4-(benzyloxy)-5-bromo-2-methylbenzaldehyde (1.5 g, 4.9 mmol) in 15 ml of THF was added dropwise over 5 mins at −78° C. The reaction mixture was stirred at −78° C. for 1 h, then was warmed up to RT. It was then quenched with aq. NH$_4$Cl solution, extracted with EtOAc three times. The combined organic layer was washed with brine, dried with Na$_2$SO$_4$ and the solvent was evaporated. The residue was purified by flash column chromatography on silica gel (40 g column, EtOAc/heptane: 0>>>15%) to yield 1.38 g (61%) of 32-A as a white solid. $^1$H NMR (CDCl$_3$) δ 7.82 (s, 1H), 7.48 (d, J=7.1 Hz, 2H), 7.39 (t, J=7.1 Hz, 2H), 7.33 (d, J=7.1 Hz, 1H), 6.71 (s, 1H), 6.63 (d, J=3.0 Hz, 1H), 6.59 (d, J=3.0 Hz, 1H), 6.01 (d, J=3.5 Hz, 1H), 5.12 (s, 2H), 2.79 (q, J=7.6 Hz, 2H), 2.29 (d, J=3.5 Hz, 1H), 2.18 (s, 3H), 1.26 (t, J=7.6 Hz, 3H). MS (ES) 439 (M+Na$^+$).

A 250 ml round bottom flask was charged with 32-A (1.03 g, 2.47 mmol) and 15 ml of DCM was added. The mixture was degassed and put under argon. To the mixture was added triethylsilane (0.59 ml, 3.7 mmol) at 0° C., followed by dropwise addition of TFA (0.25 ml, 3.2 mmol) in DCM (2 mL). The reaction mixture was kept stirring at 0° C. for 1 h. Saturated aqueous NaHCO$_3$ was added and the mixture was extracted with DCM. The organic layer was washed with brine, dried with Na$_2$SO$_4$, and evaporated to give a colorless oil, which was purified by flash column chromatography on silica gel (40 g Combiflash column, EtOAc/heptane: 0>>>10%) to afford 0.82 g (83%) of 32-B as a brown solid. $^1$H NMR (CDCl$_3$) δ 7.48 (d, J=7.6 Hz, 2H), 7.41-7.32 (m, 4H), 6.76 (s, 1H), 6.56 (d, J=3.0 Hz, 1H), 6.49 (d, J=3.0 Hz, 1H), 5.12 (s, 2H), 3.96 (s, 2H), 2.76 (q, J=7.6 Hz, 2H), 2.23 (s, 3H), 1.26 (t, J=7.6 Hz, 3H).

Compound 32-B (512 mg, 1.28 mmol) was dissolved in 2 ml of anhydrous THF, cooled to −78° C. in an acetone-dry ice bath. The solution was degassed and put under argon. To the above solution was added n-BuLi (0.80 ml, 1.6 M in hexanes) and the mixture was stirred at −78° C. for 1 h. Lactone (552 mg, 1.28 mmol) in 2 ml of anhydrous THF was added dropwise and the resulting mixture was stirred at that temperature for 4 h, quenched with aq. NH$_4$Cl, extracted with EtOAc three times. The organic extracts were dried with Na$_2$SO$_4$ and the solvent was evaporated and the residue was dried in vacuo for 2 h, then dissolved in 6 ml of anhydrous MeCN, cooled to 0° C., degassed and re-filled with argon. To the solution was added 0.25 ml of triethylsilane (1.6 mmol) and the mixture was stirred for 5 min, then 0.15 ml of BF$_3$.Et$_2$O was added and the mixture was stirred at 0° C. (ice-bath) and stirred at 0° C. for 1 h. It was quenched with saturated aq. NaHCO$_3$ solution, extracted with DCM three times. The extracts were dried with Na$_2$SO$_4$ and the drying agent was filtered off. The solvent was evaporated. The residue was purified by flash column chromatography on silica gel (12 g, EtOAc/heptane: 0>>>30%) to yield 400 mg (44.4% over two steps) of 32-C as a colorless gel (white foam after dried in vacuo). $^1$H NMR (CDCl$_3$) δ 7.38-7.14 (m, 19H), 6.98-6.96 (m, 2H), 6.71 (s, 1H), 6.49 (d, J=3.0 Hz, 1H), 6.44 (d, J=3.0 Hz, 1H), 4.97 (s, 2H), 4.68 (q, J=11.6 Hz, 3H), 4.46 (d, J=10.6 Hz, 1H), 4.45 (s, 2H), 4.09-3.95 (m, 3H), 3.78-3.71 (m, 1H), 3.61 (dd, J=10.1, 5.6 Hz, 1H), 3.46 (dd, J=10.1, 5.1 Hz, 1H), 2.67 (q J=7.6 Hz, 2H), 2.29 (m, 1H), 2.25 (s, 3H), 1.58 (q, J=11.6 Hz, 1H), 1.17 (t, J=7.6 Hz, 3H). MS (ES) 761.3 (M+Na$^+$).

To a mixture of 32-C (400 mg, 0.54 mmol) and pentamethylbenzene (722 mg, 4.9 mmol) in DCM (12 ml) was added BCl$_3$ (3.3 ml, 1M in DCM) at −78° C. under argon. The resulting brownish mixture was stirred at that temperature for 1.5 h, quenched with MeOH (1 ml). After stirring for 10 min, the volatiles were removed under reduced pressure and the residue was purified by flash column chromatography on silica gel (12 g column, EtOAc/heptanes: 0>>>100) to yield 150 mg (73%) of 32 as a white solid. $^1$H NMR (CD$_3$OD) δ 7.15 (s, 1H), 6.63 (s, 1H), 6.52 (s, 1H), 6.44 (s, 1H), 4.45 (d, J=9.6 Hz, 1H), 3.96 (s, 2H), 3.67 (br, 2H), 3.57 (s, 2H), 3.44 (t, J=9.1 Hz, 1H), 2.70 (q, J=7.1 Hz, 2H), 2.17 (s, 3H), 2.00 (bs, 1H), 1.52 (q, J=11.6 Hz, 1H), 1.22 (m, 3H). MS (ES) 401.1 (M+Na$^+$).

Example 33

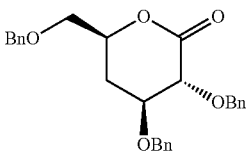 [SMILES: O=C1O[C@H](COCc2ccccc2)C[C@H](OCc2ccccc2)[C@H]1OCc1ccccc1]

3R,4S,6S)-3,4-bis(benzyloxy)-6-((benzyloxy)methyl)tetrahydro-2H-pyran-2-one (intermediate 8

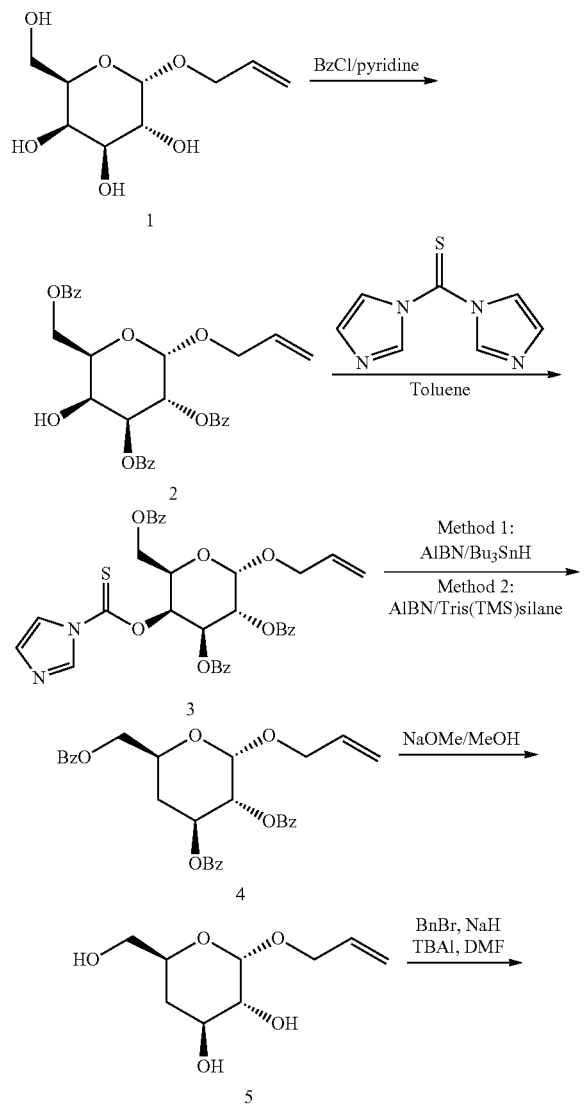

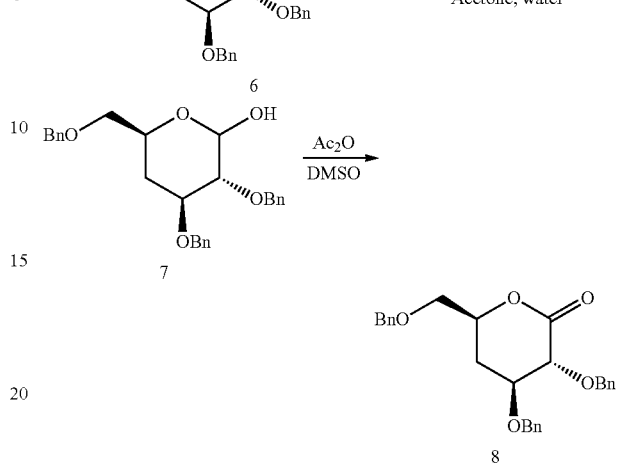

To a solution of allyl α-D-glactonpyranoside (1, 5.0 g, 22.7 mmol) in 100 mL of dry pyridine at −35~−30° C. was added benzoyl chloride dropwise with stirring. The reaction mixture was stirred at that temperature for 20 mins, then warmed to room temperature and stirred at room temperature for 48 h. The reaction was quenched by the dropwise addition of the reaction mixture to 200 ml of ice-cold saturated aqueous sodium bicarbonate with stirring. The aqueous mixture was extracted with EtOAc three times (150 ml each time). The combined extracts were washed with 1N HCl six times, brine, dried over Na$_2$SO$_4$, then evaporated to dryness in vacuo to give the crude product as light orange oil, which was purified by flash column chromatography on silica gel (150 g AnaLogix column, EtOAc/heptane: 0>>>5%>>>15%>>>35%) to yield compound 2 (8.55 g, 70.7%) as a white solid. $^1$H NMR (CDCl$_3$) δ 8.07 (s, 1H), 8.05 (d, J=1.01 Hz, 1H), 8.01 (dd, J=3.03, 1.52 Hz, 2H), 7.99 (dd, J=3.03, 1.52 Hz, 2H), 7.59 (m, 1H), 7.52 (m, 2H), 7.46 (t, J=7.58 Hz, 2H), 7.35-7.42 (4H), 5.86 (ddd, J=16.67, 11.12, 5.56 Hz, 1H), 5.79 (dd, J=11.12, 0.03 Hz, 1H), 5.70 (dd, J=10.61, 3.54 Hz, 1H), 5.35 (d, J=3.54 Hz, 1H), 5.27 (dq, J=17.18, 1.52 Hz, 1H), 5.12 (dq, J=10.61, 1.52 Hz, 1H), 4.68 (dd, J=11.62, 6.57 Hz, 1H), 4.55 (dd, J=11.12, 6.57 Hz, 1H), 4.42 (m, 2H), 4.25 (m, 1H), 4.10 (m, 1H), 2.47 (d, J=4.04 Hz, 1H). MS (ES) 554.8 (M+Na$^+$).

Thiocarbonylimidazole (976 mg, 4.93 mol) was added to a solution of 2 (1.05 g, 1.97 mmol) in dry toluene (20 ml) and the resulting mixture was heated at reflux for 4.5 h. The solvent was evaporated under reduced pressure to dryness. The residue was purified by flash column chromatography on silica gel (40 g column, EtOAc/heptane: 0>>>10%>>>45%) to afford compound 3 (1.2 g, 94.7%) as a white foam. $^1$H NMR (CDCl$_3$) δ 8.40 (s, 1H), 7.97-8.03 (4H), 7.78 (dd, J=7.07, 1.52 Hz, 2H), 7.69 (t, J=1.52 Hz, 1H), 7.37-7.60 (7H), 7.31 (t, J=8.08 Hz, 2H), 7.12 (s, 1H), 6.64 (d, J=3.03 Hz, 1H), 6.07 (dd, J=10.61, 3.54 Hz, 1H), 5.87 (ddd, J=21.73, 10.61, 5.05 Hz, 1H), 5.62 (dd, J=10.61, 3.54 Hz, 1H), 5.47 (d, J=4.04 Hz, 1H), 5.30 (dd, J=17.18, 1.52 Hz, 1H), 5.18 (dd, J=10.61, 1.52 Hz, 1H), 4.73 (t, J=6.06 Hz, 1H), 4.58 (dd, J=11.62, 6.57 Hz, 1H), 4.38 (dd, J=11.62, 6.57 Hz, 1H), 4.30 (m, 1H), 4.12 (m, 1H). MS (ES) 643.2 (MH$^+$).

Method 1:

To compound 3 (1.20 g, 1.87 mmol) in 30 ml of anhydrous toluene was added AIBN (31.3 mg, 0.19 mmol) and the mixture was degassed under high vacuum, then put under argon atmosphere. Thereto was added neat Bu$_3$SnH (0.74 ml, 2.8 mmol) and the resulting mixture was heated at reflux for 16 h. The solvent was evaporated under reduced pressure and the residue was purified by flash column chromatography on silica gel (80 g, EtOAc/heptane: 0>>>10%>>>15%) to give compound 4 (840 mg, 87.1%) as a white solid.

Method 2:

Under argon, tris(trimethylsilyl)silane (1.8 ml, 5.6 mmol) and AIBN (123 mg, 0.75 mmol) were added to a solution of compound 3 (2.40 g, 3.73 mmol) in toluene (50 ml). The mixture was heated to reflux for 7 h. Then the solvent was concentrated in vacuo. The residue was purified by flash column chromatography on silica gel (EtOAc/heptane: 0>>>10%>>>25%) to afford compound 4 (1.5 g, 77.8%) as a white foam. $^1$H NMR (CDCl$_3$) δ 8.08 (dd, J=8.08, 1.01 Hz, 2H), 8.02 (dd, J=8.59, 1.52 Hz, 2H), 7.97 (dd, J=8.59, 1.52 Hz, 2H), 7.58 (m, 1H), 7.43-7.54 (4H), 7.38 (q, J=7.58 Hz, 4H), 5.78-5.92 (2H), 5.35 (dd, J=10.11, 3.54 Hz, 1H), 5.31 (d, J=3.54 Hz, 1H), 5.29 (dq, J=17.18, 1.52 Hz, 1H), 5.13 (dq, J=10.61, 1.52 Hz, 1H), 4.40-4.50 (3H), 4.26 (ddt, J=13.64, 5.05, 1.01 Hz, 1H), 4.06 (ddt, J=13.14, 6.06, 1.52 Hz, 1H), 2.49 (ddd, J=13.14, 5.05, 1.52 Hz, 1H), 1.91 (m, 1H). MS (ES) 539.10 (M+Na$^+$).

To a suspension of compound 4 (9.0 g, 17.42 mmol) in 200 ml of anhydrous MeOH was added 30% NaOMe (1.45 ml, 7.84 mmol) in MeOH and the resulting mixture was stirred at room temperature for 16 h. The base was neutralized with Dowex 50WX8 (H+) ion-exchange resin, the suspension was filtered, and the filtrate was concentrated and the residue was purified by flash column chromatography on silica gel (40 g column, Teledyne ISCO/Combiflash, DCM/MeOH: 0>>>20%) to yield compound 5 (3.55 g, 100%) as a colorless syrup. $^1$H NMR (CD$_3$OD) δ 5.96 (m, 1H), 5.35 (dd, J=3.03, 1.52 Hz, 1H), 5.30 (dd, J=3.54, 1.52 Hz, 1H), 5.16 (dq, J=10.61, 2.02 Hz, 1H), 4.86 (d, J=4.04 Hz, 1H), 4.21 (ddt, J=12.63, 5.05, 1.52 Hz, 1H), 4.01 (ddt, J=12.63, 6.06, 1.52 Hz, 1H), 3.81-3.90 (2H), 3.52 (d, J=5.56 Hz, 2H), 3.33 (dd, J=9.09, 5.05 Hz, 1H), 1.92 (ddd, J=12.63, 5.05, 2.53 Hz, 1H), 1.36 (q, J=12.13 Hz, 1H). MS (ES) 207.1 (M+Na$^+$).

To a mixture of compound 5 (3.27 g, 16.01 mmol), sodium hydride (3.84 g, 96.07 mmol, 60% in mineral oil) and TBAI (5.91 g, 16.01 mmol) was added 100 ml of anhydrous DMF under argon atmosphere at 0° C. and the resulting mixture was stirred at 0° C. for 30 min. Neat benzyl bromide (9.13 ml, 76.9 mmol) was added and the reaction mixture was stirred at room temperature for 2 days. It was quenched with aqueous NH$_4$Cl solution and extracted with EtOAc three times. The combined organic layers were washed with brine, dried with Na$_2$SO$_4$, filtered and concentrated. The crude residue was purified by flash column chromatography on silica gel (120 g column, EtOAc/heptane: 0>>>5%) to yield compound 6 (6.89 g, 90.7%) as a colorless oil. $^1$H NMR (CDCl$_3$) δ 7.27-7.38 (15H), 5.94 (m, 1H), 5.31 (dd, J=17.18, 1.52 Hz, 1H), 5.20 (dd, J=10.61, 1.52 Hz, 1H), 4.88 (d, J=3.54 Hz, 1H), 4.82 (d, J=12.13 Hz, 1H), 4.76 (d, J=11.62 Hz, 1H), 4.68 (dd, J=12.13, 2.02 Hz, 2H), 4.55 (s, 2H), 4.17 (m, 1H), 3.93-4.06 (3H), 3.49 (dd, J=9.60, 4.04 Hz, 1H), 3.47 (d, J=4.04 Hz, 2H), 2.08 (ddd, J=12.63, 5.05, 2.02 Hz, 1H), 1.53 (q, J=11.62 Hz, 1H). MS (ES) 497.2 (M+Na$^+$).

[(Ph$_3$P)$_3$RhCl] (760 mg, 0.82 mmol) and DABCO (2300.9 mg, 20.5 mmol) was added a 250 ml round-bottle flask under argon. To which was added EtOH/H$_2$O (80 ml, 10:1 v/v) solution of compound 6 (6.49 g, 13.7 mmol) and the resulting mixture was heated under reflux overnight, then diluted with DCM (80 ml) and washed with saturated aqueous NaHCO$_3$ (20 ml) and brine (15 ml). The solvents were removed under reduced pressure. The crude residue was dissolved in acetone/H$_2$O (10:1 v/v, 88 ml). NMO (1.98 g, 16.41 mmol) and OsO$_4$ (1000 μL, 2.5% solution in i-PrOH) were added and the reaction was monitored by TLC. Until all the starting material was consumed, the reaction mixture was concentrated under reduced pressure and the residue was diluted with EtOAc (200 ml) and washed with saturated aqueous NaHCO$_3$ (20 ml) and brine (15 ml). The organic layer was dried with Na$_2$SO$_4$ and the solvent was removed under reduced pressure. The residue was purified by flash column chromatography on silica gel (EtOAc/heptane: 0>>>20%>>>30%) to yield compound 7 (4.82 g, 81.1%) as a light brown syrup. MS (ES) 457.2 (M+Na$^+$).

Compound 7 (4.82 g, 11.09 mmol) was dissolved in 30 ml of DMSO. Acetic anhydride (12.6 ml, 133.1 mmol) was added to the above solution under argon at room temperature and the reaction mixture was kept stirring at room temperature overnight. Then it was diluted with 250 ml of saturated NaHCO$_3$ solution and the resulting mixture was stirred at room temperature for 1.5 h. It was extracted with EtOAc (5×40 ml). The organic layers were combined and washed with brine, dried with Na$_2$SO$_4$, the solvent was evaporated and the residue was purified by flash column chromatography on silica gel (EtOAc/heptane: 0>>>20%, 120 g column) to yield the lactone 8 (4.13 g, 86.1%) as a colorless oil. $^1$H NMR (CDCl$_3$) δ 7.26-7.42 (15H), 5.03 (d, J=11.12 Hz, 1H), 4.71 (d, J=11.12 Hz, 1H), 4.65 (d, J=12.13 Hz, 1H), 4.59 (d, J=11.62 Hz, 1H), 4.57 (s, 2H), 4.50 (m, 1H), 4.05 (d, J=7.07 Hz, 1H), 3.91 (m, 1H), 3.61 (ddd, J=13.14, 8.59, 4.55 Hz, 2H), 2.32 (ddd, J=14.15, 5.05, 3.54 Hz, 1H), 1.91 (m, 1H). MS (ES) 473.25 (M+Na$^+$).

D) General Administration, Formulation, and Dosages

The present invention provides substituted heteroaryl ketone compounds which are useful as SGLT inhibitors.

The invention features a method for treating a subject in need thereof with an SGLT-mediated disease, said method comprising administering to the subject a therapeutically effective amount of a compound of the invention. In particular, the invention also provides a method for treating or inhibiting the progression of an SGLT-mediated disease, and associated symptoms or complications thereof in a subject, wherein the method comprises administering to the subject a therapeutically effective amount of a compound of the invention.

Embodiments of the present invention include a method wherein the compound of Formula (I) is a SGLT inhibitor.

Embodiments of the present invention include a use of the compound of Formula (I) in the manufacture of a medicament for treating an SGLT-mediated condition.

Embodiments of the present invention include a use of the compound of Formula (I) as a medicine.

The compounds of Formula (I) have an SGLT-inhibiting effect and are useful as therapeutic agents for various SGLT-mediated disorders, for example, diabetes, Syndrome X, or associated symptoms or complications. More specifically, diabetes, Syndrome X, and their associated symptoms or complications include, but are not limited to, IDDM, NIDDM, IGT, IFG, obesity, nephropathy, neuropathy, retinopathy, atherosclerosis, polycystic ovarian syndrome, hypertension, ischemia, stroke, heart disease, irritable bowel disorder, inflammation, and cataracts.

The compounds of Formula (I) may be administered orally or parenterally, and after formulation into preparations suitable for the intended administration route, they can be used as therapeutic agents for treating an SGLT-mediated condition. The following "diabetes related disorders" are diseases, disorders and conditions that are related to Type 2 diabetes, and therefore may be treated, controlled or in some cases prevented, by treatment with the compounds of this invention: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequalae, (13) vascular restenosis, (14) irritable bowel syndrome, (15) inflammatory bowel disease, including Crohn's disease and ulcerative colitis, (16) other inflammatory conditions, (17) pancreatitis, (18) abdominal obesity, (19) neurodegenerative disease, (20) retinopathy, (21) nephropathy, (22) neuropathy, (23) Syndrome X, (24) ovarian hyperandrogenism (polycystic ovarian syndrome), and other disorders where insulin resistance is a component.

One aspect of the present invention provides a method for the treatment of disorders, diseases or conditions responsive to the modulation of SGLT in a subject in need thereof which comprises administering to the subject a therapeutically or prophylactically effective amount of a compound of Formula (I) or a form thereof.

Another aspect of the present invention provides a method for the treatment of a disorder selected from the group consisting of IDDM, NIDDM, IGT, IFG, obesity, nephropathy, neuropathy, retinopathy, atherosclerosis, polycystic ovarian syndrome, hypertension, ischemia, stroke, heart disease, irritable bowel disorder, inflammation, and cataracts, in a subject in need thereof which comprises administering to the subject a therapeutically or prophylactically effective amount of a compound of Formula (I) or a form thereof.

Another aspect of the present invention provides a pharmaceutical composition comprising at least one compound of Formula (I) or a form thereof, and a pharmaceutically acceptable carrier.

The invention also features a method for treating a subject in need thereof with an SGLT-mediated disease, said method comprising administering to the subject a therapeutically effective amount of a pharmaceutical composition comprising at least one compound of the invention.

Yet another aspect of the present invention relates to the use of a compound of Formula (I) or a form thereof, for the manufacture of a medicament useful for the treatment of an SGLT-mediated disorder in a subject in need thereof.

In a clinical use of the compounds of the invention, pharmaceutically-acceptable additives may be added thereto to formulate various preparations in accordance with the intended administration route thereof, and the preparations may be administered.

Various additives generally used in the field of pharmaceutical compositions may be used herein, including, for example, gelatin, lactose, sucrose, titanium oxide, starch, crystalline cellulose, methyl cellulose, hydroxypropylmethyl cellulose, carboxymethyl cellulose, corn starch, microcrystalline wax, white petrolatum, magnesium metasilicate aluminate, anhydrous calcium phosphate, citric acid, trisodium citrate, hydroxypropyl cellulose, sorbitol, sorbitan fatty acid ester, polysorbate, sucrose fatty acid ester, polyoxyethylene, hardened castor oil, polyvinylpyrrolidone, magnesium stearate, palmitoleic acid, light silicic acid anhydride, talc, vegetable oil, benzyl alcohol, gum arabic, propylene glycol, polyalkylene glycol, cyclodextrin, and hydroxypropylcyclodextrin.

Combined with such additives, the compound of the invention may be formulated into various forms of preparations, for example, solid preparations such as tablets, capsules, granules, powders and suppositories; and liquid preparations such as syrups, elixirs and injections. These preparations can be produced in any method known in the field of pharmaceutical compositions. The liquid preparations may be in such a form that is dissolved or suspended in water or in any other suitable medium before use. Especially for injections, the preparation may be dissolved or suspended, if desired, in a physiological saline or glucose solution, and a buffer and a preservative may be added thereto.

The compounds of the invention are effective for animals, including humans and other mammals. Any ordinary physician, veterinarian or clinician may readily determine the necessity, if any, of treatment with an instant compound.

Those of skill in the treatment of disorders, diseases, or conditions mediated by SGLT can determine the effective daily amount from the test results presented hereinafter and other information. The exact dosage and frequency of administration depends on the particular compound of invention used, the particular condition being treated, the severity of the condition being treated, the age, weight and general physical condition of the particular patient as well as other medication the patient may be taking, as is well known to those skilled in the art. Furthermore, it is evident that said effective daily amount may be lowered or increased depending on the response of the treated patient and/or depending on the evaluation of the physician prescribing the compounds of the instant invention. The effective daily amount ranges mentioned herein are therefore only guidelines in practicing the present invention.

Preferably, the method for the treatment of the SGLT disorders described in the present invention using any of the compounds as defined herein, the dosage form will contain a pharmaceutically acceptable carrier containing between from about 1 mg to about 1000 mg; particularly from about 0.5 mg to about 500 mg of the compound, and may be constituted into any form suitable for the mode of administration selected. The dosages, however, may be varied depending upon the requirement of the subjects, the severity of the condition being treated and the compound being employed. The use of either daily administration or post-periodic dosing may be employed.

When the compound of the invention is, for example, put into clinical use, then its dose and its administration frequency may vary depending on the sex, the age, the body weight and the condition of the patient and on the type and the range of the necessary treatment with the compound. For oral administration, in general, the dose of the compound may be in a range of from about 0.01 mg/kg/day to about 100 mg/kg of body weight/day or in a range of from about 0.03 mg/kg/day to about 1 mg/kg/day. The oral administration frequency is preferably from one to a few times per day. For parenteral administration, the dose may be in a range of from about 0.001 mg/kg/day to about 10 mg/kg/day, in a range of from about 0.001 mg/kg/day to about 0.1 mg/kg/day or, in a range of from about 0.01 mg/kg/day to about 0.1 mg/kg/day. The parenteral administration frequency is preferably from one to a few times per day. For oral administration, the compositions are preferably provided in the form of tablets containing from about 1.0 mg to about 1000 mg of the active ingredient, particularly 1 mg, 5 mg, 10 mg, 15 mg, 20 mg, 25 mg, 50 mg, 75 mg, 100 mg, 150 mg, 200 mg, 250 mg, 300 mg, 400 mg, 500 mg, 600 mg, 750 mg, 800 mg, 900 mg, and 1000 mg of the active ingredient for the symptomatic adjustment of the dosage to the patient to be treated. The compounds may be administered on a regimen of 1 to 4 times per day, preferably once or twice per day.

When treating an SGLT mediated disorder selected from one or more of . . . disease, a therapeutic effect is expected upon administering the compounds of the present invention at a daily dosage of from about 0.1 mg to about 100 mg/kg of body weight. The dosing regimen may range from a single daily dose or a divided dose two to six times a day, or in sustained release form. For a large mammal, the total daily dosage may be in a range of from about 1 mg to about 1000 mg, or a range of from about 1 mg to about 50 mg. In the case of a 70 kg adult human, the total daily dose will generally be from about 7 mg to about 350 mg. This dosage regimen may be adjusted to provide the optimal therapeutic response.

Ordinary physicians, veterinarians and clinicians may readily determine the effective dose of the pharmaceutical compound necessary to treat, prevent, inhibit, retard or stop the intended disease, and may readily treat the diseased patient with the compound.

The pharmaceutical compositions herein will contain, per unit dosage unit, e.g., tablet, capsule, powder, injection, suppository, teaspoonful and the like, of from about 0.001 mg/kg/day to about 10 mg/kg/day (particularly from about 0.01 mg/kg/day to about 1 mg/kg/day; and, more particularly, from about 0.1 mg/kg/day to about 0.5 mg/kg/day) and may be given at a dosage of from about 0.001 mg/kg/day to about 30 mg/kg/day (particularly from about 0.01 mg/kg/day to about 2 mg/kg/day, more particularly from about 0.1 mg/kg/day to about 1 mg/kg/day and even more particularly from about 0.5 mg/kg/day to about 1 mg/kg/day).

Preferably these compositions are in unit dosage forms from such as tablets, pills, capsules, dry powders for reconstitution or inhalation, granules, lozenges, sterile parenteral solutions or suspensions, metered aerosol or liquid sprays, drops, ampoules, autoinjector devices or suppositories for administration by oral, intranasal, sublingual, intraocular, transdermal, parenteral, rectal, vaginal, dry powder inhaler or other inhalation or insufflation means. Alternatively, the composition may be presented in a form suitable for 1 to 4 times per day, preferably once or twice per day administration; for example, an insoluble salt of the active compound, such as the decanoate salt, may be adapted to provide a depot preparation for intramuscular injection.

The preparation may contain the compound of the invention in an amount in a range of from about 1.0 to about 100% by weight or, in a range of from about 1.0 to about 60% by weight of the preparation. The preparation may contain any other therapeutically-effective compound.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the subject. Conventional procedures for the selection and preparation of suitable prodrug derivatives are described, for example, in "*Design of Prodrugs*", ed. H. Bundgaard, Elsevier, 1985.

Some of the crystalline forms for the compounds may exist as polymorphs and as such are intended to be included in the present invention. In addition, some of the compounds may form solvates with water (i.e., hydrates) or common organic solvents, and such solvates are intended to be encompassed within the scope of this invention.

Where the processes for the preparation of the compounds according to the invention give rise to mixtures of stereoisomers, these isomers may be separated by conventional techniques such as preparative chromatography. The compounds may be prepared in racemic form or as individual enantiomers or diastereomers by either stereospecific synthesis or by resolution. The compounds may, for example, be resolved into their component enantiomers or diastereomers by standard techniques, such as the formation of stereoisomeric pairs by salt formation with an optically active base, followed by fractional crystallization and regeneration of the free acid. The compounds may also be resolved by formation of stereoisomeric esters or amides, followed by chromatographic separation and removal of the chiral auxiliary. Alternatively, the compounds may be resolved using a chiral HPLC column. It is to be understood that all stereoisomers, racemic mixtures, diastereomers, cis-trans isomers, and enantiomers thereof are encompassed within the scope of the present invention.

E) Use

Dosages

For preparing pharmaceutical compositions such as tablets, the principal active ingredient is mixed with a pharmaceutical carrier, e.g. conventional tableting ingredients such as diluents, binders, adhesives, disintegrants, lubricants, antiadherents and gildants. Suitable diluents include, but are not limited to, starch (i.e. corn, wheat, or potato starch, which may be hydrolized), lactose (granulated, spray dried or anhydrous), sucrose, sucrose-based diluents (confectioner's sugar; sucrose plus about 7 to 10 weight percent invert sugar; sucrose plus about 3 weight percent modified dextrins; sucrose plus invert sugar, about 4 weight percent invert sugar, about 0.1 to 0.2 weight percent cornstarch and magnesium stearate), dextrose, inositol, mannitol, sorbitol, microcrystalline cellulose (i.e. AVICEL™ microcrystalline cellulose available from FMC Corp.), dicalcium phosphate, calcium sulfate dihydrate, calcium lactate trihydrate and the like. Suitable binders and adhesives include, but are not limited to acacia gum, guar gum, tragacanth gum, sucrose, gelatin, glucose, starch, and cellulosics (i.e. methylcellulose, sodium carboxymethylcellulose, ethylcellulose, hydroxypropylmethylcellulose, hydroxypropylcellulose, and the like), water soluble or dispersible binders (i.e. alginic acid and salts thereof, magnesium aluminum silicate, hydroxyethylcellulose [i.e. TYLOSE™ available from Hoechst Celanese], polyethylene glycol, polysaccharide acids, bentonites, polyvinylpyrrolidone, polymethacrylates and pregelatinized starch) and the like. Suitable disintegrants include, but are not limited to, starches (corn, potato, etc.), sodium starch glycolates, pregelatinized starches, clays (magnesium aluminum silicate), celluloses (such as crosslinked sodium carboxymethylcellulose and microcrystalline cellulose), alginates, pregelatinized starches (i.e. corn starch, etc.), gums (i.e. agar, guar, locust bean, karaya, pectin, and tragacanth gum), crosslinked polyvinylpyrrolidone and the like. Suitable lubricants and antiadherents include, but are not limited to, stearates (magnesium, calcium and sodium), stearic acid, talc waxes, stearowet, boric acid, sodium chloride, DL-leucine, carbowax 4000, carbowax 6000, sodium oleate, sodium benzoate, sodium acetate, sodium lauryl sulfate, magnesium lauryl sulfate and the like. Suitable gildants include, but are not limited to, talc, cornstarch, silica (i.e. CAB-O-SIL™ silica available from Cabot, SYLOID™ silica available from W.R. Grace/Davison, and AEROSIL™ silica available from Degussa) and the like. Sweeteners and flavorants may be added to chewable solid dosage forms to improve the palatability of the oral dosage form. Additionally, colorants and coatings may be added or applied to the solid dosage form for ease of identification of the drug or for aesthetic purposes. These carriers are formulated with the pharmaceutical active to provide an accurate, appropriate dose of the pharmaceutical active with a therapeutic release profile.

Generally these carriers are mixed with the pharmaceutical active to form a solid preformulation composition containing a homogeneous mixture of the pharmaceutical active form of the present invention, or a pharmaceutically acceptable salt thereof. Generally the preformulation will be formed by one of three common methods: (a) wet granulation, (b) dry granulation and (c) dry blending. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.1 mg to about 500 mg of the active ingredient of the present invention. The tablets or pills containing the novel compositions may also be formulated in multilayer tablets or pills to provide a sustained or provide dual-release products. For example, a dual release tablet or pill can comprise an inner dosage and an outer dosage component, the latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric materials such as shellac, cellulose acetate (i.e. cellulose acetate phthalate, cellulose acetate trimellitate), polyvinyl acetate phthalate, hydroxypropyl methylcellulose phthalate, hydroxypropyl methylcellulose acetate succinate, methacrylate and ethylacrylate copolymers, methacrylate and methyl methacrylate copolymers and the like. Sustained release tablets may also be made by film coating or wet granulation using slightly soluble or insoluble substances in solution (which for a wet granulation acts as the binding agents) or low melting solids a molten form (which in a wet granulation may incorporate the active ingredient). These materials include natural and synthetic polymers waxes, hydrogenated oils, fatty acids and alcohols (i.e. beeswax, carnauba wax, cetyl alcohol, cetylstearyl alcohol, and the like), esters of fatty acids metallic soaps, and other acceptable materials that can be used to granulate, coat, entrap or otherwise limit the solubility of an active ingredient to achieve a prolonged or sustained release product.

The liquid forms in which the novel compositions of the present invention may be incorporated for administration orally or by injection include, but are not limited to aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable suspending agents for aqueous suspensions, include synthetic and natural gums such as, acacia, agar, alginate (i.e. propylene alginate, sodium alginate and the like), guar, karaya, locust bean, pectin, tragacanth, and xanthan gum, cellulosics such as sodium carboxymethylcellulose, methylcellulose, hydroxymethylcellulose, hydroxyethylcellulose, hydroxypropyl cellulose and hydroxypropyl methylcellulose, and combinations thereof, synthetic polymers such as polyvinyl pyrrolidone, carbomer (i.e. carboxypolymethylene), and polyethylene glycol; clays such as bentonite, hectorite, attapulgite or sepiolite; and other pharmaceutically acceptable suspending agents such as lecithin, gelatin or the like. Suitable surfactants include but are not limited to sodium docusate, sodium lauryl sulfate, polysorbate, octoxynol-9, nonoxynol-10, polysorbate 20, polysorbate 40, polysorbate 60, polysorbate 80, polyoxamer 188, polyoxamer 235 and combinations thereof. Suitable deflocculating or dispersing agents include pharmaceutical grade lecithins. Suitable flocculating agents include but are not limited to simple neutral electrolytes (i.e. sodium chloride, potassium, chloride, and the like), highly charged insoluble polymers and polyelectrolyte species, water soluble divalent or trivalent ions (i.e. calcium salts, alums or sulfates, citrates and phosphates (which can be used jointly in formulations as pH buffers and flocculating agents). Suitable preservatives include but are not limited to parabens (i.e. methyl, ethyl, n-propyl and n-butyl), sorbic acid, thimerosal, quaternary ammonium salts, benzyl alcohol, benzoic acid, chlorhexidine gluconate, phenylethanol and the like. There are many liquid vehicles that may be used in liquid pharmaceutical dosage forms; however, the liquid vehicle that is used in a particular dosage form must be compatible with the suspending agent(s). For example, nonpolar liquid vehicles such as fatty esters and oils liquid vehicles are best used with suspending agents such as low HLB (Hydrophile-Lipophile Balance) surfactants, stearalkonium hectorite, water insoluble resins, water insoluble film forming polymers and the like. Conversely, polar liquids such as water, alcohols, polyols and glycols are best used with suspending agents such as higher HLB surfactants, clays silicates, gums, water soluble cellulosics, water soluble polymers and the like. For parenteral administration, sterile suspensions and solutions are desired. Liquid forms useful for parenteral administration include sterile solutions, emulsions and suspensions. Isotonic preparations which generally contain suitable preservatives are employed when intravenous administration is desired.

Furthermore, compounds of the present invention can be administered in an intranasal dosage form via topical use of suitable intranasal vehicles or via transdermal skin patches, the composition of which are well known to those of ordinary skill in that art. To be administered in the form of a transdermal delivery system, the administration of a therapeutic dose will, of course, be continuous rather than intermittent throughout the dosage regimen.

Compounds of the present invention can also be administered in the form of liposome delivery systems, such as small unilamellar vesicles, large unilamellar vesicles, multilamellar vesicles and the like. Liposomes can be formed from a variety of phospholipids, such as cholesterol, stearylamine, phosphatidylcholines and the like.

The daily dose of a pharmaceutical composition of the present invention may be varied over a wide range from about 0.1 mg to about 5000 mg; preferably, the dose will be in the range of from about 1 mg to about 100 mg per day for an average human. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 or 500 milligrams of the active ingredient for the symptomatic adjustment of the dosage to the subject to be treated. Advantageously, a compound of the present invention may be administered in a single daily dose or the total daily dosage may be administered in divided doses of two, three or four times daily.

It is also apparent to one skilled in the art that the therapeutically effective dose for active compounds of the invention or a pharmaceutical composition thereof will vary according to the desired effect. Therefore, optimal dosages to be administered may be readily determined by those skilled in the art, and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

Compounds of this invention may be administered in any of the foregoing compositions and dosage regimens or by means of those compositions and dosage regimens established in the art whenever use of the compounds of the invention as SGLT inhibitors is required for a subject in need thereof.

In their use, the compounds of the invention may be combined with any other therapeutic agents that are useful for the treatment of an SGLT-mediated disorder.

The combination includes not only the composition of compounds of the invention and one other active substance but also the composition of compounds of the invention and two or more other active substances. The scope of possible combinations of a compound of the invention and one, two or more active substances are within the knowledge of one skilled in the art for the treatment of an SGLT-mediated disorder. For example, for the treatment and management of diabetes and Syndrome X, a combination of a compound of the invention and one, two or more active substances selected from SGLT inhibitors, RXR modulators, PPAR inhibitors, insulin, and the like is useful. In particular, a composition that also contains an glucose reabsorption agent, in addition to an insulin sensitizer agent and/or a antidiabetic agent, may exhibit a synergistic effect for treatment of diabetes or Syndrome X disease, or associated symptoms or complication thereof, which include, but are not limited to, hyperglycemia, IDDM, NIDDM, IGT, IFG, obesity, nephropathy, neuropathy, retinopathy, atherosclerosis, polycystic ovarian syndrome, hypertension, ischemia, stroke, heart disease, irritable bowel disorder, inflammation, and cataracts.

The compounds of the present invention may also be combined with a non-drug therapy such as kinesitherapy, dietetic treatment or radiation therapy. The compound and the combined compositions of the invention are effective for treating and preventing diabetes.

Formulations

To prepare the pharmaceutical compositions of this invention, one or more compounds of Formula (I) or salt thereof as the active ingredient, is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients,* published by the American Pharmaceutical Association and the Pharmaceutical Society of Great Britain.

The compounds of the present invention may be formulated into various pharmaceutical forms for administration purposes. Methods of formulating pharmaceutical compositions have been described in numerous publications such as *Pharmaceutical Dosage Forms: Tablets, Second Edition, Revised and Expanded,* Volumes 1-3, edited by Lieberman et al; *Pharmaceutical Dosage Forms: Parenteral Medications,* Volumes 1-2, edited by Avis et al; and *Pharmaceutical Dosage Forms: Disperse Systems,* Volumes 1-2, edited by Lieberman et al; published by Marcel Dekker, Inc.

F) Biological Examples

The ability of the compounds of the present invention to treat an SGLT-mediated condition was determined using the following procedures.

SGLT1 and SGLT2 were cloned in form of cDNA from human small intestine (Genbank M24847), and from human kidney (Genbank M95549), respectively. Subsequently, each full cDNA was subcloned into pcDNA with each construct's integrity verified through follow-on sequencing. To generate CHO-K1 cells that stably express human SGLT1 or human SGLT2 CHO-K1 cells were transfected using DMRIE-C reagent (Life Technologies, Gaithersburg, Md.). Transfected cells were then selected in the presence of 500 µg/ml of the antibiotic G418 (Gibco-BRL, Grand Island, N.Y.). Individual clones were then characterized using the following cell-based assay for sodium-dependent glucose transport.

First, cell lines stably expressing human SGLT1 or SGLT2 were seeded at a density of 65,000 cells per well per 200 µl cell culture medium with 10 mM of NaButyrate (Aldrich Catalog No. 30341-0) in a 96-well flat bottom plate (COSTAR, Catalog No. 3903). For human SGLT1 or SGLT2 expressing CHO-K1 cells the culture medium comprised Ham's F-12 (Invitrogen Catalog No. 31765), Fetal Bovine Serum (Invitrogen Catalog No. 16000), G418 (Geneticin, Cellgro Catalog No. 30234-CI), Phlorizidin (Sigma Catalog No. P3449), DPBS (Cellgro Catalog No. 21030-CV), $^{14}$C-methyl-α-D-glucopyranoside (Amersham Catalog No. CFB 76), and Methyl-α-D-glucopyranoside (Sigma Catalog No. M-9376).

The cells were allowed to incubate for 24 hours. Subsequently, the medium was aspirated from the plates and the cells were washed one time with 150 µl assay buffer and incubate 15 min with another 150 µl assay buffer which comprised 50 mM HEPES pH 7.4, 20 mM Tris Base, 5 mM KCl, 1 mM $MgCl_2$, 1 mM $CaCl_2$, and 137 mM NaCl. After removing the wash buffer, 40 µl assay buffer and 10 µl compound solution was added to each well, which was again allowed to incubate for 10 min.

Following the 10 min incubation, 10 µl of serial diluted Methyl-α-D-glucopyranoside (Sigma Catalog No. M-9376) containing 0.07 µCi $^{14}$C-methyl-α-D-glucopyranoside (Amersham Catalog No. CFB 76) was added to the appropriate well and allowed to incubate for another 2 hours. $^{14}$C-methyl-α-D-glucopyranoside (Sigma Catalog No. M-9376, St. Louis, Mo.) is a non-metabolizable glucose analog specific for sodium-dependent glucose transporters as previously described by H. Peng and J. E. Lever in "Post-transcriptional regulation of Na+/glucose cotransporter (SGLT1) gene expression in LLC-PK1 cells," *J. Biol. Chem.* 270, 20536-42 (1995).

Next, the plates were twice washed with 150 µl of ice-cold DPBS (Cellgro Catalog No. 21030) that was then completely removed from the plates before adding 50 µl of MicroScint™-20 (Packard Catalog No. 6013621) to each well for a 20 min or longer incubation time.

Sodium-dependent $^{14}$C-methyl-α-D-glucopyranoside uptake was quantified by measuring radioactivity. Plates were counted in a TopCount (Packard, Meriden, Conn.). Results are reported as the %-inhibition or $IC_{50}$ value from a representative experiment. Variability for the functional assay was typically within 20%. The %-inhibition or $IC_{50}$ data derived from the best curve fit is shown in Tables 2 and 3.

TABLE 2

In Vitro Potency in SGLT1 and SGLT2 assays

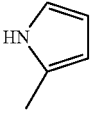

(I)

| Cpd | $R_1$ | $R_3$ | $R_2$ | $R_6$ | SGLT1 IC$_{50}$ (nM) | SGLT2 IC$_{50}$ (nM) | $R_4/R_5$ |
|---|---|---|---|---|---|---|---|
| 1 | OH | CH$_3$ | H | H | 117 | 16 | H/H |
| 2 | OH | OCH$_3$ | H | H | 155 | 114 | H/H |
| 3 | OH | Cl | H | H | 115 | 22 | H/H |
| 4 | OH | F | H | H | 893 | 128 | H/H |
| 5 | OH | OCH$_3$ | H | H | 0%@3 μM | 0%@3 μM | C=O |
| 6 | OH | CH$_3$ | H | H | 0%@3 μM | 0%@3 μM | C=O |
| 7 | OH | OCH$_3$ | H | H | 43%@3 μM | 6%@3 μM | =CH$_2$ |
| 8 | OH | CH$_3$ | H | H | 41%@3 μM | 25%@3 μM | =CH$_2$ |
| 9 | OH | OCH$_3$ | H | H | 49%@3 μM | 57%@3 μM | cy-C$_3$H$_5$ |
| 10 | OH | CH$_3$ | H | H | >3000 | 223 | cy-C$_3$H$_5$ |
| 11 | OH | C$_2$H$_5$ | H | H | 95%@3 μM | 61 | H/H |
| 12 | OH | cy-C$_3$H$_5$ | H | H | 99 | 683 | H/H |
| 13 | OH | CN | H | H | 57%@3 μM | 73%@0.3 μM | H/H |
| 14 | OH | OCH$_3$ | H | H | 46%@0.3 μM | 54%@0.3 μM | CH$_3$/CH$_3$ |
| 15 | OH | CH$_3$ | H | H | 52%@3 μM | 25%@0.3 μM | CH$_3$/CH$_3$ |
| 16 | OH | CF$_3$ | H | H | 240 | 77%@0.1 μM | H/H |
| 17 | OH | CH=CH$_2$ | H | H | 58%@0.1 μM | 64%@0.1 μM | H/H |
| 18 | OH | OH | H | H | 19%@3 μM | 13%@0.3 μM | C=O |
| 19 | OH | CH$_3$ | H | F | 220 | 41 | H/H |
| 20 | OH | CH$_3$ | H | Cl | 20%@0.1 μM | 84%@0.1 μM | H/H |
| 21 | OH | OCH$_3$ | F | H | 26%@0.1 μM | 78%@0.1 μM | H/H |
| 22 | OH | CH$_3$ | CH$_3$ | H | 39%@0.1 μM | 67%@0.1 μM | H/H |
| 23 | OCH$_3$ | CH$_3$ | CH$_3$ | H | 50%@0.1 μM | 70%@0.1 μM | H/H |
| 24 | OCH$_2$—CH=CH$_2$ | CH$_3$ | CH$_3$ | H | 31%@0.1 μM | 40%@0.1 μM | H/H |
| 25 | Br | CH$_3$ | H | H | 26%@0.1 μM | 47%@0.1 μM | H/H |
| 26 | 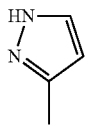 | CH$_3$ | H | H | 33%@0.1 μM | 57%@0.1 μM | H/H |
| 27 | HN-N (pyrazolyl with CH$_3$) | CH$_3$ | H | H | 734 | 10 | H/H |

TABLE 3

In Vitro Potency in SGLT1 and SGLT2 assays

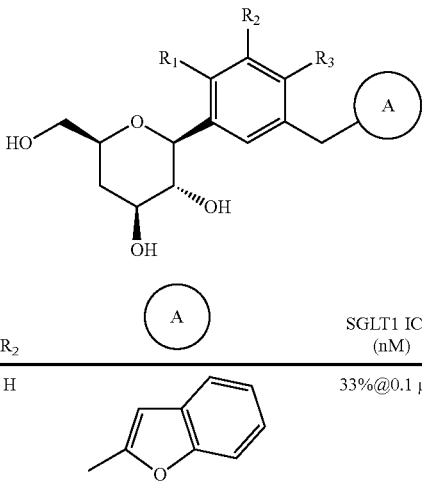

| Cpd | R$_1$ | R$_3$ | R$_2$ | A | SGLT1 IC$_{50}$ (nM) | SGLT2 IC$_{50}$ (nM) |
|---|---|---|---|---|---|---|
| 28 | OH | CH$_3$ | H | 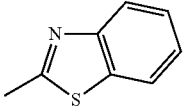 | 33%@0.1 μM | 69%@0.1 μM |
| 29 | OH | CH$_3$ | H | 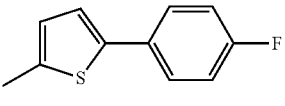 | 22%@0.1 μM | 41%@0.1 μM |
| 30 | Br | CH$_3$ | H | 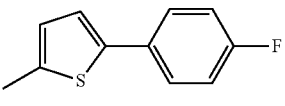 | 44%@0.1 μM | 73%@0.1 μM |
| 31 | OH | CH$_3$ | H | 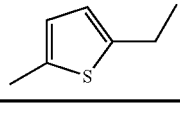 | 272 | 58%@0.1 μM |
| 32 | OH | CH$_3$ | H | | 97 | 4 |

Throughout this application, various publications are cited. The disclosure of these publications is hereby incorporated by reference into this application to describe more fully the state of the art to which this invention pertains.

While the foregoing specification teaches the principles of the present invention, with examples provided for the purpose of illustration, it will be understood that the practice of the invention encompasses all of the usual variations, adaptations and modifications as come within the scope of the following claims and their equivalents.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

The invention claimed is:
1. A compound of Formula (I)

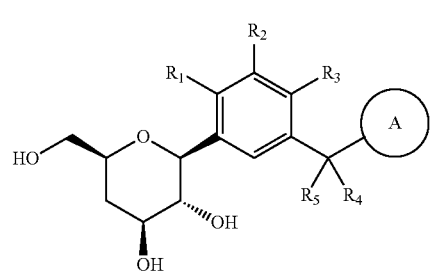

wherein
R₁ is hydroxyl, C₁₋₄alkoxy, heteroaryl, or halogen;
R₂ is H, C₁₋₂alkyl, or halogen;
R₃ is C₁₋₄alkyl, halogen, C₁₋₄alkoxy, hydroxyl, C₃₋₅cycloalkyl, cyano, or C₁₋₂alkenyl; wherein said C₁₋₄alkyl may be substituted with halogen;
R₄ is H or C₁₋₄alkyl;
R₅ is H or C₁₋₄alkyl; or alternatively R₄ is linked together to R₅ to form a cycloalkyl, alkenyl, or oxo;
A is selected from the group consisting of:

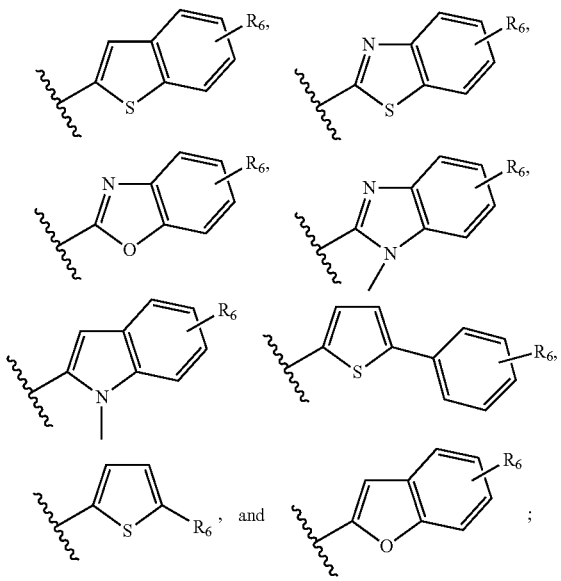

and
R₆ is H, halogen, or C₁₋₄alkyl;
or an optical isomer, enantiomer, diastereomer, cis-trans isomer, racemate or pharmaceutically acceptable salt thereof.

2. The compound of claim 1, wherein
R₁ is OH, —OCH₃, —OCH₂—CH=CH₂,

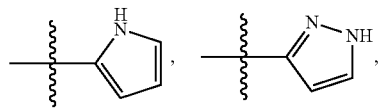

or —Br;
R₂ is H, —CH₃, or —F;
R₃ is —CH₃, —CF₃, —CH₂CH₃, —Cl, —F, —OCH₃, —CH=CH₂, —CN, or

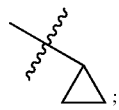 [SMILES: *C1CC1]

R₄ is H or —CH₃;
R₅ is H or —CH₃; or alternatively R₄ is linked together to R₅ to form

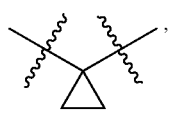 [SMILES: *C1(*)CC1]

=CH₂, or =O;

A is selected from the group consisting of:

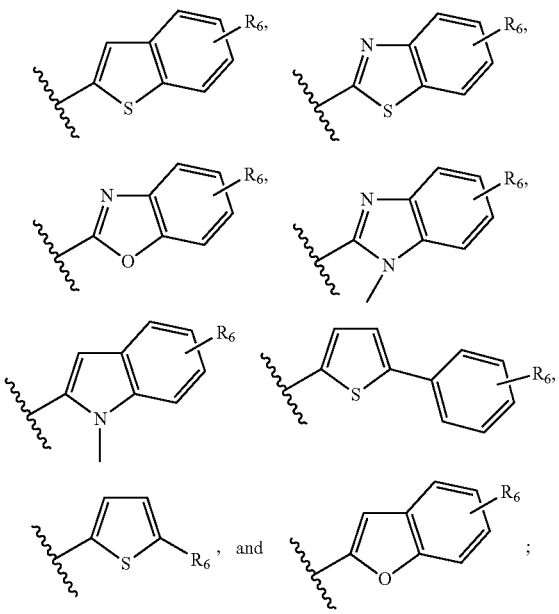

and
R₆ is H, —F, —Cl, or —CH₂CH₃;
or an optical isomer, enantiomer, diastereomer, cis-trans isomer, racemate or pharmaceutically acceptable salt thereof.

3. The compound of claim 1, wherein
R₁ is —OH, —OCH₃, —OCH₂—CH=CH₂,

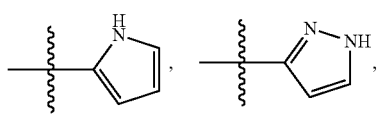 [SMILES: *c1ccc[nH]1 ; *c1cc[nH]n1]

or —Br;
R₂ is —H, —CH₃, or —F;
R₃ is —CH₃, —CF₃, —CH₂CH₃, —Cl, —OCH₃, —CH=CH₂, —CN, or

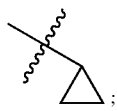 [SMILES: *C1CC1]

R₄ is H or —CH₃;
R₅ is H or —CH₃; or alternatively R₄ is linked together to R₅ to form

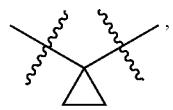

=CH₂, or =O;

A is selected from the group consisting of:

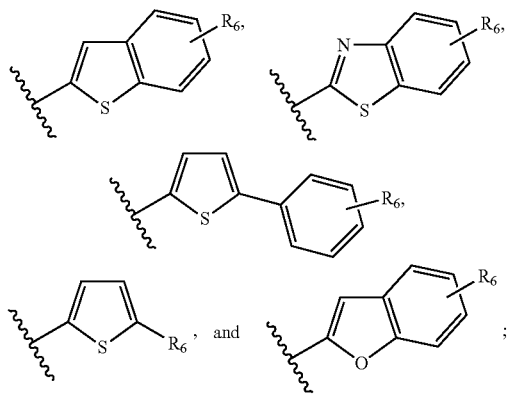

and
R$_6$ is H, —F, —Cl, or —CH$_2$CH$_3$;
or an optical isomer, enantiomer, diastereomer, cis-trans isomer, racemate or pharmaceutically acceptable salt thereof.

4. The compound of claim 1, wherein
R$_1$ is —OH;
R$_2$ is H, —CH$_3$, or —F;
R$_3$ is —CH$_3$, —CF$_3$, —CH$_2$CH$_3$, —F, —Cl, —OCH$_3$, —CH=CH2, or

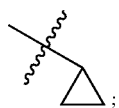

R$_4$ is H;
R$_5$ is H;
A is selected from the group consisting of:

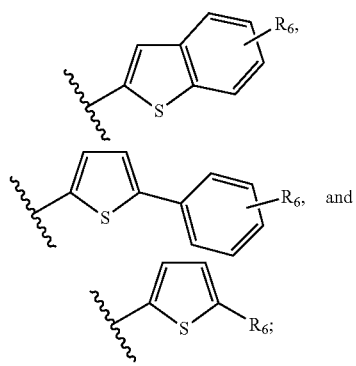

and
R$_6$ is H, —F, —Cl, or —CH$_2$CH$_3$;
or an optical isomer, enantiomer, diastereomer, cis-trans isomer, racemate or pharmaceutically acceptable salt thereof.

5. The compound of claim 1, wherein
R$_1$ is —OH;
R$_2$ is H or —F;
R$_3$ is —CH$_3$, —CH$_2$CH$_3$, —Cl or —OCH$_3$;
R$_4$ is H;
R$_5$ is H;

A is selected from the group consisting of:

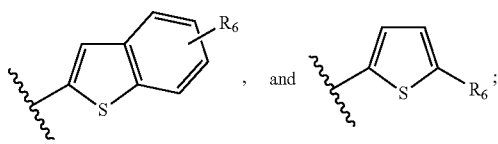

and
R$_6$ is H, —F or —CH$_2$CH$_3$;
or an optical isomer, enantiomer, diastereomer, cis-trans isomer, racemate or pharmaceutically acceptable salt thereof.

6. The compound of claim 1, wherein
R$_1$ is —OH;
R$_2$ is H or —F;
R$_3$ is —CH$_3$, —CH$_2$CH$_3$, —Cl, or —OCH$_3$;
R$_4$ is H;
R$_5$ is H;
A is

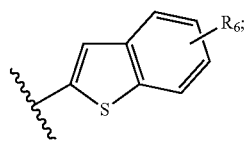

and
R$_6$ is H or —F;
or an optical isomer, enantiomer, diastereomer, cis-trans isomer, racemate or pharmaceutically acceptable salt thereof.

7. The compound of claim 1, wherein
R$_1$ is —OH;
R$_2$ is H;
R$_3$ is —CH$_3$;
R$_4$ is H;
R$_5$ is H;
A is

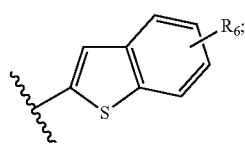

and
R$_6$ is H;
or an optical isomer, enantiomer, diastereomer, cis-trans isomer, racemate or pharmaceutically acceptable salt thereof.

8. The compound of claim 1, wherein
R$_1$ is —OH or —Br;
R$_2$ is H;
R$_3$ is —CH$_3$;
R$_4$ is H;
R$_5$ is H;

127

A is selected from the group consisting of:

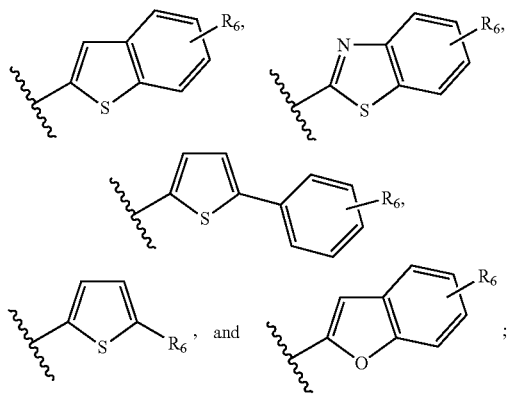

and

R$_6$ is H, CH$_2$CH$_3$, or —F or an optical isomer, enantiomer, diastereomer, cis-trans isomer, racemate or pharmaceutically acceptable salt thereof.

9. The compound of claim 1 wherein the compound is selected from:
(2S,3R,4S,6S)-2-(5-(benzo[b]thiophen-2-ylmethyl)-2-hydroxy-4-methylphenyl)-6-(hydroxymethyl)tetrahydro-2H-pyran-3,4-diol,
(2S,3R,4S,6S)-2-(5-(benzo[b]thiophen-2-ylmethyl)-2-hydroxy-4-methoxyphenyl)-6-(hydroxymethyl)tetrahydro-2H-pyran-3,4-diol,
(2S,3R,4S,6S)-2-(5-(benzo[b]thiophen-2-ylmethyl)-4-chloro-2-hydroxyphenyl)-6-(hydroxymethyl)tetrahydro-2H-pyran-3,4-diol,
(2S,3R,4S,6S)-2-(5-(benzo[b]thiophen-2-ylmethyl)-4-fluoro-2-hydroxyphenyl)-6-(hydroxymethyl)tetrahydro-2H-pyran-3,4-diol,
(2S,3R,4S,6S)-2-(5-(benzo[b]thiophen-2-ylmethyl)-4-ethyl-2-hydroxyphenyl)-6-(hydroxymethyl)tetrahydro-2H-pyran-3,4-diol,
(2S,3R,4S,6S)-2-(5-(benzo[b]thiophen-2-ylmethyl)-4-cyclopropyl-2-hydroxyphenyl)-6-(hydroxymethyl)tetrahydro-2H-pyran-3,4-diol,
(2S,3R,4S,6S)-2-(5-(benzo[b]thiophen-2-ylmethyl)-2-hydroxy-4-(trifluoromethyl)phenyl)-6-(hydroxymethyl)tetrahydro-2H-pyran-3,4-diol,
(2S,3R,4S,6S)-2-(5-(benzo[b]thiophen-2-ylmethyl)-2-hydroxy-4-vinylphenyl)-6-(hydroxymethyl)tetrahydro-2H-pyran-3,4-diol,
(2S,3R,4S,6S)-2-(5-((5-fluorobenzo[b]thiophen-2-yl)methyl)-2-hydroxy-4-methylphenyl)-6-(hydroxymethyl)tetrahydro-2H-pyran-3,4-diol,
(2S,3R,4S,6S)-2-(5-((5-chlorobenzo[b]thiophen-2-yl)methyl)-2-hydroxy-4-methylphenyl)-6-(hydroxymethyl)tetrahydro-2H-pyran-3,4-diol,
(2S,3R,4S,6S)-2-(5-(benzo[b]thiophen-2-ylmethyl)-3-fluoro-2-hydroxy-4-methoxyphenyl)-6-(hydroxymethyl)tetrahydro-2H-pyran-3,4-diol,
(2S,3R,4S,6S)-2-(5-(benzo[b]thiophen-2-ylmethyl)-2-hydroxy-3,4-dimethylphenyl)-6-(hydroxymethyl)tetrahydro-2H-pyran-3,4-diol,
(2S,3R,4S,6S)-2-(5-((5-(4-fluorophenyl)thiophen-2-yl)methyl)-2-hydroxy-4-methylphenyl)-6-(hydroxymethyl)tetrahydro-2H-pyran-3,4-diol, and

128

(2S,3R,4S,6S)-2-(5-((5-ethylthiophen-2-yl)methyl)-2-hydroxy-4-methylphenyl)-6-(hydroxymethyl)tetrahydro-2H-pyran-3,4-diol.

10. The compound of claim 9 wherein the compound is selected from:
(2S,3R,4S,6S)-2-(5-(benzo[b]thiophen-2-ylmethyl)-2-hydroxy-4-methylphenyl)-6-(hydroxymethyl)tetrahydro-2H-pyran-3,4-diol,
(2S,3R,4S,6S)-2-(5-(benzo[b]thiophen-2-ylmethyl)-4-chloro-2-hydroxyphenyl)-6-(hydroxymethyl)tetrahydro-2H-pyran-3,4-diol,
(2S,3R,4S,6S)-2-(5-(benzo[b]thiophen-2-ylmethyl)-3-fluoro-2-hydroxy-4-methoxyphenyl)-6-(hydroxymethyl)tetrahydro-2H-pyran-3,4-diol,
(2S,3R,4S,6S)-2-(5-(benzo[b]thiophen-2-ylmethyl)-4-ethyl-2-hydroxyphenyl)-6-(hydroxymethyl)tetrahydro-2H-pyran-3,4-diol,
(2S,3R,4S,6S)-2-(5-((5-fluorobenzo[b]thiophen-2-yl)methyl)-2-hydroxy-4-methylphenyl)-6-(hydroxymethyl)tetrahydro-2H-pyran-3,4-diol, and
(2S,3R,4S,6S)-2-(5-((5-ethylthiophen-2-yl)methyl)-2-hydroxy-4-methylphenyl)-6-(hydroxymethyl)tetrahydro-2H-pyran-3,4-diol.

11. A pharmaceutical composition comprising at least one compound of claim 1 and at least one pharmaceutically acceptable carrier.

12. The pharmaceutical composition of claim 11 wherein the compound is selected from:
(2S,3R,4S,6S)-2-(5-(benzo[b]thiophen-2-ylmethyl)-2-hydroxy-4-methylphenyl)-6-(hydroxymethyl)tetrahydro-2H-pyran-3,4-diol,
(2S,3R,4S,6S)-2-(5-(benzo[b]thiophen-2-ylmethyl)-2-hydroxy-4-methoxyphenyl)-6-(hydroxymethyl)tetrahydro-2H-pyran-3,4-diol,
(2S,3R,4S,6S)-2-(5-(benzo[b]thiophen-2-ylmethyl)-4-chloro-2-hydroxyphenyl)-6-(hydroxymethyl)tetrahydro-2H-pyran-3,4-diol,
(2S,3R,4S,6S)-2-(5-(benzo[b]thiophen-2-ylmethyl)-4-fluoro-2-hydroxyphenyl)-6-(hydroxymethyl)tetrahydro-2H-pyran-3,4-diol,
(2S,3R,4S,6S)-2-(5-(benzo[b]thiophen-2-ylmethyl)-4-ethyl-2-hydroxyphenyl)-6-(hydroxymethyl)tetrahydro-2H-pyran-3,4-diol,
(2S,3R,4S,6S)-2-(5-(benzo[b]thiophen-2-ylmethyl)-4-cyclopropyl-2-hydroxyphenyl)-6-(hydroxymethyl)tetrahydro-2H-pyran-3,4-diol,
(2S,3R,4S,6S)-2-(5-(benzo[b]thiophen-2-ylmethyl)-2-hydroxy-4-(trifluoromethyl)phenyl)-6-(hydroxymethyl)tetrahydro-2H-pyran-3,4-diol,
(2S,3R,4S,6S)-2-(5-(benzo[b]thiophen-2-ylmethyl)-2-hydroxy-4-vinylphenyl)-6-(hydroxymethyl)tetrahydro-2H-pyran-3,4-diol,
(2S,3R,4S,6S)-2-(5-((5-fluorobenzo[b]thiophen-2-yl)methyl)-2-hydroxy-4-methylphenyl)-6-(hydroxymethyl)tetrahydro-2H-pyran-3,4-diol,
(2S,3R,4S,6S)-2-(5-((5-chlorobenzo[b]thiophen-2-yl)methyl)-2-hydroxy-4-methylphenyl)-6-(hydroxymethyl)tetrahydro-2H-pyran-3,4-diol,
(2S,3R,4S,6S)-2-(5-(benzo[b]thiophen-2-ylmethyl)-3-fluoro-2-hydroxy-4-methoxyphenyl)-6-(hydroxymethyl)tetrahydro-2H-pyran-3,4-diol,
(2S,3R,4S,6S)-2-(5-(benzo[b]thiophen-2-ylmethyl)-2-hydroxy-3,4-dimethylphenyl)-6-(hydroxymethyl)tetrahydro-2H-pyran-3,4-diol,
(2S,3R,4S,6S)-2-(5-((5-(4-fluorophenyl)thiophen-2-yl)methyl)-2-hydroxy-4-methylphenyl)-6-(hydroxymethyl)tetrahydro-2H-pyran-3,4-diol, and (2S,3R,4S,6S)-2-(5-((5-ethylthiophen-2-yl)methyl)-2-hydroxy-4-methylphenyl)-6-(hydroxymethyl)tetrahydro-2H-pyran-3,4-diol.

13. The pharmaceutical composition of claim 12 wherein the compound is selected from:

(2S,3R,4S,6S)-2-(5-(benzo[b]thiophen-2-ylmethyl)-2-hydroxy-4-methylphenyl)-6-(hydroxymethyl)tetrahydro-2H-pyran-3,4-diol, (2S,3R,4S,6S)-2-(5-(benzo[b]thiophen-2-ylmethyl)-4-chloro-2-hydroxyphenyl)-6-(hydroxymethyl)tetrahydro-2H-pyran-3,4-diol, (2S,3R,4S,6S)-2-(5-(benzo[b]thiophen-2-ylmethyl)-3-fluoro-2-hydroxy-4-methoxyphenyl)-6-(hydroxymethyl)tetrahydro-2H-pyran-3,4-diol, (2S,3R,4S,6S)-2-(5-(benzo[b]thiophen-2-ylmethyl)-4-ethyl-2-hydroxyphenyl)-6-(hydroxymethyl)tetrahydro-2H-pyran-3,4-diol, (2S,3R,4S,6S)-2-(5-((5-fluorobenzo[b]thiophen-2-yl)methyl)-2-hydroxy-4-methylphenyl)-6-(hydroxymethyl)tetrahydro-2H-pyran-3,4-diol, and (2S,3R,4S,6S)-2-(5-((5-ethylthiophen-2-yl)methyl)-2-hydroxy-4-methylphenyl)-6-(hydroxymethyl)tetrahydro-2H-pyran-3,4-diol.

14. A method of treating a subject suffering from or diagnosed with a disease, disorder, or condition mediated by SGLT activity, comprising administering to the subject a therapeutically effective amount of at least one compound of claim 1.

15. A method according to claim 14, wherein the disease, disorder, or medical condition is selected from the group consisting of diabetes and Syndrome X.

16. A method according to claim 14, wherein the disease, disorder, or condition is selected from the group consisting of IDDM, NIDDM, IGT, IFG, obesity, nephropathy, neuropathy, retinopathy, atherosclerosis, polycystic ovarian syndrome, hypertension, ischemia, stroke, heart disease, irritable bowel disorder, inflammation, and cataracts.

17. A method according to claim 14, wherein the disease, disorder, or condition is selected from the group consisting of IDDM, NIDDM, and obesity.

18. A method according to claim 14, wherein the disease, disorder, or condition is selected from the group consisting of IDDM, NIDDM, IGT, IFG, obesity, nephropathy, neuropathy, retinopathy, atherosclerosis, hypertension, ischemia, stroke, and heart disease.

19. The method of claim 14 wherein the therapeutically effective amount of the compound of Formula (I) is from about 0.1 mg/dose to about 5 g/dose.

20. A process for making a pharmaceutical composition comprising admixing any of the compounds according to claim 1 and a pharmaceutically acceptable carrier.

* * * * *